United States Patent
Yu et al.

(10) Patent No.: US 10,385,060 B2
(45) Date of Patent: Aug. 20, 2019

(54) PIPERIDINE DERIVATIVE AND PREPARATION METHOD AND PHARMACEUTICAL USE THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Shanghai Yu, Shanghai (CN); Fanglong Yang, Shanghai (CN); Lei Chen, Shanghai (CN); Jingjing Yan, Shanghai (CN); Xiqian Zhang, Shanghai (CN); Zhichao Xie, Shanghai (CN); Lingxiang Chen, Shanghai (CN); Mingxun He, Shanghai (CN)

(73) Assignees: Jiangsu Hengrui Medicine Co., Ltd., Lianyungang, Jiangsu (CN); Shanghai Hangrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/012,958

(22) Filed: Jun. 20, 2018

(65) Prior Publication Data

US 2018/0298020 A1    Oct. 18, 2018

Related U.S. Application Data

(62) Division of application No. 15/736,898, filed as application No. PCT/CN2016/083636 on May 27, 2016, now Pat. No. 10,087,191.

(30) Foreign Application Priority Data

Jun. 16, 2015   (CN) ........................... 2015 1 0334700
Dec. 18, 2015   (CN) ........................... 2015 1 0954294

(51) Int. Cl.
| | | |
|---|---|---|
| *A61K 31/4725* | (2006.01) | |
| *A61K 31/4741* | (2006.01) | |
| *C07D 491/056* | (2006.01) | |
| *A61K 31/4743* | (2006.01) | |
| *C07D 217/14* | (2006.01) | |
| *C07D 401/04* | (2006.01) | |
| *C07D 401/06* | (2006.01) | |
| *C07D 417/04* | (2006.01) | |
| *C07D 491/048* | (2006.01) | |
| *C07D 495/04* | (2006.01) | |
| *C07D 217/16* | (2006.01) | |
| *C07D 401/10* | (2006.01) | |

(Continued)

(52) U.S. Cl.
CPC ...... *C07D 491/056* (2013.01); *A61K 31/4741* (2013.01); *A61K 31/4743* (2013.01); *C07D 217/14* (2013.01); *C07D 217/16* (2013.01); *C07D 401/04* (2013.01); *C07D 401/06* (2013.01); *C07D 401/10* (2013.01); *C07D 405/12* (2013.01); *C07D 413/10* (2013.01); *C07D 417/04* (2013.01); *C07D 471/04* (2013.01); *C07D 491/048* (2013.01); *C07D 495/04* (2013.01)

(58) Field of Classification Search
CPC ....................... A61K 31/4725; A61K 31/4741
USPC ................................................. 514/307, 291
See application file for complete search history.

(56) References Cited

U.S. PATENT DOCUMENTS 9,155,727 B2 * 10/2015 Bradbury .............. C07C 57/145

FOREIGN PATENT DOCUMENTS

| EP | 1113007 A1 | 7/2001 |
|---|---|---|
| WO | 2008068974 A1 | 6/2008 |

(Continued)

OTHER PUBLICATIONS

Bioorganic & Medicinal Chemistry, 2002, 10(4), 1085-1092.

(Continued)

*Primary Examiner* — Charanjit Aulakh
(74) *Attorney, Agent, or Firm* — Panitch Schwarze Belisario & Nadel LLP

(57) ABSTRACT

The present invention relates to a piperidine derivative and the preparation method and a pharmaceutical use thereof. In particular, the present invention relates to the piperidine derivative as shown by general formula (I) and the preparation method thereof and a pharmaceutical composition containing the same, and the use thereof as an estrogen receptor modulator in the treatment of estrogen receptor mediated or dependent diseases or conditions, the diseases preferably being breast cancer. In the abstract, the definition of each substituent of the general formula (I) is the same as that in the description.

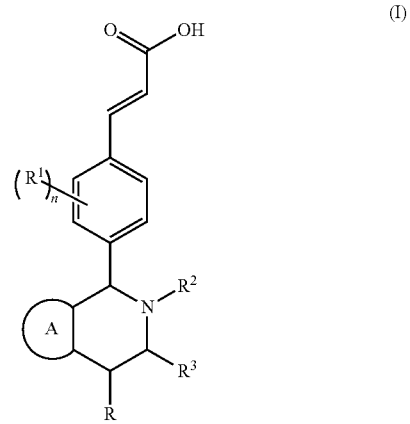

(I)

17 Claims, No Drawings

(51) Int. Cl.
*C07D 405/12* (2006.01)
*C07D 413/10* (2006.01)
*C07D 471/04* (2006.01)

(56) References Cited

FOREIGN PATENT DOCUMENTS

| | | | |
|---|---|---|---|
| WO | 2008080015 | A3 | 7/2008 |
| WO | 2009068177 | A1 | 6/2009 |
| WO | 2009117097 | A1 | 9/2009 |
| WO | 2011153359 | A1 | 12/2011 |
| WO | 2013162061 | A1 | 10/2013 |
| WO | 2014031937 | A1 | 2/2014 |
| WO | 2014106848 | A1 | 7/2014 |
| WO | 2014141292 | A3 | 9/2014 |
| WO | 2014151899 | A1 | 9/2014 |
| WO | 2014153214 | A1 | 9/2014 |
| WO | 2014159224 | A1 | 10/2014 |
| WO | 2014165723 | A3 | 10/2014 |
| WO | 2014135834 | A8 | 11/2014 |
| WO | 2014180735 | A1 | 11/2014 |
| WO | 2014191726 | A1 | 12/2014 |
| WO | 2015092634 | A1 | 6/2015 |

OTHER PUBLICATIONS

Journal of Organic Chemistry, 2005, 70(6), 2372-2375.
Khimiya Geterotsiklicheskikh Soedinenii, 1987, (7), 889-93.
Bioorganic & Medicinal Chemistry, 2005, 13(14), 4450-4457.
Journal of Medicinal Chemistry, 56(24), 10045-10065, 2013.
Bioorganic & Medicinal Chemistry, 9(3), 2001, 677-694.
Tetrahedron Letters, 50(49), 2009, 6783-6786.
Bioorganic & Medicinal Chemistry Letters, 2008, 18(19), 5299-5302.
Journal of Heterocyclic Chemistry, 41(6), 2004, 931-939.
Bioorganic & Medicinal Chemistry, 2013, 21(21), 6804-6820.
Journal of the American Chemical Society, 2014, 136(11), 4287-4299.
Tetrahedron Letters, 2002, 43(23), 4285-4287.
Organic & Biomolecular Chemistry, 2014, 12(44), 8952-8965.
Bioorganic & Medicinal Chemistry, 2011, 19(3), 1106-1114.
Applied Organometallic Chemistry, 2014, 28(7), 529-536.
Organometallics, 2015, 34(19), 4732-4740.
Environmental Science and Pollution Research, 2014, 21(7), 4861-4870.
ChemMedChem, 2009, 4(2), 249-260.
Journal of Medicinal Chemistry, 2011, 54(18), 6342-6363.
Organic & Biomolecular Chemistry, 2014, 12(37), 7318-7327.
Organic Letters, 2012, 14(2), 600-603.
Journal of Medicinal Chemistry, 2011, 54(15), 5395-5402.
ACS Medicinal Chemistry Letters, vol. 7, No. 5, Dec. 19, 2015.

\* cited by examiner

PIPERIDINE DERIVATIVE AND PREPARATION METHOD AND PHARMACEUTICAL USE THEREOF

CROSS-REFERENCE TO RELATED APPLICATION

This application is a Divisional of Ser. No. 15/736,898, which was filed on Dec. 15, 2017, which is a Section 371 of International Application No. PCT/CN2016/083636, which was published on Dec. 22, 2016 in the Chinese language, under International Publication No. WO2016/202161, which claims priority to Chinese Application No. 201510334700.9, filed on Jun. 16, 2016 and Chinese Application No. 201510954294.6, filed on Dec. 18, 2015, the disclosures of which are incorporated herein by reference in their entireties.

FIELD OF THE INVENTION

The present invention belongs to the field of medicine, and relates to a piperidine derivative and a preparation method thereof and a pharmaceutical use thereof. In particular, the present invention relates to a piperidine derivative as shown by general formula (I), a preparation method thereof, and a pharmaceutical composition containing same, and a use thereof as an estrogen receptor modulator in treating an estrogen receptor mediated or dependent disease or condition, particularly preferably breast cancer.

BACKGROUND OF THE INVENTION

After a long period of basic research and clinical monitoring, it is found that diseases such as breast cancer, ovarian cancer, osteoporosis, schizophrenia and Alzheimer's disease are closely related to the abnormality of the estrogen signaling pathway. Estrogen is a steroid hormone secreted by the endocrine system, and plays an important role in the reproductive system, bone tissue, cardiovascular system, immune system and central nervous system. Estrogen signal transduction system plays an important role in the regulation of cell growth, differentiation and apoptosis. The occurrence and development of estrogen-dependent tumors, such as breast cancer, ovarian cancer, and endometrial cancer, are closely related to estrogen. Currently, the main chemotherapy for breast cancer is the use of antiestrogen agents, such as Tamoxifen. However, Tamoxifen exerts estrogen agonist properties in the uterus, thereby stimulating cancer cells in the uterus. Due to these serious side effects, it is imperative to seek a new safe and effective treatment.

One important protein of the estrogen signaling pathway is estrogen receptor (ER). ER is a steroid hormone receptor, and belongs to a ligand-activated transcription factor of the nuclear receptor superfamily that contains two subtypes: ERα (discovered in 1950) and ERβ (discovered in 1996), encoded by different genes, respectively. ERα and ERβ show a high degree of similarity at the amino acid level, and their similarity in the DNA binding domain is up to 97%, and the similarity in the ligand binding domain is up to 56%, but only 24% low homology in the N terminus. ER contains 6 domains from A to F, which comprise four main functional areas. The functional area of the N terminal A/B domain is a ligand independent transcriptional activation function AF-1, and AF-1 has a constitutive activity. The transcription of target genes is activated by interaction with basic transcription factors, reactivation factors and other transcription factors. There are multiple phosphorylation sites in this function, and it is reported that the role of AF-1 depends on protein phosphorylation. The DNA binding domain (DBD) composed of the C domain is highly conservative and contains 2 zinc finger domains that can specifically bind to the target DNA, simultaneously, and this domain plays an important role in the dimerization of receptors. The D domain is a hinge region that connects the DBD and the ligand binding domain (LBD), with low conservatism (only 30% homology between two subtypes). The ligand binding domain (LBD) composed of the C terminal E domain determines the specific binding of ER to ligands such as estrogen, selective estrogen receptor modulator (SERM), and selective estrogen receptor downregulator (SERD). LBD has a ligand dependent transcriptional activation function AF-2, which has a synergistic reaction with AF-1 to exert ER receptor's role in activating the transcription of target genes. At the same time, LBD has a strong dimerization interface and still can function without ligands. Therefore, LBD is the key site for receptor dimerization.

ERα is mainly distributed in the uterus, ovary, testis, pituitary, kidney, epididymis and adrenal gland, while ERβ is mainly distributed in the prostate, ovary, lung, bladder, brain and blood vessels. Due to the serious side effects of full agonists or full antagonists, the study of SERM arises. The "selectivity" means that SERM acts as an agonist in some tissues such as bone, liver and the cardiovascular system that are rich in ERβ, whereas it acts as an antagonist in some other tissues such as mammary glands. In the uterus, the significant region of ERα, it can be either an agonist or antagonist. So far, commercially available SERMs include Tamoxifen, Raloxifene, Bazedoxifene, Toremifene and the like. However, studies have found that commercially available SERMs still have serious side effects, for example, the long-term use of Tamoxifen and Toremifene can cause endometrial hyperplasia, polyps and endometrial cancer, and the common side effects of Raloxifene include hot flashes, leg pain, breast tenderness and venous thrombosis and the like. Therefore, the research and development of new compounds are still urgent problems to be solved.

Tamoxifen belongs to a class of compounds known as selective estrogen receptor modulators (SERMs), and has the ability to stabilize ERα and slightly upregulate the level of ERα receptors. In contrast, fulvestrant induces rapid degradation of ERα and intensifies the blockage of the ER receptor signaling pathway, and such compounds are called selective estrogen receptor downregulators (SERDs). The differences in the mechanisms of actions of these SERMs and SERDs seem to be the mechanisms responsible for the resistance of these compounds. A large number of tumors that are tamoxifen resistant and ER positive are still sensitive to fulvestrant. It is found clinically that SERDs such as fulvestrant can effectively treat some breast cancers that are ERα positive and tamoxifen resistant. Therefore, the compounds responsible for degradation of ERα can be used to prolong the duration of efficacy in breast cancer patients successfully treated with anti-estrogen therapy, whereas different SERMs, aromatase inhibitiors and SERDs can be used successively.

The patent applications disclosing selective estrogen receptor mediated modulators include WO2014165723, WO2014151899, WO2014141292, WO2014135834 and WO2014106848.

In order to achieve better therapeutic effects and to better meet the needs of the market, the inventors hope to develop a new generation of highly effective and low toxicity SERDs targeting the estrogen signaling pathway. The present invention provides a novel structure of a SERD, and it is found that the compounds with such a structure have good activity and show excellent ER receptor antagonism.

SUMMARY OF THE INVENTION

The present invention is directed to a compound of formula (I), or a tautomer, mesomer, racemate, enantiomer, diastereomer, or mixture thereof, or a pharmaceutically acceptable salt thereof, wherein the structure of the compound of formula (I) is as follows:

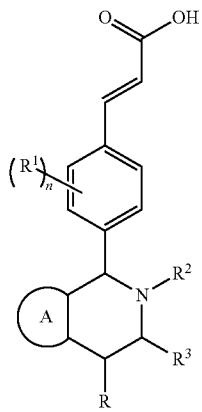

(I)

or a tautomer, mesomer, racemate, enantiomer, diastereomer, or mixture thereof, or a pharmaceutically acceptable salt thereof,
wherein:
ring A is selected from the group consisting of:

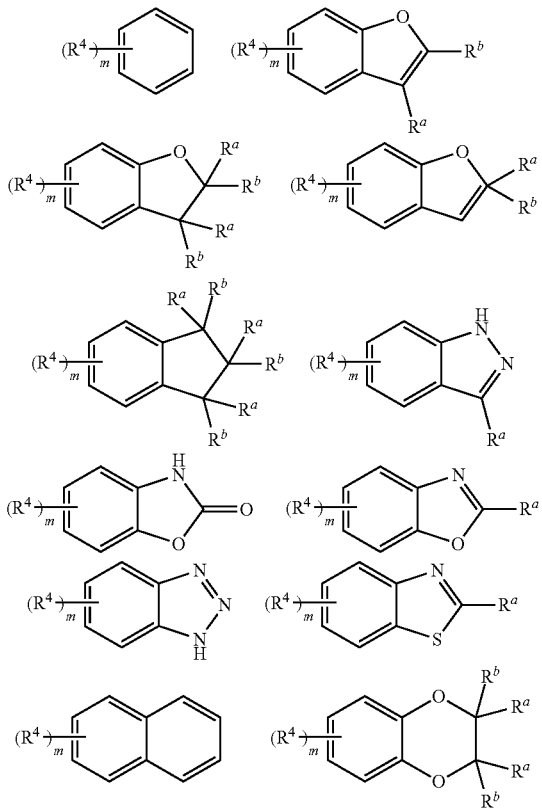

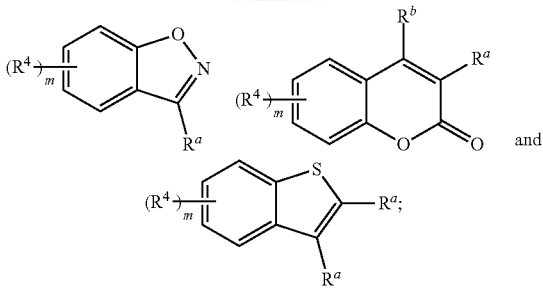

R is selected from the group consisting of hydrogen, alkyl and cycloalkyl, wherein the alkyl and cycloalkyl are each optionally substituted by one or more groups selected from the group consisting of halogen, amino, cyano, hydroxy, alkoxy, carboxy, cycloalkyl, aryl and heteroaryl;

each $R^1$ is identical or different and each is independently selected from the group consisting of hydrogen, alkyl, halogen, cyano and alkoxy, wherein the alkyl and alkoxy are each optionally substituted by one or more groups selected from the group consisting of halogen, amino, cyano and hydroxy;

$R^2$ is selected from the group consisting of alkyl, haloalkyl and cycloalkyl, wherein the alkyl and cycloalkyl are each optionally substituted by one or more groups selected from the group consisting of halogen, amino, cyano, hydroxy, alkoxy, carboxy, cycloalkyl, aryl and heteroaryl;

$R^3$ is selected from the group consisting of hydrogen, alkyl and cycloalkyl, wherein the alkyl and cycloalkyl are each optionally substituted by one or more groups selected from the group consisting of alkyl, halogen, amino, cyano, hydroxy, alkoxy, carboxy and cycloalkyl;

each $R^4$ is identical or different and each is independently selected from the group consisting of hydrogen, alkyl, cycloalkyl, alkoxy, amino, halogen, cyano, carboxy, alkenyl, alkynyl, heterocyclyl, aryl, heteroaryl, $-OR^5$, $-NHC(O)OR^5$ and $-NHC(O)NR^6R^7$, wherein the alkyl, alkenyl, alkynyl, cycloalkyl, alkoxy, heterocyclyl, aryl and heteroaryl are each optionally substituted by one or more groups selected from the group consisting of $R^c$, alkyl, haloalkyl, hydroxyalkyl, halogen, amino, nitro, cyano, hydroxy, oxo, hydroxyalkyl, alkoxy, cycloalkyl, heterocyclyl, aryl and heteroaryl;

$R^c$ is selected from the group consisting of alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl and $-C(O)NR^6R^7$;

$R^6$ and $R^7$ are identical or different and each is independently selected from the group consisting of hydrogen, alkyl, hydroxy, halogen, cyano, amino, nitro, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^a$ and $R^b$ are identical or different and each is independently selected from the group consisting of hydrogen, alkyl, hydroxy, halogen, cyano, amino, nitro, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, —$OR^5$, aryl and heteroaryl;

m is 0, 1, 2, 3 or 4; and n is 0, 1, 2, 3 or 4.

In a preferred embodiment of the present invention, in a compound of formula (I), or a tautomer, mesomer, racemate, enantiomer, diastereomer, or mixture thereof, or a pharmaceutically acceptable salt thereof, ring A is selected from the group consisting of:

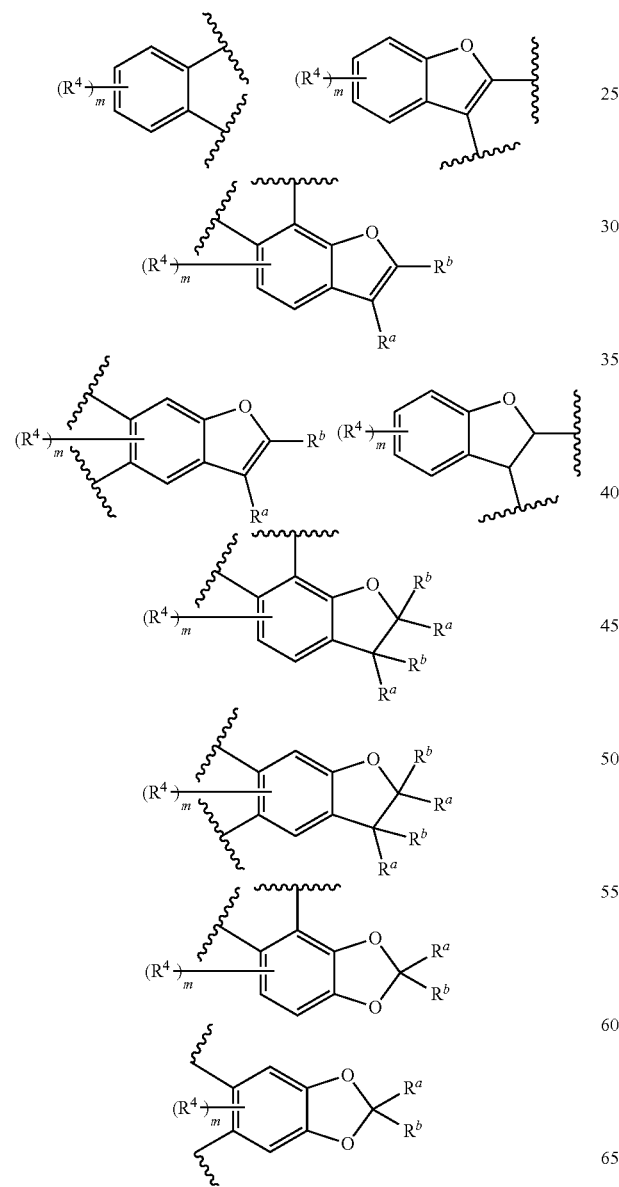

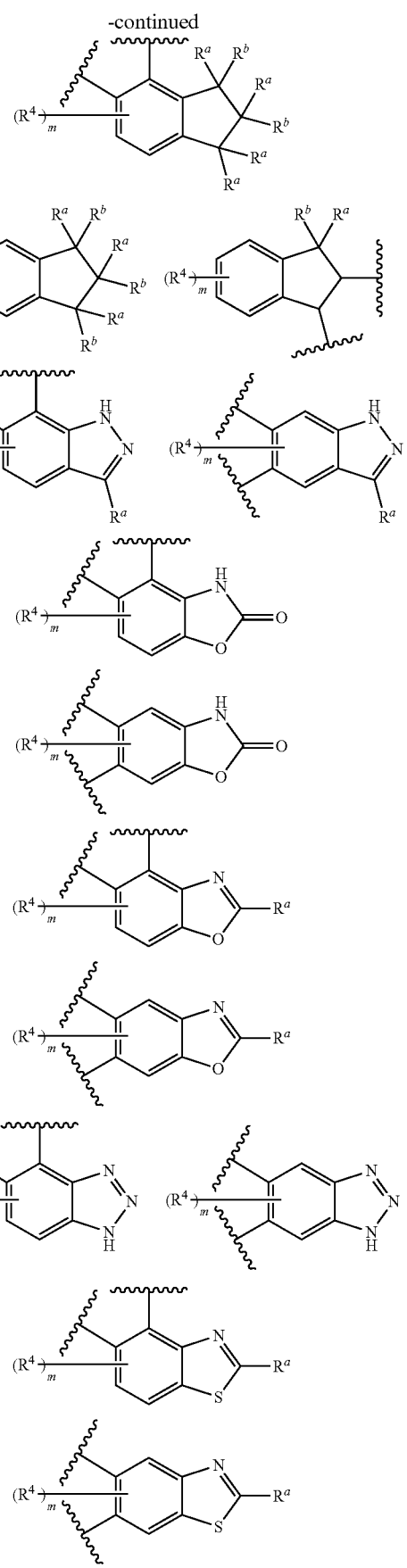

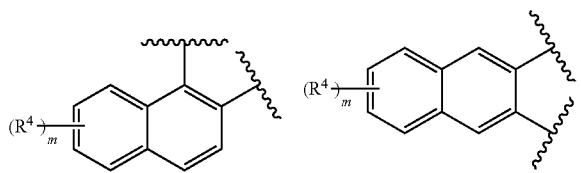
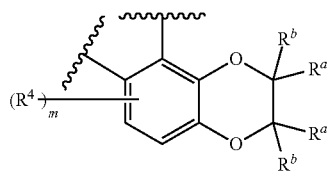
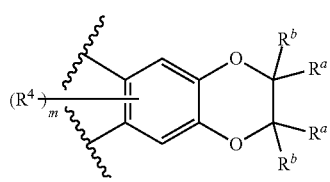
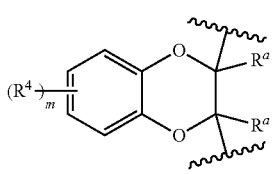
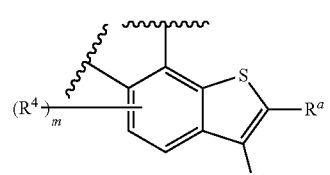
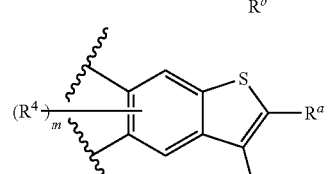
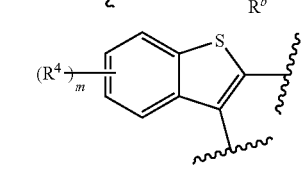
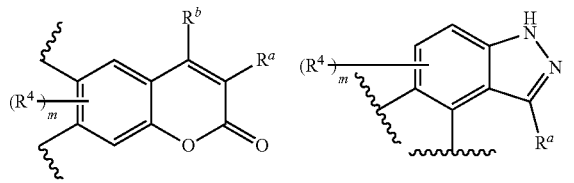
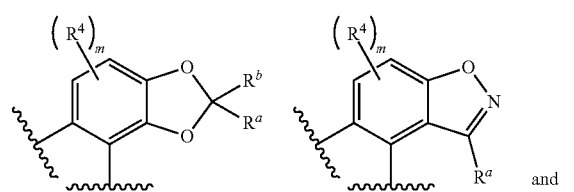

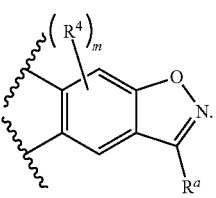

In a preferred embodiment of the present invention, in a compound of formula (I), or a tautomer, mesomer, racemate, enantiomer, diastereomer, or mixture thereof, or a pharmaceutically acceptable salt thereof, n is 2.

In a preferred embodiment of the present invention, in a compound of formula (I), or a tautomer, mesomer, racemate, enantiomer, diastereomer, or mixture thereof, or a pharmaceutically acceptable salt thereof, $R^1$ is halogen.

In a preferred embodiment of the present invention, in a compound of formula (I), or a tautomer, mesomer, racemate, enantiomer, diastereomer, or mixture thereof, or a pharmaceutically acceptable salt thereof, $R^2$ is alkyl, wherein the alkyl is optionally substituted by one or more groups selected from the group consisting of halogen, amino, cyano, hydroxy, alkoxy, carboxy and cycloalkyl; preferably alkyl or haloalkyl.

In a preferred embodiment of the present invention, in a compound of formula (I), or a tautomer, mesomer, racemate, enantiomer, diastereomer, or mixture thereof, or a pharmaceutically acceptable salt thereof, $R^3$ is alkyl.

In a preferred embodiment of the present invention, in a compound of formula (I), or a tautomer, mesomer, racemate, enantiomer, diastereomer, or mixture thereof, or a pharmaceutically acceptable salt thereof, R is hydrogen or alkyl.

In a preferred embodiment of the present invention, a compound of formula (I), or a tautomer, mesomer, racemate, enantiomer, diastereomer, or mixture thereof, or a pharmaceutically acceptable salt thereof, is optionally selected from the group consisting of a compound of formula (I-A), formula (I-B) and formula (I-C):

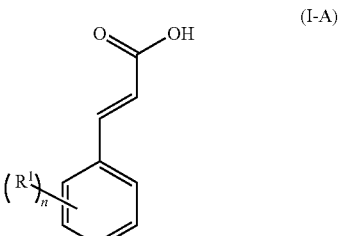

(I-A)

-continued

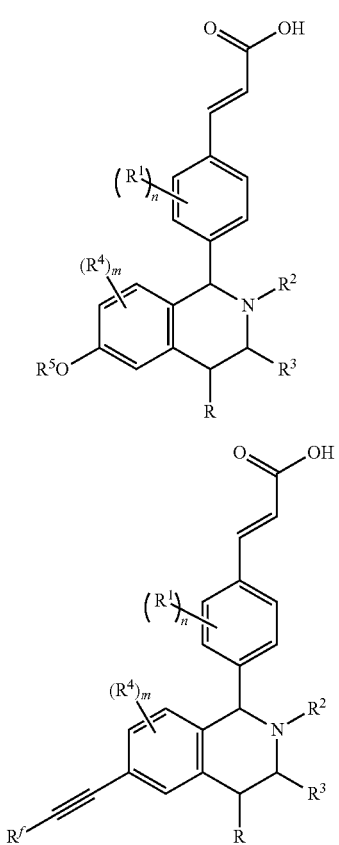

(I-B)

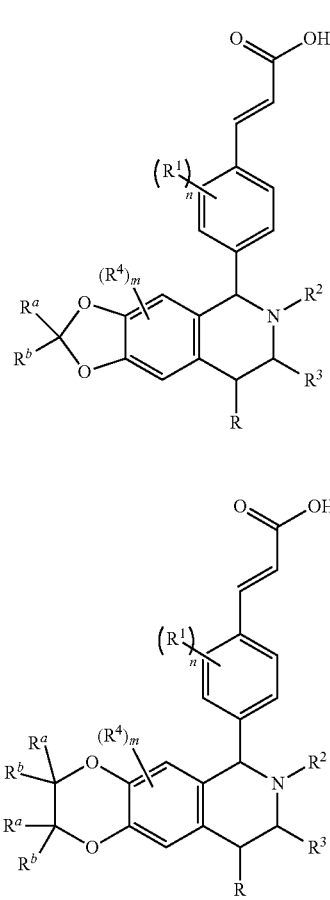

(II)

(I-C)

(III)

or a tautomer, mesomer, racemate, enantiomer, diastereomer, or mixture thereof, or a pharmaceutically acceptable salt thereof, wherein:

ring B is selected from the group consisting of cycloalkyl, heterocyclyl, aryl and heteroaryl;

$R^d$ is selected from the group consisting of hydrogen, alkyl, halogen, haloalkyl, hydroxyalkyl, oxo, amino, cyano, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^f$ is selected from the group consisting of hydrogen, alkyl, halogen, haloalkyl, hydroxyalkyl, hydroxyalkyl, amino, cyano, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl; and R to $R^5$, m and n are as defined in formula (I).

In a preferred embodiment of the present invention, a compound of formula (I), or a tautomer, mesomer, racemate, enantiomer, diastereomer, or mixture thereof, or a pharmaceutically acceptable salt thereof, is optionally selected from the group consisting of a compound of formula (II), formula (III) and formula (IV):

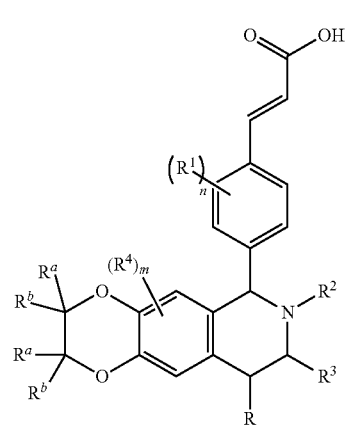

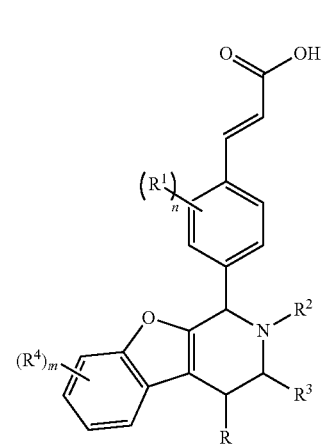

(IV)

or a tautomer, mesomer, racemate, enantiomer, diastereomer, or mixture thereof, or a pharmaceutically acceptable salt thereof, wherein:

R to $R^3$, $R^a$, $R^b$, m and n are as defined in formula (I).

In a preferred embodiment of the present invention, a compound of formula (I), or a tautomer, mesomer, racemate, enantiomer, diastereomer, or mixture thereof, or a pharmaceutically acceptable salt thereof, is optionally a compound of formula (I-D):

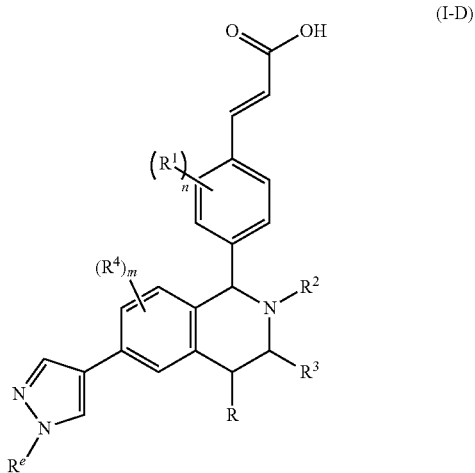

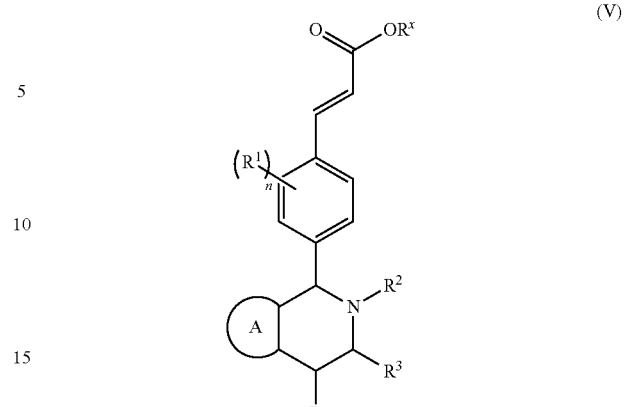

or a tautomer, mesomer, racemate, enantiomer, diastereomer, or mixture thereof, or a pharmaceutically acceptable salt thereof, wherein:

$R^e$ is selected from the group consisting of alkyl, haloalkyl, hydroxyalkyl, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl; and R to $R^5$ and n are as defined in formula (I).

In a preferred embodiment of the present invention, a compound of formula (I), or a tautomer, mesomer, racemate, enantiomer, diastereomer, or mixture thereof, or a pharmaceutically acceptable salt thereof, is optionally a compound of formula (I-I):

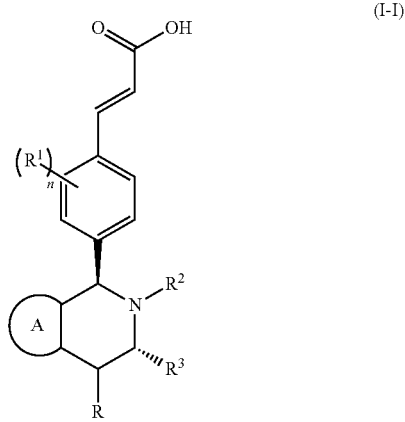

or a tautomer, mesomer, racemate, enantiomer, diastereomer, or mixture thereof, or a pharmaceutically acceptable salt thereof, wherein:

ring A, R to $R^3$ and n are as defined in formula (I).

The present invention further provides a compound of formula (V), or a tautomer, mesomer, racemate, enantiomer, diastereomer, or mixture thereof, or a pharmaceutically acceptable salt thereof, wherein:

$R^x$ is alkyl or cycloalkyl, wherein said alkyl and cycloalkyl are each optionally substituted by one or more groups selected from the group consisting of alkyl, halogen, amino, cyano, hydroxy, alkoxy, carboxy and cycloalkyl; and ring A, R, $R^1$ to $R^3$ and n are as defined in formula (I).

The present invention further provides a process for preparing the compound of formula (I), or a tautomer, mesomer, racemate, enantiomer, diastereomer, or mixture thereof, or a pharmaceutically acceptable salt thereof, comprising a step of:

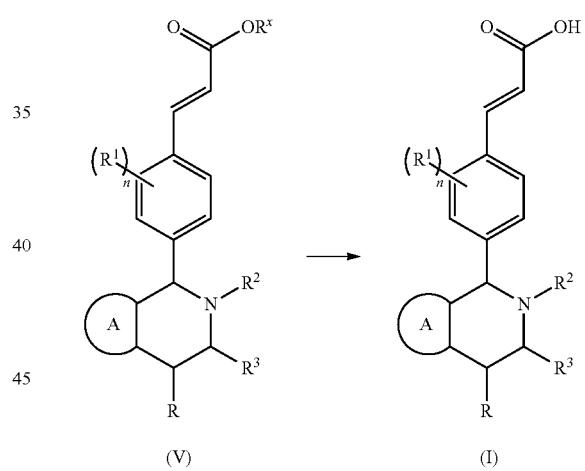

under an alkaline condition, hydrolyzing a compound of formula (V) to obtain the compound of formula (I), wherein:

ring A, $R^1$ to $R^3$ and n are as defined in formula (I).

Another aspect of this invention is directed to a pharmaceutical composition comprising a therapeutically effective amount of the compound of each aforementioned formula, or a tautomer, mesomer, racemate, enantiomer, diastereomer, or mixture thereof, or a pharmaceutically acceptable salt thereof, and one or more pharmaceutically acceptable carriers, diluents or excipients. The present invention is further directed to a process for preparing the aforementioned pharmaceutical composition, comprising a step of mixing the compound of each aforementioned formula, or a tautomer, mesomer, racemate, enantiomer, diastereomer, or mixture thereof, or a pharmaceutically acceptable salt thereof, with one or more pharmaceutically acceptable carriers, diluents or excipients.

The present invention is further directed to a use of the compound of formula (I), or a tautomer, mesomer, racemate, enantiomer, diastereomer, or mixture thereof, or a pharmaceutically acceptable salt thereof, or the pharmaceutical composition comprising the same, in the preparation of an estrogen receptor modulator.

The present invention is further directed to a use of the compound of formula (I), or a tautomer, mesomer, racemate, enantiomer, diastereomer, or mixture thereof, or a pharmaceutically acceptable salt thereof, or the pharmaceutical composition comprising the same, in the preparation of a medicament for treating an estrogen receptor mediated or dependent disease or condition, wherein the estrogen receptor mediated or dependent disease or condition is selected from the group consisting of cancer, central nervous system (CNS) defects, cardiovascular system defects, hematological system defects, immune and inflammation diseases, susceptibility to infection, metabolic defects, neurological defects, psychiatric defects and reproductive defects; wherein the cancer can be breast cancer, endometrial cancer, cervical cancer, skin cancer, prostate cancer, ovarian cancer, fallopian tube tumor, ovarioncus, hemophilia or leukemia; preferably breast cancer, ovarian cancer, endometrial cancer, prostate cancer or uterine cancer; more preferably breast cancer; wherein the central nervous system (CNS) defects can be alcoholism or migraine; wherein the cardiovascular system defects can be aortic aneurysm, susceptibility to myocardial infarction, aortic valve sclerosis, cardiovascular diseases, coronary artery disease or hypertension; wherein the immune and inflammation diseases can be Grave's disease, arthritis, multiple sclerosis or cirrhosis; wherein the susceptibility to infection can be hepatitis B or chronic liver disease; wherein the metabolic defects can be cholestasis, hypospadias, obesity, osteoarthritis, osteopenia or osteoporosis; wherein the neurological defects can be Alzheimer's disease, Parkinson's disease, migraine, or dizziness; wherein the psychiatric defects can be anorexia nervosa, attention deficit hyperactivity disorder (ADHD), dementia, severe depressive disorder or psychosis; and wherein the reproductive defects can be menarche age, endometriosis and infertility, and the like.

The present invention is further directed to the compound of formula (I), or a tautomer, mesomer, racemate, enantiomer, diastereomer, or mixture thereof, or a pharmaceutically acceptable salt thereof, for use as a medicament for treating an estrogen receptor mediated or dependent disease or condition. Wherein the estrogen receptor mediated or dependent disease or condition is selected from the group consisting of cancer, central nervous system (CNS) defects, cardiovascular system defects, hematological system defects, immune and inflammation diseases, susceptibility to infection, metabolic defects, neurological defects, psychiatric defects and reproductive defects; wherein the cancer can be breast cancer, endometrial cancer, cervical cancer, skin cancer, prostate cancer, ovarian cancer, fallopian tube tumor, ovarioncus, hemophilia or leukemia; preferably breast cancer, ovarian cancer, endometrial cancer, prostate cancer or uterine cancer; more preferably breast cancer; wherein the central nervous system (CNS) defects can be alcoholism or migraine; wherein the cardiovascular system defects can be aortic aneurysm, susceptibility to myocardial infarction, aortic valve sclerosis, cardiovascular diseases, coronary artery disease or hypertension; wherein the immune and inflammation diseases can be Grave's disease, arthritis, multiple sclerosis or cirrhosis; wherein the susceptibility to infection can be hepatitis B or chronic liver disease; wherein the metabolic defects can be cholestasis, hypospadias, obesity, osteoarthritis, osteopenia or osteoporosis; wherein the neurological defects can be Alzheimer's disease, Parkinson's disease, migraine, or dizziness; wherein the psychiatric defects can be anorexia nervosa, attention deficit hyperactivity disorder (ADHD), dementia, severe depressive disorder or psychosis; and wherein the reproductive defects can be menarche age, endometriosis and infertility, and the like.

The present invention is further directed to a method for treating an estrogen receptor mediated or dependent disease or condition, comprising a step of administering to a patient in need thereof a therapeutically effective amount of the compound of formula (I), or a tautomer, mesomer, racemate, enantiomer, diastereomer, or mixture thereof, or a pharmaceutically acceptable salt thereof. This method shows outstanding efficacy and fewer side effects. The estrogen receptor mediated or dependent disease or condition is selected from the group consisting of cancer, central nervous system (CNS) defects, cardiovascular system defects, hematological system defects, immune and inflammation diseases, susceptibility to infection, metabolic defects, neurological defects, psychiatric defects and reproductive defects; wherein the cancer can be breast cancer, endometrial cancer, cervical cancer, skin cancer, prostate cancer, ovarian cancer, fallopian tube tumor, ovarioncus, hemophilia or leukemia; preferably breast cancer, ovarian cancer, endometrial cancer, prostate cancer or uterine cancer; more preferably breast cancer; wherein the central nervous system (CNS) defects can be alcoholism or migraine; wherein the cardiovascular system defects can be aortic aneurysm, susceptibility to myocardial infarction, aortic valve sclerosis, cardiovascular diseases, coronary artery disease or hypertension; wherein the immune and inflammation diseases can be Grave's disease, arthritis, multiple sclerosis or cirrhosis; wherein the susceptibility to infection can be hepatitis B or chronic liver disease; wherein the metabolic defects can be cholestasis, hypospadias, obesity, osteoarthritis, osteopenia or osteoporosis; wherein the neurological defects can be Alzheimer's disease, Parkinson's disease, migraine, or dizziness; wherein the psychiatric defects can be anorexia nervosa, attention deficit hyperactivity disorder (ADHD), dementia, severe depressive disorder or psychosis; and wherein the reproductive defects can be menarche age, endometriosis and infertility, and the like.

In another aspect, the present invention is directed to the compound of formula (I), or a tautomer, mesomer, racemate, enantiomer, diastereomer, or mixture thereof, or a pharmaceutically acceptable salt thereof, for use as a medicament for treating cancer. It shows outstanding efficacy and fewer side effects in treating cancer. The cancer can be selected from the group consisting of breast cancer, endometrial cancer, cervical cancer, skin cancer, prostate cancer, ovarian cancer, fallopian tube tumor, ovarioncus, hemophilia and leukemia; preferably breast cancer, ovarian cancer, endometrial cancer, prostate cancer or uterine cancer; more preferably breast cancer.

In another aspect, the present invention is directed to a method for treating cancer, comprising a step of administering to a patient in need thereof a therapeutically effective amount of the compound of formula (I), or a tautomer, mesomer, racemate, enantiomer, diastereomer, or mixture thereof, or a pharmaceutically acceptable salt thereof. This method shows outstanding efficacy and fewer side effects. The cancer can be selected from the group consisting of breast cancer, endometrial cancer, cervical cancer, skin cancer, prostate cancer, ovarian cancer, fallopian tube tumor, ovarioncus, hemophilia and leukemia; preferably breast cancer, ovarian cancer, endometrial cancer, prostate cancer or uterine cancer; more preferably breast cancer.

In another aspect, the present invention is directed to the compound of formula (I), or a tautomer, mesomer, racemate, enantiomer, diastereomer, or mixture thereof, or a pharmaceutically acceptable salt thereof for use as a medicament for treating bone cancer, breast cancer, colorectal cancer, endometrial cancer, prostate cancer, ovarian cancer, uterine cancer, cervical cancer, lung cancer, leiomyomata, uterine leiomyomas, alcoholism, migraine, aortic aneurysm, susceptibility to myocardial infarction, aortic valve sclerosis, cardiovascular disease, coronary artery disease, hypertension, deep vein thrombosis, Grave's disease, arthritis, multiple sclerosis, cirrhosis, hepatitis B, chronic liver disease, cholestasis, hypospadias, obesity, osteoarthritis, osteoporosis, osteoporosis, Alzheimer's disease, Parkinson's disease, migraine, dizziness, anorexia nervosa, attention deficit hyperactivity disorder (adhd), dementia, severe depressive disorder, psychosis, menarche age, endometriosis or infertility in mammals.

In another aspect, the present invention is directed to a method for treating bone cancer, breast cancer, colorectal cancer, endometrial cancer, prostate cancer, ovarian cancer, uterine cancer, cervical cancer, lung cancer, leiomyomata, uterine leiomyomas, alcoholism, migraine, aortic aneurysm, susceptibility to myocardial infarction, aortic valve sclerosis, cardiovascular disease, coronary artery disease, hypertension, deep vein thrombosis, Grave's disease, arthritis, multiple sclerosis, cirrhosis, hepatitis B, chronic liver disease, cholestasis, hypospadias, obesity, osteoarthritis, osteoporosis, osteoporosis, Alzheimer's disease, Parkinson's disease, migraine, dizziness, anorexia nervosa, attention deficit hyperactivity disorder (adhd), dementia, severe depressive disorder, psychosis, menarche age, endometriosis or infertility in mammals, comprising a step of administering to a patient in need thereof a therapeutically effective amount of the compound of formula (I), or a tautomer, mesomer, racemate, enantiomer, diastereomer, or mixture thereof, or a pharmaceutically acceptable salt thereof.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical compositions. Such compositions can contain one or more additives selected from the group consisting of sweeteners, flavoring agents, colorants and preservatives, in order to provide a pleasing and palatable pharmaceutical preparation. Tablets contain the active ingredient and nontoxic pharmaceutically acceptable excipients suitable for the manufacture of tablets. These excipients can be inert excipients, granulating agents, disintegrating agents, and lubricants. The tablet can be uncoated or coated by means of a known technique to mask the taste of the drug or delay the disintegration and absorption of the drug in the gastrointestinal tract, thereby providing sustained release over an extended period.

Oral formulations can also be provided as soft gelatin capsules in which the active ingredient is mixed with an inert solid diluent, or the active ingredient is mixed with a water soluble carrier or an oil medium, or Olive oil.

An aqueous suspension contains the active ingredient in admixture with excipients suitable for the manufacture of an aqueous suspension. Such excipients are suspending agents, dispersants or humectants. The aqueous suspension can also contain one or more preservatives, one or more colorants, one or more flavoring agents, and one or more sweeteners.

An oil suspension can be formulated by suspending the active ingredient in a vegetable oil, or in a mineral oil. The oil suspension can contain a thickener. The aforementioned sweeteners and flavoring agents can be added to provide a palatable preparation. These compositions can be preserved by adding an antioxidant.

The active ingredient and the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added.

The present pharmaceutical composition can also be in the form of an oil-in-water emulsion. The oil phase can be a vegetable oil, or a mineral oil, or mixture thereof. Suitable emulsifying agents can be naturally occurring phosphatides or partial esters. The emulsion can also contain sweeteners, flavoring agents, preservatives and antioxidants. The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, sterile fixed oils can easily be used as a solvent or suspending medium.

The present compound can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors, including but not limited to, the following factors: activity of the specific compound, age, weight, general health, behavior, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms, and more preferably an alkyl having 1 to 6 carbon atoms.

Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Cycloalkyl" refers to a saturated and/or partially unsaturated monocyclic or polycyclic hydrocarbon group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

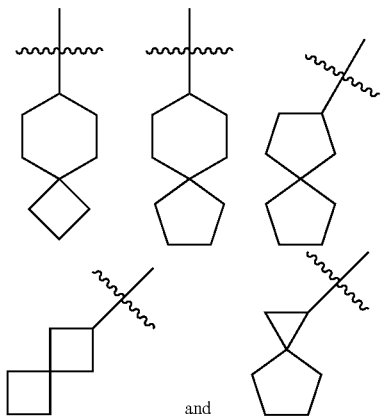

and

"Fused cycloalkyl" refers to a 5 to 20 membered full-carbon polycyclic group wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyl include:

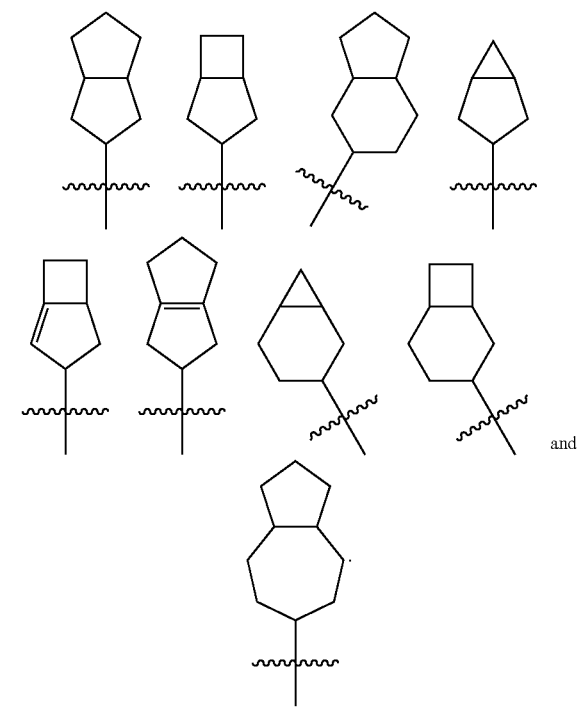

and

"Bridged cycloalkyl" refers to a 5 to 20 membered full-carbon polycyclic group, wherein every two rings in the system share two disconnected atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Non-limiting examples of bridged cycloalkyls include:

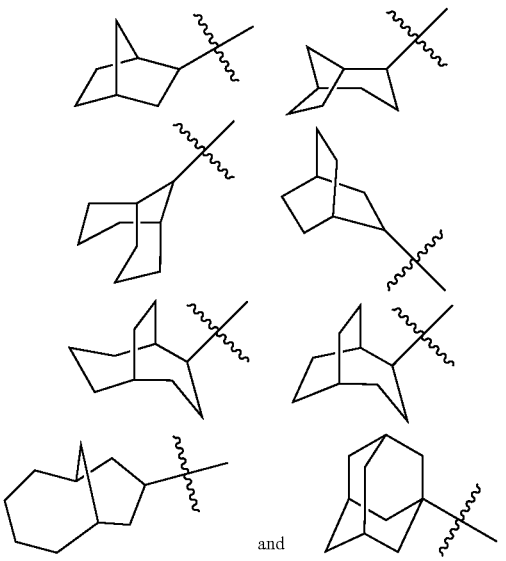

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms wherein 1 to 4 atoms are heteroatoms, more preferably 3 to 6 atoms, and most preferably 5 to 6 atoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl and the like, preferably pyranyl, piperazinyl, morpholinyl, tetrahydrofuranyl, piperidinyl, or pyrrolidinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein said rings have one or more heteroatoms selected from the group consisting of N, O, and S(O)m (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

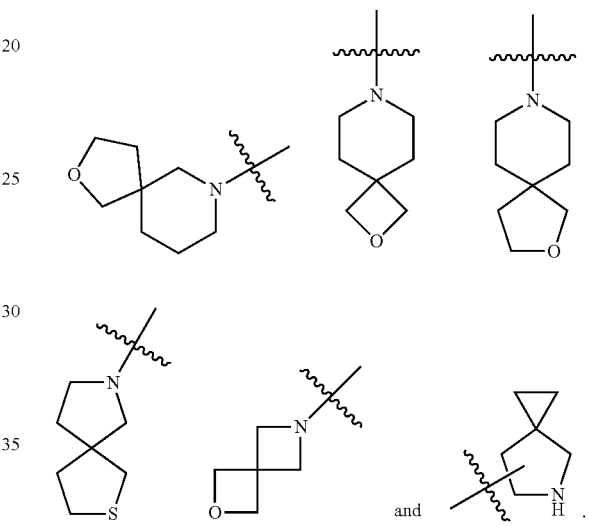

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein said rings have one or more heteroatoms selected from the group consisting of N, O, and S(O)m (wherein m is an integer of 0 to 2) as ring atoms, with the remaining ring atoms being carbon atoms, preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyl include:

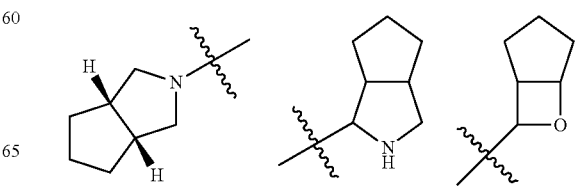

-continued

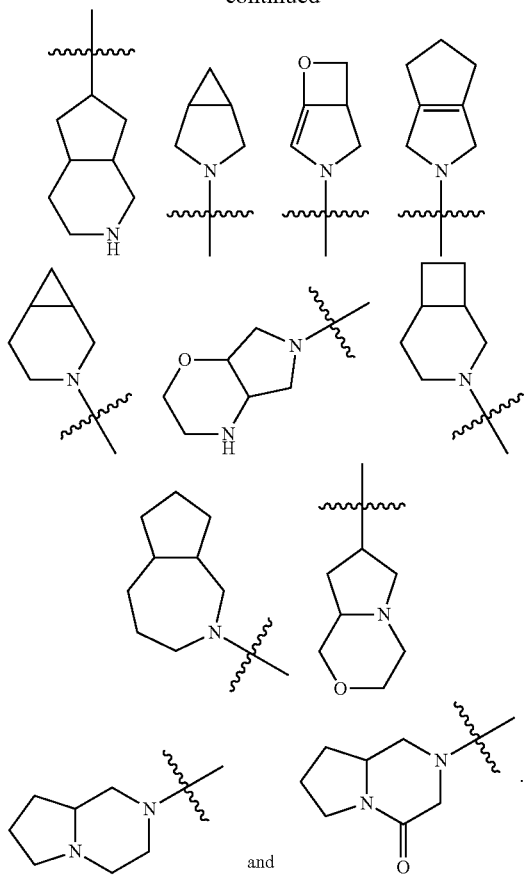

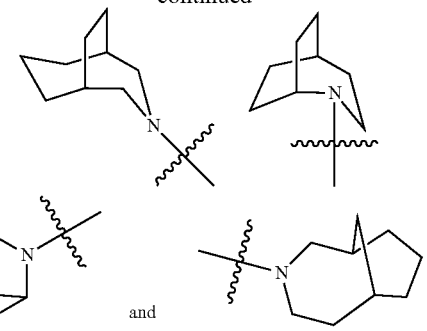

and

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S (O)m (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Non-limiting examples of bridged heterocyclyls include:

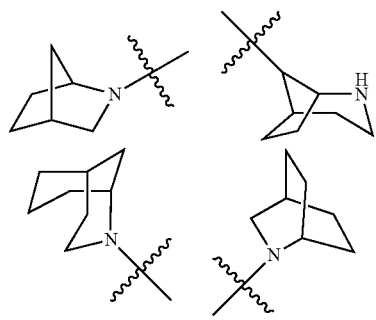

The heterocyclyl ring can be fused to the ring of aryl, heteroaryl or cycloalkyl, wherein the ring bound to the parent structure is heterocyclyl. Non-limiting examples include:

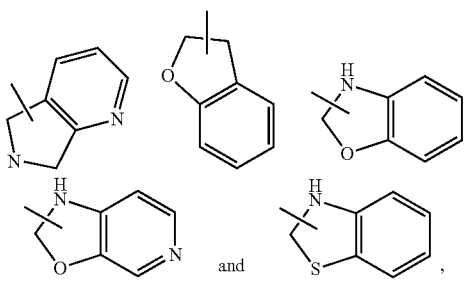

and and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Aryl" refers to a 6 to 14 membered full-carbon monocyclic ring or polycyclic fused ring (i.e. each ring in the system shares an adjacent pair of carbon atoms with another ring in the system) having a completely conjugated pi-electron system, preferably 6 to 10 membered aryl, for example, phenyl and naphthyl. The aryl ring can be fused to the ring of heteroaryl, heterocyclyl or cycloalkyl, wherein the ring bound to the parent structure is aryl ring. Non-limiting examples include:

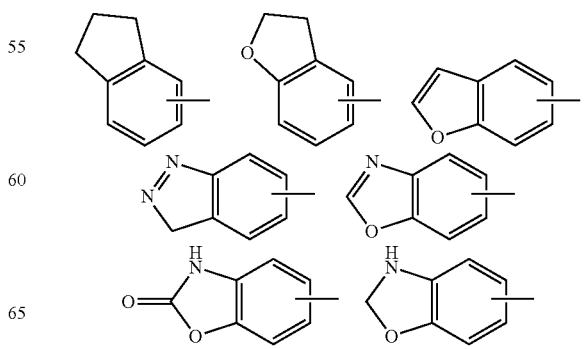

-continued

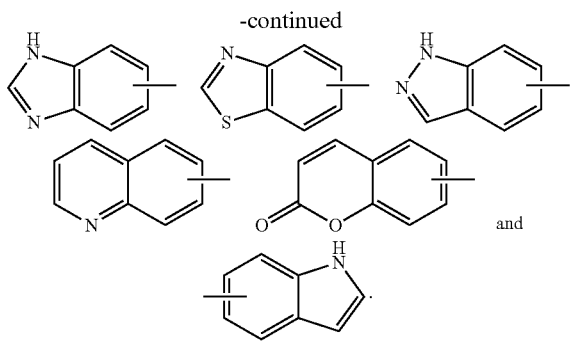

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, carboxy and alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl, more preferably 5 or 6 membered heteroaryl, for example, imidazolyl, furyl, thienyl, thiazolyl, pyrazolyl, oxazolyl, pyrrolyl, tetrazolyl, pyridinyl, pyrimidinyl, thiadiazole, pyrazinyl and the like, preferably imidazolyl, pyrazolyl, pyrimidinyl, pyridinyl, thiazolyl or tetrazolyl; more preferably pyrazolyl. The heteroaryl ring can be fused to the ring of aryl, heterocyclyl or cycloalkyl, wherein the ring bound to the parent structure is heteroaryl ring. Non-limiting examples include:

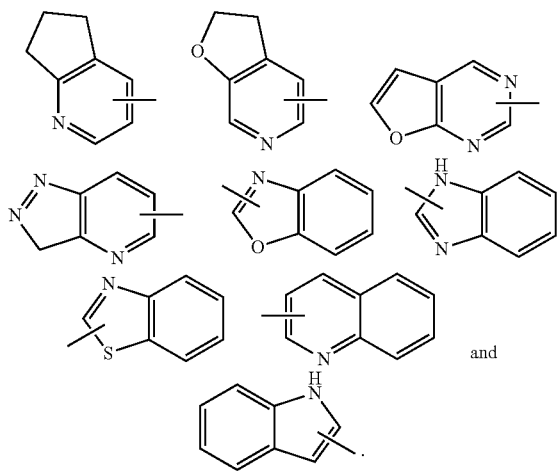

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Hydroxyalkyl" refers to an alkyl substituted by hydroxy, wherein the alkyl is as defined above.

"Hydroxy" refers to an —OH group.

"Halogen" refers to fluorine, chlorine, bromine or iodine.

"Amino" refers to a —NH$_2$ group.

"Cyano" refers to a —CN group.

"Nitro" refers to a —NO$_2$ group.

"Carboxy" refers to a —C(O)OH group.

"Alkoxycarbonyl" refers to a —C(O)O(alkyl) or (cycloalkyl) group, wherein the alkyl and cycloalkyl are as defined above.

"Acyl halide" refers to a compound comprising a —C(O)-halogen group.

"Optional" or "optionally" means that the event or circumstance described subsequently can, but need not, occur, and such a description includes the situation in which the event or circumstance does or does not occur. For example, "the heterocyclic group optionally substituted by an alkyl" means that an alkyl group can be, but need not be, present, and such a description includes the situation of the heterocyclic group being substituted by an alkyl and the heterocyclic group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient, thus displaying biological activity.

"Pharmaceutically acceptable salt" refers to a salt of the compound of the present invention, which is safe and effective in mammals and has the desired biological activity.

In the present invention, different terms, such as "X is selected from the group consisting of A, B or C", "X is selected from the group consisting of A, B and C", "X is A, B or C" and "X is A, B and C", are the same meaning. It means that X can be any one or more of A, B, and C.

Synthesis Method of the Compound of the Present Invention

In order to achieve the object of the present invention, the present invention applies the following synthesis technical solutions.

A process for preparing a compound of formula (I) of the present invention, or a tautomer, mesomer, racemate, enantiomer, diastereomer, or mixture thereof, or a pharmaceutically acceptable salt thereof, comprises the following steps:

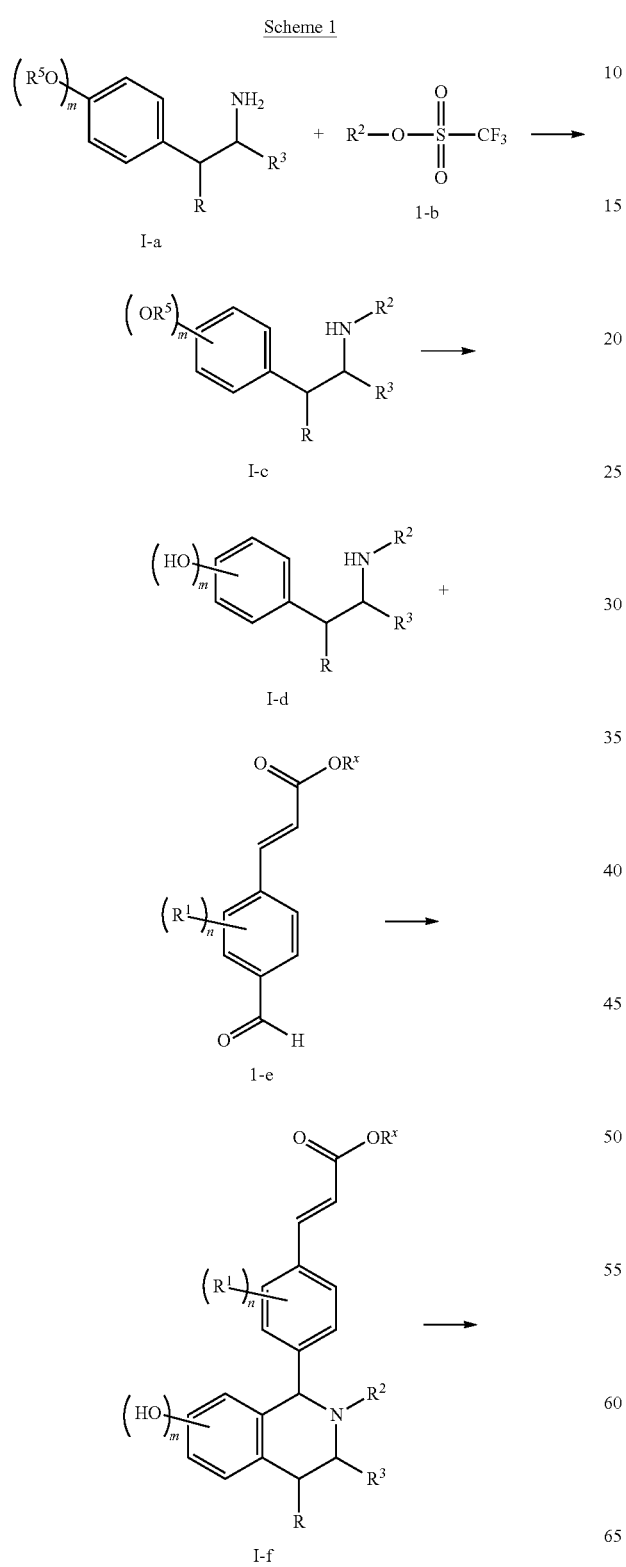

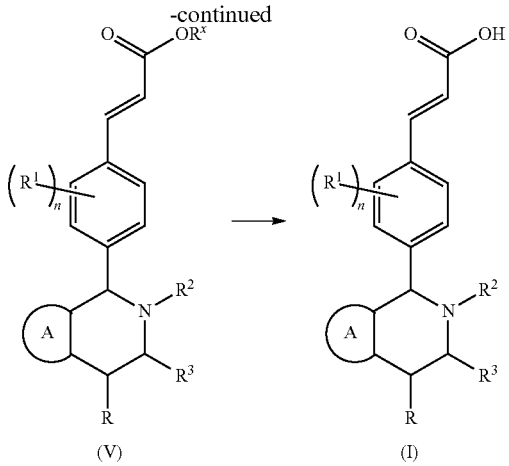

A compound of formula (I-a) is reacted with a compound of formula (I-b) at high temperature under an alkaline condition to obtain a compound of formula (I-c), wherein the alkaline reagent that provides the alkaline condition for this reaction is preferably N,N-diisopropylethylamine. The resulting compound of formula (I-c) is reduced at room temperature to obtain a compound of formula (I-d), wherein the catalyst under this condition is preferably palladium on carbon, and the reducing agent is preferably hydrogen. The resulting compound of formula (I-d) is subjected to a cyclization reaction with a compound of formula (I-e) under heating under an acidic condition to obtain a compound of formula (I-f), wherein the acidic reagent that provides the acidic condition for this reaction is preferably acetic acid. The resulting compound of formula (I-f) is optionally subjected to a cyclization reaction with a dihalide at high temperature under an alkaline condition to obtain a compound of formula (V), wherein the alkaline reagent that provides the alkaline condition for the reaction is preferably cesium carbonate. The resulting compound of formula (V) is hydrolyzed under an alkaline condition to obtain a compound of formula (I), wherein the alkaline reagent that provides the alkaline condition for the reaction is preferably lithium hydroxide and sodium hydroxide.

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate or cesium carbonate, sodium hydroxide and lithium hydroxide.

The reagent that provides an acidic condition includes, but is not limited to, formic acid, acetic acid, hydrochloric acid, sulfuric acid, and methanesulfonic acid.

The reducing agent used herein includes, but is not limited to, Fe powder, Zn powder, $H_2$, sodium borohydride, sodium triacetoxyborohydride, sodium nitrile sodium borohydride and lithium aluminum hydride.

The solvent used herein includes, but is not limited to, acetic acid, methanol, ethanol, toluene, tetrahydrofuran, dichloromethane, dimethylsulfoxide, 1,4-dioxane, water and N,N-dimethylformamide.

Wherein:
ring A, $R^1$ to $R^3$, $R^5$, m and n are as defined in formula (I).

The compounds of formula (I) of the present invention also can be prepared as follows:

Scheme 2

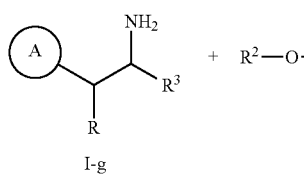 + 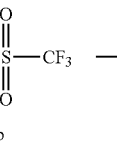

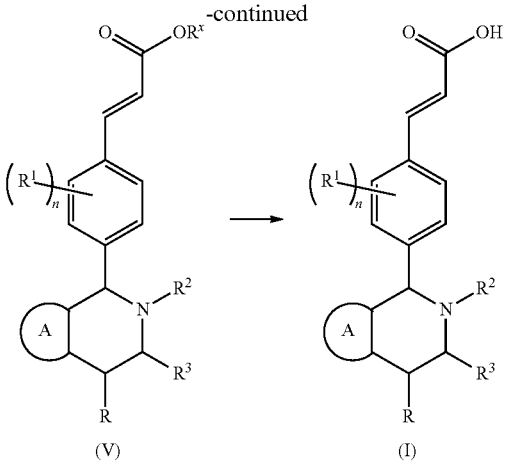

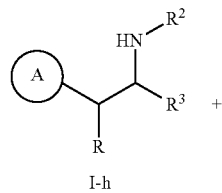

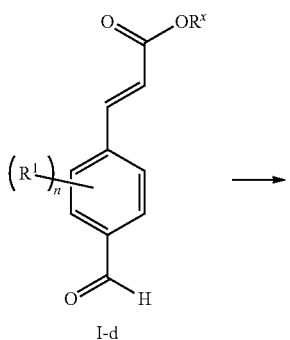

A compound of formula (I-g) is reacted with a compound of formula (I-b) under heating and under an alkaline condition to obtain a compound of formula (I-h), wherein the alkaline reagent that provides the alkaline condition for the reaction is preferably N,N-diisopropylethylamine. The resulting compound of formula (I-h) is subjected to a cyclization reaction with triisopropylsilyl chloride and a compound of formula (I-d) under heating to obtain a compound of formula (V). The resulting compound of formula (V) is hydrolyzed under an alkaline condition to obtain a compound of formula (I), wherein the alkaline reagent that provides the alkaline condition for the reaction is preferably lithium hydroxide and sodium hydroxide.

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate or cesium carbonate, sodium hydroxide and lithium hydroxide.

The solvent used herein includes, but is not limited to, acetic acid, methanol, ethanol, toluene, tetrahydrofuran, dichloromethane, dimethylsulfoxide, 1,4-dioxane, water and N,N-dimethylformamide.

Wherein:
ring A, $R^1$ to $R^3$ and n are as defined in formula (I).

Scheme 3

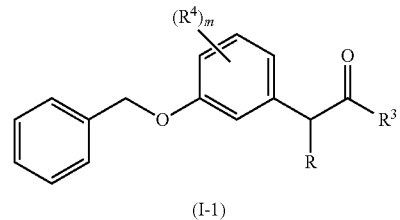 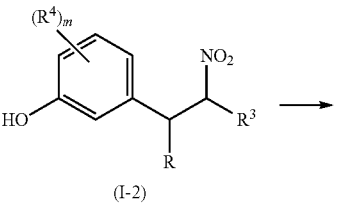

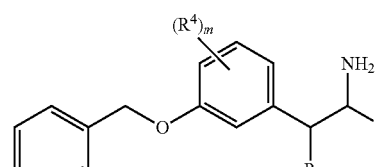 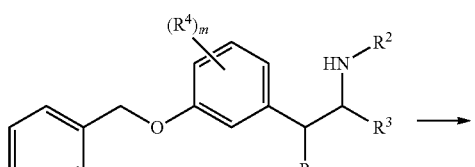

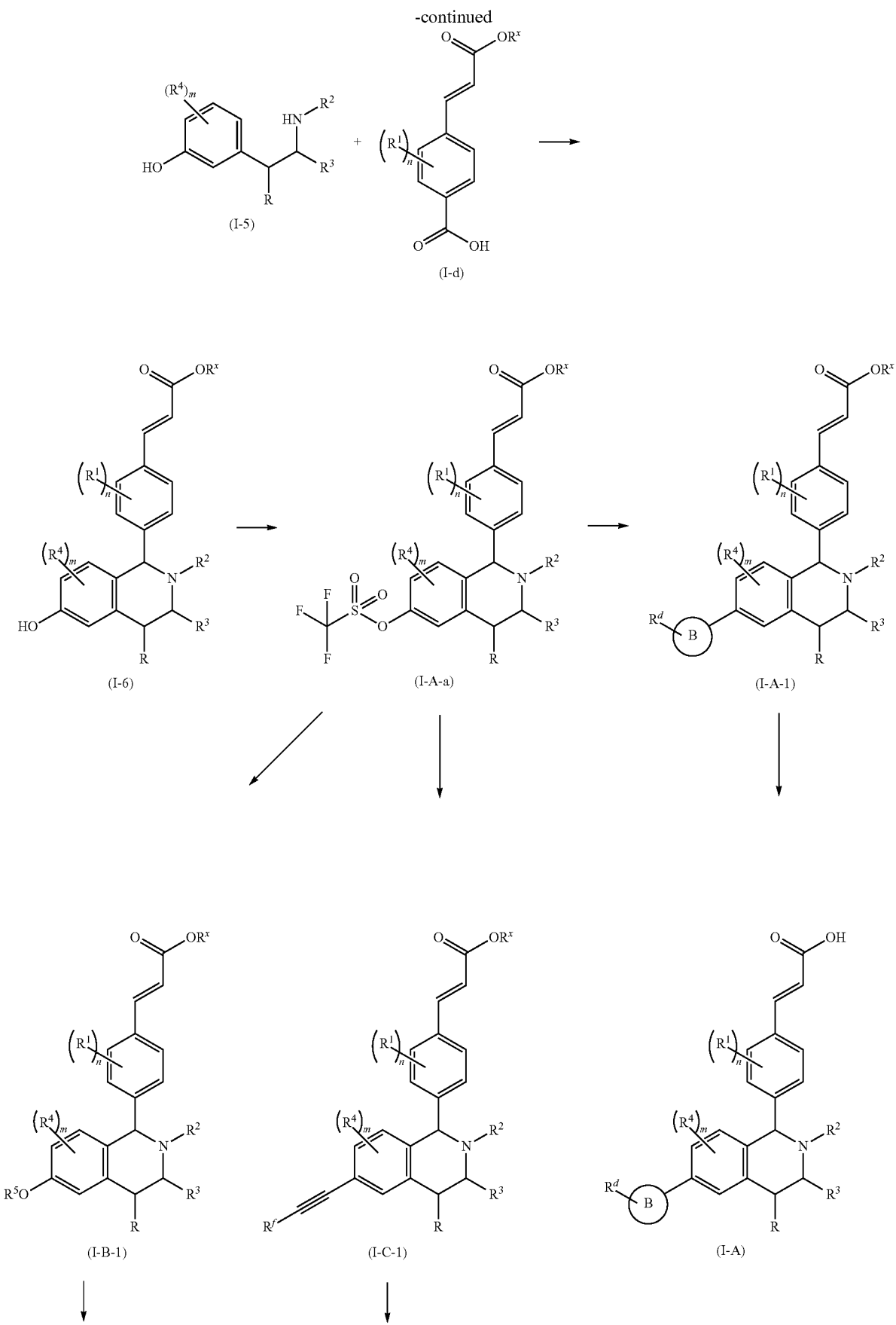

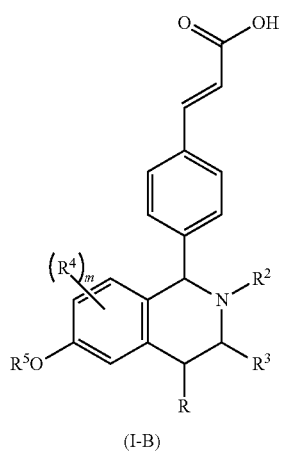

(I-B)

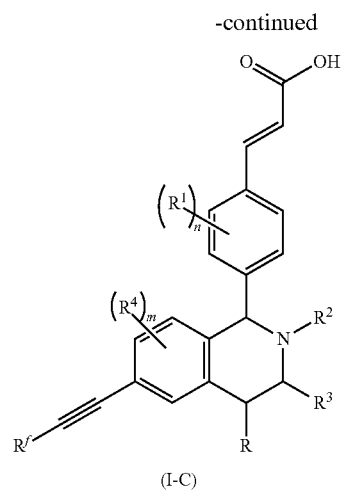

(I-C)

A compound of formula (I-1) is reacted with ammonium acetate and nitroethane at high temperature to obtain a compound of formula (I-2). The resulting compound of formula (I-2) is reduced with a reducing agent in this condition to obtain a compound of formula (I-3), wherein the reducing agent is preferably lithium aluminum hydride. The resulting compound of formula (I-3) is reacted with a haloalkyl trifluoromethanesulfonate at high temperature under an alkaline condition to obtain a compound of formula (I-4), wherein the alkaline reagent that provides the alkaline condition is preferably N,N-diisopropylethylamine. The resulting compound of formula (I-4) is subjected to high temperature and an acidic condition to obtain a compound of formula (I-5), wherein the acidic reagent that provides the acidic condition is preferably trifluoroacetic acid. The resulting compound of formula (I-5) is reacted with a compound of formula (I-d) at high temperature under an acidic condition to obtain a compound of formula (I-6), wherein the acidic reagent that provides the acidic condition is preferably acetic acid. The resulting compound of formula (I-6) is reacted with trifluoromethanesulfonic anhydride under an alkaline condition at low temperature to obtain a compound of formula (I-A-a), wherein the alkaline reagent that provides the alkaline condition is preferably 2,6-lutidine. The resulting compound of formula (I-A-a) is reacted under different conditions to obtain a compound of the corresponding formula.

(1) The compound of formula (I-A-a) is reacted with a borate at high temperature in the presence of a catalyst under an alkaline condition to obtain a compound of formula (I-A-1), wherein the alkaline reagent that provides the alkaline condition is preferably sodium carbonate, and the catalyst is preferably tetrakis(triphenylphosphine) palladium. The resulting compound of formula (I-A-1) is hydrolyzed under an alkaline condition to obtain a compound of formula (I-A), wherein the alkaline reagent that provides the alkaline condition is preferably lithium hydroxide.

(2) The compound of formula (I-A-a) is reacted with an $R^5$-containing halide to obtain a compound of formula (I-B-1). The resulting compound of formula (I-B-1) is hydrolyzed under an alkaline condition to obtain a compound of formula (I-B), wherein the alkaline reagent that provides the alkaline condition is preferably sodium hydroxide.

(3) The compound of formula (I-A-a) is reacted with cuprous iodide and an alkynyl-containing compound at high temperature in the presence of a catalyst under an alkaline condition to obtain a compound of formula (I-C-1), wherein the alkaline reagent that provides the alkaline condition is preferably N,N-diisopropylethylamine, and the catalyst is preferably bis(triphenylphosphine)palladium(II) dichloride. The resulting compound of formula (I-C-1) is hydrolyzed under an alkaline condition to obtain a compound of formula (I-C), wherein the alkaline reagent that provides the alkaline condition is preferably sodium hydroxide.

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate or cesium carbonate, sodium hydroxide and lithium hydroxide.

The reagent that provides an acidic condition includes, but is not limited to, formic acid, acetic acid, hydrochloric acid, sulfuric acid, and methanesulfonic acid.

The reducing agent used herein includes, but is not limited to, Fe powder, Zn powder, $H_2$, sodium borohydride, sodium triacetoxyborohydride, sodium nitrile sodium borohydride and lithium aluminum hydride.

The solvent used herein includes, but is not limited to, acetic acid, methanol, ethanol, toluene, tetrahydrofuran, dichloromethane, dimethylsulfoxide, 1,4-dioxane, water and N,N-dimethylformamide.

The catalyst includes, but is not limited to, tetrakistriphenylphosphine palladium, bis(triphenylphosphine)palladium(II) dichloride, palladium dichloride, palladium acetate, [1,1'-bis(diphenylphosphino)ferrocene]dichloropalladium(II) or tris(dibenzylideneacetone) dipalladium.

wherein ring B, $R^1$ to $R^5$, $R^x$, m and n are as defined in formula (I) and formula (V).

PREFERRED EMBODIMENTS

The present invention will be further described with reference to the following examples, but the examples should not be considered as limiting the scope of the invention.

EXAMPLES

The structures of the compounds were identified by nuclear magnetic resonance (NMR) and/or mass spectrometry (MS). NMR chemical shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

Chiral HPLC was determined on a LC-10A vp (Shimadzu) or SFC-analytical (Berger Instruments Inc.).

The average kinase inhibition rates and IC$_{50}$ values were determined by a NovoStar ELISA (BMG Co., Germany).

Yantai Huanghai HSGF254 or Qingdao GF254 silica gel plate was used for thin-layer silica gel chromatography (TLC). The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel is used as a carrier for column chromatography.

Prep Star SD-1 (Varian Instruments Inc.) or SFC-multigram (Berger Instruments Inc.) is used for chiral preparation column chromatography.

CombiFlash rapid preparation instrument is Teledyne Isco CombiFlash®Rf200 from America.

The known starting materials of the present invention can be prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressurized hydrogenation reactions were performed with a Parr 3916EKX hydrogenation instrument and a QL-500 hydrogen generator or HC2-SS hydrogenation instrument.

In hydrogenation reactions, the reaction system is generally vacuumed and filled with hydrogen, with the above operation repeated three times.

CEM Discover-S 908860 type microwave reactor was used in microwave reactions.

Unless otherwise stated, the solution used in the reactions refers to an aqueous solution.

Unless otherwise stated, the reaction temperature in the reactions refers to room temperature from 20° C. to 30° C.

The reaction process was monitored by thin layer chromatography (TLC), and the developing solvent system included: A: dichloromethane and methanol, B: n-hexane and ethyl acetate, C: petroleum ether and ethyl acetate, D: acetone. The ratio of the volume of the solvent was adjusted according to the polarity of the compounds. The elution system for purification of the compounds by column chromatography, thin layer chromatography and CombiFlash flash rapid preparation instrument included: A: dichloromethane and methanol, B: n-hexane and ethyl acetate, C: dichloromethane and acetone. The ratio of the volume of the solvent was adjusted according to the polarity of the compounds, and sometimes a little alkaline reagent such as triethylamine or acidic reagent such as acetic acid was added.

Example 1

(E)-3-(3,5-difluoro-4-((5S,7R/5R,7S)-6-(2-fluoro-2-methylpropyl)-7-methyl-5,6,7,8-tetrahydro-[1,3]dioxolo[4,5-g]isoquinolin-5-yl)phenyl)acrylic Acid

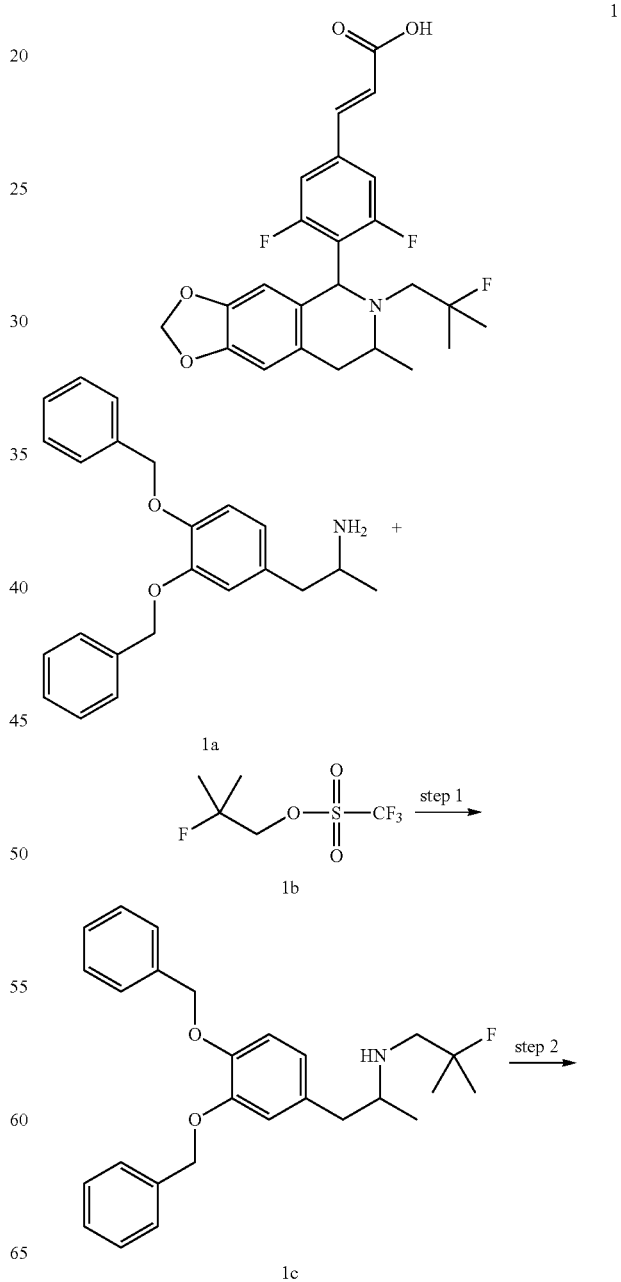

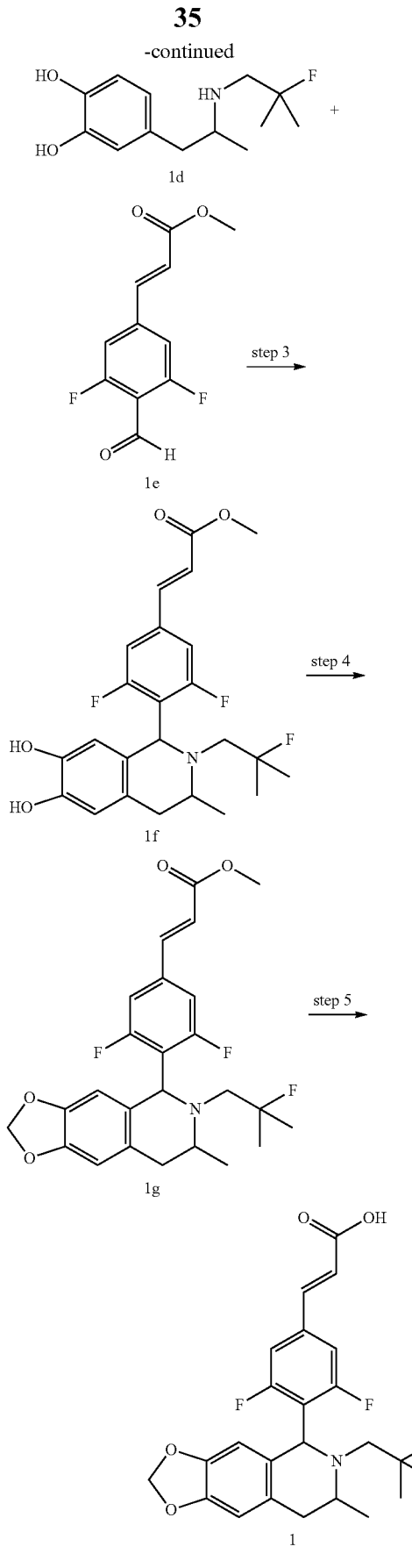

Step 1

N-(1-(3,4-bis(benzyloxy)phenyl)propan-2-yl)-2-fluoro-2-methylpropan-1-amine 1-(3,4-bis(benzyloxy)phenyl)propan-2-amine 1a (0.8 g, 2.3 mmol, prepared by a well-known method disclosed in "*Bioorganic & Medicinal Chemistry,* 2002, 10(4), 1085-1092"), 2-fluoro-2-methylpropyl trifluoromethanesulfonate 1b (671 mg, 3 mmol, prepared by a well-known method disclosed in "*Journal of Organic Chemistry,* 2005, 70(6), 2372-2375") and N,N-diisopropylethylamine (595 mg, 4.6 mmol) were dissolved in 8 mL of 1,4-dioxane. The resulting mixture was stirred for 12 hours at 90° C. The reaction was stopped, and the reaction solution was concentrated under reduced pressure. The residue was purified by silica gel column chromatography with elution system A to obtain the title compound N-(1-(3,4-bis(benzyloxy)phenyl)propan-2-yl)-2-fluoro-2-methylpropan-1-amine 1c (527 mg, yield 54.3%) as a yellow oil.

Step 2

4-(2-((2-fluoro-2-methylpropyl)amino)propyl)benzene-1,2-diol

N-(1-(3,4-bis(benzyloxy)phenyl)propan-2-yl)-2-fluoro-2-methylpropan-1-amine 1c (100 mg, 0.237 mmol) was dissolved in 10 mL of methanol, Pd/C (20 mg) was added under an argon atmosphere, and then the reaction system was purged with hydrogen three times. The reaction was stirred for 12 hours at normal pressure and temperature. The reaction was stopped and filtered. The filtrate was concentrated under reduced pressure to obtain the crude title compound 4-(2-((2-fluoro-2-methylpropyl)amino)propyl)benzene-1,2-diol 1d (57 mg) as a light yellow oil, which was used directly in the next step.

Step 3

(E)-methyl 3-(3,5-difluoro-4-((1S,3R/1R,3S)-2-(2-fluoro-2-methylpropyl)-6,7-dihydroxy-3-methyl-1,2,3,4-tetrahydroisoquinolin-1-yl)phenyl)acrylate The crude 4-(2-((2-fluoro-2-methylpropyl)amino)propyl)benzene-1,2-diol 1d (57 mg, 0.236 mmol) was dissolved in 1.5 mL of methanol, then (E)-methyl 3-(3,5-difluoro-4-formylphenyl)acrylate 1e (53.4 mg, 0.236 mmol, prepared by a method disclosed in the patent application "WO2014191726") and acetic acid (28.4 mg, 0.472 mmol) were added. The resulting mixture was heated to 55° C. and stirred for 12 hours. After the reaction was completed, the reaction solution was concentrated under reduced pressure to remove methanol and acetic acid, dichloromethane was added, and the residue was purified by silica gel column chromatography with elution system A to obtain the title compound (E)-methyl 3-(3,5-difluoro-4-((1S,3R/1R,3S)-2-(2-fluoro-2-methylpropyl)-6,7-dihydroxy-3-methyl-1,2,3,4-tetrahydroisoquinolin-1-yl)phenyl)acrylate 1f (51 mg, yield 48%) as a brown oil.

Step 4

(E)-methyl 3-(3,5-difluoro-4-((5S,7R/5R,7S)-6-(2-fluoro-2-methylpropyl)-7-methyl-5,6,7,8-tetrahydro-[1,3]dioxolo[4,5-g]isoquinolin-5-yl)phenyl)acrylate (E)-methyl 3-(3,5-difluoro-4-((1S,3R/1R,3S)-2-(2-fluoro-2-methylpropyl)-6,7-dihydroxy-3-methyl-1,2,3,4-tetrahydroisoquinolin-1-yl)phenyl)acrylate 1f (51 mg, 0.113 mmol) was dissolved in 15 mL of N,N-dimethylformamide, then dibromomethane (29.6 mg, 0.17 mmol) and cesium carbonate (55.5 mg, 0.17 mmol) were added. The resulting mixture was heated to 110° C. and stirred for 3 hours. The reaction was stopped. The reaction solution was concentrated under reduced pressure. Ethyl acetate (10 mL) was added, then the mixture was washed with water (10 mL) and saturated sodium chloride solution (10 mL), dried over anhydrous sodium sulfate and filtered. The filtrate was concentrated under reduced pressure to obtain the crude title compound (E)-methyl 3-(3,5-difluoro-4-((5S,7R/5R,7S)-6-(2-fluoro-2-methylpropyl)-7-methyl-5,6,7,8-tetrahydro-[1,3]dioxolo[4,5-g]isoquinolin-5-yl)phenyl)acrylate 1g (50 mg) as a brown solid, which was used directly in the next step.

Step 5

(E)-3-(3,5-difluoro-4-((5S,7R/5R,7S)-6-(2-fluoro-2-methylpropyl)-7-methyl-5,6,7,8-tetrahydro-[1,3]dioxolo[4,5-g]isoquinolin-5-yl)phenyl)acrylic Acid The crude (E)-methyl 3-(3,5-difluoro-4-(6-(2-fluoro-2-methylpropyl)-7-methyl-5,6,7,8-tetrahydro-[1,3]dioxolo[4,5-g]isoquinolin-5-yl)phenyl)acrylate 1g (50 mg, 0.11 mmol) was dissolved in 2 mL of a mixture of tetrahydrofuran and methanol (V/V=3:1). The reaction mixture was cooled to 0° C., then 0.54 mL of 1 M lithium hydroxide aqueous solution was added. The reaction mixture was naturally warmed up to room temperature and stirred for 0.5 hour. The reaction was stopped, and the reaction solution was concentrated under reduced pressure to remove methanol and tetrahydrofuran. Diluted hydrochloric acid (0.5 N) was added dropwise to adjust the pH to 5, and the mixture was extracted with ethyl acetate (5 mL×3). The organic phases were combined, dried over anhydrous sodium sulfate, and filtered. The filtrate was concentrated under reduced pressure, and the residue was purified by high performance liquid chromatography to obtain the title compound (E)-3-(3,5-difluoro-4-((5S,7R/5R,7S)-6-(2-fluoro-2-methylpropyl)-7-methyl-5,6,7,8-tetrahydro-[1,3]dioxolo[4,5-g]isoquinolin-5-yl)phenyl)acrylic acid 1 (10 mg, yield 20.6%) as a yellow solid.

MS m/z (ESI): 448.4 [M+1]

$^1$H NMR (400 MHz, CDCl$_3$) δ 7.52 (d, 1H), 7.04 (d, 2H), 6.65 (s, 1H), 6.37 (d, 1H), 6.30 (s, 1H), 5.94 (d, 2H), 5.78 (s, 1H), 4.15-4.17 (m, 1H), 3.22-3.41 (m, 2H), 2.98 (t, 1H), 2.71 (dd, 1H), 1.58 (d, 3H), 1.26-1.43 (m, 7H).

Example 2

(E)-3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylic Acid

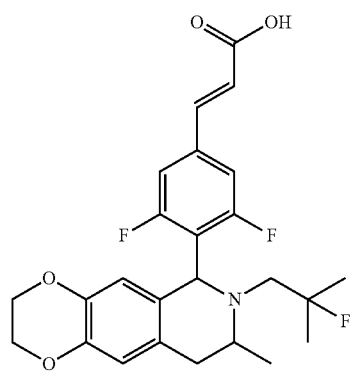

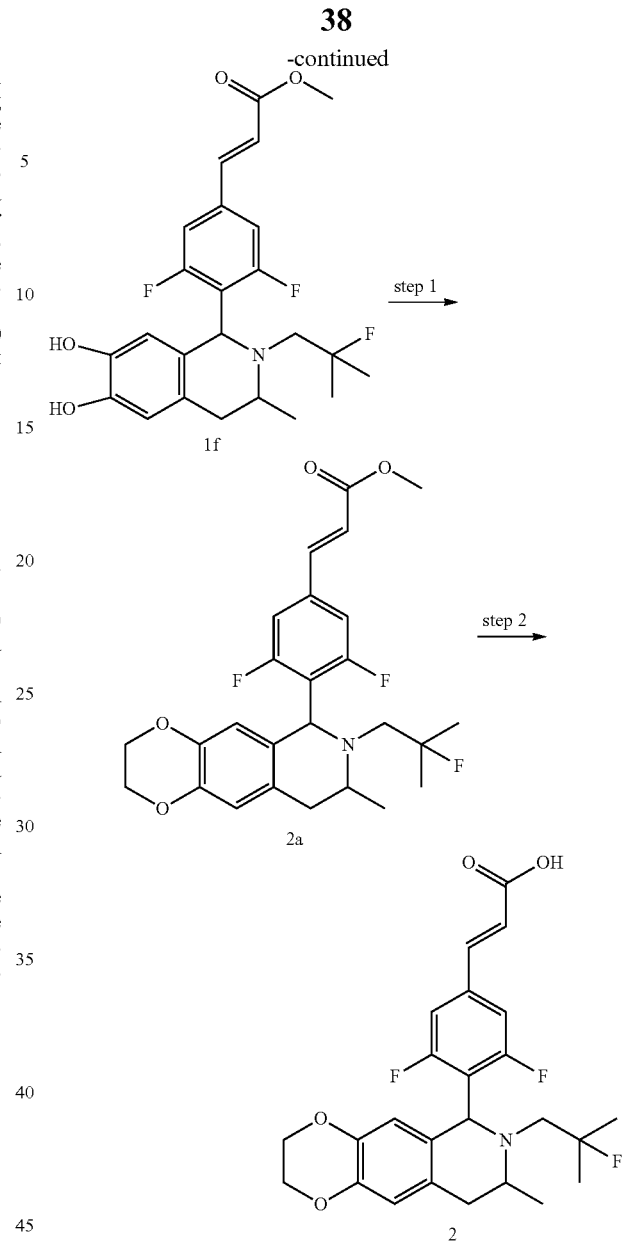

Step 1

(E)-methyl 3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylate (E)-methyl 3-(3,5-difluoro-4-((1S,3R/1R,3S)-2-(2-fluoro-2-methylpropyl)-6,7-dihydroxy-3-methyl-1,2,3,4-tetrahydroisoquinolin-1-yl)phenyl)acrylate 1f (58 mg, 0.129 mmol) was dissolved in 1.5 mL of N,N-dimethylformamide, then 1,2-dibromomethane (36.4 mg, 0.194 mmol) and cesium carbonate (63 mg, 0.194 mmol) were added. The resulting mixture was heated to 70° C. and stirred for 16 hours. The reaction was stopped. The reaction solution was concentrated under reduced pressure. Ethyl acetate (10 mL) was added, and the mixture was washed with water (10 mL) and saturated sodium chloride solution (10 mL), dried over anhydrous sodium sulfate and filtered. The filtrate was concentrated under reduced pressure to obtain the crude title compound (E)-methyl 3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylate 2a (61 mg) as a brown solid, which was used directly in the next step.

Step 2

(E)-3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylic Acid The crude (E)-methyl 3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylate 2a (61 mg, 0.128 mmol) was dissolved in 2 mL of a mixture of tetrahydrofuran and methanol (V/V=3:1). The reaction mixture was cooled to 0° C., and 0.65 mL of 1 M lithium hydroxide aqueous solution was added. The reaction mixture was naturally warmed up to room temperature and stirred for 0.5 hour. The reaction was stopped, and the reaction solution was concentrated under reduced pressure to remove methanol and tetrahydrofuran. Diluted hydrochloric acid (0.5 N) was added dropwise to adjust the pH to 5, and the mixture was extracted with ethyl acetate (5 mL×3). The organic phases were combined, dried over anhydrous sodium sulfate, and filtered. The filtrate was concentrated under reduced pressure, and the residue was purified by high performance liquid chromatography to obtain the title compound (E)-3-(3,5-difluoro-4-((6S,8R/6R,8S)-7-(2-fluoro-2-methylpropyl)-8-methyl-2,3,6,7,8,9-hexahydro-[1,4]dioxino[2,3-g]isoquinolin-6-yl)phenyl)acrylic acid 2 (45 mg, yield 76%) as a white solid.

MS m/z (ESI): 462.4 [M+1]

$^1$H NMR (400 MHz, CDCl$_3$) δ7.52 (d, 1H), 7.03 (d, 2H), 6.69 (s, 1H), 6.41-6.37 (m, 2H), 5.69 (s, 1H), 4.20-4.25 (m, 4H), 3.17-3.40 (m, 3H), 2.90 (t, 1H), 2.66 (dd, 1H), 1.52 (d, 3H), 1.26-1.40 (m, 6H).

Example 3

(E)-3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylic Acid

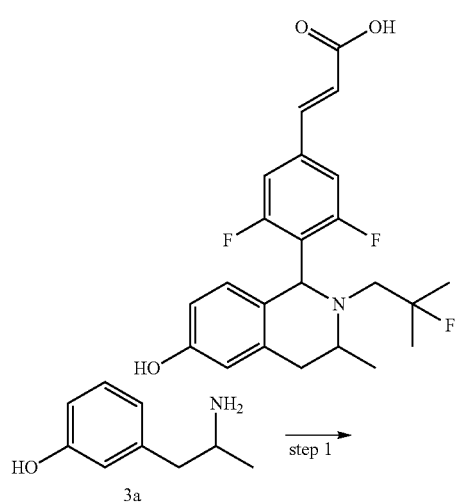

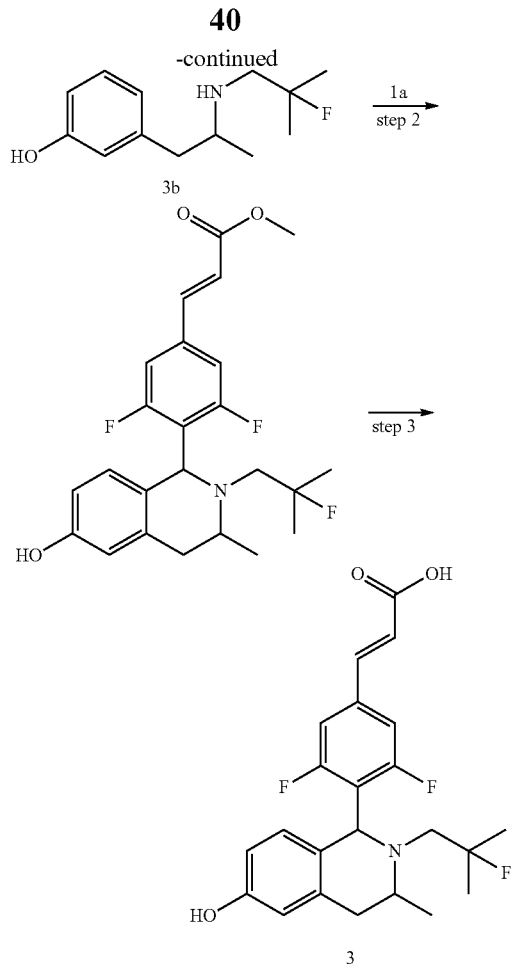

Step 1

3-(2-((2-fluoro-2-methylpropyl)amino)propyl)phenol 3-(2-aminopropyl)phenol 3a (220 mg, 2.3 mmol, prepared by a method disclosed in the patent application "WO2009068177"), 2-fluoro-2-methylpropyl trifluoromethanesulfonate 1b (651 mg, 2.9 mmol) and N,N-diisopropylethylamine (559 mg, 4.365 mmol) were dissolved in 5 mL of 1,4-dioxane. The resulting mixture was heated to 90° C. and stirred for 12 hours under an argon atmosphere. The reaction was stopped, and the reaction solution was concentrated under reduced pressure. The residue was purified by silica gel column chromatography with elution system A to obtain the title compound 3-(2-((2-fluoro-2-methylpropyl)amino)propyl)phenol 3b (113 mg, yield 35%) as a brown liquid.

Step 2

(E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3-(2-((2-fluoro-2-methylpropyl)amino)propyl)phenol 3b (113 mg, 0.5 mmol) was dissolved in 3 mL of methanol, then (E)-methyl 3-(3,5-difluoro-4-formylphenyl) acrylate 1e (113 mg, 0.5 mmol) and acetic acid (60 mg, 1 mmol) were added. The resulting mixture was heated to 55° C. and stirred for 12 hours. After the reaction was stopped, the reaction solution was concentrated under reduced pressure to obtain the title compound (E)-methyl 3-(3,5-difluoro-4-((1S,3R/1R,3S)-2-(2-fluoro-2-methylpropyl)-6-hydroxy-3-methyl-1,2, 3,4-tetrahydroisoquinolin-1-yl)phenyl)acrylate 3c (15 mg, yield 7%) as a yellow solid.

Step 3

(E)-3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (15 mg, 0.0346 mmol) was dissolved in 5 mL of methanol, then 2 mL of sodium hydroxide aqueous solution (14 mg, 0.346 mmol) was added. The reaction was stirred for 12 hours at room temperature. The reaction was stopped. 0.5 N diluted hydrochloric acid was added dropwise to adjust the pH to 2, and the mixture was extracted with dichloromethane (5 mL×3). The organic phases were combined, dried over anhydrous sodium sulfate and filtered. The filtrate was concentrated under reduced pressure. The residue was purified by thin-layer chromatography with elution system A to obtain the title compound (E)-3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylic acid 3 (5 mg, yield 34.5%) as a yellow solid.

MS m/z (ESI): 420.4 [M+1]

$^1$H NMR (400 MHz, CD$_3$OD) δ 7.18-7.60 (m, 4H), 6.51-6.56 (m, 3H), 5.17 (s, 1H), 3.69 (s, 1H), 3.01 (s, 1H), 2.07-2.55 (m, 3H), 0.92-1.19 (m, 9H).

Example 4

(E)-3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylic Acid

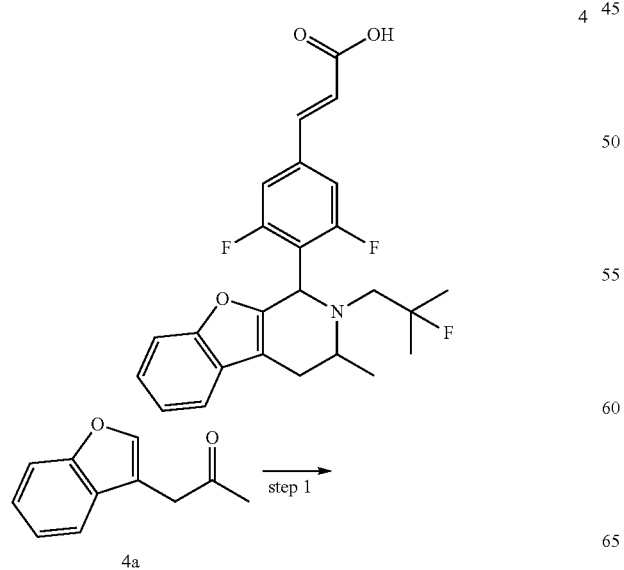

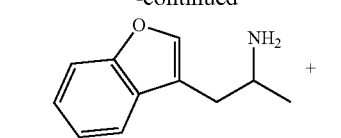

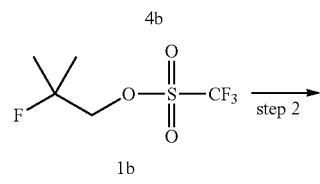

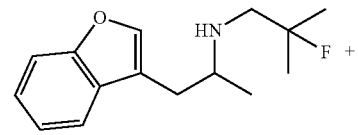

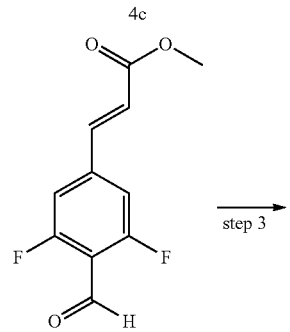

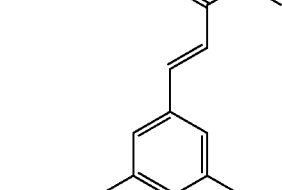

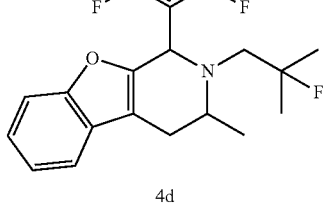

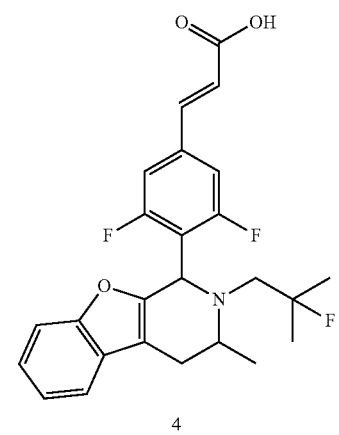

Step 1

1-(benzofuran-3-yl)propan-2-amine 1-(benzofuran-3-yl)propan-2-one 4a (1 g, 5.74 mmol, prepared by a well-known method disclosed in "*Khimiya Geterotsiklicheskikh Soedinenii*, 1987, (7), 889-93"), ammonium acetate (4.42 g, 57.4 mmol) and sodium acetate (470 mg, 5.74 mmol) were dissolved in 30 mL of methanol. Sodium cyanoborohydride (540 mg, 8.6 mmol) was added, and 10 drops of acetic acid were added dropwise. After the resulting mixture was stirred for 12 hours at 25° C., the reaction was stopped. Then, 1 N NaOH solution was added dropwise to adjust the pH to 7-8. The mixture was dried over anhydrous sodium sulfate and filtered. The filtrate was concentrated under reduced pressure. The residue was purified by silica gel column chromatography with elution system A to obtain the title compound 1-(benzofuran-3-yl)propan-2-amine 4b (600 mg, yield 60%) as a brown liquid.

Step 2

N-(1-(benzofuran-3-yl)propan-2-yl)-2-fluoro-2-methylpropan-1-amine 1-(benzofuran-3-yl)propan-2-amine 4b (50 mg, 0.285 mmol), 2-fluoro-2-methylpropyl trifluoromethanesulfonate 1b (128 mg, 0.57 mmol, prepared by a well-known method disclosed in "*Journal of Organic Chemistry*, 2005, 70(6), 2372-2375") and N,N-diisopropylethylamine (109 mg, 0.855 mmol) were dissolved in 3 mL of 1,4-dioxane. The resulting mixture was heated to 90° C. and stirred for 12 hours under an argon atmosphere. The reaction was stopped, and the reaction solution was concentrated under reduced pressure. The residue was purified by silica gel column chromatography with elution system A to obtain the title compound N-(1-(benzofuran-3-yl)-propan-2-yl)-2-fluoro-2-methylpropan-1-amine 4c (50 mg, yield 70%) as a brown liquid.

Step 3

(E)-methyl 3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylate N-(1-(benzofuran-3-yl)propan-2-yl)-2-fluoro-2-methylpropan-1-amine 4c (50 mg, 0.2 mmol), (E)-methyl 3-(3,5-difluoro-4-formylphenyl) acrylate 1e (90 mg, 0.4 mmol, prepared by a method disclosed in the patent application publication "WO2014191726") and triisopropylsilyl chloride (193 mg, 1 mmol) were dissolved in 2 mL of N,N-dimethylformamide and placed in a sealed tube. The reaction mixture was heated to 130° C. After stirring for 3 hours, the reaction was stopped. The reaction solution was concentrated under reduced pressure. The resulting residue was purified by thin-layer chromatography with elution system A to obtain the title compound (E)-methyl 3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylate 4d (15 mg, yield 16%) as a white solid.

Step 4

(E)-3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylic Acid (E)-methyl 3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylate 4d (15 mg, 0.033 mmol) was dissolved in 5 mL of methanol. Then, 2 mL of sodium hydroxide (13 mg, 0.33 mmol) aqueous solution was added. After stirring for 12 hours at room temperature, the reaction was stopped. Citric acid was added dropwise to adjust the pH to 2-3, and the mixture was extracted with dichloromethane (5 mL×3). The organic phases were combined, dried over anhydrous sodium sulfate and filtered. The filtrate was concentrated under reduced pressure, and the resulting residue was purified by silica gel column chromatography with elution system A to obtain the title compound (E)-3-(3,5-difluoro-4-((1R,3R/1S,3S)-2-(2-fluoro-2-methylpropyl)-3-methyl-1,2,3,4-tetrahydrobenzofuro[2,3-c]pyridin-1-yl)phenyl)acrylic acid 4 (10 mg, yield 67%) as a yellow solid.

MS m/z (ESI): 444 [M+1]

$^1$H NMR (400 MHz, CD$_3$OD) δ 7.60-7.64 (m, 2H), 7.27-7.40 (m, 5H), 6.61 (d, 1H), 5.60 (s, 1H), 3.86-3.88 (m, 1H), 3.10-3.25 (m, 2H), 2.76-2.78 (m, 2H), 1.28-1.37 (m, 9H).

Example 5

(E)-3-(3,5-difluoro-4-((1R,3R/1S,3S)-2-(2-fluoro-2-methylpropyl)-3-methyl-1,2,3,4-tetrahydrobenzo[4,5]thieno[2,3-c]pyridin-1-yl)phenyl)acrylic Acid

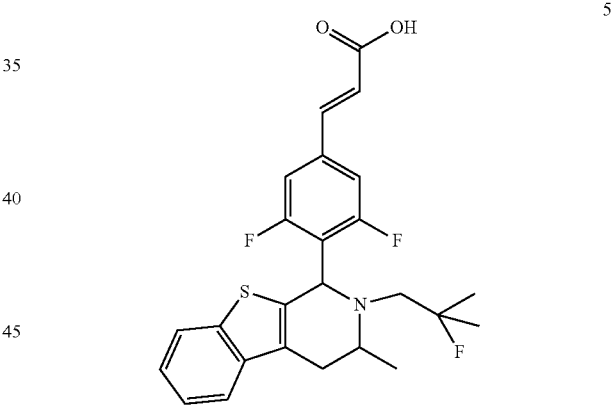

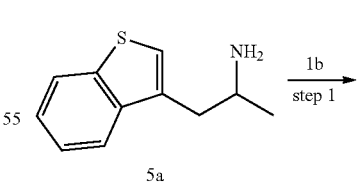

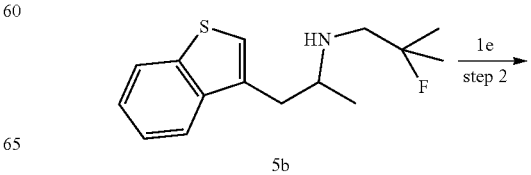

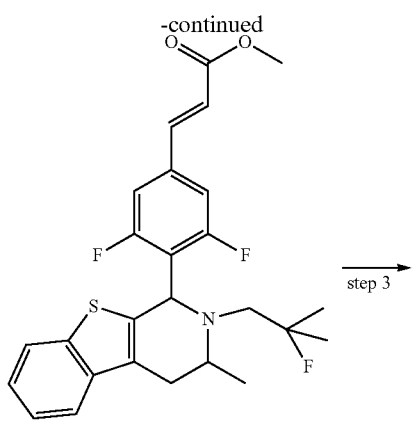

5c

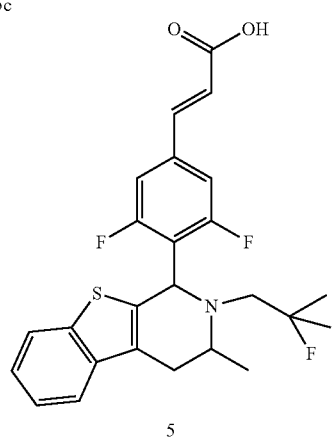

5

Step 1

N-(1-(benzo[b]thiophen-3-yl)propan-2-yl)-2-fluoro-2-methylpropan-1-amine 1-(benzo[b]thiophen-3-yl)propan-2-amine 5a (100 mg, 0.523 mmol, prepared by a well-known method disclosed in "*Bioorganic & Medicinal Chemistry*, 2005, 13(14), 4450-4457"), 2-fluoro-2-methylpropyl trifluoromethanesulfonate 1b (152 mg, 0.680 mmol) and N,N-diisopropylethylamine (135 mg, 1.046 mmol) were dissolved in 4 mL of 1,4-dioxane. After stirring for 3 hours at 90° C., the reaction was stopped. The reaction solution was concentrated under reduced pressure. The resulting residue was purified by thin-layer chromatography with elution system A to obtain the title compound N-(1-(benzo[b]thiophen-3-yl)propan-2-yl)-2-fluoro-2-methylpropan-1-amine 5b (100 mg, yield 72%) as a yellow oil.

Step 2

(E)-methyl 3-(3,5-difluoro-4-((1R,3R/1S,3S)-2-(2-fluoro-2-methylpropyl)-3-methyl-1,2,3,4-tetrahydrobenzo[4,5]thieno[2,3-c]pyridin-1-yl)phenyl)acrylate N-(1-(benzo[b]thiophen-3-yl)propan-2-yl)-2-fluoro-2-methylpropan-1-amine 5b (30 mg, 0.113 mmol), (E)-methyl 3-(3,5-difluoro-4-formylphenyl)acrylate 1e (31 mg, 0.136 mmol) and triisopropylsilyl chloride (109 mg, 0.565 mmol) were dissolved in 1.5 mL of N,N-dimethylformamide and placed in a sealed tube. The reaction mixture was heated to 140° C. After stirring for 6 hours, the reaction was stopped. The reaction solution was concentrated under reduced pressure and extracted with ethyl acetate (5 mL×3). The organic phases were combined and concentrated under reduced pressure.

The residue was purified by silica gel column chromatography with elution system A to obtain the title compound (E)-methyl 3-(3,5-difluoro-4-((1R,3R/1S,3S)-2-(2-fluoro-2-methylpropyl)-3-methyl-1,2,3,4-tetrahydrobenzo[4,5]thieno[2,3-c]pyridin-1-yl)phenyl)acrylate 5c (10 mg, yield 20%) as a yellow oil.

Step 3

(E)-3-(3,5-difluoro-4-((1R,3R/1S,3S)-2-(2-fluoro-2-methylpropyl)-3-methyl-1,2,3,4-tetrahydrobenzo[4,5]thieno[2,3-c]pyridin-1-yl)phenyl)acrylic Acid (E)-methyl 3-(3,5-difluoro-4-(2-(2-fluoro-2-methylpropyl)-3-methyl-1,2,3,4-tetra hydrobenzo[4,5]thieno[2,3-c]pyridin-1-yl)phenyl)acrylate 5c (10 mg, 0.021 mmol) and sodium hydroxide (4 mg, 0.105 mmol) were dissolved in 3 mL of methanol. After stirring for 3 hours at 50° C., the reaction was stopped. Then, 1 N hydrochoric acid was added dropwise to adjust the pH to 2-3, and the mixture was extracted with ethyl acetate (5 mL×3). The organic phases were combined, dried over anhydrous sodium sulfate and filtered. The filtrate was concentrated under reduced pressure, and the residue was purified by silica gel column chromatography with elution system A to obtain the title compound (E)-3-(3,5-difluoro-4-((1R,3R/1S,3S)-2-(2-fluoro-2-methylpropyl)-3-methyl-1,2,3,4-tetrahydrobenzo[4,5]thieno[2,3-c]pyridin-1-yl)phenyl)acrylic acid 5 (2.5 mg, yield 26%) as a yellow solid.

MS m/z (ESI): 460.2 [M+1]

$^1$H NMR (400 MHz, CDCl$_3$) δ 7.74 (d, 1H), 7.69 (d, 1H), 7.58 (d, 1H), 7.37 (t, 1H), 7.32 (t, 1H), 7.24 (d, 1H), 6.97 (d, 1H), 6.57 (d, 1H), 5.39 (s, 1H), 3.27 (s, 1H), 3.10-3.14 (m, 1H), 2.99-3.04 (m, 1H), 2.75-2.79 (m, 1H), 2.35-2.46 (m, 1H), 1.25 (d, 3H), 1.19 (d, 6H).

Example 6

(E)-3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylic Acid

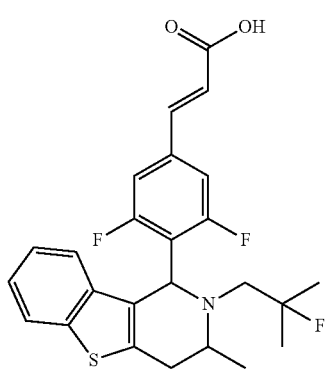

6

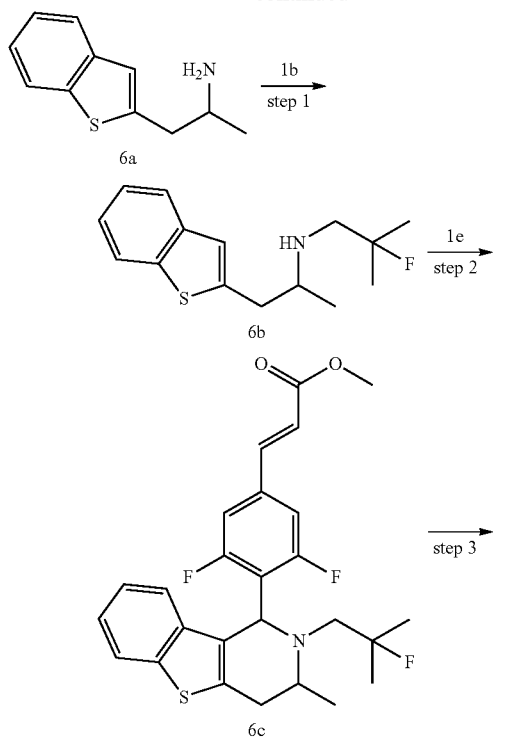

Step 2

(E)-methyl 3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylate N-(1-(benzo[b]thiophen-2-yl)propan-2-yl)-2-fluoro-2-methylpropan-1-amine 6b (82 mg, 0.309 mmol) and (E)-methyl 3-(3,5-difluoro-4-formylphenyl) acrylate 1e (84 mg, 0.371 mmol) were dissolved in 2 mL of toluene, then acetic acid (37 mg, 0.618 mmol) was added. The resulting mixture was stirred under reflux for 24 hours, then the reaction was stopped. The reaction solution was concentrated under reduced pressure, and the residue was purified by thin-layer chromatography with elution system B to obtain the title compound (E)-methyl 3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylate 6c (32 mg, yield 22%) as a yellow solid.

MS m/z (ESI): 373.9 [M+1]

Step 3

(E)-3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylic Acid (E)-methyl 3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylate 6c (32 mg, 0.068 mmol) was dissolved in 2 mL of a mixture of tetrahydrofuran and methanol (V/V=3:1), then 0.12 mL of 6 N sodium hydroxide (27.2 mg, 0.68 mmol) aqueous solution was added. After stirring for 2 hours at room temperature, the reaction was stopped. Then, 10% citric acid was added dropwise to adjust the pH to 3-4, and the mixture was extracted with dichloromethane (5 mL×3). The organic phases were combined, dried over anhydrous sodium sulfate and filtered. The filtrate was concentrated under reduced pressure, and the residue was purified by thin-layer chromatography with elution system B to obtain the title compound (E)-3-(3,5-difluoro-4-((1R,3R/1S,3S)-2-(2-fluoro-2-methylpropyl)-3-methyl-1,2,3,4-tetrahydrobenzo[4,5]thieno[3,2-c]pyridin-1-yl)phenyl)acrylic acid 6 (8 mg, yield 26%) as a light yellow solid.

MS m/z (ESI): 460.3 [M+1]

$^1$H NMR (400 MHz, CDCl$_3$) δ 7.66-7.80 (m, 1H), 7.42-7.56 (m, 1H), 6.43-7.23 (m, 5H), 6.27-6.42 (m, 1H), 5.32 (s, 1H), 3.63-3.81 (m, 1H), 3.22-3.37 (m, 1H), 2.82-3.01 (m, 1H), 2.61-2.80 (m, 1H), 2.27-2.49 (m, 1H), 1.26 (s, 3H), 1.12-1.22 (m, 3H), 1.07 (s, 3H).

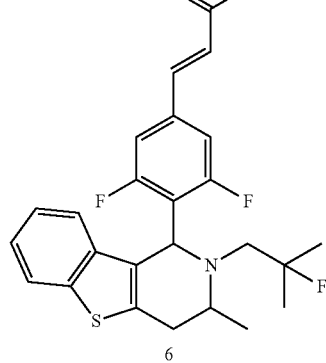

Step 1

N-(1-(benzo[b]thiophen-2-yl)propan-2-yl)-2-fluoro-2-methylpropan-1-amine 1-(benzo[b]thiophen-2-yl)propan-2-amine 6a (155 mg, 0.811 mmol, prepared by a method disclosed in the patent application publication "WO2009117097") and 2-fluoro-2-methylpropyl trifluoromethanesulfonate 1b (545 mg, 2.43 mmol) were dissolved in 3 mL of 1,4-dioxane, then N,N-diisopropylethylamine (524 mg, 4.055 mmol) was added. After stirring for 5 hours at 90° C., the reaction was stopped. The reaction mixture was concentrated under reduced pressure. The residue was purified by thin-layer chromatography with elution system B to obtain the title compound N-(1-(benzo[b]thiophen-2-yl)propan-2-yl)-2-fluoro-2-methylpropan-1-amine 6b (75 mg, yield 35%) as a yellow oil.

Example 7

(E)-3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic Acid

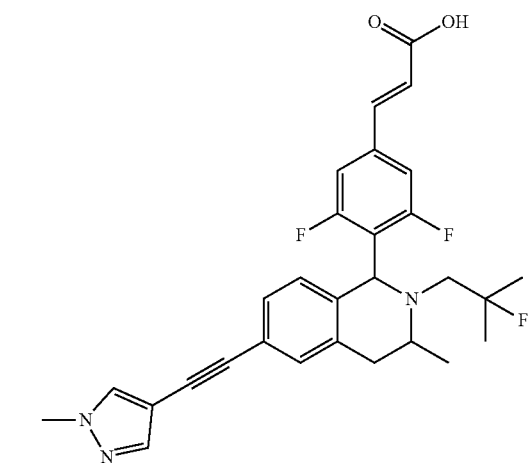

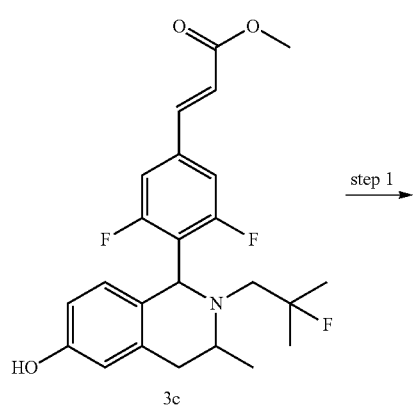

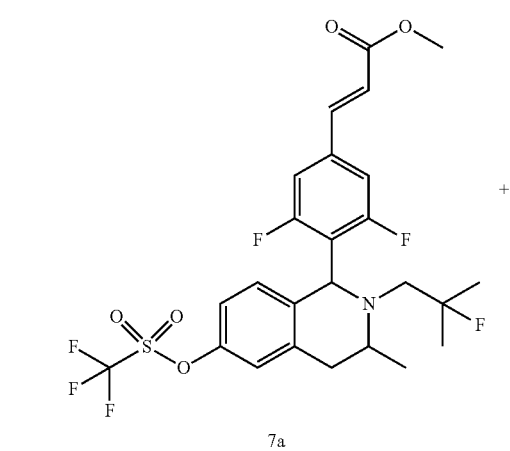

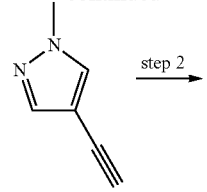

Step 1

(E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (43 mg, 0.1 mmol) was dissolved in 1 mL of dichloromethane, then 2,6-lutidine (21 mg, 0.2 mmol) was added. Trifluoromethanesulfonic anhydride (42 mg, 0.15 mmol) was added dropwise at 0° C. The reaction mixture was warmed up to room temperature. After stirring for 2 hours, the reaction was stopped. The reaction solution was concentrated under reduced pressure, and the residue was purified by thin-layer chromatography with elution system B to obtain the title compound (E)- methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (38 mg, yield 68%) as a yellow oil.

Step 2

(E)-methyl 3-(3,5-difluoro-4-(2-((1S,3R/1R,3S)-2-fluoro-2-methylpropyl)-3-methyl-6-((1-methyl-1H-pyrazol-4-yl)ethynyl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (38 mg, 0.067 mmol) and 4-ethynyl-1-methyl-1H-pyrazole 7b (17 mg, 0.16 mmol, prepared by a well-known method disclosed in "*Journal of Medicinal Chemistry*, 56(24), 10045-10065; 2013") were dissolved in 1 mL of N,N-dimethylformamide, then bis(triphenylphosphine)palladium(II) dichloride (5 mg, 0.0067 mmol), cuprous iodide (1.3 mg, 0.0067 mmol) and N,N-diisopropylethylamine (28 mg, 0.214 mmol) were added. The reaction was warmed up to 120° C. After stirring for 12 hours, the reaction was stopped. The reaction solution was cooled to room temperature and concentrated under reduced pressure. Water was added to the residue, and the mixture was extracted with ethyl acetate three times. The organic phases were combined, dried over anhydrous sodium sulfate and filtered. The filtrate was concentrated under reduced pressure. The residue was purified by thin-layer chromatography with elution system B to obtain the title compound (E)-methyl 3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylate 7c (15 mg, yield 43%) as a yellow solid.

Step 3

(E)-3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylate 7c (15 mg, 0.029 mmol) was dissolved in 1 mL of a mixture of tetrahydrofuran and methanol (V/V=3:1), then 0.05 mL of 6 M sodium hydroxide solution was added. After stirring for 2 hours, the reaction was stopped. Then, 10% citric acid was added dropwise to adjust the pH to 3-4, and the mixture was extracted with ethyl acetate. The organic phases were combined, dried over anhydrous sodium sulfate and filtered. The filtrate was concentrated under reduced pressure, and the residue was purified by thin-layer chromatography with elution system A to obtain the title compound (E)-3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic acid 7 (5 mg, yield 33%) as a light yellow solid.

MS m/z (ESI): 508.1[M+1]

$^1$H NMR (400 MHz, CD$_3$OD) δ 7.82 (s, 1H), 7.61 (s, 1H), 7.45 (dd, 1H), 7.24 (s, 1H), 7.12-7.17 (m, 3H), 6.71 (dd, 1H), 6.54 (dd, 1H), 5.22 (s, 1H), 3.92 (s, 3H) 3.72 (s, 1H), 3.49 (dd, 1H), 3.00 (t, 1H), 2.61 (dd, 1H), 2.35-2.24 (t, 1H), 1.18-1.10 (t, 6H), 1.02 (t, 3H).

Examples 8, 9

(E)-3-(3,5-difluoro-4-((1S,3R)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic Acid (E)-3-(3,5-difluoro-4-((1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic Acid

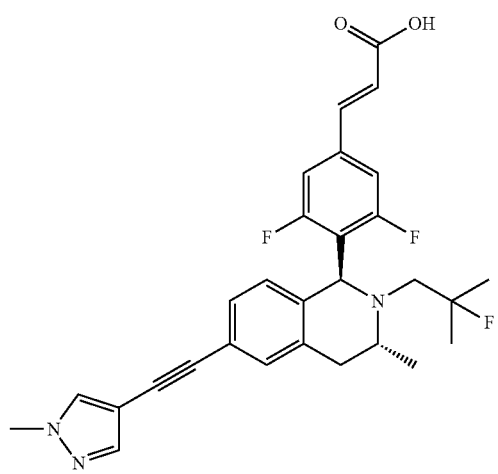

8

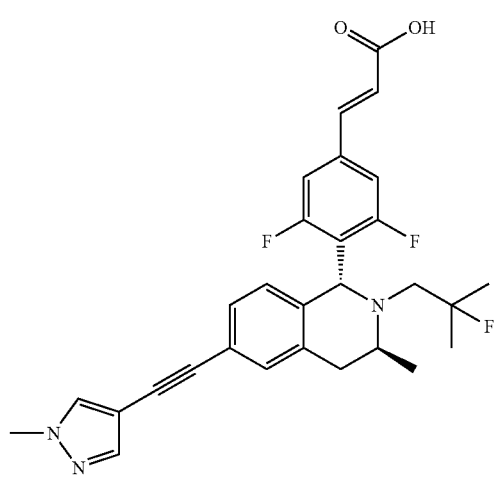

9

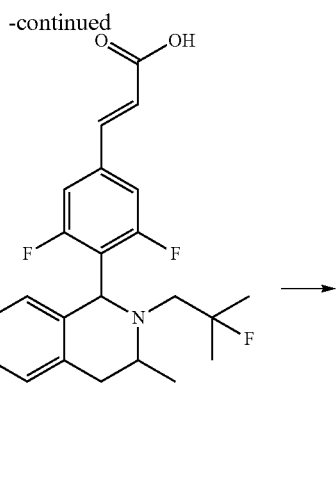

7

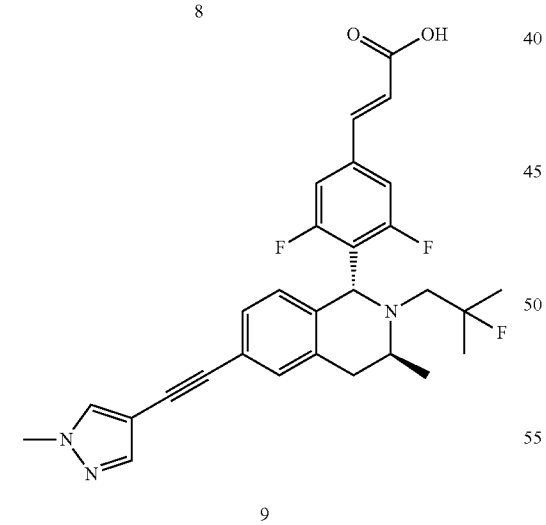

8

9

(E)-3-(3,5-difluoro-4-((1S,3R/1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic acid 7 (242 mg, 0.48 mmol) was separated chirally (separation conditions: chiral preparative column CHIRALPAK AD, 2.5 cm I.D.×25 cm L; mobile phase: n-hexane:ethanol:trifluoroacetic acid=70:30:0.1, flow rate: 30 mL/min). The corresponding fractions were collected and concentrated under reduced pressure to obtain the title compounds (E)-3-(3,5-difluoro-4-((1S,3R)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic acid 8 (65 mg, a yellow solid) and (E)-3-(3,5-difluoro-4-((1R,3S)-2-(2-fluoro-2-methylpropyl)-3-methyl-6-((1-methyl-1H-pyrazol-4-yl)ethynyl)-1,2,3,4-tetrahydroisoquinolin-1-yl)phenyl)acrylic acid 9 (70 mg, a yellow solid).

Example 8

MS m/z (ESI): 508.1 [M+1];

Chiral HPLC analysis: retention time 7.340 minutes, chiral purity: 99.240% (chromatographic column: CHIRALPAK AD-H, 0.46 cm I.D.×15 cm L; mobile phase: n-hexane/ethanol/trifluoroacetic acid=70/30/0.1 (v/v/v));

$^1$H NMR (400 MHz, CD$_3$OD) δ 7.82 (s, 1H), 7.61 (s, 1H), 7.45 (dd, 1H), 7.24 (s, 1H), 7.12-7.17 (m, 3H), 6.71 (dd, 1H), 6.54 (dd, 1H), 5.22 (s, 1H), 3.92 (s, 3H) 3.72 (s, 1H), 3.49 (dd, 1H), 3.00 (t, 1H), 2.61 (dd, 1H), 2.35-2.24 (t, 1H), 1.18-1.10 (t, 6H), 1.02 (t, 3H).

Example 9

MS m/z (ESI): 508.1 [M+1];

Chiral HPLC analysis: retention time 3.948 minutes, chiral purity: 98.052% (chromatographic column: CHIRALPAK AD-H, 0.46 cm I.D.×15 cm L; mobile phase: n-hexane/ethanol/trifluoroacetic acid=70/30/0.1 (v/v/v));

$^1$H NMR (400 MHz, CD$_3$OD) δ 7.82 (s, 1H), 7.61 (s, 1H), 7.45 (dd, 1H), 7.24 (s, 1H), 7.12-7.17 (m, 3H), 6.71 (dd, 1H), 6.54 (dd, 1H), 5.22 (s, 1H), 3.92 (s, 3H) 3.72 (s, 1H), 3.49 (dd, 1H), 3.00 (t, 1H), 2.61 (dd, 1H), 2.35-2.24 (t, 1H), 1.18-1.10 (t, 6H), 1.02 (t, 3H).

Example 10

(E)-3-(3,5-difluoro-4-((1S,3R/1R,3S)-2-(2-fluoro-2-methylpropyl)-3-methyl-6-(2-methylthiazol-5-yl)-1,2,3,4-tetrahydroisoquinolin-1-yl)phenyl)acrylic Acid

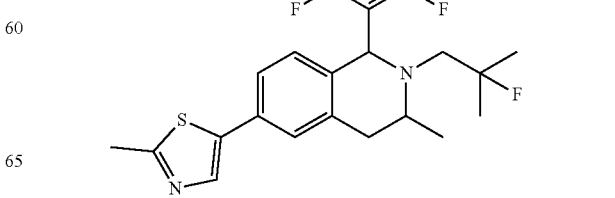

10

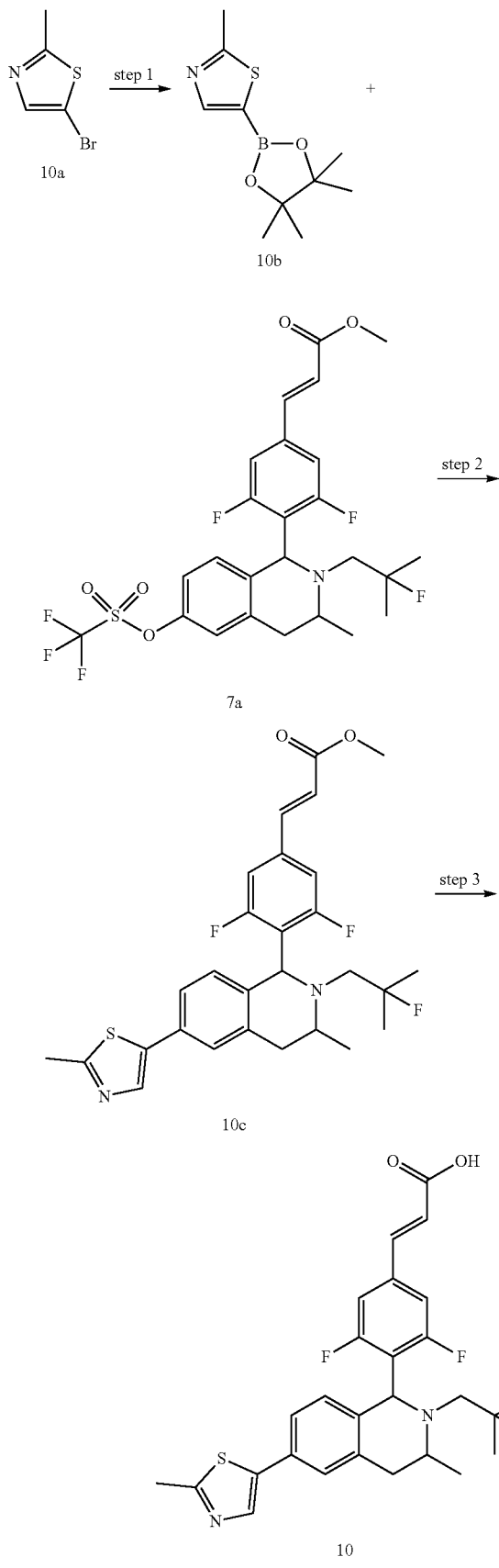

Step 1

2-methyl-5-(4,4,5,5-tetramethyl-1,3,2-dioxaborolan-2-yl)thiazole 5-bromo-2-methylthiazole 10a (2 g, 11.23 mmol) was dissolved in 70 mL of tetrahydrofuran, and 5.6 mL of a solution of 2.4 M n-butyllithium was added at −78° C. After the mixture was stirred for 30 minutes, 2-isopropoxy-4,4,5,5-tetramethyl-1,3,2-dioxaborolane (2.5 g, 13.44 mmol) was added. The reaction was stirred for 1.5 hours, then stopped. The reaction solution was warmed up to room temperature, then 10 mL of a mixture of saturated ammonium chloride solution and water (V/V=1:1) were added to quench the reaction. Then, 50 mL of ethyl acetate was added, and two phases were separated. The aqueous phase was extracted with 30 mL of ethyl acetate. The organic phases were combined, dried over anhydrous sodium sulfate and filtered. The filtrate was concentrated under reduced pressure, and the residue was purified by silica gel column chromatography with elution system B to obtain the title compound 2-methyl-5-(4,4,5,5-tetramethyl-1,3,2-dioxaborolan-2-yl)thiazole 10b (1.6 g, yield 64%) as a light yellow oil.

MS m/z (ESI): 226.1 [M+1]

Step 2

(E)-methyl 3-(3,5-difluoro-4-((1S,3R/1R,3S)-(2-(2-fluoro-2-methylpropyl)-3-methyl-6-(2-methylthiazol-5-yl)-1,2,3,4-tetrahydroisoquinolin-1-yl)phenyl)acrylate (E)-methyl 3-(3,5-difluoro-4-((1S,3R/1R,3S)-(2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (3.3 g, 5.835 mmol) was dissolved in 36 mL of a mixture of 1,4-dioxane and water (V/V=35:1). Then, 2-methyl-5-(4,4,5,5-tetramethyl-1,3,2-dioxaborolan-2-yl)thiazole 10b (1.6 g, 7.107 mmol), tetrakis(triphenylphosphine) palladium (0.674 g, 0.583 mmol) and sodium carbonate (1.86 g, 17.55 mmol) were added. The resulting mixture was warmed up to 90° C. After stirring for 12 hours, the reaction was stopped. The reaction solution was cooled to room temperature, filtered and the filtrate was concentrated under reduced pressure. The residue was purified by silica gel column chromatography with eluent system B to obtain the title compound (E)-methyl 3-(3,5-difluoro-4-((1S,3R/1R,3S)-(2-(2-fluoro-2-methylpropyl)-3-methyl-6-(2-methylthiazol-5-yl)-1,2,3,4-tetrahydroisoquinolin-1-yl)phenyl)acrylate 10c (650 mg, yield 22%) as a yellow oil.

MS m/z (ESI): 515.0 [M+1]

Step 3

(E)-3-(3,5-difluoro-4-((1S,3R/1R,3S)-2-(2-fluoro-2-methylpropyl)-3-methyl-6-(2-methylthiazol-5-yl)-1,2,3,4-tetrahydroisoquinolin-1-yl)phenyl)acrylic Acid (E)-methyl 3-(3,5-difluoro-4-((1S,3R/1R,3S)-(2-(2-fluoro-2-methylpropyl)-3-methyl-6-(2-methylthiazol-5-yl)-1,2,3,4-tetrahydroisoquinolin-1-yl)phenyl)acrylate 10c (650 mg, 1.263 mmol) was dissolved in 12 mL of a mixture of tetrahydrofuran and methanol (V/V=5:1), then 6.5 mL of 1 M lithium hydroxide solution was added. After stirring for 2 hours, the reaction was stopped. Then, 10% citric acid was added dropwise to adjust the pH to 3-4, and 50 mL of ethyl acetate was added. Two phases were separated, and the aqueous phase was extracted with ethyl acetate (30 mL). The organic phases were combined, dried over anhydrous sodium sulfate and filtered. The filtrate was concentrated under reduced pressure, and the residue was purified by silica gel column chromatography with elution system A to obtain the title compound (E)-3-(3,5-difluoro-4-((1S,3R/1R,3S)-2-(2-fluoro-2-methylpropyl)-3-methyl-6-(2-methylthiazol-5-yl)-1,2,3,4-tetrahydroisoquinolin-1-yl)phenyl) acrylic acid 10 (250 mg, yield 40%) as a yellow solid.

MS m/z (ESI): 501.4 [M+1]

$^1$H NMR (400 MHz, CDCl$_3$) δ 7.95 (s, 1H), 7.64 (d, 1H), 7.35 (s, 1H), 7.25 (d, 1H), 7.07 (d, 2H), 6.86 (d, 1H), 6.45 (d, 1H), 5.43 (s, 1H), 3.88 (s, 1H), 3.54-3.47 (m, 1H), 3.08 (t, 1H), 2.88 (s, 3H), 2.73 (dd, 1H), 2.52-2.41 (m, 1H), 1.35-1.14 (m, 9H).

Examples 11, 12

(E)-3-(3,5-difluoro-4-((1S,3R)-2-(2-fluoro-2-methylpropyl)-3-methyl-6-(2-methylthiazol-5-yl)-1,2,3,4-tetrahydroisoquinolin-1-yl)phenyl)acrylic Acid (E)-3-(3,5-difluoro-4-((1R,3S)-2-(2-fluoro-2-methylpropyl)-3-methyl-6-(2-methylthiazol-5-yl)-1,2,3,4-tetrahydroisoquinolin-1-yl)phenyl)acrylic Acid

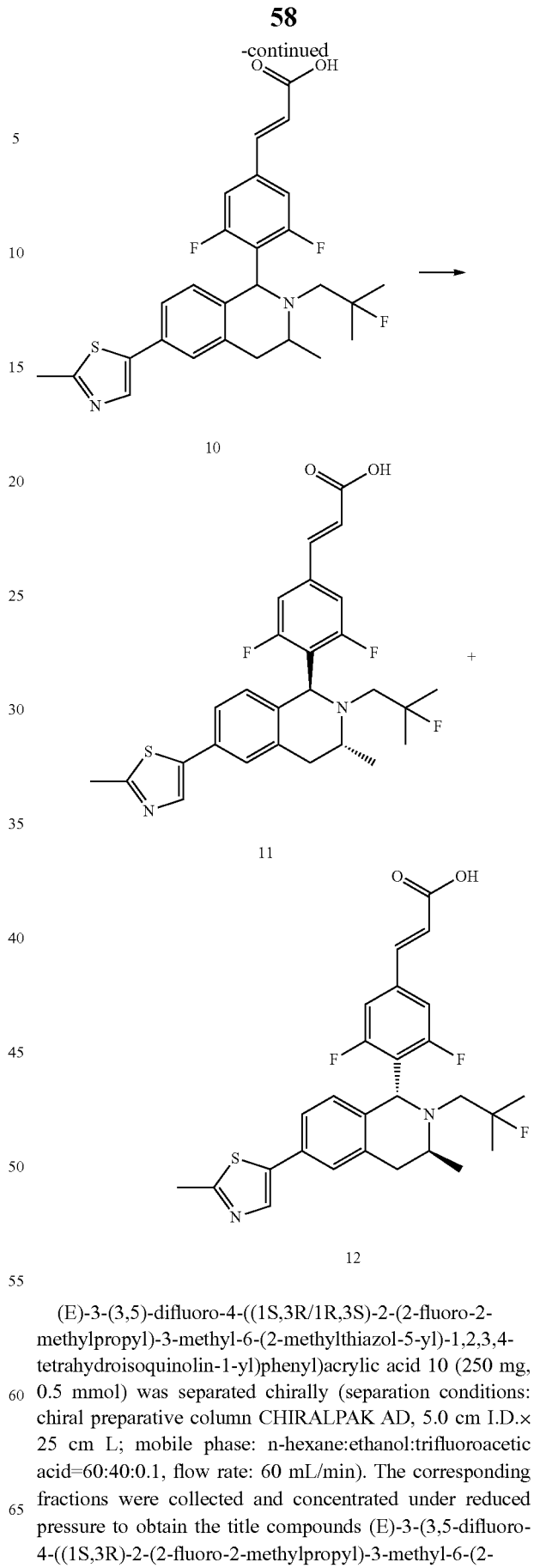

(E)-3-(3,5)-difluoro-4-((1S,3R/1R,3S)-2-(2-fluoro-2-methylpropyl)-3-methyl-6-(2-methylthiazol-5-yl)-1,2,3,4-tetrahydroisoquinolin-1-yl)phenyl)acrylic acid 10 (250 mg, 0.5 mmol) was separated chirally (separation conditions: chiral preparative column CHIRALPAK AD, 5.0 cm I.D.× 25 cm L; mobile phase: n-hexane:ethanol:trifluoroacetic acid=60:40:0.1, flow rate: 60 mL/min). The corresponding fractions were collected and concentrated under reduced pressure to obtain the title compounds (E)-3-(3,5-difluoro-4-((1S,3R)-2-(2-fluoro-2-methylpropyl)-3-methyl-6-(2- methylthiazol-5-yl)-1,2,3,4-tetrahydroisoquinolin-1-yl)phenyl)acrylic acid 11 (117.9 mg, a yellow solid) and (E)-3-(3,5-difluoro-4-((1R,3S)-2-(2-fluoro-2-methylpropyl)-3-methyl-6-(2-methylthiazol-5-yl)-1,2,3,4-tetrahydroisoquinolin-1-yl)phenyl)acrylic acid 12 (116.7 mg, a yellow solid).

Example 11

MS m/z (ESI): 501.4 [M+1];

Chiral HPLC analysis: retention time 8.585 minutes, chiral purity: 99.989% (chromatographic column: CHIRALPAK AD-H, 0.46 cm I.D.×15 cm L; mobile phase: n-hexane/ethanol/trifluoroacetic acid=60/40/0.1 (v/v/v));

$^1$H NMR (400 MHz, CD$_3$OD) δ 7.85 (s, 1H), 7.60-7.56 (m, 1H), 7.38 (s, 1H), 7.30-7.21 (m, 3H), 6.80-6.78 (d, 1H), 6.57-6.53 (d, 1H), 5.25 (s, 1H), 3.74 (s, 1H), 3.42-3.39 (m, 1H), 3.05-2.98 (m, 1H), 2.72 (s, 3H), 2.36-2.19 (m, 2H), 1.32-0.91 (m, 9H).

Example 12

MS m/z (ESI): 501.4 [M+1];

Chiral HPLC analysis: retention time 5.254 minutes, chiral purity: 99.804% (chromatographic column: CHIRALPAK AD-H, 0.46 cm I.D.×25 cm L; mobile phase: n-hexane/ethanol/trifluoroacetic acid=60/40/0.1 (v/v/v));

$^1$H NMR (400 MHz, CD$_3$OD) δ 7.85 (s, 1H), 7.60-7.56 (m, 1H), 7.38 (s, 1H), 7.30-7.21 (m, 3H), 6.80-6.78 (d, 1H), 6.57-6.53 (d, 1H), 5.25 (s, 1H), 3.74 (s, 1H), 3.42-3.39 (m, 1H), 3.05-2.98 (m, 1H), 2.72 (s, 3H), 2.36-2.19 (m, 2H), 1.32-0.91 (m, 9H).

Example 13

(E)-3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic Acid

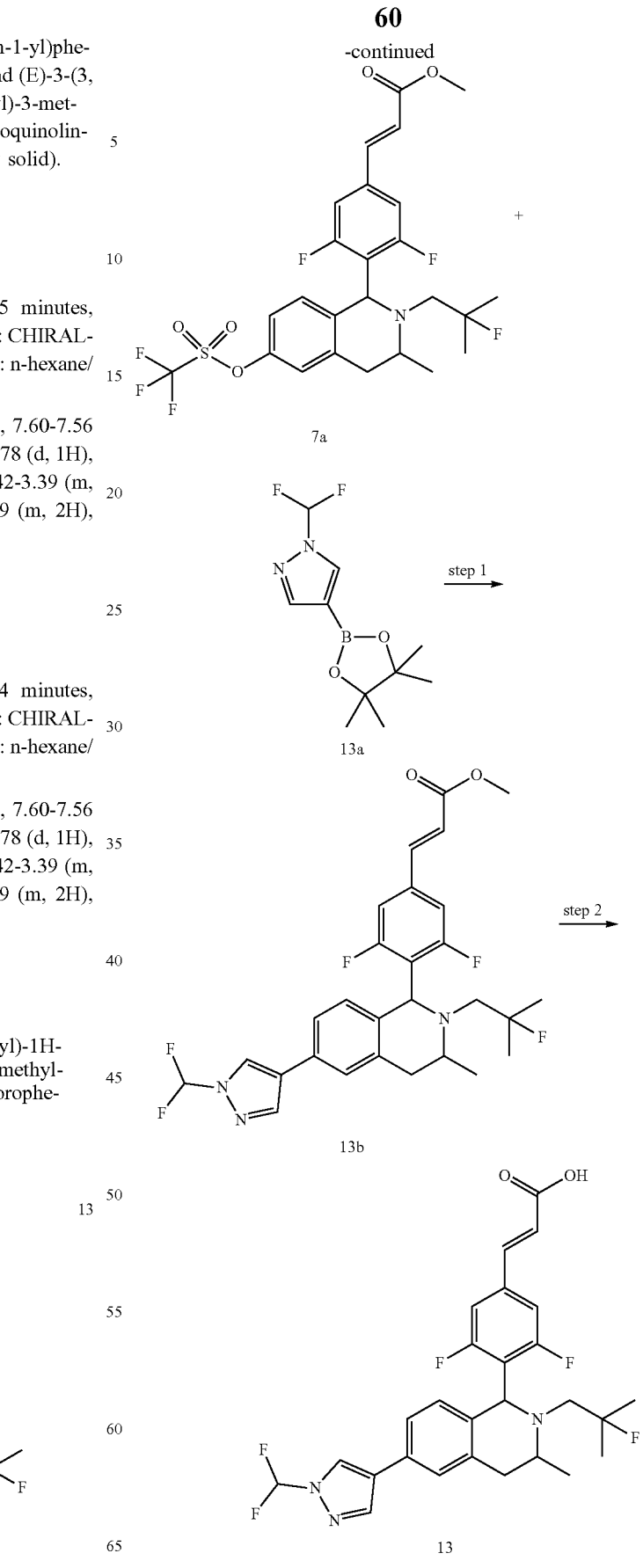

Step 1

(E)-methyl 3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (200 mg, 0.353 mmol), 1-(difluoromethyl)-4-(4,4,5,5-tetramethyl-1,3,2-dioxaborolan-2-yl)-1H-pyrazole 13a (129 mg, 0.529 mmol, prepared by a method disclosed in the patent application publication "WO2014159224") and potassium carbonate (146 mg, 1.06 mmol) were dissolved in 5.5 mL of a mixture of 1,4-dioxane and water (V/V=10:1), then [1,1'-bis(diphenylphosphino)ferrocene]dichloropalladium(II) (12.9 mg, 0.0176 mmol) was added. The reaction was warmed up to 80° C. After stirring for 18 hours, the reaction was stopped. The reaction solution was cooled to room temperature. Ethyl acetate was added, and the mixture was washed with water. The organic phase was dried over anhydrous sodium sulfate and filtered. The filtrate was concentrated under reduced pressure. The residue was purified by thin-layer chromatography with elution system A to obtain the title compound (E)-methyl 3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylate 13b (52 mg, yield 27.6%) as a yellow solid.

Step 2

(E)-3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic Acid (E)-methyl 3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylate 13b (50 mg, 0.093 mmol) was dissolved in 3.5 mL of a mixture of tetrahydrofuran and methanol (V/V=6:1), then 0.5 mL of 1 M lithium hydroxide solution was added. After stirring for 3 hours, the reaction was stopped. Then, 10% citric acid was added dropwise to adjust the pH to 3-4, and the mixture was extracted with ethyl acetate three times. The organic phases were combined, dried over anhydrous sodium sulfate and filtered. The filtrate was concentrated under reduced pressure, and the residue was purified by thin-layer chromatography with elution system A to obtain the title compound (E)-3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic acid 13 (18 mg, yield 37%) as a yellow solid.

MS m/z (ESI): 520.2 [M+1]

$^1$H NMR (400 MHz, DMSO-$d_6$) δ 8.66 (s, 1H), 8.23 (s, 1H), 7.97-7.68 (m, 1H), 7.55-7.45 (m, 4H), 7.36 (d, 1H), 6.73 (d, 1H), 6.65 (d, 1H), 5.15 (s, 1H), 3.63-3.54 (m, 1H), 3.29-3.21 (m, 1H), 3.00-2.89 (m, 1H), 2.70-2.62 (s, 1H), 2.29-2.23 (m, 1H), 1.25-0.94 (m, 9H).

Examples 14, 15

(E)-3-(4-((1S,3R)-6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl) acrylic Acid (E)-3-(4-((1R,3S)-6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl) acrylic Acid

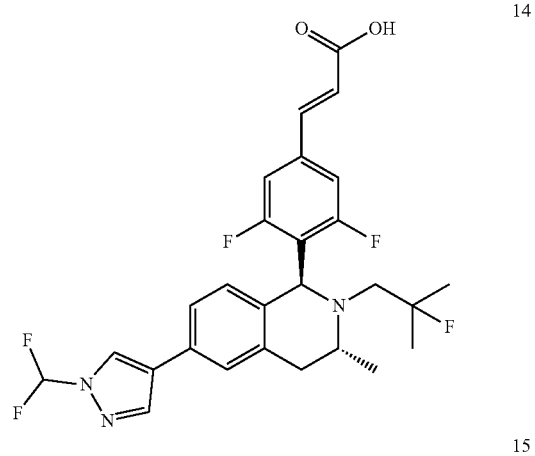

14

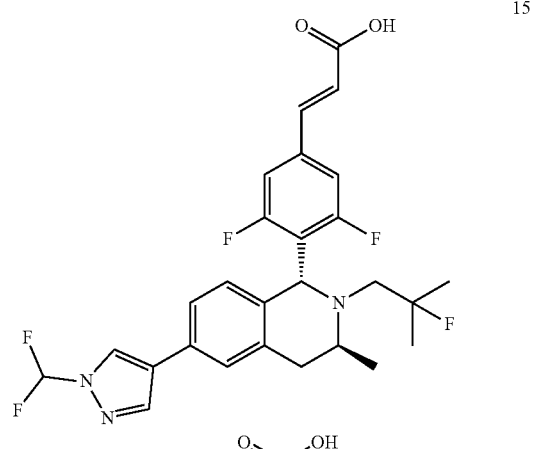

15

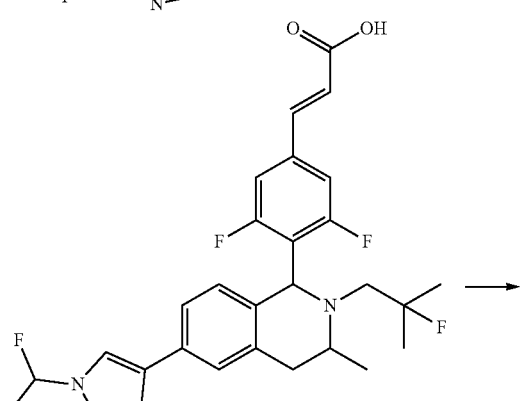

13

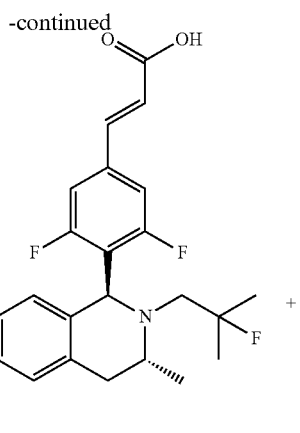

14

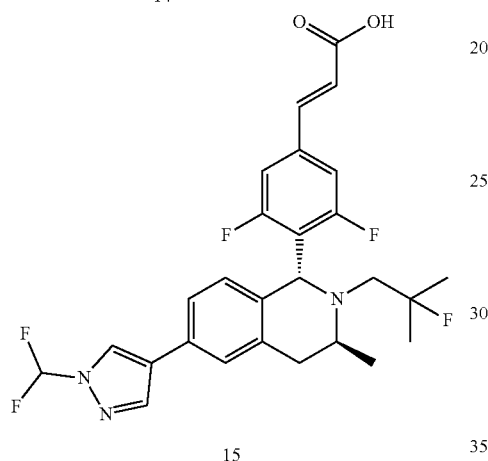

15

(E)-3-(4-((1S,3R/1R,3S)-(6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic acid 13 (1.4 g, 2.7 mmol) was separated chirally (separation conditions: chiral preparative column CHIRALPAK AD, 5.0 cm I.D.×25 cm L: mobile phase: n-hexane:ethanol:trifluoroacetic acid=85:15:0.1, flow rate: 60 mL/min). The corresponding fractions were collected and concentrated under reduced pressure to obtain the title compounds (E)-3-(4-((1S,3R)-6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic acid 14 (210 mg, a yellow solid) and (E)-3-(4-((1R,3S)-6-(1-(difluoromethyl)-1H-pyrazol-4-yl)-2-(2-fluoro-2-methylpropyl)-3-methyl-1,2,3,4-tetrahydroisoquinolin-1-yl)-3,5-difluorophenyl)acrylic acid 15 (200 mg, a yellow solid).

Example 14

MS m/z (ESI): 520.2 [M+1];
Chiral HPLC analysis: retention time 15.403 minutes, chiral purity: 99.90% (chromatographic column: CHIRALPAK AD-H, 0.46 cm I.D.×15 cm L; mobile phase: n-hexane/ethanol/trifluoroacetic acid=85/15/0.1 (v/v/v));
$^1$H NMR (400 MHz, DMSO-d$_6$) δ 8.66 (s, 1H), 8.23 (s, 1H), 7.97-7.68 (m, 1H), 7.55-7.45 (m, 4H), 7.36 (d, 1H), 6.73 (d, 1H), 6.65 (d, 1H), 5.15 (s, 1H), 3.63-3.54 (m, 1H), 3.29-3.21 (m, 1H), 3.00-2.89 (m, 1H), 2.70-2.62 (s, 1H), 2.29-2.23 (m, 1H), 1.25-0.94 (m, 9H).

Example 15

MS m/z (ESI): 520.2 [M+1];
Chiral HPLC analysis: retention time 10.902 min, chiral purity: 99.90% (chromatographic column: CHIRALPAK AD-H, 0.46 cm I.D.×15 cm L; mobile phase: n-hexane/ethanol/trifluoroacetic acid=85/15/0.1 (v/v/v));
$^1$H NMR (400 MHz, DMSO-d$_6$) δ 8.66 (s, 1H), 8.23 (s, 1H), 7.97-7.68 (m, 1H), 7.55-7.45 (m, 4H), 7.36 (d, 1H), 6.73 (d, 1H), 6.65 (d, 1H), 5.15 (s, 1H), 3.63-3.54 (m, 1H), 3.29-3.21 (m, 1H), 3.00-2.89 (m, 1H), 2.70-2.62 (s, 1H), 2.29-2.23 (m, 1H), 1.25-0.94 (m, 9H).

Example 16

(E)-3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylic Acid

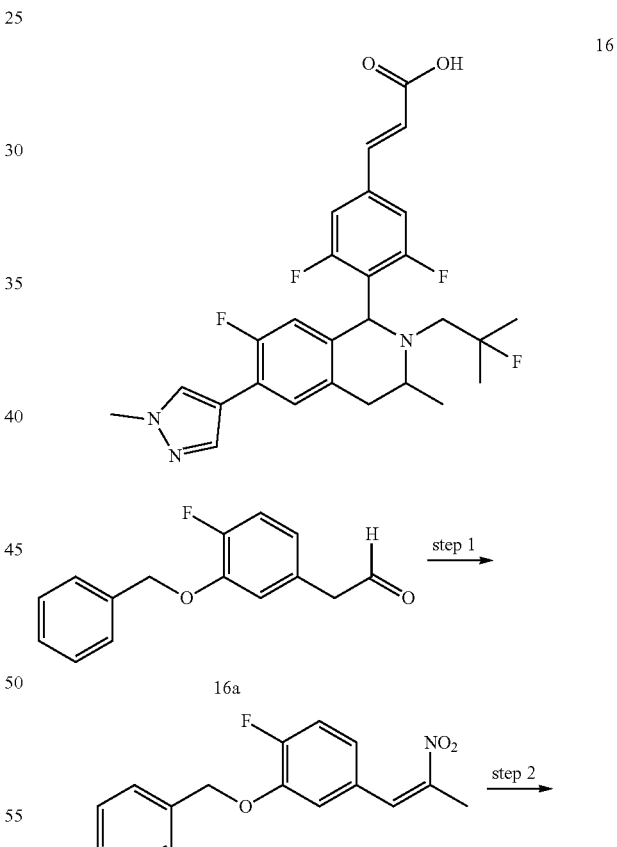

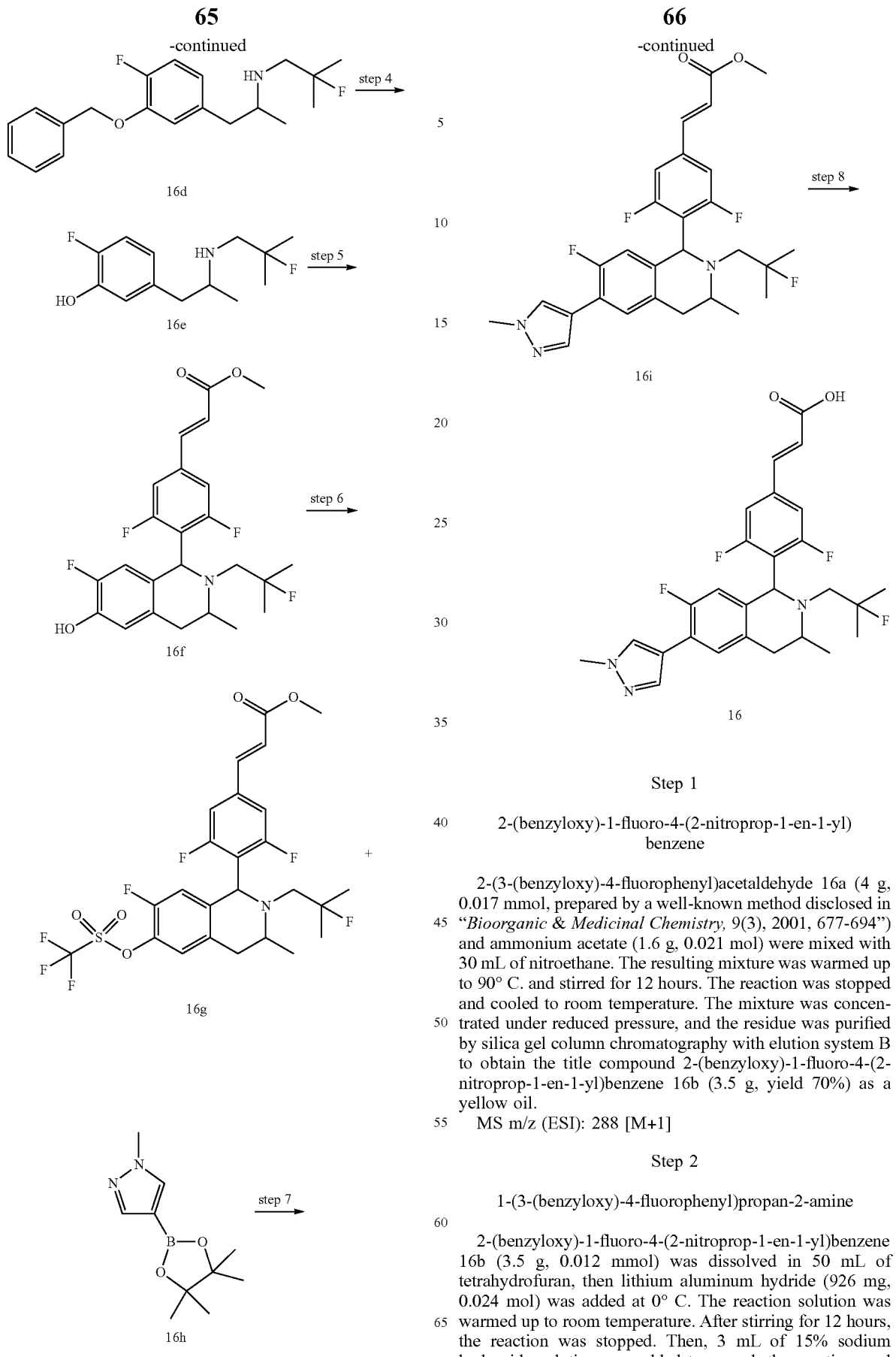

Step 1

2-(benzyloxy)-1-fluoro-4-(2-nitroprop-1-en-1-yl)benzene 2-(3-(benzyloxy)-4-fluorophenyl)acetaldehyde 16a (4 g, 0.017 mmol, prepared by a well-known method disclosed in "*Bioorganic & Medicinal Chemistry,* 9(3), 2001, 677-694") and ammonium acetate (1.6 g, 0.021 mol) were mixed with 30 mL of nitroethane. The resulting mixture was warmed up to 90° C. and stirred for 12 hours. The reaction was stopped and cooled to room temperature. The mixture was concentrated under reduced pressure, and the residue was purified by silica gel column chromatography with elution system B to obtain the title compound 2-(benzyloxy)-1-fluoro-4-(2-nitroprop-1-en-1-yl)benzene 16b (3.5 g, yield 70%) as a yellow oil.

MS m/z (ESI): 288 [M+1]

Step 2

1-(3-(benzyloxy)-4-fluorophenyl)propan-2-amine 2-(benzyloxy)-1-fluoro-4-(2-nitroprop-1-en-1-yl)benzene 16b (3.5 g, 0.012 mmol) was dissolved in 50 mL of tetrahydrofuran, then lithium aluminum hydride (926 mg, 0.024 mol) was added at 0° C. The reaction solution was warmed up to room temperature. After stirring for 12 hours, the reaction was stopped. Then, 3 mL of 15% sodium hydroxide solution was added to quench the reaction, and the reaction solution was filtered. The filtrate was concentrated under reduced pressure to obtain the title compound 1-(3-(benzyloxy)-4-fluorophenyl) propan-2-amine 16c (3.1 g) as a yellow oil, which was used directly in next step without further purification.

Step 3

N-(1-(3-(benzyloxy)-4-fluorophenyl)propan-2-yl)-2-fluoro-2-methylpropan-1-amine

The crude 1-(3-(benzyloxy)-4-fluorophenyl)propan-2-amine 16c (3.1 g, 0.012 mmol), 2-fluoro-2-methylpropyl trifluoromethanesulfonate 1b (4.02 g, 0.018 mmol) and N,N-diisopropylethylamine (3.1 g, 0.024 mmol) were dissolved in 30 mL of 1,4-dioxane. The resulting mixture was warmed up to 90° C. After stirring for 12 hours, the reaction was stopped. The reaction solution was cooled to room temperature and concentrated under reduced pressure. The residue was purified by silica gel column chromatography with elution system B to obtain the title compound N-(1-(3-(benzyloxy)-4-fluorophenyl)propan-2-yl)-2-fluoro-2-methylpropan-1-amine 16d (1.3 g, yield 30%) as a yellow liquid.

MS m/z (ESI): 334.0 [M+1]

Step 4

2-fluoro-5-(2-((2-fluoro-2-methylpropyl)amino)propyl)phenol

N-(1-(3-(benzyloxy)-4-fluorophenyl)propan-2-yl)-2-fluoro-2-methylpropan-1-amine 16d (1 g, 3 mmol) was dissolved in 8 mL of trifluoroacetic acid. The resulting mixture was warmed up to 50° C. After stirring for 48 hours, the reaction was stopped. The solution was cooled to room temperature and concentrated under reduced pressure. A solution of saturated sodium bicarbonate was added to the residue to adjust the pH to 8-9. The mixture was extracted with ethyl acetate. The organic phases were combined, dried over anhydrous sodium sulfate, and filtered. The filtrate was concentrated under reduced pressure, and the residue was purified by silica gel column chromatography with elution system A to obtain the title compound 2-fluoro-5-(2-((2-fluoro-2-methylpropyl)amino) propyl)phenol 16e (300 mg, yield 41%) as a yellow oil.

MS m/z (ESI): 244.0 [M+1]

Step 5

(E)-methyl 3-(3,5-difluoro-4-((1S,3R/1R,3S)-7-fluoro-2-(2-fluoro-2-methylpropyl)-6-hydroxy-3-methyl-1,2,3,4-tetrahydroisoquinolin-1-yl)phenyl)acrylate 2-fluoro-5-(2-((2-fluoro-2-methylpropyl)amino)propyl) phenol 16e (300 mg, 1.233 mmol) was dissolved in 5 mL of methanol, then (E)-methyl 3-(3,5-difluoro-4-formylphenyl) acrylate 1e (418 mg, 1.896 mmol) and acetic acid (740 mg, 12.33 mmol) were added. The resulting mixture was heated to 80° C. and stirred for 48 hours. After the reaction was stopped, the reaction solution was cooled to room temperature. A solution of 1M sodium bicarbonate was added to the reaction solution to adjust the pH to 7-8. The mixture was extracted with ethyl acetate. The organic phases were combined, dried over anhydrous sodium sulfate, and filtered. The filtrate was concentrated under reduced pressure, and the residue was purified by silica gel column chromatography with elution system B to obtain the title compound (E)-methyl 3-(3,5-difluoro-4-((1S,3R/1R,3S)-7-fluoro-2-(2-fluoro-2-methylpropyl)-6-hydroxy-3-methyl-1,2,3,4-tetrahydroisoquinolin-1-yl)phenyl)acrylate 16f (300 mg, yield 54%) as a yellow oil.

MS m/z (ESI): 451.9 [M+1]

Step 6

(E)-methyl 3-(3,5-difluoro-4-((1S,3R/1R,3S)-7-fluoro-2-(2-fluoro-2-methylpropyl)-3-methyl-6-(((trifluoromethyl)sulfonyl)oxy)-1,2,3,4-tetrahydroisoquinolin-1-yl)phenyl)acrylate (E)-methyl 3-(3,5-difluoro-4-((1S,3R/1R,3S)-7-fluoro-2-(2-fluoro-2-methylpropyl)-6-hydroxy-3-methyl-1,2,3,4-tetrahydroisoquinolin-1-yl)phenyl)acrylate 16f (300 mg, 0.664 mmol) was dissolved in 10 mL of dichloromethane, then 2,6-lutidine (142 mg, 1.329 mmol) and trifluoromethanesulfonic anhydride (281 mg, 0.996 mmol) were added at 0° C. The reaction was stirred for 2 hours at 0° C. After the reaction was stopped, the reaction solution was warmed up to room temperature. Water was added, and the mixture was extracted with dichloromethane. The organic phase was concentrated under reduced pressure. The residue was purified by silica gel column chromatography with elution system B to obtain the title compound (E)-methyl 3-(3,5-difluoro-4-((1S,3R/1R,3S)-7-fluoro-2-(2-fluoro-2-methylpropyl)-3-methyl-6-(((trifluoromethyl)sulfonyl)oxy)-1,2,3,4-tetrahydroisoquinolin-1-yl)phenyl)acrylate 16g (300 mg, yield 77%) as a yellow oil.

MS m/z (ESI): 583.8 [M+1]

Step 7

(E)-methyl 3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylate (E)-methyl 3-(3,5-difluoro-4-((1S,3R/1R,3S)-7-fluoro-2-(2-fluoro-2-methylpropyl)-3-methyl-6-(((trifluoromethyl) sulfonyl)oxy)-1,2,3,4-tetrahydroisoquinolin-1-yl)phenyl) acrylate 16g (350 mg, 0.6 mmol), 1-methyl-4-(4,4,5,5-tetramethyl-1,3,2-dioxaborolan-2-yl)-1H-pyrazole 16h (250 mg, 1.2 mmol, prepared by a well-known method disclosed in "*Tetrahedron Letters*, 50(49), 2009, 6783-6786") and potassium carbonate (248 mg, 1.8 mmol) were dissolved in 10 mL of a mixture of 1,4-dioxane and water (V/V=8:1), then [1,1'-bis(diphenylphosphino)ferrocene]dichloropalladium(II) (44 mg, 0.06 mmol) was added. The reaction was warmed up to 90° C. After stirring for 12 hours, the reaction was stopped. The reaction solution was cooled to room temperature and filtered. The filtrate was concentrated under reduced pressure to obtain the crude title compound (E)-methyl 3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylate 16i (300 mg) as a brown oil, which was used directly in next step without further purification.

MS m/z (ESI): 515.9 [M+1]

Step 8

(E)-3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylic Acid The crude (E)-methyl 3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylate 16i (300 mg, 0.582 mmol) was dissolved in 10 mL of methanol, then 2 mL of 3 M sodium hydroxide solution was added. After stirring for 12 hours, the reaction was stopped. Then, 1M hydrochloric acid was added dropwise to adjust the pH to 5-6. The mixture was extracted with ethyl acetate. The organic phases were combined, dried over anhydrous sodium sulfate and filtered. The filtrate was concentrated under reduced pressure, and the residue was purified by high performance liquid chromatography to obtain the title compound (E)-3-(3,5-difluoro-4-((1S,3R/1R,3S)-7-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylic acid 16 (120 mg, yield 41%) as a yellow solid.

MS m/z (ESI): 502.5 [M+1]

$^1$H NMR (400 MHz, CD$_3$OD): δ 8.01 (s, 1H), 7.89 (s, 1H), 7.66 (d, 1H), 7.50 (d, 1H), 7.31 (d, 2H), 6.59 (d, 2H), 5.52 (s, 1H), 3.95 (s, 3H), 3.83-3.78 (m, 1H), 3.37-3.34 (m, 1H), 3.32-3.30 (m, 1H), 2.82 (s, 2H), 1.38-1.11 (m, 9H).

Example 17

(E)-3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylic Acid

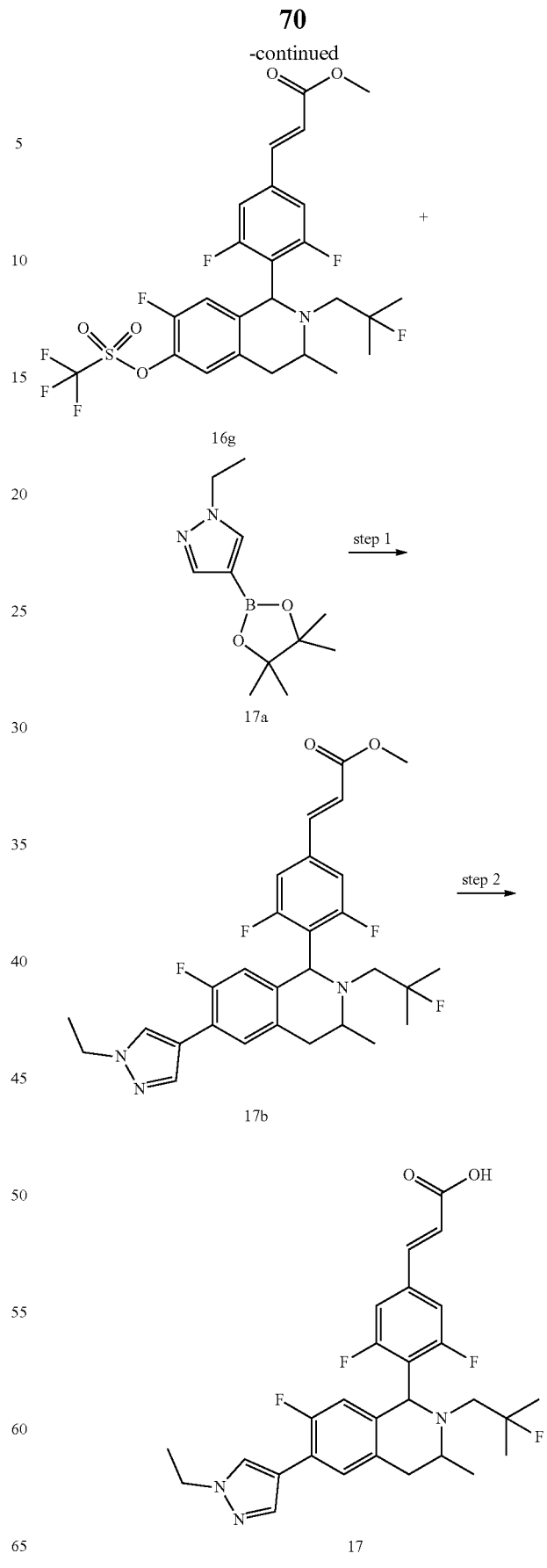

Example 18

(E)-3-(3,5-difluoro-4-((1S,3R/1R,3S)-2-(2-fluoro-2-methylpropyl)-3-methyl-6-(1-propyl-1H-pyrazol-4-yl)-1,2,3,4-tetrahydroisoquinolin-1-yl)phenyl)acrylic Acid

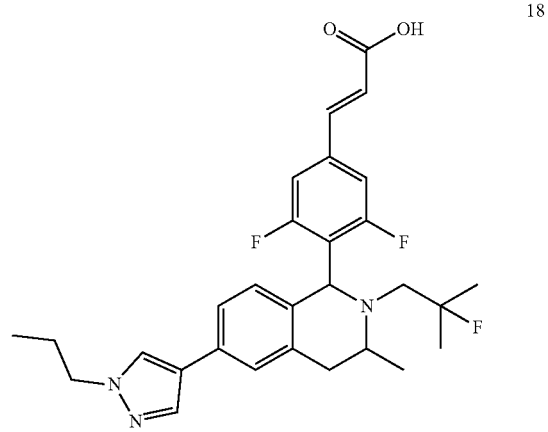

18

Step 1

(E)-methyl 3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-7-fluoro-2-(2-fluoro-2-methylpropyl)-3-methyl-6-(((trifluoromethyl)sulfonyl)oxy)-1,2,3,4-tetrahydroisoquinolin-1-yl)phenyl)acrylate 16g (300 mg, 0.514 mmol), 1-ethyl-4-(4,4,5,5-tetramethyl-1,3,2-dioxaborolan-2-yl)-1H-pyrazole 17a (228 mg, 1.028 mmol, prepared by a well-known method disclosed in "*Bioorganic & Medicinal Chemistry Letters,* 2008, 18(19), 5299-5302") and potassium carbonate (213 mg, 1.542 mmol) were dissolved in 12 mL of a mixture of 1,4-dioxane and water (V/V=5:1), [1,1'-bis(diphenylphosphino)ferrocene]dichloropalladium(II) (37 mg, 0.051 mmol) was added. The reaction was warmed up to 85° C. After stirring for 12 hours, the reaction was stopped. The reaction solution was cooled to room temperature and filtered. The filtrate was concentrated under reduced pressure to obtain the crude title compound (E)-methyl 3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylate 17b (250 mg) as a brown oil, which was used directly in next step without further purification.

MS m/z (ESI): 530.0 [M+1]

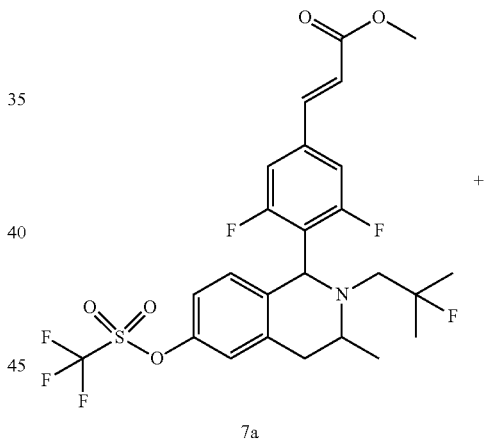

7a

Step 2

(E)-3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylic Acid The crude (E)-methyl 3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylate 17b (250 mg, 0.472 mmol) was dissolved in 10 mL of methanol, then 2 mL of 4 M sodium hydroxide solution was added. The reaction was cooled to room temperature and stirred 1 hour, then the reaction was stopped. After the reaction mixture was cooled to room temperature, 1M citric acid was added dropwise to adjust the pH to 5-6. The mixture was extracted with ethyl acetate. The organic phases were combined, dried over anhydrous sodium sulfate and filtered. The filtrate was concentrated under reduced pressure, and the residue was purified by high performance liquid chromatography to obtain the title compound (E)-3-(4-((1S,3R/1R,3S)-6-(1-ethyl-1H-pyrazol-4-yl)-7-fluoro-2-(2-fluoro-2-methylpropyl)-3-methyl-1,2,3,4-tetrahydroisoquinolin-1-yl)-3,5-difluorophenyl)acrylic acid 17 (30 mg, yield 13%) as a yellow solid.

MS m/z (ESI): 515.9 [M+1]

$^1$H NMR (400 MHz, CD$_3$OD) δ 8.06 (s, 1H), 7.91 (s, 1H), 7.61 (d, 1H), 7.53 (d, 1H), 7.32 (d, 2H), 6.68-6.58 (m, 2H), 5.58 (s, 1H), 4.22-4.24 (m, 2H), 3.86 (s, 1H), 3.37-3.34 (m, 1H), 3.32-3.30 (m, 1H), 2.86 (s, 2H), 1.51 (t, 3H), 1.34-1.22 (m, 9H).

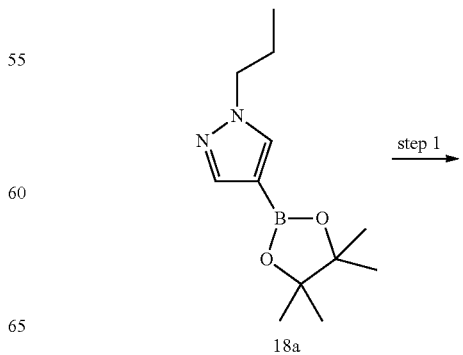

18a

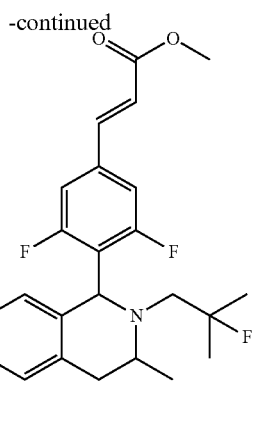

18b step 2

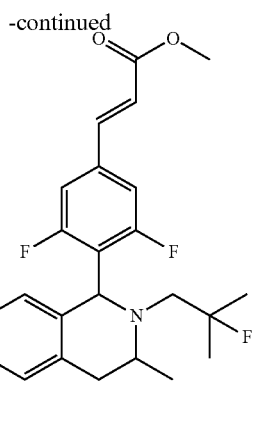

18

Step 1

(E)-methyl 3-(3,5-difluoro-4-((1S,3R/1R,3S)-2-(2-fluoro-2-methylpropyl)-3-methyl-6-(1-propyl-1H-pyrazol-4-yl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (200 mg, 0.35 mmol), 1-propyl-4-(4,4,5,5-tetramethyl-1,3,2-dioxaborolan-2-yl)-1H-pyrazole 18a (167 mg, 0.70 mmol, prepared by a well-known method disclosed in "*Journal of Heterocyclic Chemistry*, 41(6), 2004, 931-939") and potassium carbonate (145 mg, 1.05 mmol) were dissolved in 5 mL of a mixture of 1,4-dioxane and water (V/V=4:1), then [1,1'-bis(diphenylphosphino)ferrocene]dichloropalladium (II) (12.8 mg, 0.0175 mmol) was added. The reaction was warmed up to 90° C. After stirring for 12 hours, the reaction was stopped. The reaction solution was cooled to room temperature and filtered. The filtrate was concentrated under reduced pressure. The residue was purified by silica gel column chromatography with elution system B to obtain the title compound (E)-methyl 3-(3,5-difluoro-4-((1S,3R/1R,3S)-2-(2-fluoro-2-methylpropyl)-3-methyl-6-(1-propyl-1H-pyrazol-4-yl)-1,2,3,4-tetrahydroisoquinolin-1-yl)phenyl)acrylate 18b (128 mg, yield 69.9%) as an oily liquid.

Step 2

(E)-3-(3,5-difluoro-4-((1S,3R/1R,3S)-2-(2-fluoro-2-methylpropyl)-3-methyl-6-(1-propyl-1H-pyrazol-4-yl)-1,2,3,4-tetrahydroisoquinolin-1-yl)phenyl)acrylic Acid (E)-methyl 3-(3,5-difluoro-4-(2-(2-fluoro-2-methylpropyl)-3-methyl-6-(1-propyl-1H-pyrazol-4-yl)-1,2,3,4-tetrahydroisoquinolin-1-yl)phenyl)acrylate 18b (58 mg, 0.11 mmol) was dissolved in 10 mL of methanol, then 1 mL of 1 M sodium hydroxide solution was added. After stirring for 4 hours, the reaction was stopped. The reaction solution was concentrated under reduced pressure, and the residue was purified by silica gel column chromatography with elution system A to obtain the title compound (E)-3-(3,5-difluoro-4-((1S,3R/1R,3S)-2-(2-fluoro-2-methylpropyl)-3-methyl-6-(1-propyl-1H-pyrazol-4-yl)-1,2,3,4-tetrahydroisoquinolin-1-yl)phenyl)acrylic acid 18 (29 mg, yield 51.8%) as a yellow solid.

MS m/z (ESI): 510.5 [M−1]

$^1$H NMR (400 MHz, CD$_3$OD) δ 7.94 (s, 1H), 7.79 (s, 1H), 7.56 (d, 1H) 7.33 (s, 1H), 7.21 (t, 3H), 6.71 (d, 1H), 6.53 (d, 1H), 5.23 (s, 1H), 4.13 (t, 2H), 3.70-3.74 (m, 1H), 3.38-3.42 (dd, 1H), 3.01 (t, 1H), 2.69-2.64 (dd, 1H), 2.36-2.25 (m, 1H), 1.93-1.88 (m, 2H), 1.19-1.10 (dd, 6H), 1.03 (d, 3H), 0.94 (t, 3H).

Example 19

(E)-3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl)acrylic Acid

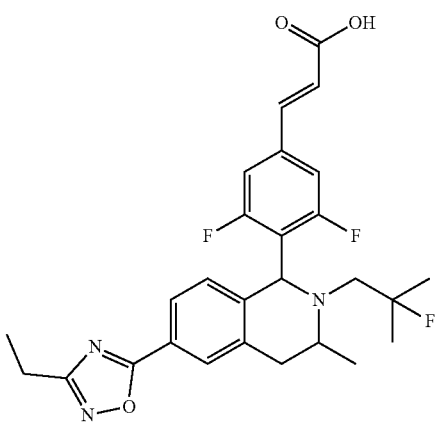

19

75

-continued

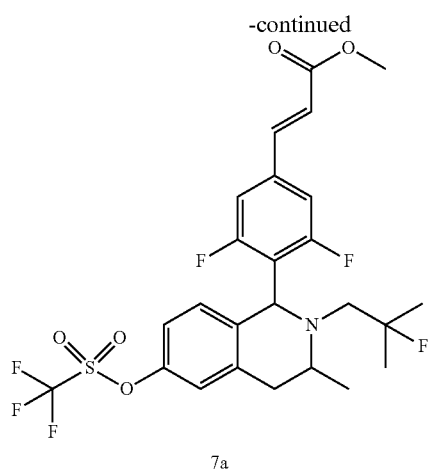

7a

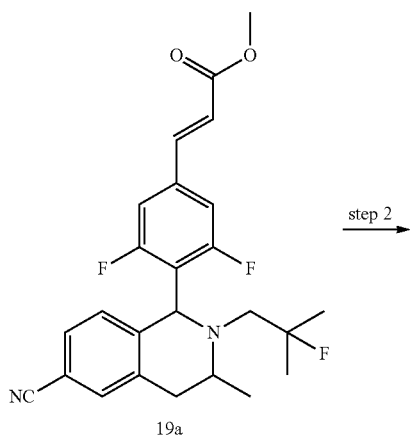

19a

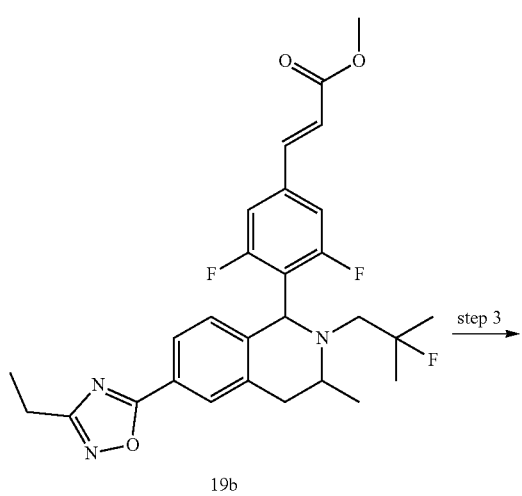

19b

76

-continued

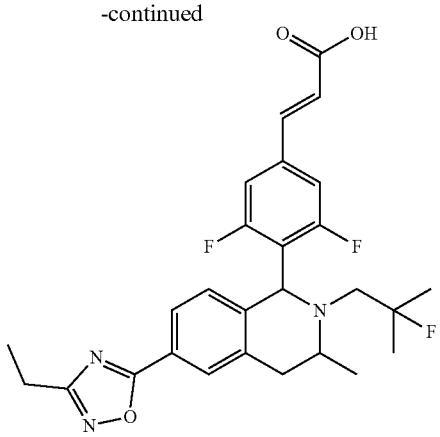

19

Step 1

(E)-methyl 3-(4-((1S,3R/1R,3S)-6-cyano-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (2 g, 3.54 mmol), zinc cyanide (0.41 g, 3.54 mmol), zinc powder (368 mg, 5.66 mmol) and [1,1'-bis(diphenylphosphino)ferrocene]dichloropalladium(II) (155 mg, 0.21 mmol) were dissolved in 65 mL of a mixture of of N,N-diethylacetamide and water (V/V=12:1). The reaction was warmed up to 120° C. After stirring for 12 hours, the reaction was stopped. The reaction solution was cooled to room temperature and filtered. Water was added, and the mixture was extracted with ethyl acetate (50 mL). The organic phases were combined, washed with water, dried over anhydrous sodium sulphate and filtered. The filtrate was concentrated under reduced pressure. The residue was purified by silica gel column chromatography with elution system B to obtain the title compound (E)-methyl 3-(4-((1S,3R/1R,3S)-6-cyano-2-(2-fluoro-2-methylpropyl)-3-methyl-1,2,3,4-tetrahydroisoquinolin-1-yl)-3,5-difluorophenyl)acrylate 19a (1.17 g, yield 75%) as a white solid.

Step 2

(E)-methyl 3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl)acrylate (E)-methyl 3-(4-((1S,3R/1R,3S)-6-cyano-2-(2-fluoro-2-methylpropyl)-3-methyl-1,2, 3,4-tetrahydroisoquinolin-1-yl)-3,5-difluorophenyl)acrylate 19a (200 mg, 0.45 mmol), N-hydroxypropionamidine (40 mg, 0.45 mmol), 0.15 mL of a solution of 1 M zinc chloride in diethyl ether, and p-toluenesulfonic acid hydrate (25.7 mg, 0.135 mmol) were successively added to 5 mL of N,N-dimethylformamide. The reaction was warmed up to 80° C. After stirring for 12 hours, the reaction was stopped. The reaction solution was cooled to room temperature and concentrated under reduced pressure. The residue was purified by silica gel column chromatography with elution system B to obtain the title compound (E)-methyl 3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl)acrylate 19b (210 mg, yield 90.5%) as a colorless oil.

MS m/z (ESI): 514.0 [M+1]

Step 3

(E)-3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl) acrylic Acid (E)-methyl 3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl)acrylate 19b (210 mg, 0.41 mmol) was dissolved in 5 mL of methanol, then 1 mL of 2M sodium hydroxide solution was added. After stirring for 12 hours, the reaction was stopped. The reaction solution was concentrated under reduced pressure, and hydrochloric acid was added dropwise to adjust the pH to 3. The mixture was extracted with ethyl acetate. The organic phases were combined, dried over anhydrous sodium sulfate and filtered. The filtrate was concentrated under reduced pressure, and the residue was purified by high performance liquid chromatography to obtain the title compound (E)-3-(4-((1S,3R/1R,3S)-6-(3-ethyl-1,2,4-oxadiazol-5-yl)-2-(2-fluoro-2-methylpropyl)-3-methyl-1,2,3,4-tetrahydroisoquinolin-1-yl)-3,5-difluorophenyl)acrylic acid 19 (20 mg, yield 10%) as a yellow solid.

MS m/z (ESI): 500.5 [M+1]

$^1$H NMR (400 MHz, DMSO-$d_6$): δ 12.04 (s, 1H), 7.91 (s, 1H), 7.78 (d, 1H), 7.53-7.46 (m, 3H), 6.99 (d, 1H), 6.68 (d, 1H), 5.23 (s, 1H), 3.61-3.56 (m, 1H), 2.93 (t, 1H), 2.76 (d, 1H), 2.55 (q, 2H), 2.27-2.17 (m, 2H), 1.11 (dd, 6H), 1.02 (t, 3H), 0.97 (d, 3H).

Example 20

(E)-3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl) acrylic Acid

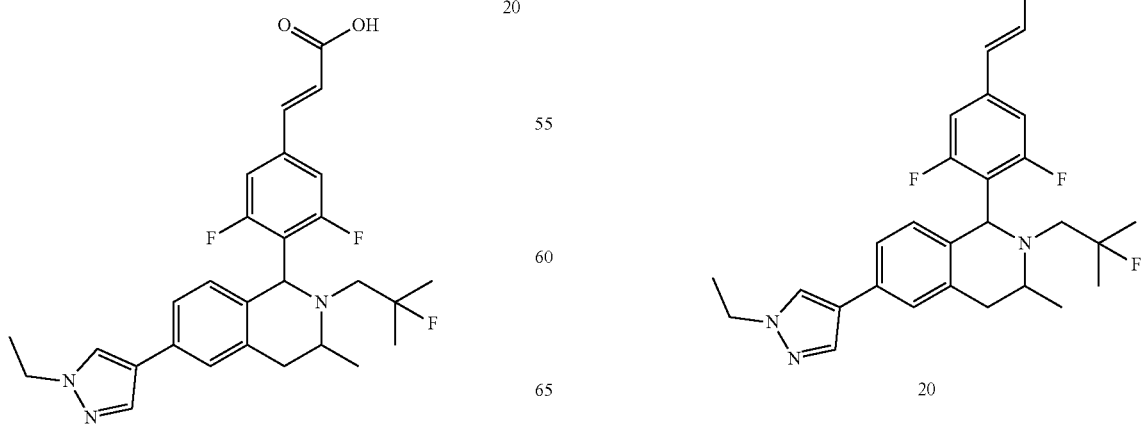

Step 1

(E)-methyl 3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (3.9 g, 6.896 mmol), 1-ethyl-4-(4,4,5,5-tetramethyl-1,3,2-dioxaborolan-2-yl)-1H-pyrazole 17a (3 g, 13.792 mmol) and potassium carbonate (2.86 g, 20.689 mmol) were dissolved in 60 mL of a mixture of 1,4-dioxane and water (V/V=5:1), then [1,1'-bis (diphenylphosphino)ferrocene]dichloropalladium(II) (503 mg, 0.689 mmol) was added. The reaction was warmed up to 80° C. After stirring for 12 hours, the reaction was stopped. The reaction solution was cooled to room temperature and filtered. The filtrate was extracted with ethyl acetate, and the organic phase was concentrated under reduced pressure. The residue was purified by silica gel column chromatography with elution system B to obtain the title compound (E)-methyl 3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylate 20a (3.2 g, yield 91%) as a yellow solid.

MS m/z (ESI): 512.0 [M+1]

Step 2

(E)-3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylic Acid (E)-methyl 3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylate 20a (3.2 g, 6.255 mmol) was dissolved in 30 mL of methanol, then 3 mL of 6 M sodium hydroxide solution was added. After stirring for 12 hours, the reaction was stopped. Then, 1M hydrochloric acid was added dropwise until the pH of the reaction solution was acidic. The mixture was extracted with ethyl acetate. The organic phase was washed with saturated sodium bicarbonate solution, dried over anhydrous sodium sulfate and filtered. The filtrate was concentrated under reduced pressure, and the residue was purified by silica gel column chromatography with elution system A to obtain the title compound (E)-3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylic acid 20 (1.5 g, yield 48%) as a yellow solid.

MS m/z (ESI): 498.5 [M+1]

$^1$H NMR (400 MHz, CD$_3$OD) δ 7.96 (s, 1H), 7.80 (s, 1H), 7.56 (d, 1H), 7.33 (s, 1H), 7.25-7.17 (m, 3H), 6.71 (d, 1H), 6.58-6.50 (m, 1H), 5.23 (s, 1H), 4.25-4.18 (m, 2H), 3.76-3.69 (m, 1H), 3.44-3.37 (m, 1H), 3.06-2.96 (m, 1H), 2.70-2.63 (m, 1H), 2.37-2.23 (m, 1H), 1.51-1.48 (m, 3H), 1.22-1.03 (m, 9H).

Examples 21, 22

(E)-3-(4-((1S,3R)-6-(1-ethyl-1H-pyrazol-4-yl)-2-(2-fluoro-2-methylpropyl)-3-methyl-1, 2,3,4-tetrahydroisoquinolin-1-yl)-3,5-difluorophenyl)acrylic Acid

(E)-3-(4-((1R,3S)-6-(1-ethyl-1H-pyrazol-4-yl)-2-(2-fluoro-2-methylpropyl)-3-methyl-1, 2,3,4-tetrahydroisoquinolin-1-yl)-3,5-difluorophenyl)acrylic Acid

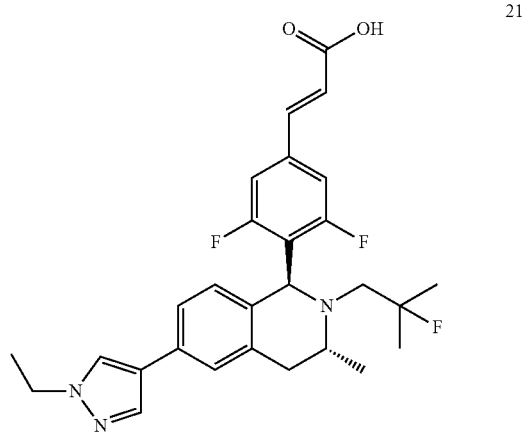

21

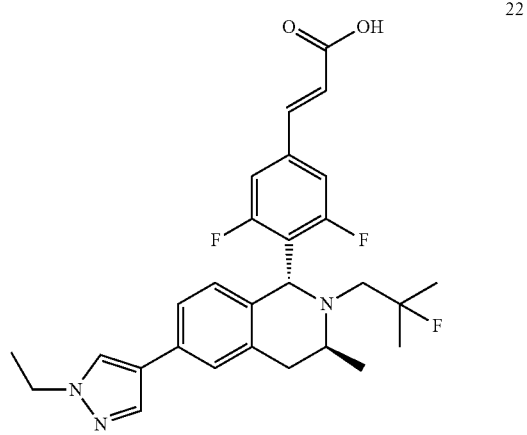

22

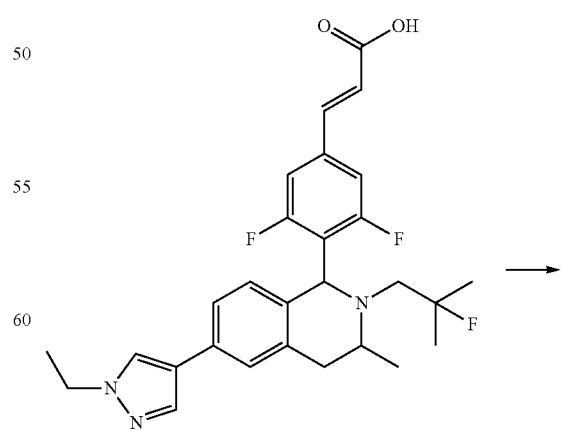

20

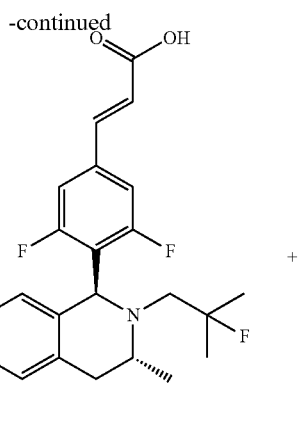

21

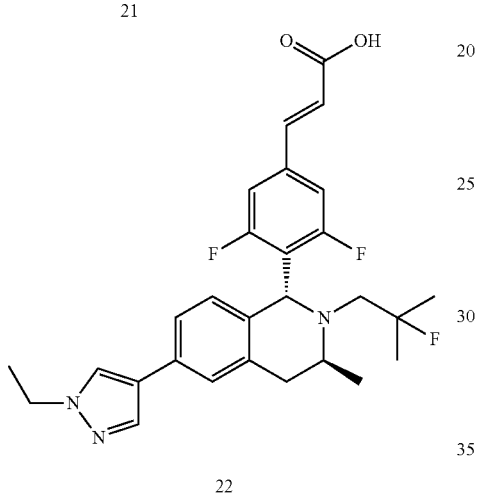

22

(E)-3-(4-((1S,3R/1R,3S)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylic acid 20 (1.5 g, 3.01 mmol) was separated chirally (separation conditions: chiral preparative column Superchiral S-AD (Chiralway), 2 cm I.D.*25 cm Length, 5 μm; mobile phase: carbon dioxide: ethanol:diethylamine=65:35:0.05, flow rate: 50 g/min). The corresponding fractions were collected and concentrated under reduced pressure to obtain the title compounds (E)-3-(4-((1S,3R)-6-(1-ethyl-1H-pyrazol-4-yl)-2-(2-fluoro-2-methylpropyl)-3-methyl-1,2,3,4-tetrahydroisoquinolin-1-yl)-3,5-difluorophenyl)acrylic acid 21 (650 mg, a yellow solid) and (E)-3-(4-((1R,3S)-6-(1-ethyl-1H-pyrazol-4-yl)-2-(2-fluoro-2-methylpropyl)-3-methyl-1, 2,3,4-tetrahydroisoquinolin-1-yl)-3,5-difluorophenyl)acrylic acid 22 (600 mg, a yellow solid).

Example 21

MS m/z (ESI): 498.0 [M+1];
Chiral HPLC analysis: retention time 5.292 minutes, chiral purity: 99.512% (chromatographic column: Superchiral S-AD, 0.46 cm I.D.×25 cm L; mobile phase: carbon dioxide/ethanol/diethylamine=65/35/0.05 (v/v/v));
$^1$H NMR (400 MHz, CD$_3$OD) δ 8.05 (s, 1H), 7.86 (s, 1H), 7.62 (d, 1H), 7.50 (s, 1H), 7.42-7.37 (m, 3H), 7.00 (s, 1H), 6.63 (d, 1H), 5.96 (s, 1H), 4.27-4.20 (m, 2H), 4.02 (s, 1H), 3.57 (s, 1H), 3.44-3.38 (dd, 1H), 3.06 (s, 2H), 1.52-1.32 (m, 12H).

Example 22

MS m/z (ESI): 498.6 [M+1];
Chiral HPLC analysis: retention time 4.568 minutes, chiral purity: 100% (chromatographic column: Superchiral S-AD, 0.46 cm I.D.×25 cm L; mobile phase: carbon dioxide/ethanol/diethylamine=65/35/0.05 (v/v/v));
$^1$H NMR (400 MHz, CD$_3$OD) δ 7.95 (s, 1H), 7.79 (s, 1H), 7.58 (d, 1H), 7.33 (s, 1H), 7.24-7.19 (m, 3H), 6.70 (d, 1H), 6.53 (d, 1H), 5.23 (s, 1H), 4.21 (q, 2H), 3.71 (s, 1H), 3.40 (dd, 1H), 3.01 (t, 1H), 2.65 (d, 1H), 2.30 (q, 1H), 1.50 (t, 3H), 1.02-1.19 (m, 9H).

Example 23

(E)-3-(3,5-difluoro-4-((1S,3R/1R,3S)-2-(2-fluoro-2-methylpropyl)-6-(1-(2-hydroxyethyl)-1H-pyrazol-4-yl)-3-methyl-1,2,3,4-tetrahydroisoquinolin-1-yl)phenyl)acrylic Acid

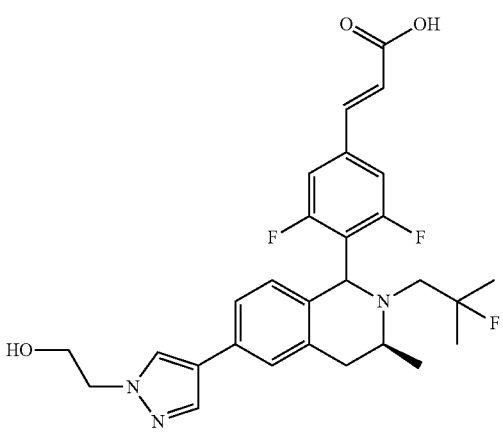

23

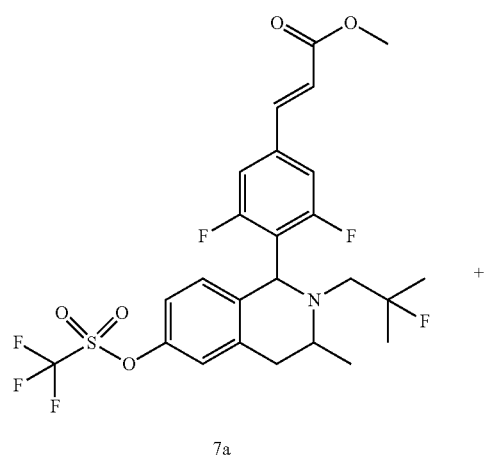

7a

-continued

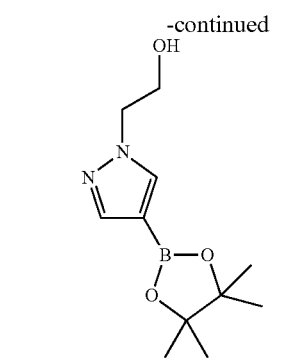

23a

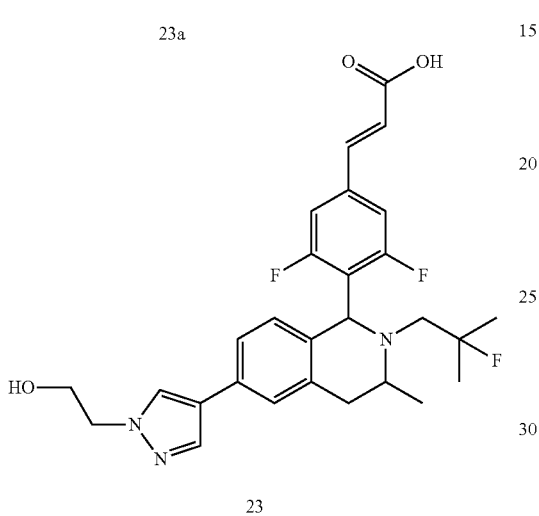

23

(E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (60 mg, 0.106 mmol), 2-(4-(4,4,5,5-tetramethyl-1,3,2-dioxaborolan-2-yl)-1H-pyrazol-1-yl)ethanol 23a (38 mg, 0.16 mmol, prepared by a well-known method disclosed in "Bioorganic & Medicinal Chemistry, 2013, 21(21), 6804-6820") and potassium carbonate (36.6 mg, 0.265 mmol) were dissolved in 3.5 mL of a mixture of 1,4-dioxane and water (V/V=6:1), then [1,1'-bis(diphenylphosphino)ferrocene]dichloropalladium(II) (7.8 mg, 0.0106 mmol) was added. The reaction was warmed up to 80° C. After stirring for 18 hours, the reaction was stopped. The reaction solution was cooled to room temperature. Ethyl acetate was added, and the mixture was washed with water. The organic phase was dried over anhydrous sodium sulfate and filtered. The filtrate was concentrated under reduced pressure. The residue was purified by thin-layer chromatography with elution system A to obtain the title compound (E)-3-(3,5-difluoro-4-((1S,3R/1R,3S)-2-(2-fluoro-2-methylpropyl)-6-(1-(2-hydroxyethyl)-1H-pyrazol-4-yl)-3-methyl-1,2,3,4-tetrahydroisoquinolin-1-yl)phenyl)acrylic acid 23 (9 mg, yield 20%) as a yellow solid.

MS m/z (ESI): 514.5 [M+1]

$^1$H NMR (400 MHz, CD$_3$OD) δ 7.96 (s, 1H), 7.80 (s, 1H), 7.56 (d, 1H), 7.33 (s, 1H), 7.25-7.17 (m, 3H), 6.71 (d, 1H), 6.50-6.58 (m, 1H), 5.23 (s, 1H), 4.02 (t, 2H), 3.72-3.62 (m, 2H), 3.76-3.69 (m, 1H), 3.44-3.37 (m, 1H), 3.06-2.96 (m, 1H), 2.70-2.63 (m, 1H), 2.37-2.23 (m, 1H), 1.22-1.03 (m, 9H).

Example 24

(E)-3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylic Acid

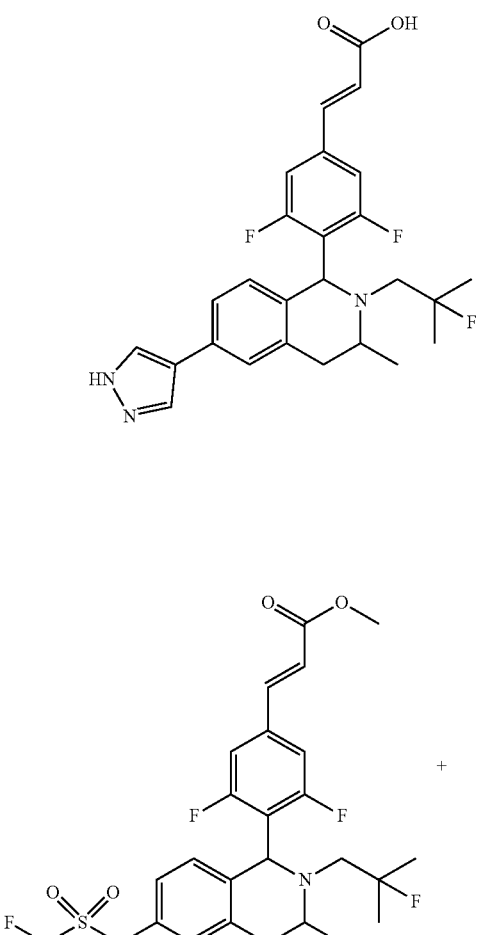

24

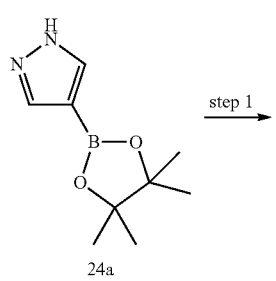

24a step 1

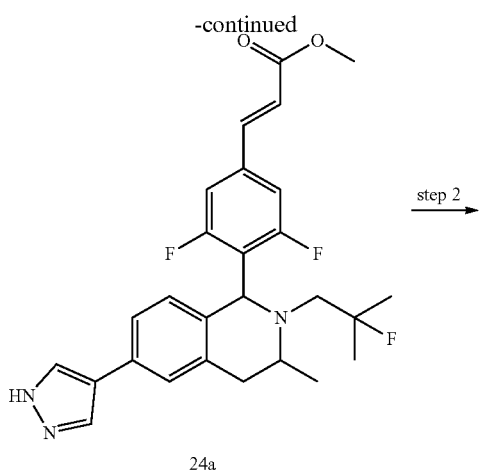

24a

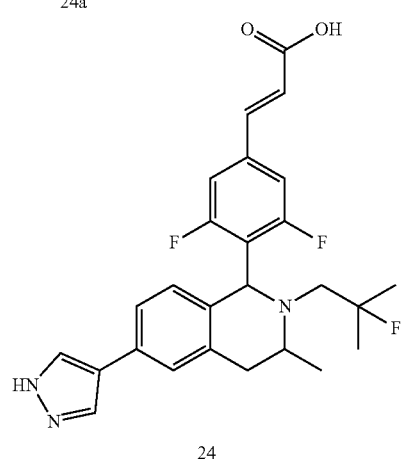

24

Step 1

(E)-methyl 3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (100 mg, 0.177 mmol), 4-(4,4,5,5-tetramethyl-1,3,2-dioxaborolan-2-yl)-1H-pyrazole 24a (75 mg, 0.265 mmol, prepared by a well-known method disclosed in "*Journal of the American Chemical Society*, 2014, 136(11), 4287-4299") and potassium carbonate (73 mg, 0.531 mmol) were dissolved in 20 mL of a mixture of 1,4-dioxane and water (V/V=9:1), then [1,1'-bis(diphenylphosphino)ferrocene]dichloropalladium(II) (12.9 mg, 0.0177 mmol) was added. The reaction was warmed up to 95° C. After stirring for 22 hours, the reaction was stopped. The reaction solution was cooled to room temperature. Water was added, and the mixture was extracted with ethyl acetate. The organic phases were combined, dried over anhydrous sodium sulfate, and filtered. The filtrate was concentrated under reduced pressure. The residue was purified by thin-layer chromatography with elution system A to obtain the title compound (E)-methyl 3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylate 24b (31 mg, yield 36%) as a yellow solid.

Step 2

(E)-3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylate 24b (30 mg, 0.062 mmol) was dissolved in 3 mL of ethanol, then 2 mL of 1 M sodium hydroxide solution was added. After stirring for 2 hours, the reaction was stopped. A solution of 10% citric acid was added dropwise to adjust the pH to 6-7. The mixture was extracted with ethyl acetate. The organic phase was washed with saturated sodium bicarbonate solution, dried over anhydrous sodium sulfate and filtered. The filtrate was concentrated under reduced pressure, and the residue was purified by thin-layer chromatography with elution system A to obtain the title compound (E)-3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylic acid 24 (5 mg, yield 16.6%) as a yellow solid.

MS m/z (ESI): 470.4 [M+1]

$^1$H NMR (400 MHz, CD$_3$OD) δ 8.04 (s, 2H), 7.63 (d, 1H), 7.58 (br, 1H), 7.51-7.41 (m, 3H), 7.08 (d, 1H), 6.65 (d, 1H), 6.14-6.09 (m, 1H), 4.12-4.06 (m, 1H), 3.77-3.68 (m, 1H), 3.46-3.40 (m, 1H), 3.20-3.13 (m, 2H), 1.61-1.49 (m, 9H).

Examples 25, 26

(E)-3-(3,5-difluoro-4-((1S,3R)-2-(2-fluoro-2-methylpropyl)-3-methyl-6-(1H-pyrazol-4-yl)-1,2,3,4-tetrahydroisoquinolin-1-yl)phenyl)acrylic Acid (E)-3-(3,5-difluoro-4-((1R,3S)-2-(2-fluoro-2-methylpropyl)-3-methyl-6-(1H-pyrazol-4-yl)-1,2,3,4-tetrahydroisoquinolin-1-yl)phenyl)acrylic Acid

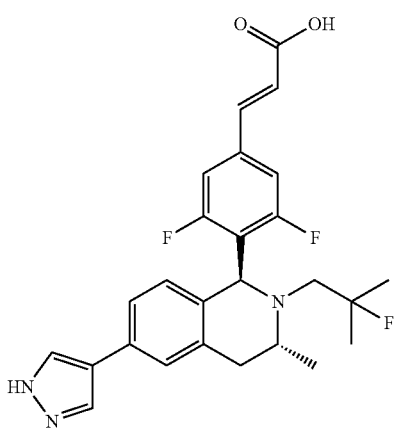

25

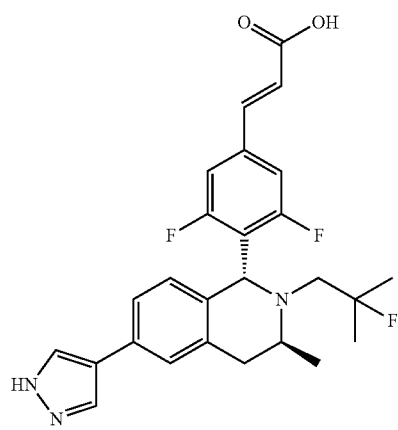

26

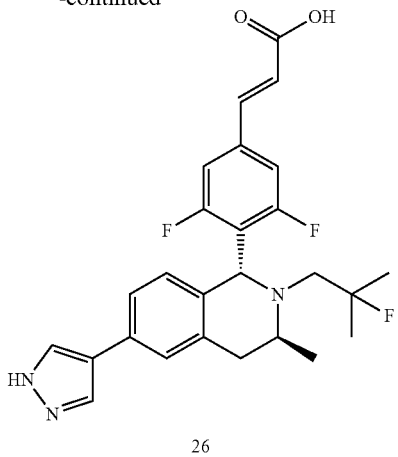

26

(E)-3-(3,5-difluoro-4-((1S,3R/1R,3S)-2-(2-fluoro-2-methylpropyl)-3-methyl-6-(1H-pyrazol-4-yl)-1,2,3,4-tetrahydroisoquinolin-1-yl)phenyl)acrylic acid 24 (860 mg, 1.83 mmol) was separated chirally (separation conditions: chiral preparative column CHIRALPAK IE, 5.0 cm I.D.×25 cm L; mobile phase: n-hexane:ethanol:trifluoroacetic acid=70:30:0.1, flow rate: 60 mL/min). The corresponding fractions were collected and concentrated under reduced pressure to obtain the title compounds (E)-3-(3,5-difluoro-4-((1S,3R)-2-(2-fluoro-2-methylpropyl)-3-methyl-6-(1H-pyrazol-4-yl)-1,2,3,4-tetrahydroisoquinolin-1-yl)phenyl)acrylic acid 25 (250 mg, a yellow solid) and (E)-3-(3,5-difluoro-4-((1R,3S)-2-(2-fluoro-2-methylpropyl)-3-methyl-6-(1H-pyrazol-4-yl)-1,2,3,4-tetrahydroisoquinolin-1-yl)phenyl)acrylic acid 26 (240 mg, a yellow solid).

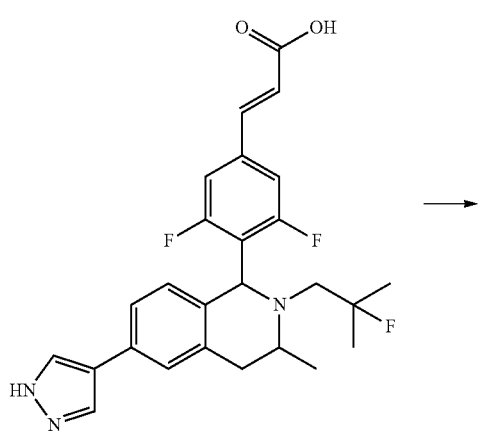

24

→

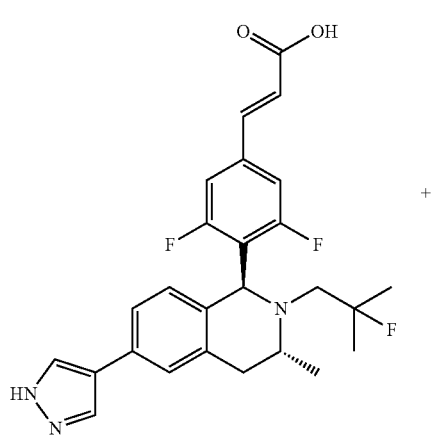

25

+

Example 25

MS m/z (ESI): 470.4 [M+1];

Chiral HPLC analysis: retention time 4.266 minutes, chiral purity: 99.767% (chromatographic column: CHIRALPAK IE, 0.46 cm I.D.×15 cm L; mobile phase: n-hexane/ethanol/trifluoroacetic acid=70/30/0.1 (V/V/V));

$^1$H NMR (400 MHz, CD$_3$OD) δ 8.04 (s, 2H), 7.63 (d, 1H), 7.58 (br, 1H), 7.51-7.41 (m, 3H), 7.08 (d, 1H), 6.65 (d, 1H), 6.14-6.09 (m, 1H), 4.12-4.06 (m, 1H), 3.77-3.68 (m, 1H), 3.46-3.40 (m, 1H), 3.20-3.13 (m, 2H), 1.61-1.49 (m, 9H).

Example 26

MS m/z (ESI): 470.4 [M+1];

Chiral HPLC analysis: retention time 3.138 minutes, chiral purity: 96.048% (chromatographic column: CHIRALPAK IE, 0.46 cm I.D.×15 cm L; mobile phase: n-hexane/ethanol/trifluoroacetic acid=70/30/0.1 (V/V/V));

$^1$H NMR (400 MHz, CD$_3$OD) δ 8.04 (s, 2H), 7.63 (d, 1H), 7.58 (br, 1H), 7.51-7.41 (m, 3H), 7.08 (d, 1H), 6.65 (d, 1H), 6.14-6.09 (m, 1H), 4.12-4.06 (m, 1H), 3.77-3.68 (m, 1H), 3.46-3.40 (m, 1H), 3.20-3.13 (m, 2H), 1.61-1.49 (m, 9H).

Example 27

(E)-3-(4-((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylic Acid

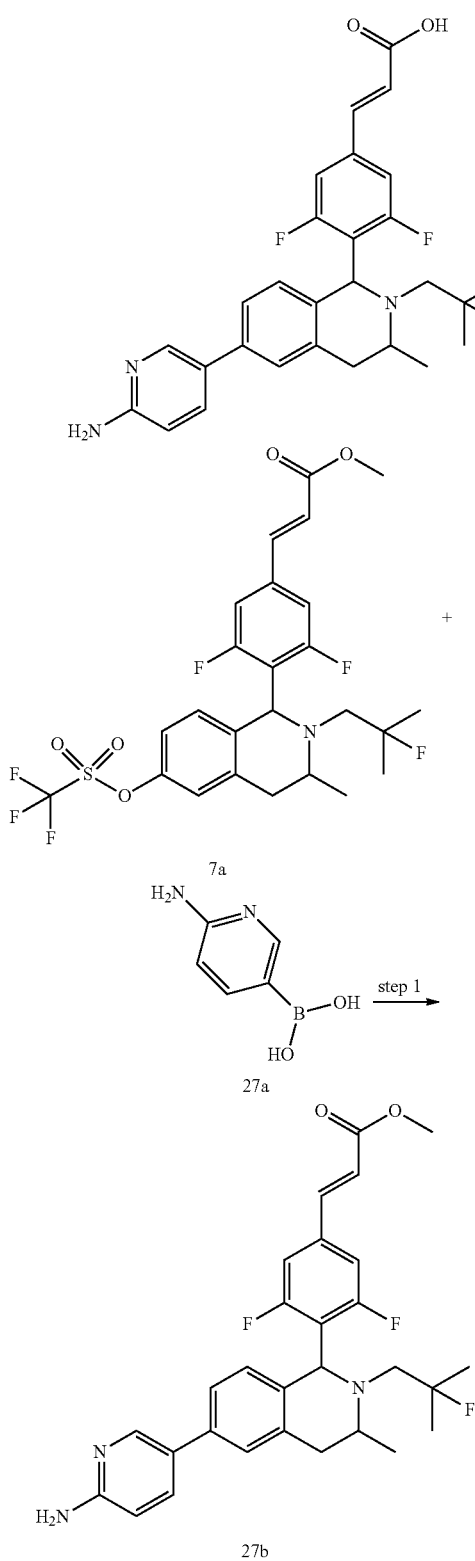

Step 1

(E)-methyl 3-(4-((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylate

(E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (100 mg, 0.177 mmol), (6-aminopyridin-3-yl)boronic acid 27a (36.6 mg, 0.265 mmol, prepared by a method disclosed in the patent application "WO2014180735") and potassium carbonate (73.4 mg, 0.531 mmol) were dissolved in 3.5 mL of a mixture of 1,4-dioxane and water (V/V=6:1), then [1,1'-bis(diphenylphosphino)ferrocene]dichloropalladium(II) (6.5 mg, 0.00885 mmol) was added. The reaction was warmed up to 80° C. After stirring for 18 hours, the reaction was stopped. The reaction solution was cooled to room temperature. Ethyl acetate was added, and the mixture was washed with water. The organic phase was dried over anhydrous sodium sulfate and filtered. The filtrate was concentrated under reduced pressure. The residue was purified by thin-layer chromatography with elution system A to obtain the title compound (E)-methyl 3-(4-((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylate 27b (20 mg, yield 22%) as a yellow solid.

Step 2

(E)-3-(4-((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylic Acid

(E)-methyl 3-(4-((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylate 27b (15 mg, 0.029 mmol) was dissolved in 3 mL of ethanol, then 0.15 mL of 1 M lithium hydroxide solution was added. After stirring for 3 hours, the reaction was stopped. 10% citric acid was added dropwise until the pH of the reaction solution was neutral. The mixture was extracted with ethyl acetate. The organic phase was dried over anhydrous sodium sulfate and filtered. The filtrate was concentrated under reduced pressure, and the residue was purified by thin-layer chromatography with elution system A to obtain the title compound (E)-3-(4-(((1S,3R/1R,3S)-6-(6-aminopyridin-3-yl)-2-(2-fluoro-2-methylpropyl)-3-methyl-1,2,3,4-tetrahydroisoquinolin-1-yl)-3,5-difluorophenyl)acrylic acid 27 (9 mg, yield 62%) as a yellow solid.

MS m/z (ESI): 496.5[M+1]

¹H NMR (400 MHz, CD₃OD) δ 8.44 (s, 1H), 8.20-8.17 (□m, 1H), 7.55 (d, 1H), 7.44 (s, 1H), 7.33 (d, 1H), 7.21 (d, 2H), 7.16-7.14 (m, 1H), 6.87 (d, 1H), 6.58-6.54 (m, 1H), 5.29 (s, 1H), 3.78-3.75 (m, 1H), 3.47-3.43 (m, 1H), 3.07-2.99 (m, 1H), 2.77-2.73 (m, 1H), 2.38-2.27 (s, 1H), 1.20-1.20 (m, 9H).

Example 28

(E)-3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylic Acid

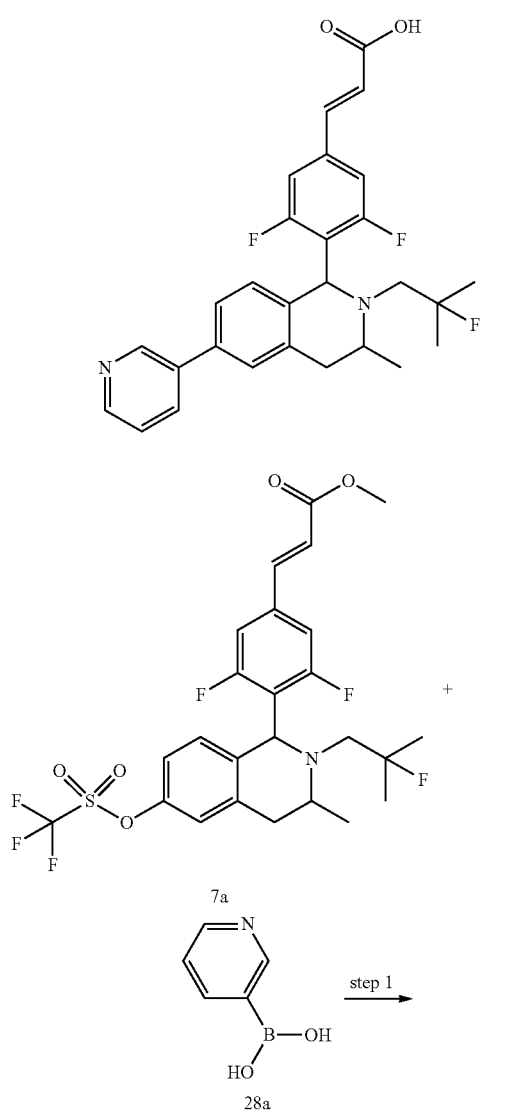

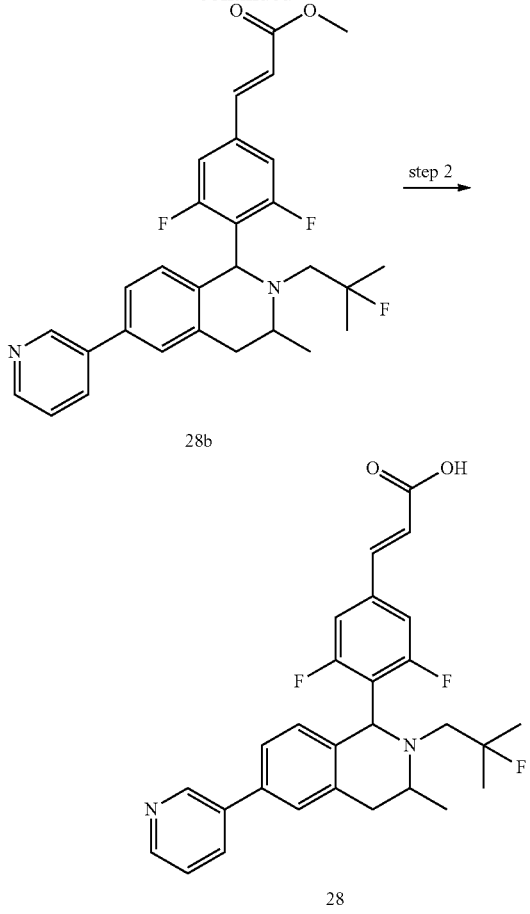

Step 1

(E)-methyl 3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (100 mg, 0.177 mmol), pyridin-3-ylboronic acid 28a (28 mg, 0.23 mmol, prepared by a well-known method disclosed in "*Tetrahedron Letters,* 2002, 43(23), 4285-4287") and potassium carbonate (74 mg, 0.531 mmol) were dissolved in 3.5 mL of a mixture of 1,4-dioxane and water (V/V=6:1), then [1,1'-bis(diphenylphosphino)ferrocene]dichloropalladium(II) (6.5 mg, 0.00885 mmol) was added. The reaction was warmed up to 80° C. After stirring for 18 hours, the reaction was stopped. The reaction solution was cooled to room temperature. Ethyl acetate was added, and the mixture was washed with water. The organic phase was dried over anhydrous sodium sulfate and filtered. The filtrate was concentrated under reduced pressure. The residue was purified by thin-layer chromatography with elution system A to obtain the title compound (E)-methyl 3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylate 28b (25 mg, yield 28.5%) as a yellow solid.

93

Step 2

(E)-3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylate 28b (50 mg, 0.1 mmol) was dissolved in 2.5 mL of ethanol, then 0.5 mL of 1 M lithium hydroxide solution was added. After stirring for 2 hours, the reaction was stopped. 10% citric acid was added dropwise until the pH of the reaction solution was neutral. The mixture was extracted with ethyl acetate. The organic phase was dried over anhydrous sodium sulfate and filtered. The filtrate was concentrated under reduced pressure, and the residue was purified by thin-layer chromatography with elution system A to obtain the title compound (E)-3-(3,5-difluoro-4-((1S,3R/1R,3S)-2-(2-fluoro-2-methylpropyl)-3-methyl-6-(pyridin-3-yl)-1,2,3,4-tetrahydroisoquinolin-1-yl)phenyl)acrylic acid 28 (16.9 mg, yield 35%) as a yellow solid.

MS m/z (ESI): 481.5 [M+1]

$^1$H NMR (400 MHz, CD$_3$OD) δ 8.80 (s, 1H), 8.51 (d, 1H), 8.10 (d, 1H), 7.60-7.48 (m, 3H), 7.37 (m, 1H), 7.23 (d, 2H), 6.68 (d, 1H), 6.55 (d, 1H), 5.30 (s, 1H), 3.79-3.75 (m, 1H), 3.49-3.44 (m, 1H), 3.07-3.00 (m, 1H), 2.77-2.74 (m, 1H), 2.38-2.27 (m, 1H), 1.20-1.05 (m, 9H)

Example 29

(E)-3-(3,5-difluoro-4-((1S,3R/1R,3S)-2-(2-fluoro-2-methylpropyl)-3-methyl-6-(3-methylureido)-1,2,3,4-tetrahydroisoquinolin-1-yl)phenyl)acrylic Acid

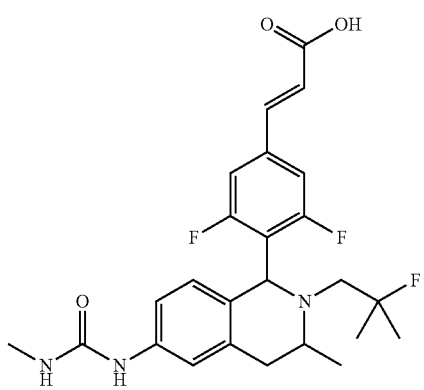

In accordance with the synthetic route of Example 10, the starting material 2-methyl-5-(4,4,5,5-tetramethyl-1,3,2-dioxaborolan-2-yl)thiazole 10b used in step 2 was replaced with 1-methylurea, accordingly, the title compound (E)-3-(3,5-difluoro-4-((1S,3R/1R,3S)-2-(2-fluoro-2-methylpropyl)-3-methyl-6-(3-methylureido)-1,2,3,4-tetrahydroisoquinolin-1-yl)phenyl)acrylic acid 29 was prepared.

MS m/z (ESI): 476.5 [M+1]

$^1$H NMR (400 MHz, CD$_3$OD) δ 7.58-7.54 (d, 1H), 7.39-7.35 (m, 1H), 7.23-7.17 (m, 3H), 6.61-6.51 (m, 2H), 5.18 (s, 1H), 3.69 (s, 1H), 3.50-3.33 (m, 1H), 3.03-2.95 (m, 1H), 2.77 (s, 3H), 2.59-2.56 (m, 1H), 2.34-2.23 (m, 1H), 1.18-0.92 (m, 9H).

94

Example 30

(E)-3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylic Acid

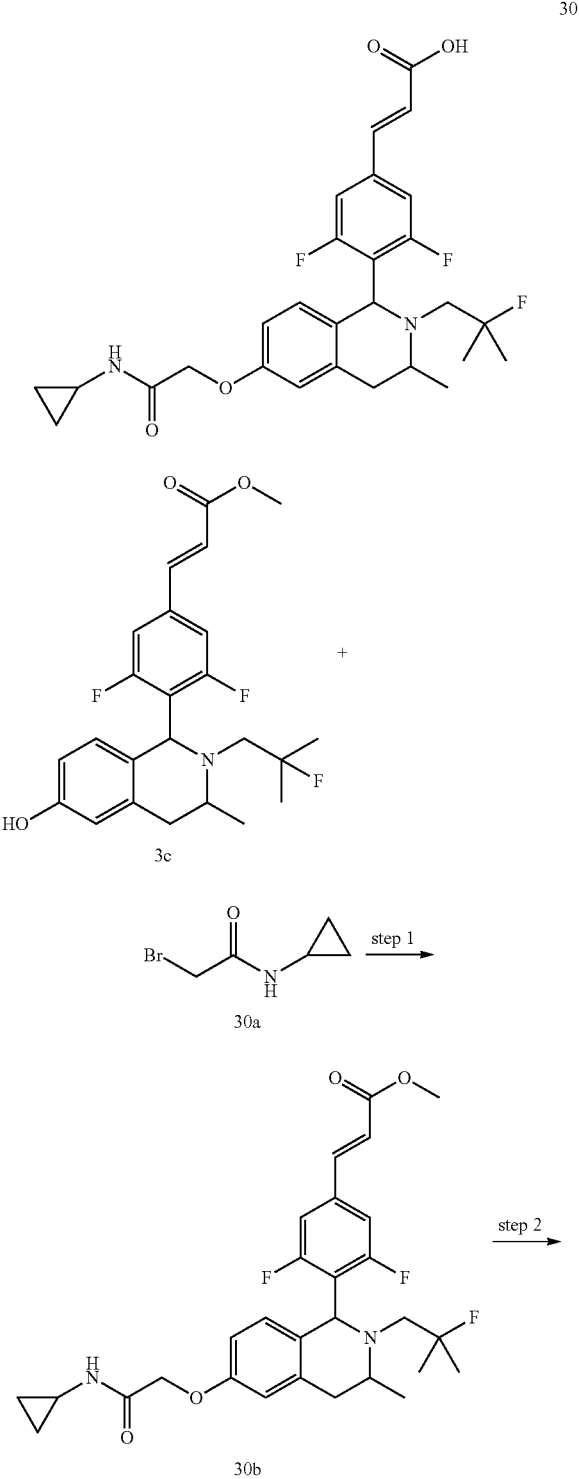

-continued

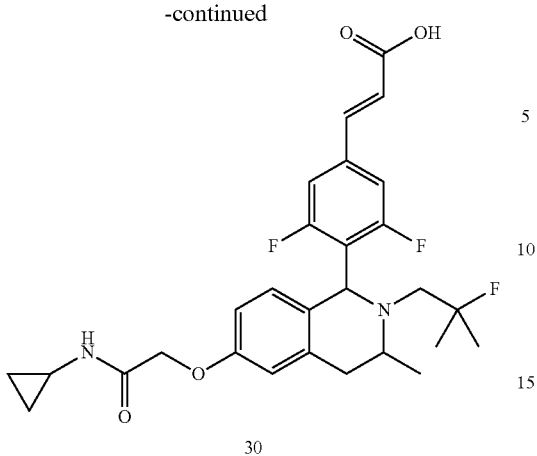

30

Step 1

(E)-methyl 3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (173 mg, 0.4 mmol) and 2-bromo-N-cyclopropylacetamide 30a (107 mg, 0.6 mmol, prepared by a well-known method disclosed in "*Organic & Biomolecular Chemistry*, 2014, 12(44), 8952-8965") were dissolved in 3 mL of N,N-dimethylformamide, then potassium carbonate (110 mg, 0.8 mmol) was added. The reaction was warmed up to 90° C. and stirred for 12 hours. After cooling to room temperature, the reaction solution was concentrated under reduced pressure. The resulting residue was purified by thin-layer chromatography with elution system B to obtain the title compound (E)-methyl 3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylate 30b (12 mg, yield 5.6%) as a light yellow solid.

Step 2

(E)-3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylic Acid (E)-methyl 3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylate 30b (12 mg, 0.023 mmol) was dissolved in 2.5 mL of a mixture of methanol and tetrahydrofuran (V/V=1:4), then 0.04 mL of 6 M sodium hydroxide solution was added. The reaction was stirred for 12 hours at room temperature. 1M hydrochloric acid was added dropwise to adjust the pH to 5-6. The mixture was extracted with ethyl acetate (5 mL×3). The organic phases were combined, dried over anhydrous sodium sulfate, and filtered. The filtrate was concentrated under reduced pressure, and the resulting residue was purified by thin-layer chromatography with elution system A to obtain the title compound (E)-3-(4-((1S,3R/1R,3S)-6-(2-(cyclopropylamino)-2-oxoethoxy)-2-(2-fluoro-2-methylpropyl)-3-methyl-1,2,3,4-tetrahydroisoquinolin-1-yl)-3,5-difluorophenyl)acrylic acid 30 (8 mg, yield 67.2%) as a light yellow solid.

MS m/z (ESI): 517.5 [M+1]

$^1$H NMR (400 MHz, CD$_3$OD) δ 7.35 (d, 1H), 7.10 (d, 2H), 6.74 (s, 1H), 6.67-6.64 (m, 2H), 6.52 (d, 1H), 5.51 (s, 1H), 5.16 (s, 1H), 4.45 (s, 2H), 3.69 (s, 1H), 3.37 (s, 1H), 2.98 (t, 1H), 2.73 (s, 1H), 2.59 (d, 1H), 2.33-2.21 (m, 1H), 1.17-1.12 (m, 6H), 1.06 (d, 3H), 0.75 (d, 2H), 0.56 (d, 2H).

Example 31

(E)-3-(4-((1S,3R/1R,3S)-6-((tert-butoxycarbonyl)amino)-2-(2-fluoro-2-methylpropyl)-3-methyl-1,2,3,4-tetrahydroisoquinolin-1-yl)-3,5-difluorophenyl)acrylic Acid

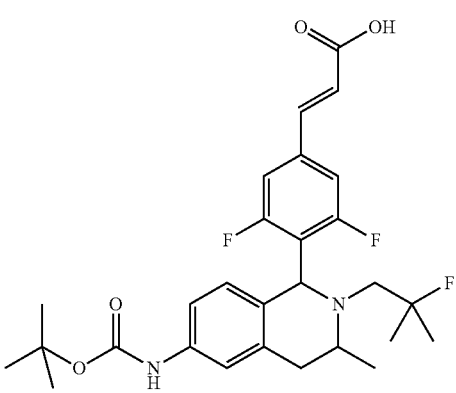

31

In accordance with the synthetic route of Example 10, the starting material 2-methyl-5-(4,4,5,5-tetramethyl-1,3,2-dioxaborolan-2-yl)thiazole 10b used in step 2 was replaced with tert-butyl carbamate, accordingly, the title compound (E)-3-(4-((1S,3R/1R,3S)-6-((tert-butoxycarbonyl)amino)-2-(2-fluoro-2-methylpropyl)-3-methyl-1,2,3,4-tetrahydroisoquinolin-1-yl)-3,5-difluorophenyl)acrylic acid 31 was prepared.

MS m/z (ESI): 519.6 [M+1]

$^1$H NMR (400 MHz, CD$_3$OD) δ 7.60-7.56 (d, 1H), 7.27-7.18 (m, 3H), 7.07-7.05 (m, 1H), 6.62-6.51 (m, 2H), 5.18 (s, 1H), 3.70 (s, 1H), 3.37-3.36 (m, 1H), 3.03-2.95 (m, 1H), 2.60-2.55 (m, 1H), 2.33-2.21 (m, 1H), 1.38 (s, 9H), 1.18-0.92 (m, 9H).

Example 32

(E)-3-(3,5-difluoro-4-((1S,3R/1R,3S)-2-(2-fluoro-2-methylpropyl)-3-methyl-6-(2-(methylamino)-2-oxoethoxy)-1,2,3,4-tetrahydroisoquinolin-1-yl)phenyl)acrylic Acid

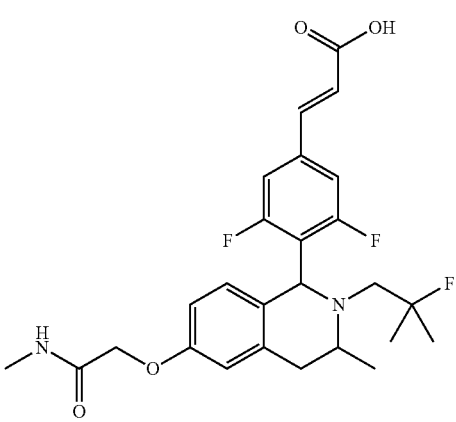

32

In accordance with the synthetic route of Example 30, the starting material 2-bromo-N-cyclopropylacetamide 30a used in step 1 was replaced with 2-bromo-N-methylacetamide that was prepared by a well-known method disclosed in "*Bioorganic & Medicinal Chemistry*, 2011, 19(3), 1106-1114", accordingly, the title compound (E)-3-(3,5-difluoro-4-((1S,3R/1R,3S)-2-(2-fluoro-2-methylpropyl)-3-methyl-6-(2-(methylamino)-2-oxoethoxy)-1,2,3,4-tetrahydroisoquinolin-1-yl)phenyl)acrylic acid 32 was prepared.

MS m/z (ESI): 491.5 [M+1]

$^1$H NMR (400 MHz, CD$_3$OD) δ 7.54 (d, 1H), 7.17 (d, 2H), 6.77 (s, 1H), 6.68-6.63 (m, 2H), 6.53 (d, 1H), 5.18 (s, 1H), 4.47 (s, 2H), 3.69 (s, 1H), 3.38 (s, 1H), 2.98 (t, 1H), 2.80 (s, 3H), 2.60 (s, 1H), 2.40-2.20 (m, 1H), 1.18-1.09 (m, 6H), 1.00 (d, 3H).

Example 33

(E)-3-(4-((1S,3R/1R,3S)-6-(cyanomethoxy)-2-(2-fluoro-2-methylpropyl)-3-methyl-1,2,3,4-tetrahydroisoquinolin-1-yl)-3,5-difluorophenyl)acrylic Acid

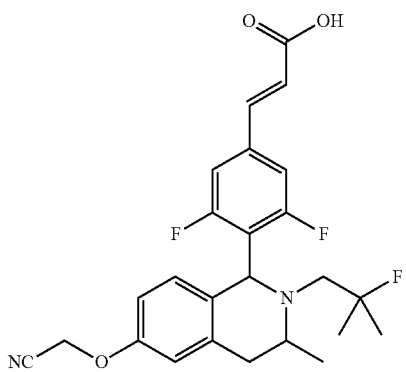

33

In accordance with the synthetic route of Example 30, the starting material 2-bromo-N-cyclopropylacetamide 30a used in step 1 was replaced with 2-bromoacetonitrile, accordingly, the title compound (E)-3-(4-((1S,3R/1R,3S)-6-(cyanomethoxy)-2-(2-fluoro-2-methylpropyl)-3-methyl-1,2,3,4-tetrahydroisoquinolin-1-yl)-3,5-difluorophenyl)acrylic acid 33 was prepared.

MS m/z (ESI): 459.5 [M+1]

$^1$H NMR (400 MHz, CD$_3$OD) δ 7.64-7.60 (d, 1H), 7.35 (s, 2H), 6.99-6.93 (m, 3H), 6.64-6.60 (d, 1H), 6.00-5.89 (m, 1H), 5.02 (s, 2H), 4.11 (s, 1H), 3.41-3.37 (m, 2H), 3.18-2.88 (m, 2H), 1.49-1.31 (m, 9H).

Example 34

(E)-3-(4-((1S,3R/1R,3S)-6-cyclopropyl-2-(2-fluoro-2-methylpropyl)-3-methyl-1,2,3,4-tetrahydroisoquinolin-1-yl)-3,5-difluorophenyl)acrylic Acid

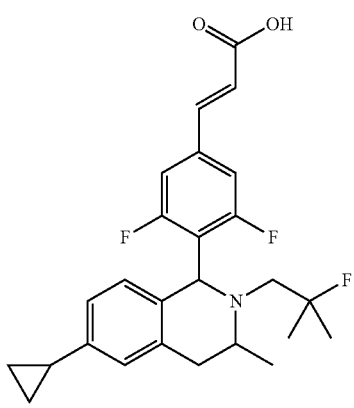

34

In accordance with the synthetic route of Example 10, the staring material 2-methyl-5-(4,4,5,5-tetramethyl-1,3,2-dioxaborolan-2-yl)thiazole 10b used in step 2 was replaced with cyclopropylborate, accordingly, the title compound (E)-3-(4-((1S,3R/1R,3S)-6-cyclopropyl-2-(2-fluoro-2-methylpropyl)-3-methyl-1,2,3,4-tetrahydroisoquinolin-1-yl)-3,5-difluorophenyl)acrylic acid 34 was prepared.

MS m/z (ESI): 444.4 [M+1]

$^1$H NMR (400 MHz, CD$_3$OD) δ 7.60-7.55 (m, 2H), 7.40 (d, 1H), 7.23 (d, 2H), 6.93 (d, 1H), 6.56 (d, 1H), 5.30 (s, 1H), 3.78-3.70 (m, 1H), 3.67-3.41 (m, 1H), 3.04-2.96 (m, 1H), 2.75-2.70 (m, 1H), 2.36-2.25 (m, 1H), 1.52-1.48 (m, 1H), 1.33-1.01 (m, 13H).

Example 35

(E)-3-(4-((1R,3R/1S,3S)-2-(2-fluoro-2-methylpropyl)-7,8-dimethoxy-3-methyl-1,2,3,4-tetrahydroisoquinolin-1-yl)phenyl)acrylic Acid

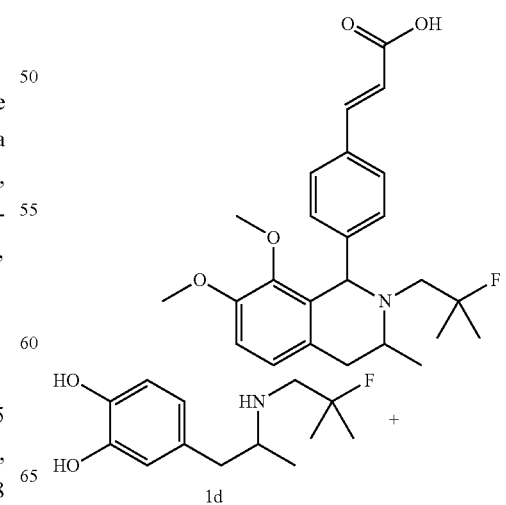

35

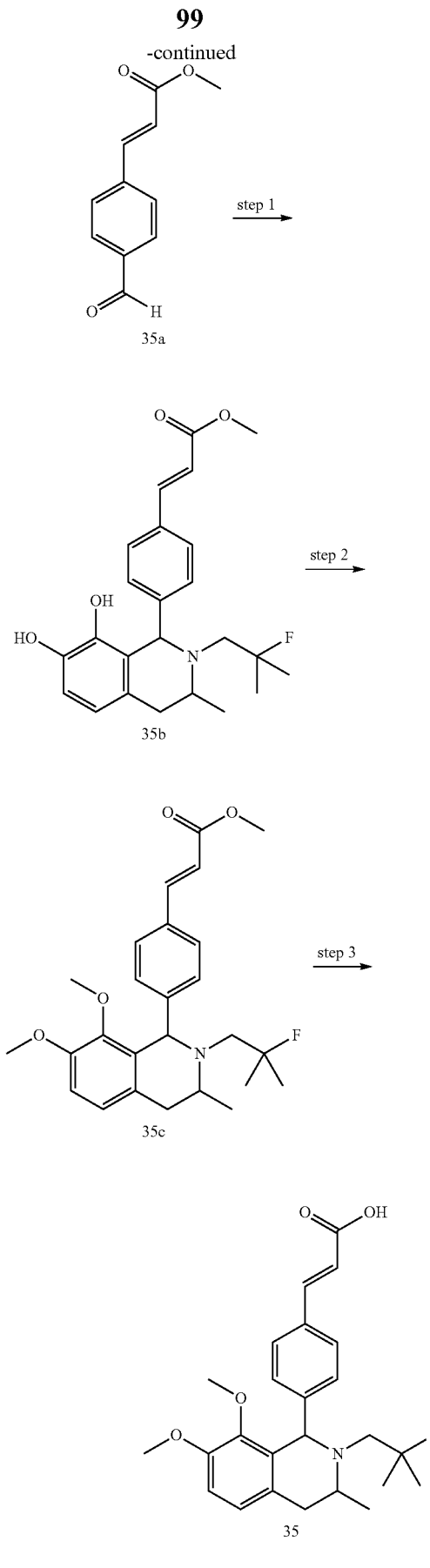

Step 1

(E)-methyl 3-(4-((1R,3R/1S,3S)-2-(2-fluoro-2-methylpropyl)-7,8-dihydroxy-3-methyl-1,2,3,4-tetrahydroisoquinolin-1-yl)phenyl)acrylate The crude 4-(2-((2-fluoro-2-methylpropyl)amino)propyl)benzene-1,2-diol 1d (200 mg, 0.83 mmol) was dissolved in 8 mL of methanol, then (E)-methyl 3-(4-formylphenyl)acrylate 35a (165 mg, 0.87 mmol, prepared by a well-known method disclosed in "*Applied Organometallic Chemistry,* 2014, 28(7), 529-536") and acetic acid (100 mg, 1.66 mmol) were added. The resulting mixture was heated to 55° C. and stirred for 5 hours. The reaction solution was concentrated under reduced pressure to remove methanol and acetic acid. Dichloromethane was added, and the mixture was purified by silica gel column chromatography with elution system A to obtain the title compound (E)-methyl 3-(4-((1R,3R/1S,3S)-2-(2-fluoro-2-methylpropyl)-7,8-dihydroxy-3-methyl-1,2,3,4-tetrahydroisoquinolin-1-yl)phenyl)acrylate 35b (100 mg, yield 29%) as a brown oil.

Step 2

(E)-methyl 3-(4-((1R,3R/1S,3S)-2-(2-fluoro-2-methylpropyl)-7,8-dimethoxy-3-methyl-1,2,3,4-tetrahydroisoquinolin-1-yl)phenyl)acrylate (E)-methyl 3-(4-((1R,3R/1S,3S)-2-(2-fluoro-2-methylpropyl)-7,8-dihydroxy-3-methyl-1,2,3,4-tetrahydroisoquinolin-1-yl)phenyl)acrylate 35b (100 mg, 0.24 mmol) was dissolved in 3 mL of acetone, then dimethyl sulfate (92 mg, 0.72 mmol) and potassium carbonate (133 mg, 0.96 mmol) were added. The resulting mixture was stirred under reflux for 12 hours. After cooling to room temperature, the reaction mixture was concentrated under reduced pressure. 100 mL of ethyl acetate was added to the residue, then the mixture was washed with saturated sodium chloride solution (100 mL×2), dried over anhydrous sodium sulfate, and filtered. The filtrate was concentrated under reduced pressure, and the residue was purified by silica gel column chromatography with elution system A to obtain the title compound (E)-methyl 3-(4-((1R,3R/1S,3S)-2-(2-fluoro-2-methylpropyl)-7,8-dimethoxy-3-methyl-1,2,3,4-tetrahydroisoquinolin-1-yl)phenyl)acrylate 35c (18 mg, yield 17%) as a brown solid.

Step 3

(E)-3-(4-((1R,3R/1S,3S)-2-(2-fluoro-2-methylpropyl)-7,8-dimethoxy-3-methyl-1,2,3,4-tetrahydroisoquinolin-1-yl)phenyl)acrylic Acid (E)-methyl 3-(4-((1R,3R/1S,3S)-2-(2-fluoro-2-methylpropyl)-7,8-dimethoxy-3-methyl-1,2,3,4-tetrahydroisoquinolin-1-yl)phenyl)acrylate 35c (18 mg, 0.04 mmol) was dissolved in 4 mL of a mixture of tetrahydrofuran and methanol (V/V=1:1), then 0.5 mL of 1M sodium hydroxide solution was added. The reaction was stirred for 10 hours at room temperature. Hydrochloric acid (1 M) was added dropwise to adjust the pH to 6. The mixture was extracted with ethyl acetate (50 mL). The organic phase was washed with saturated sodium chloride solution (50 mL), dried over anhydrous sodium sulfate, and filtered. The filtrate was concentrated under reduced pressure, and the residue was purified by thin-layer chromatography with elution system A to obtain the title compound (E)-3-(4-((1R,3R/1S,3S)-2-(2- fluoro-2-methylpropyl)-7,8-dimethoxy-3-methyl-1,2,3,4-tetrahydroisoquinolin-1-yl)phenyl)acrylic acid 35 (5 mg, yield 28%) as a light yellow solid.

MS m/z (ESI): 428.4 [M+1]

¹H NMR (400 MHz, CDCl₃) δ 7.76-7.72 (d, 1H), 7.44-7.42 (d, 2H), 7.29-7.26 (m 2H), 6.87 (s 2H), 6.41-6.37 (d 1H), 5.37 (s, 1H), 3.85 (s 3H), 3.52 (s 3H), 3.12-3.05 (m 1H), 2.64-2.44 (m, 4H), 1.35-1.25 (m, 6H), 0.99-0.97 (m, 3H).

Example 36

(E)-3-(3,5-difluoro-4-((1S,3R/1R,3S)-2-(2-fluoro-2-methylpropyl)-3-methyl-6-((tetrahydro-2H-pyran-4-yl)oxy)-1,2,3,4-tetrahydroisoquinolin-1-yl)phenyl)acrylic Acid

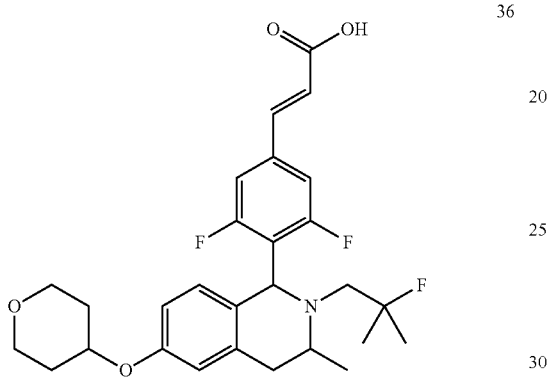

36

In accordance with the synthetic route of Example 30, the starting material 2-bromo-N-cyclopropylacetamide 30a used in step 1 was replaced with tetrahydro-4-pyranol, accordingly, the title compound (E)-3-(3,5-difluoro-4-((1S, 3R/1R,3S)-2-(2-fluoro-2-methylpropyl)-3-methyl-6-((tetrahydro-2H-pyran-4-yl)oxy)-1,2,3,4-tetrahydroisoquinolin-1-yl)phenyl)acrylic acid 36 was prepared.

MS m/z (ESI): 504.5 [M+1]

¹H NMR (400 MHz, CD₃OD) δ 7.57 (d, 1H), 7.19 (d, 2H), 6.73 (s, 1H), 6.64-6.60 (m, 2H), 6.53 (d, 1H), 5.17 (s, 1H), 4.50 (s, 1H), 3.98-3.91 (m, 2H), 3.68 (s, 1H), 3.59 (t, 1H), 3.36 (s, 1H), 2.99 (t, 1H), 2.58 (d, 1H), 2.34-2.22 (m, 2H), 2.12-2.01 (m, 2H), 1.70-1.66 (m, 2H), 1.17-1.09 (m, 6H), 1.01 (d, 3H).

Example 37

(E)-3-(3,5-difluoro-4-((1S,3R/1R,3S)-2-(2-fluoro-2-methylpropyl)-3-methyl-6-(((S)-tetrahydrofuran-3-yl)oxy)-3,4-tetrahydroisoquinolin-1-yl)phenyl)acrylic Acid

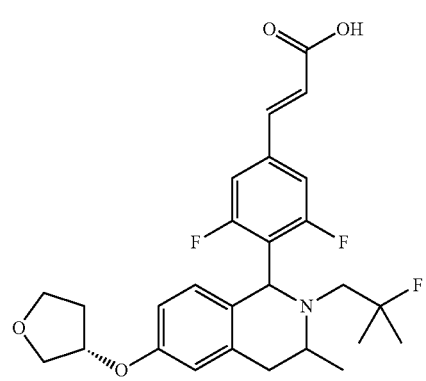

37

In accordance with the synthetic route of Example 30, the starting material 2-bromo-N-cyclopropylacetamide 30a used in step 1 was replaced with (R)-3-hydroxytetrahydrofuran, accordingly, the title compound (E)-3-(3,5-difluoro-4-((1S,3R/1R,3S)-2-(2-fluoro-2-methylpropyl)-3-methyl-6-(((S)-tetrahydrofuran-3-yl)oxy)-1,2,3,4-tetrahydroisoquinolin-1-yl)phenyl)acrylic acid 37 was prepared.

MS m/z (ESI): 490.4 [M+1]

¹H NMR (400 MHz, CDCl₃) δ 7.51 (d, 1H), 7.03 (d, 2H), 6.76 (d, 1H), 6.69-6.66 (m, 2H), 6.35 (d, 1H), 5.79 (s, 1H), 4.91 (s, 1H), 4.17 (d, 1H), 4.03-3.92 (m, 4H), 3.27-3.20 (m, 2H), 2.99-2.95 (m, 1H), 2.75 (dd, 1H), 2.21-2.16 (m, 2H), 1.54 (d, 3H), 1.41-1.26 (m, 6H).

Example 38

(E)-3-(3,5-difluoro-4-((1S,3R/1R,3S)-2-(2-fluoro-2-methylpropyl)-3-methyl-6-(2-methylmorpholino)-1,2,3,4-tetrahydroisoquinolin-1-yl)phenyl)acrylic Acid

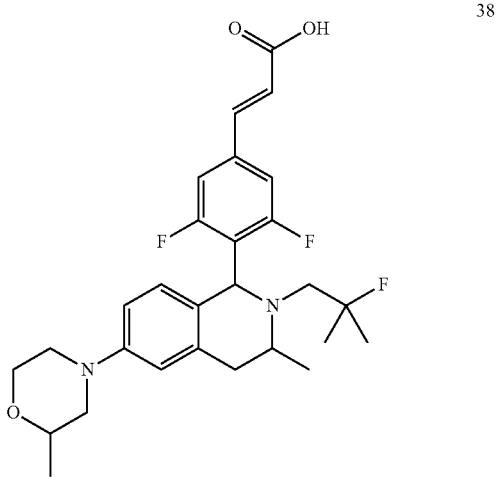 [SMILES: CC1CN(c2ccc3c(c2)CC(C)N(CC(C)(C)F)C3c2c(F)cc(/C=C/C(=O)O)cc2F)CCO1]

38

In accordance with the synthetic route of Example 10, the starting material, 2-methyl-5-(4,4,5,5-tetramethyl-1,3,2-dioxaborolan-2-yl)thiazole 10b used in step 2, was replaced with 2-methylmorpholine, accordingly, the title compound (E)-3-(3,5-difluoro-4-((1S,3R/1R,3S)-2-(2-fluoro-2-methylpropyl)-3-methyl-6-(2-methylmorpholino)-1,2,3,4-tetrahydroisoquinolin-1-yl)phenyl)acrylic acid 38 was prepared.

MS m/z (ESI): 503.5 [M+1]

¹H NMR (400 MHz, CD₃OD) δ 7.43-7.39 (m, 1H), 7.15-7.01 (m, 3H), 6.74-6.48 (m, 3H), 5.22-5.14 (m, 1H), 4.05-3.95 (m, 1H), 3.82-3.37 (m, 4H), 3.25-3.19 (m, 1H), 2.81-2.21 (m, 6H), 1.23-0.99 (m, 12H).

Example 39

(E)-3-(3,5-difluoro-4-((1S,3R/1R,3S)-2-(2-fluoro-2-methylpropyl)-3-methyl-6-(4-methyl-3-oxopiperazin-1-yl)-1,2,3,4-tetrahydroisoquinolin-1-yl)phenyl)acrylic Acid

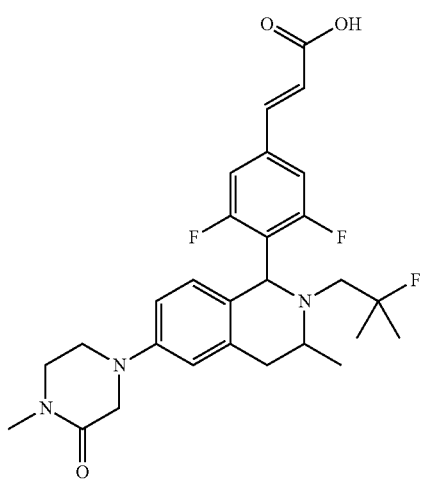

In accordance with the synthetic route of Example 10, the starting material 2-methyl-5-(4,4,5,5-tetramethyl-1,3,2-dioxaborolan-2-yl)thiazole 10b used in step 2 was replaced with 1-methylpiperazin-2-one, accordingly, the title compound (E)-3-(3,5-difluoro-4-((1S,3R/1R,3S)-2-(2-fluoro-2-methylpropyl)-3-methyl-6-(4-methyl-3-oxopiperazin-1-yl)-1,2,3,4-tetrahydroisoquinolin-1-yl)phenyl)acrylic acid 39 was prepared.

MS m/z (ESI): 516.5 [M+1]

$^1$H NMR (400 MHz, CD$_3$OD) δ 7.68-7.55 (m, 2H), 7.44 (d, 1H), 7.19-7.08 (m, 2H), 6.82-6.60 (m, 2H), 6.56-6.50 (m, 1H), 5.24-5.15 (m, 1H), 4.01-3.94 (m, 1H), 3.78-3.37 (m, 6H), 3.16-2.91 (m, 5H), 2.68-2.56 (m, 1H), 2.33-2.22 (m, 1H), 1.19-0.99 (m, 9H).

Example 40

(E)-3-(3,5-difluoro-4-((1S,3R/1R,3S)-2-(2-fluoro-2-methylpropyl)-3-methyl-6-(3-methylmorpholino)-1,2,3,4-tetrahydroisoquinolin-1-yl)phenyl)acrylic Acid

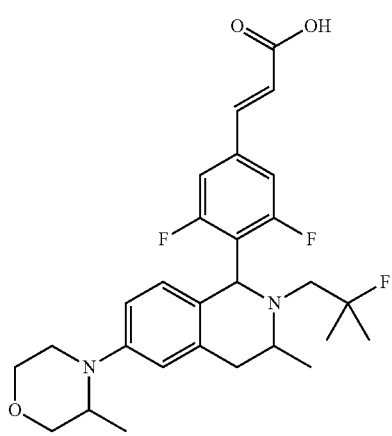

In accordance with the synthetic route of Example 10, the starting material 2-methyl-5-(4,4,5,5-tetramethyl-1,3,2-dioxaborolan-2-yl)thiazole 10b used in step 2 was replaced with 3-methylmorpholine, accordingly, the title compound (E)-3-(3,5-difluoro-4-((1S,3R/1R,3S)-2-(2-fluoro-2-methylpropyl)-3-methyl-6-(3-methylmorpholino)-1,2,3,4-tetrahydroisoquinolin-1-yl)phenyl)acrylic acid 40 was prepared.

MS m/z (ESI): 503.0 [M+1]

$^1$H NMR (400 MHz, CD$_3$OD) δ 7.59 (d, 1H), 7.22 (d, 2H), 6.83-6.77 (m, 2H), 6.75-6.71 (m, 1H), 6.54 (d, 1H), 5.29 (s, 1H), 3.95 (d, 1H), 3.87 (d, 1H), 3.77-3.66 (m, 4H), 3.38-3.37 (m, 1H), 3.26-3.18 (m, 2H), 3.18-3.08 (m, 1H), 2.73-2.69 (m, 1H), 2.41-2.21 (m, 1H), 1.18-1.02 (m, 12H).

Example 41

(E)-3-(3,5-difluoro-4-((1S,3R/1R,3S)-2-(2-fluoro-2-methylpropyl)-3-methyl-6-morpholino-1,2,3,4-tetrahydroisoquinolin-1-yl)phenyl)acrylic Acid

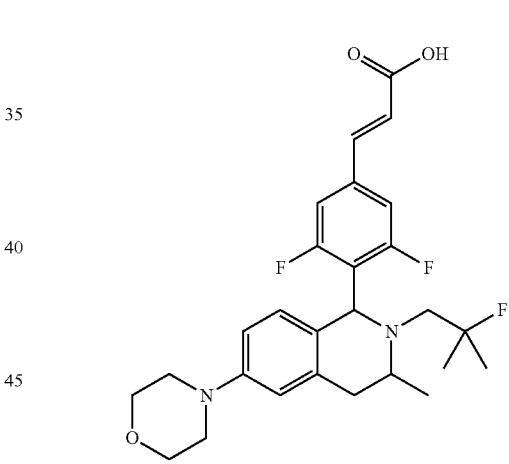

In accordance with the synthetic route of Example 10, the starting material 2-methyl-5-(4,4,5,5-tetramethyl-1,3,2-dioxaborolan-2-yl)thiazole 10b used in step 2 was replaced with morpholine, accordingly, the title compound (E)-3-(3,5-difluoro-4-((1S,3R/1R,3S)-2-(2-fluoro-2-methylpropyl)-3-methyl-6-morpholino-1,2,3,4-tetrahydroisoquinolin-1-yl)phenyl)acrylic acid 41 was prepared.

MS m/z (ESI): 489.5[M+1]

$^1$H NMR (400 MHz, CD$_3$OD) δ 7.60-7.55 (m, 2H), 7.40 (d, 1H), 7.23 (d, 2H), 6.93 (d, 1H), 6.56 (d, 1H), 5.30 (s, 1H), 3.78-3.70 (m, 1H), 3.67-3.41 (m, 5H), 3.04-2.80 (m, 5H), 2.75-2.70 (m, 1H), 2.36-2.25 (m, 1H), 1.33-1.01 (m, 9H).

Example 42

(E)-3-(3,5-difluoro-4-((1S,3R/1R,3S)-2-(2-fluoro-2-methylpropyl)-3-methyl-6-(1H-pyrrolo[3,4-c]pyridin-2(3H)-yl)-1,2,3,4-tetrahydroisoquinolin-1-yl)phenyl)acrylic Acid

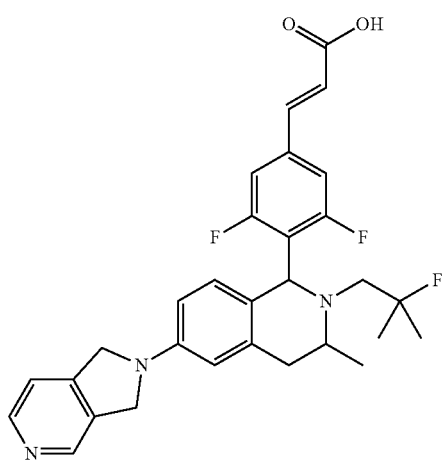

In accordance with the synthetic route of Example 10, the starting material 2-methyl-5-(4,4,5,5-tetramethyl-1,3,2-dioxaborolan-2-yl)thiazole 10b used in step 2 was replaced with 2,3-dihydro-1H-pyrrolo[3,4-c]pyridine hydrochloride, accordingly, the title compound (E)-3-(3,5-difluoro-4-((1S,3R/1R,3S)-2-(2-fluoro-2-methylpropyl)-3-methyl-6-(1H-pyrrolo[3,4-c]pyridin-2(3H)-yl)-1,2,3,4-tetrahydroisoquinolin-1-yl)phenyl)acrylic acid 42 was prepared.

MS m/z (ESI): 522.6 [M+1]

$^1$H NMR (400 MHz, CD$_3$OD) δ 8.60-8.48 (m, 2H), 7.90-7.83 (m, 1H), 7.65-7.57 (m, 2H), 7.23-7.16 (m, 2H), 6.65-6.52 (m 3H), 5.19 (s, 1H), 4.69 (s, 4H), 3.71 (s 1H), 3.05-3.01 (m, 1H), 2.64-2.61 (m, 1H), 2.35-2.22 (m, 2H), 1.22-0.93 (m, 9H).

Example 43

(E)-3-(3,5-difluoro-4-((1S,3R/1R,3S)-2-(2-fluoro-2-methylpropyl)-3-methyl-6-(5-methylthiophen-2-yl)-1,2,3,4-tetrahydroisoquinolin-1-yl)phenyl)acrylic Acid

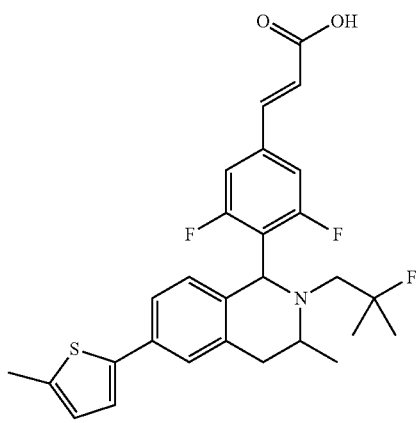

In accordance with the synthetic route of Example 10, the starting material 2-methyl-5-(4,4,5,5-tetramethyl-1,3,2-dioxaborolan-2-yl)thiazole 10b used in step 2 was replaced with 4,4,5,5-tetramethyl-2-(5-methylthiophen-2-yl)-1,3,2-dioxaborolane that was prepared by a well-known method disclosed in "Organometallics, 2015, 34(19), 4732-4740", accordingly, the title compound (E)-3-(3,5-difluoro-4-((1S,3R/1R,3S)-2-(2-fluoro-2-methylpropyl)-3-methyl-6-(5-methylthiophen-2-yl)-1,2,3,4-tetrahydroisoquinolin-1-yl)phenyl)acrylic acid 43 was prepared.

MS m/z (ESI): 500.4 [M+1]

$^1$H NMR (400 MHz, CD$_3$OD) δ 7.60-7.56 (d, 1H), 7.33 (s, 1H), 7.26-7.20 (m, 3H), 7.13 (s, 1H), 6.74-6.70 (m 2H), 6.56-6.52 (d 1H), 5.23 (s, 1H), 3.73 (s 1H), 3.41-3.37 (m 1H), 3.05-2.97 (m, 1H), 2.68-2.64 (m, 1H), 2.49 (s, 3H), 2.36-2.25 (m, 1H), 1.19-0.92 (m, 9H).

Example 44

(E)-3-(4-((1S,3R/1R,3S)-6-(3,3-dimethylureido)-2-(2-fluoro-2-methylpropyl)-3-methyl-1,2,3,4-tetrahydroisoquinolin-1-yl)-3,5-difluorophenyl)acrylic Acid

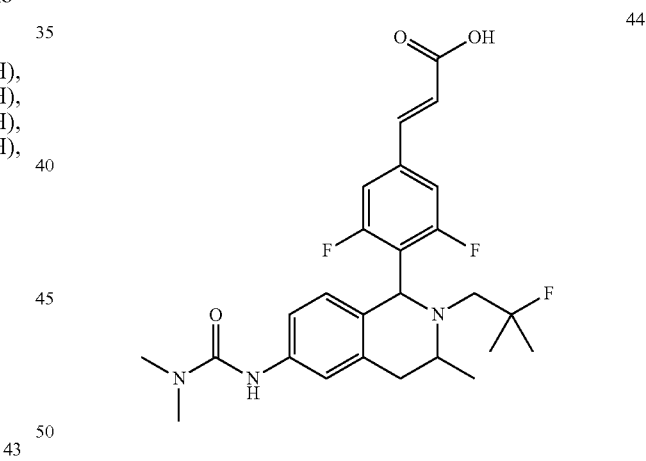

In accordance with the synthetic route of Example 10, the starting material 2-methyl-5-(4,4,5,5-tetramethyl-1,3,2-dioxaborolan-2-yl)thiazole 10b used in step 2 was replaced with 1-isopropylurea, accordingly, the title compound (E)-3-(4-((1S,3R/1R,3S)-6-(3,3-dimethylureido)-2-(2-fluoro-2-methylpropyl)-3-methyl-1,2,3,4-tetrahydroisoquinolin-1-yl)-3,5-difluorophenyl)acrylic acid 44 was prepared.

MS m/z (ESI): 490.5 [M+1]

$^1$H NMR (400 MHz, CDCl$_3$) δ 7.58 (d, 1H), 7.00 (m, 3H), 6.64 (d, 1H), 6.40 (d, 1H), 6.24 (s, 1H), 5.17 (s, 1H), 3.36 (dd, 1H), 3.02 (s, 6H), 2.94 (t, 1H), 2.55 (dd, 1H), 2.24 (m, 1H), 1.93 (s, 1H), 1.32-1.09 (m, 6H), 0.99 (d, 3H).

Example 45

(E)-3-(3,5-difluoro-4-((1S,3R/1R,3S)-5-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylic Acid

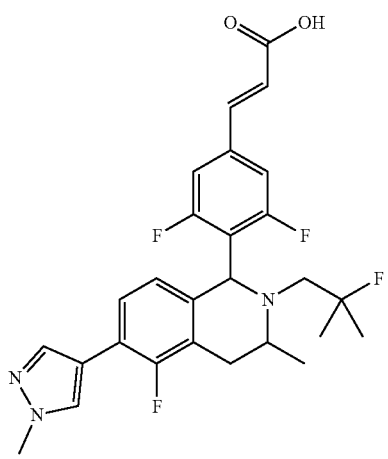

In accordance with the synthetic route of Example 16, the starting material 2-(3-(benzyloxy)-4-fluorophenyl)acetaldehyde 16a used in step 1 was replaced with 2-(3-(benzyloxy)-2-fluorophenyl)acetaldehyde that was prepared by a well-known method disclosed in "*Environmental Science and Pollution Research*, 2014, 21(7), 4861-4870"), accordingly, the title compound (E)-3-(3,5-difluoro-4-((1S,3R/1R,3S)-5-fluoro-2-(2-fluoro-2-methylpropyl)-3-methyl-6-(1-methyl-1H-pyrazol-4-yl)-1,2,3,4-tetrahydroisoquinolin-1-yl)phenyl)acrylic acid 45 was prepared. MS m/z (ESI): 502.5 [M+1]

$^1$H NMR (400 MHz, CD$_3$OD) δ 8.05 (s, 1H), 7.90 (s, 1H), 7.61 (d, 1H), 7.49-7.47 (m, 1H), 7.36-7.33 (m, 2H), 6.80 (s, 1H), 6.61 (d, 1H), 5.79 (s, 1H), 3.97-3.94 (m, 4H), 3.30-3.27 (m, 2H), 3.03-2.68 (m, 2H), 1.42-1.33 (m, 9H).

Example 46

(E)-3-(4-(((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl)acrylic Acid

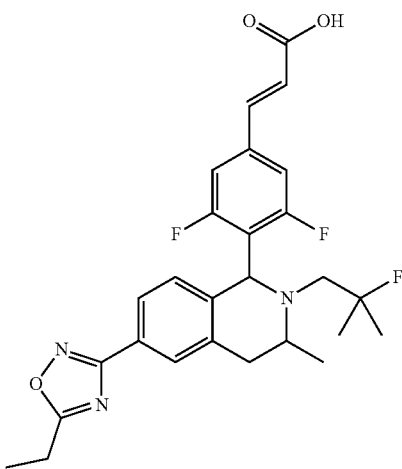

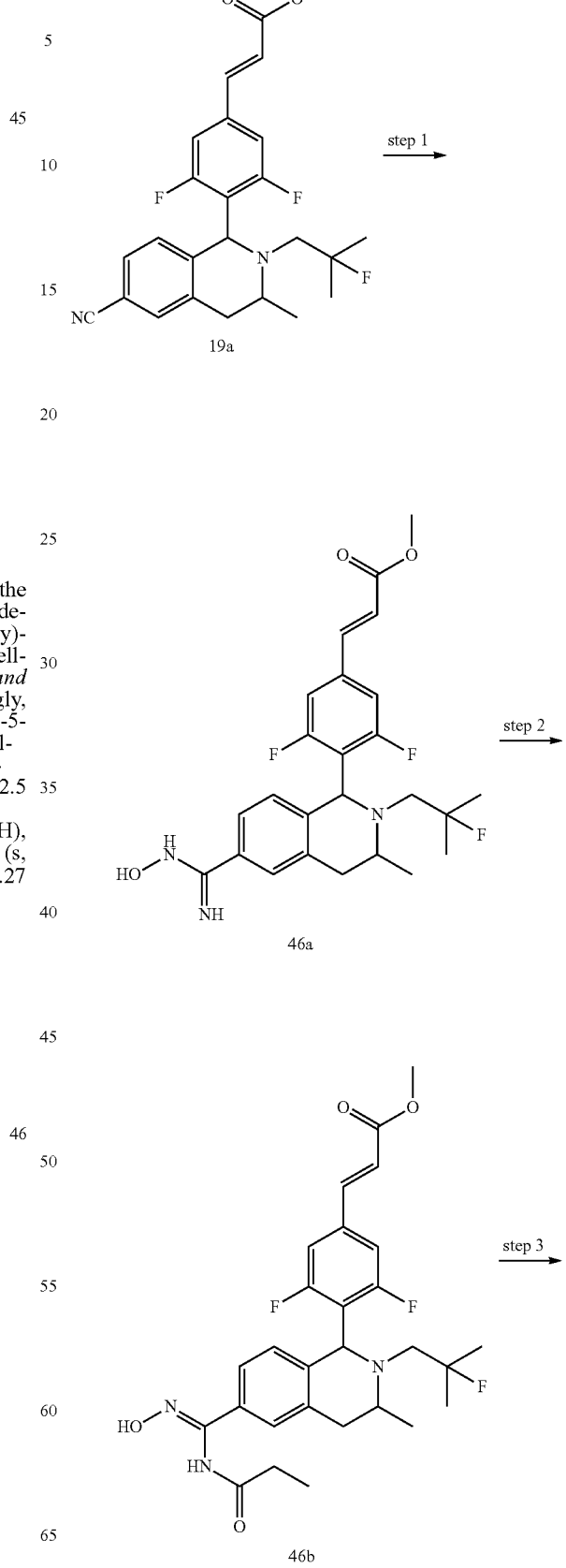

-continued

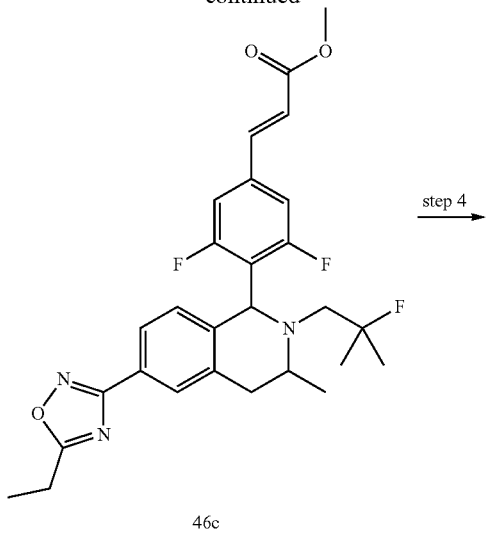

46c

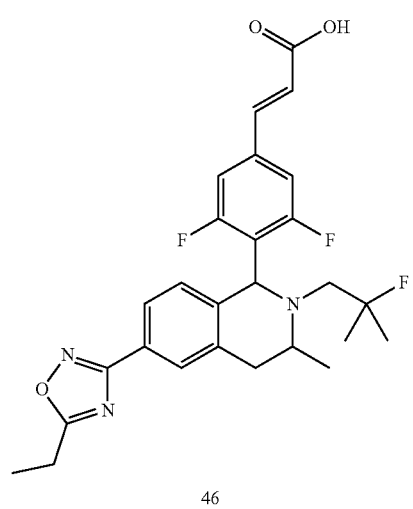

46

Step 1

(E)-methyl 3-(3,5-difluoro-4-((1S,3R/1R,3S)-2-(2-fluoro-2-methylpropyl)-6-(N-hydroxycarbamimidoyl)-3-methyl-1,2,3,4-tetrahydroisoquinolin-1-yl)phenyl)acrylate (E)-methyl 3-(4-((1S,3R/1R,3S)-6-cyano-2-(2-fluoro-2-methylpropyl)-3-methyl-1,2,3,4-tetrahydroisoquinolin-1-yl)-3,5-difluorophenyl)acrylate 19a (300 mg, 0.68 mmol), hydroxylamine hydrochloride (56 mg, 0.81 mmol) and triethylamine (151 mg, 1.49 mmol) were dissolved in 10 mL of ethanol. The resulting mixture was stirred under reflux for 12 hours. The reaction solution was cooled to room temperature and concentrated under reduced pressure to obtain the crude title compound (E)-methyl 3-(3,5-difluoro-4-((1S,3R/1R,3S)-2-(2-fluoro-2-methylpropyl)-6-(N-hydroxycarbamimidoyl)-3-methyl-1,2,3,4-tetrahydroisoquinolin-1-yl)phenyl)acrylate 46a (350 mg) as a yellow oil, which was used directly in next step without further purification.

Step 2

(E)-methyl 3-(3,5-difluoro-4-((1S,3R/1R,3S)-2-(2-fluoro-2-methylpropyl)-6-((Z)—N'-hydroxy-N-propionylcarbamimidoyl)-3-methyl-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-6-(N-hydroxycarbamimidoyl)-3-methyl-1,2,3,4-tetrahydroisoquinolin-1-yl)phenyl)acrylate 46a (350 mg, 0.68 mmol) and potassium carbonate (187 mg, 1.36 mmol) were dissolved in acetone, and propionyl chloride (94 mg, 1.02 mmol) was added dropwise. The reaction was stirred for 12 hours at room temperature. Water was added and the mixture was extracted with ethyl acetate (50 mL×2). The organic phases were combined and dried over anhydrous sodium sulfate, and filtered. The filtrate was concentrated under reduced pressure to obtain the crude title compound (E)-methyl 3-(3,5-difluoro-4-((1S,3R/1R,3S)-2-(2-fluoro-2-methylpropyl)-6-((Z)—N'-hydroxy-N-propionylcarbamimidoyl)-3-methyl-1,2,3,4-tetrahydroisoquinolin-1-yl)phenyl)acrylate 46b (350 mg) as a yellow oil, which was used directly in next step without further purification.

Step 3

(E)-methyl 3-(4-((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl)acrylate The crude (E)-methyl 3-(3,5-difluoro-4-((1S,3R/1R,3S)-2-(2-fluoro-2-methylpropyl)-6-((Z)—N'-hydroxy-N-propionylcarbamimidoyl)-3-methyl-1,2,3,4-tetrahydroisoquinolin-1-yl)phenyl)acrylate 46b (350 mg, 0.68 mmol) was dissolved in 15 mL of toluene. The reaction mixture was warmed up to 90° C. and stirred for 12 hours. The reaction solution was cooled to room temperature and concentrated under reduced pressure. The resulting residue was purified by silica gel column chromatography with elution system A to obtain the title compound (E)-methyl 3-(4-((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl)acrylate 46c (50 mg, yield 14.3%) as a yellow oil.

Step 4

(E)-3-(4-((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl) acrylic Acid (E)-methyl 3-(4-((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl)acrylate 46c (50 mg, 0.1 mmol) was dissolved in 2 mL of methanol, then 0.3 mL of 1M lithium hydroxide solution was added. The reaction was stirred for 12 hours at room temperature. The reaction solution was concentrated under reduced pressure to remove methanol. 1M hydrochloric acid was added dropwise to adjust the pH to 3. The mixture was extracted with ethyl acetate (30 mL×2 mL). The organic phases were combined, dried over anhydrous sodium sulfate, and filtered. The filtrate was concentrated under reduced pressure, and the resulting residue was purified by thin-layer chromatography with elution system A to obtain the title compound (E)-3-(4-((1S,3R/1R,3S)-6-(5-ethyl-1,2,4-oxadiazol-3-yl)-2-(2-fluoro-2-methylpropyl)-3-methyl-1,2,3,4-tetrahydroisoquinolin-1-yl)-3,5-difluorophenyl)acrylic acid 46 (10 mg, yield 20%) as a yellow solid.

MS m/z (ESI): 500.5 [M+1]

$^1$H NMR (400 MHz, DMSO-d$_6$) δ 12.57 (s, 1H), 7.80 (d, 1H), 7.68 (d, 1H), 7.55-7.46 (m, 3H), 6.90 (d, 1H), 6.66 (d, 1H), 5.21 (s, 1H), 3.60-3.53 (m, 1H), 3.30-3.24 (m, 1H), 3.04-2.91 (m, 3H), 2.75 (dd, 1H), 2.29-2.18 (m, 1H), 1.33 (t, 3H), 1.18-1.04 (m, 6H), 0.97 (d, 3H).

Example 47

(E)-3-(4-((1S,3R/1R,3S)-6-(1-ethyl-1H-pyrazol-4-yl)-5-fluoro-2-(2-fluoro-2-methylpropyl)-3-methyl-1,2,3,4-tetrahydroisoquinolin-1-yl)-3,5-difluorophenyl)acrylic Acid

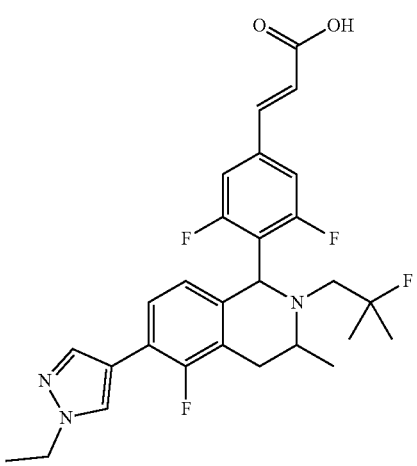

In accordance with the synthetic route of Example 16, the starting material 2-(3-(benzyloxy)-4-fluorophenyl)acetaldehyde 16a used in step 1 was replaced with 2-(3-(benzyloxy)-2-fluorophenyl)acetaldehyde that was prepared by a well-known method disclosed in "*Environmental Science and Pollution Research*, 2014, 21(7), 4861-4870", and the starting material 1-methyl-4-(4,4,5,5-tetramethyl-1,3,2-dioxaborolan-2-yl)-1H-pyrazole 16h used in step 7 was replaced with 1-ethyl-4-(4,4,5,5-tetramethyl-1,3,2-dioxaborolane-2-yl)-1H-pyrazol to obtain the title compound (E)-3-(4-((1S,3R/1R,3S)-6-(1-ethyl-1H-pyrazol-4-yl)-5-fluoro-2-(2-fluoro-2-methylpropyl)-3-methyl-1,2,3,4-tetrahydroisoquinolin-1-yl)-3,5-difluorophenyl)acrylic acid 47.

MS m/z (ESI): 516.5 [M+1]

$^1$H NMR (400 MHz, CD$_3$OD) δ 8.03 (s, 1H), 7.87 (s, 1H), 7.59 (d, 1H), 7.36-7.32 (m, 1H), 7.23 (d, 2H), 6.59-6.53 (m, 2H), 5.27 (s, 1H), 4.27-4.22 (m, 2H), 3.76 (s, 1H), 3.15-2.84 (m, 3H), 2.37-2.26 (m, 1H), 1.52-1.50 (m, 3H), 1.21-1.05 (m, 9H).

Example 48

(E)-3-(3,5-difluoro-4-((1S,3R/1R,3S)-2-(2-fluoro-2-methylpropyl)-6-(1-(2-fluoroethyl)-1H-pyrazol-4-yl)-3-methyl-1,2,3,4-tetrahydroisoquinolin-1-yl)phenyl)acrylic Acid

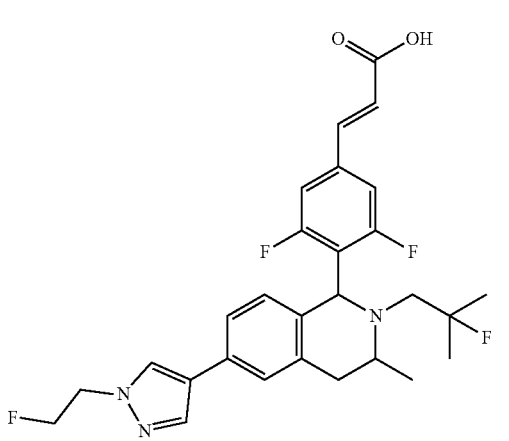

In accordance with the synthetic route of Example 10, the starting material 2-methyl-5-(4,4,5,5-tetramethyl-1,3,2-dioxaborolan-2-yl)thiazole 10b used in step 2 was replaced with 1-(2-fluoroethyl)-4-(4,4,5,5-tetramethyl-1,3,2-dioxaborolan-2-yl)-1H-pyrazole that was prepared by a method disclosed in the patent application publication "WO2013162061"), accordingly, the title compound (E)-3-(3,5-difluoro-4-((1S,3R/1R,3S)-2-(2-fluoro-2-methylpropyl)-6-(1-(2-fluoroethyl)-1H-pyrazol-4-yl)-3-methyl-1,2,3,4-tetrahydroisoquinolin-1-yl)phenyl)acrylic acid 48 was prepared.

MS m/z (ESI): 516.0 [M+1]

$^1$H NMR (400 MHz, CD$_3$OD) δ 7.99 (s, 1H), 7.85 (s, 1H), 7.56 (d, 1H), 7.34 (s, 1H), 7.25-7.19 (m, 3H), 6.73-6.71 (d, 1H), 6.56-6.52 (d, 1H), 5.23 (s, 1H), 4.84-4.82 (m, 1H), 4.73-4.70 (m, 1H), 4.52-4.49 (m, 1H), 4.45-4.43 (m, 1H), 4.75-4.71 (m, 1H), 3.43-3.38 (m, 1H), 3.05-2.97 (s, 1H), 2.69-2.64 (m, 1H), 2.36-2.25 (m, 1H), 1.19-1.03 (m, 9H).

Example 49

(E)-3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylic Acid

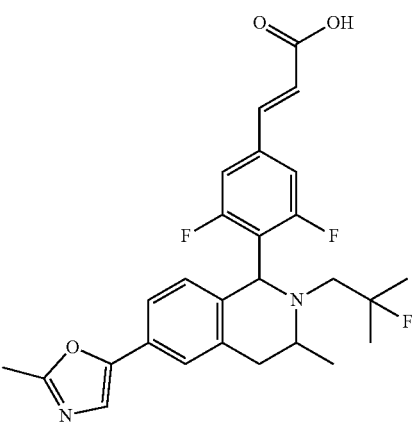

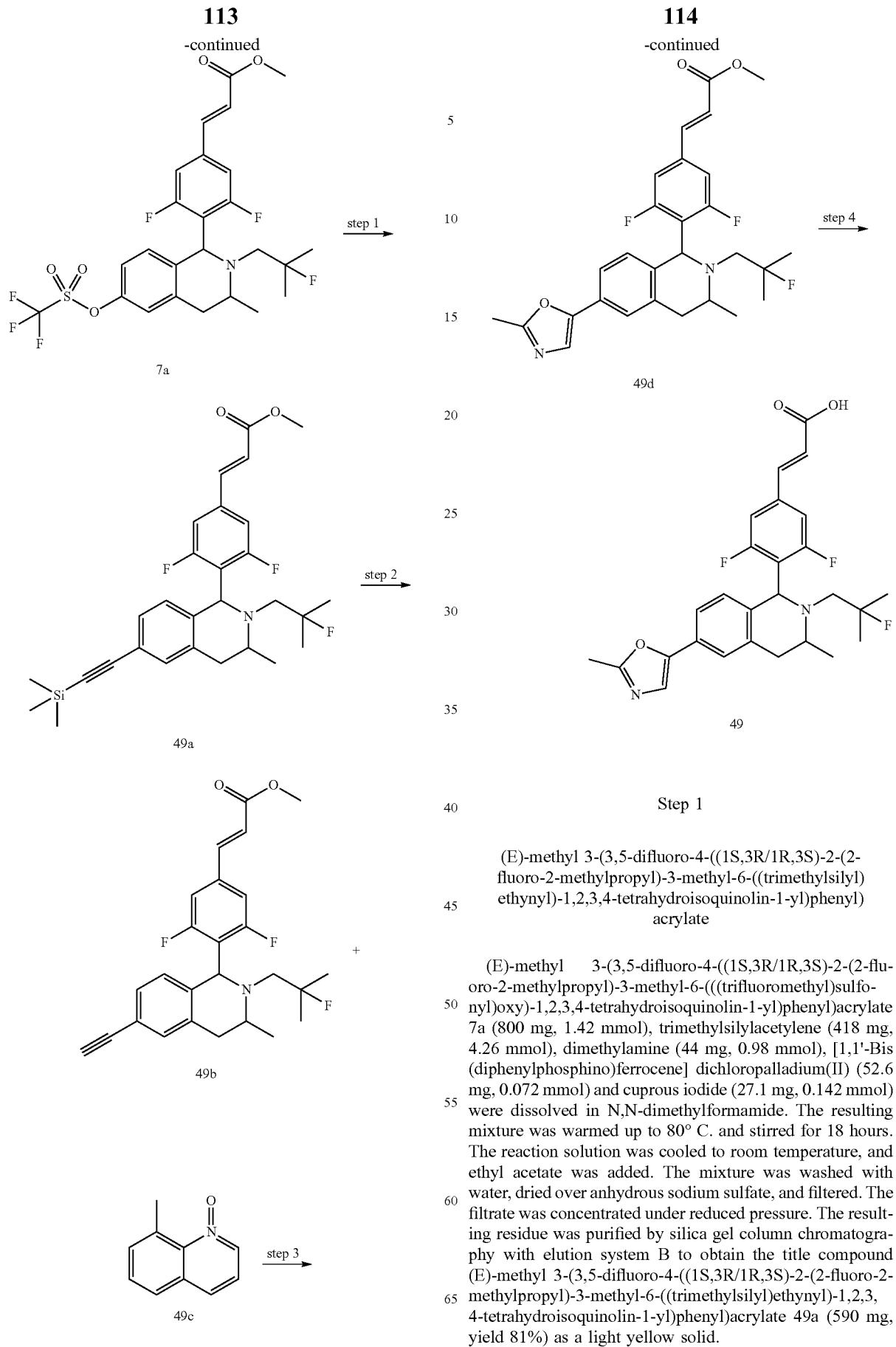

Step 1

(E)-methyl 3-(3,5-difluoro-4-((1S,3R/1R,3S)-2-(2-fluoro-2-methylpropyl)-3-methyl-6-((trimethylsilyl)ethynyl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (800 mg, 1.42 mmol), trimethylsilylacetylene (418 mg, 4.26 mmol), dimethylamine (44 mg, 0.98 mmol), [1,1'-Bis(diphenylphosphino)ferrocene] dichloropalladium(II) (52.6 mg, 0.072 mmol) and cuprous iodide (27.1 mg, 0.142 mmol) were dissolved in N,N-dimethylformamide. The resulting mixture was warmed up to 80° C. and stirred for 18 hours. The reaction solution was cooled to room temperature, and ethyl acetate was added. The mixture was washed with water, dried over anhydrous sodium sulfate, and filtered. The filtrate was concentrated under reduced pressure. The resulting residue was purified by silica gel column chromatography with elution system B to obtain the title compound (E)-methyl 3-(3,5-difluoro-4-((1S,3R/1R,3S)-2-(2-fluoro-2-methylpropyl)-3-methyl-6-((trimethylsilyl)ethynyl)-1,2,3,4-tetrahydroisoquinolin-1-yl)phenyl)acrylate 49a (590 mg, yield 81%) as a light yellow solid.

Step 2

(E)-methyl 3-(4-((1S,3R/1R,3S)-6-ethynyl-2-(2-fluoro-2-methylpropyl)-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-3-methyl-6-((trimethylsilyl)ethynyl)-1,2,3,4-tetrahydroisoquinolin-1-yl)phenyl)acrylate 49a (590 mg, 1.15 mmol) was dissolved in 5 mL of 1 M tetrabutylammonium fluoride. The reaction was stirred for 5 hours at room temperature. Water was added, and the mixture was extracted three times with ethyl acetate. The organic phases were combined, dried over anhydrous sodium sulfate and filtered. The filtrate was concentrated under reduced pressure. The resulting residue was purified by silica gel column chromatography with elution system B to obtain the title compound (E)-methyl 3-(4-((1S,3R/1R,3S)-6-ethynyl-2-(2-fluoro-2-methylpropyl)-3-methyl-1,2,3,4-tetrahydroisoquinolin-1-yl)-3,5-difluorophenyl)acrylate 49b (60 mg, yield 11.8%) as a white solid.

Step 3

(E)-methyl 3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylate (E)-methyl 3-(4-((1S,3R/1R,3S)-6-ethynyl-2-(2-fluoro-2-methylpropyl)-3-methyl-1,2,3,4-tetrahydroisoquinolin-1-yl)-3,5-difluorophenyl)acrylate 49b (20 mg, 0.045 mmol) was dissolved in 4 mL of acetonitrile, then 8-methylquinoline-1-oxide 49c (9.4 mg, 0.058 mmol, prepared by a well-known method disclosed in "*Chem Med Chem*, 2009, 4(2), 249-260") and [bis(trifluoromethanesulfonyl)imidate](triphenylphosphine)gold(I) (1.7 mg, 0.00225 mmol) were added, and the reaction was warmed up to 60° C. and stirred for 3 hours. The reaction solution was cooled to room temperature, and the resulting residue was purified by silica gel column chromatography with elution system B to obtain the title compound (E)-methyl 3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylate 49d (13 mg, yield 58%) as a light yellow solid.

Step 4

(E)-3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylate 49d (13 mg, 0.026 mmol) was dissolved in 1 mL of methanol, then 1 mL of 1 M lithium hydroxide solution was added, and the mixture was stirred for 1 hour at room temperature. A solution of 10% citric acid was added dropwise to adjust the pH to 6-7. The resulting mixture was extracted with ethyl acetate, dried over anhydrous sodium sulfate, and filtered. The filtrate was concentrated under reduced pressure. The resulting residue was purified by thin layer silica gel chromatography with elution system A to obtain the title compound (E)-3-(3,5-difluoro-4-((1S,3R/1R,3S)-2-(2-fluoro-2-methylpropyl)-3-methyl-6-(2-methyloxazol-5-yl)-1,2,3,4-tetrahydroisoquinolin-1-yl)phenyl)acrylic acid 49 (6 mg, yield 48%) as a yellow solid.

MS m/z (ESI): 485.5 [M+1]

$^1$H NMR (400 MHz, CD$_3$OD) δ 7.63 (d, 1H), 7.47 (s, 1H), 7.36 (d, 1H), 7.31 (s, 1H), 7.22 (d, 2H), 6.80 (d, 1H), 6.55 (d, 1H), 5.26 (s, 1H), 3.76-3.72 (m, 1H), 3.43-3.39 (m, 1H), 3.05-2.98 (m, 1H), 2.72-2.68 (m, 1H), 2.52 (s, 3H), 2.37-2.25 (m, 1H), 1.20-1.03 (m, 9H).

Example 50

(E)-3-(3,5-difluoro-4-((1S,3R/1R,3S)-2-(2-fluoro-2-methylpropyl)-6-(1-isopropyl-1H-pyrazol-4-yl)-3-methyl-1,2,3,4-tetrahydroisoquinolin-1-yl)phenyl) acrylic Acid

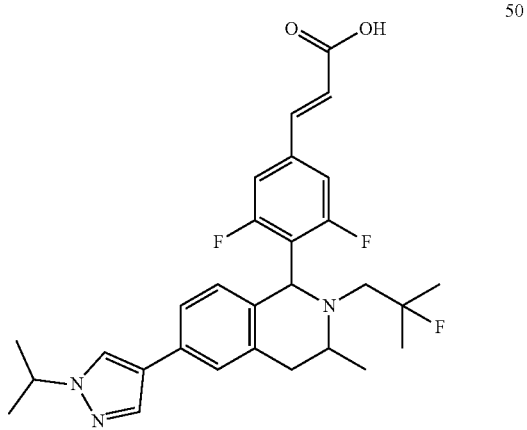 [SMILES: CC1Cc2cc(-c3cnn(C(C)C)c3)ccc2C(c2c(F)cc(/C=C/C(=O)O)cc2F)N1CC(C)(C)F]

In accordance with the synthetic route of Example 10, the starting material 2-methyl-5-(4,4,5,5-tetramethyl-1,3,2-dioxaborolan-2-yl)thiazole 10b used in step 2 was replaced with 1-isopropyl-4-(4,4,5,5-tetramethyl-1,3,2-dioxaborolan-2-yl)-1H-pyrazole that was prepared by a well-known method disclosed in "*Journal of Medicinal Chemistry*, 2011, 54(18), 6342-6363", accordingly, the title compound (E)-3-(3,5-difluoro-4-((1S,3R/1R,3S)-2-(2-fluoro-2-methylpropyl)-6-(1-isopropyl-1H-pyrazol-4-yl)-3-methyl-1,2,3,4-tetrahydroisoquinolin-1-yl)phenyl)acrylic acid 50 was prepared.

MS m/z (ESI): 510.5 [M−1]

$^1$H NMR (400 MHz, CD$_3$OD) δ 7.99 (s, 1H), 7.79 (s, 1H), 7.59 (d, 1H), 7.34 (s, 1H), 7.22 (t, 3H), 6.71 (d, 1H), 6.54 (d, 1H), 5.24 (s, 1H), 3.70-3.74 (m, 1H), 3.38-3.42 (dd, 1H), 3.01 (t, 1H), 2.69-2.64 (dd, 1H), 2.36-2.25 (m, 2H), 1.53 (d, 6H), 1.19-1.10 (dd, 6H), 1.04 (s, 3H).

Example 51

(E)-3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylic Acid

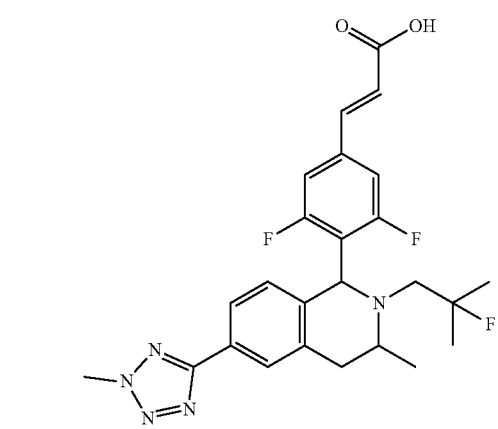

51

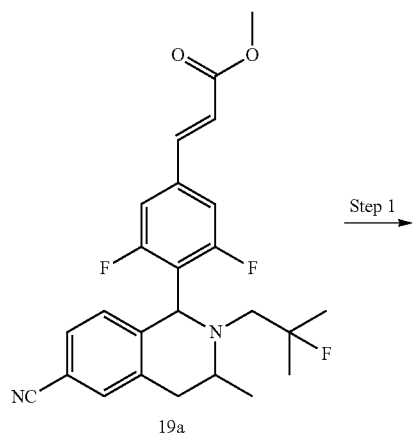

19a

Step 1 →

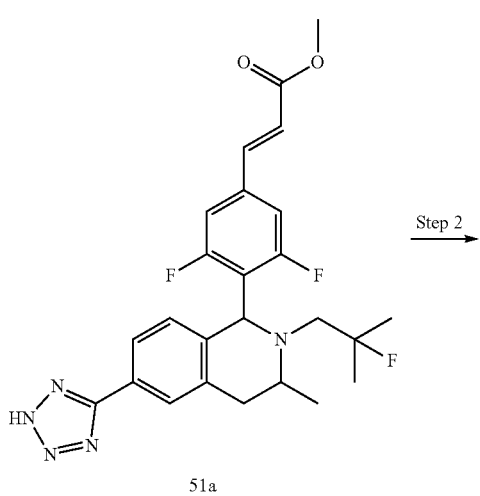

51a

Step 2 →

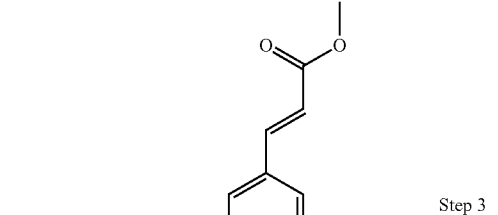

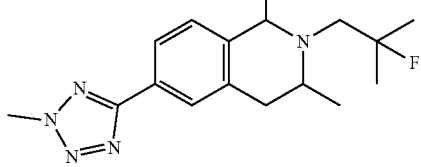

51b

Step 3 →

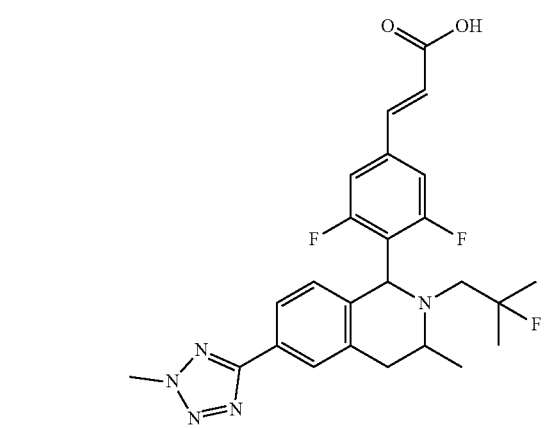

51

Step 1

(E)-methyl 3-(3,5-difluoro-4-((1S,3R/1R,3S)-2-(2-fluoro-2-methylpropyl)-3-methyl-6-(2H-tetrazol-5-yl)-1,2,3,4-tetrahydroisoquinolin-1-yl)phenyl)acrylate (E)-methyl 3-(4-((1S,3R/1R,3S)-6-cyano-2-(2-fluoro-2-methylpropyl)-3-methyl-1,2,3,4-tetrahydroisoquinolin-1-yl)-3,5-difluorophenyl)acrylate 19a (20 mg, 0.045 mmol), sodium azide (17 mg, 0.271 mmol) and ammonium chloride (15 mg, 0.271 mmol) were added to N,N-dimethylformamide. The mixture was warmed up to 150° C. and stirred in a microwave for 1 hour. The reaction solution was cooled to room temperature, and water was added. The mixture was extracted with ethyl acetate (20 ml×2). The organic phases were combined, dried over anhydrous sodium sulfate and filtered. The filtrate was concentrated under reduced pressure to obtain the crude title compound (E)-methyl 3-(3,5-difluoro-4-((1S,3R/1R,3S)-2-(2-fluoro-2-methylpropyl)-3-methyl-6-(2H-tetrazol-5-yl)-1,2,3,4-tetrahydroisoquinolin-1-yl)phenyl)acrylate 51a (20 mg) as a yellow solid, which was used directly in the next step without further purification.

Step 2

(E)-methyl 3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-3-methyl-6-(2H-tetrazol-5-yl)-1,2,3,4-tetrahydroisoquinolin-1-yl)phenyl)acrylate 51a (20 mg, 0.041 mmol), methyl iodide (9 mg, 0.061 mmol) and potassium carbonate (11 mg, 0.082 mmol) were dissolved in 1 mL of N,N-dimethylformamide. The reaction mixture was stirred for 12 hours at room temperature. Water was added, and the reaction solution was extracted with ethyl acetate (20 ml×2). The organic phases were combined, dried over anhydrous sodium sulfate and filtered. The filtrate was concentrated under reduced pressure to obtain the crude title compound (E)-methyl 3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylate 51b (20 mg) as a yellow solid, which was used directly in the next step without further purification.

Step 3

(E)-3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylic Acid The crude (E)-methyl 3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylate 51b (20 mg, 0.04 mmol) was dissolved in 1.5 mL of a mixture of methanol and tetrahydrofuran (V/V=2:1), then 0.2 mL of 1M lithium hydroxide solution was added. After stirring at room temperature for 12 hours, the reaction solution was concentrated under reduced pressure, and 1 M HCl was added to the residue until the pH was 4. The mixture was extracted with ethyl acetate (20 mL×2). The organic phases were combined, dried over anhydrous sodium sulfate and filtered. The filtrate was concentrated under reduced pressure. The resulting residue was purified by thin layer chromatography with elution system A to obtain the title compound (E)-3-(3,5-difluoro-4-((1S,3R/1R,3S)-2-(2-fluoro-2-methylpropyl)-3-methyl-6-(2-methyl-2H-tetrazol-5-yl)-1,2,3,4-tetrahydroisoquinolin-1-yl)phenyl)acrylic acid 51 (10 mg, yield 50%) as a white solid.

MS m/z (ESI): 486.2 [M+1]

$^1$H NMR (400 MHz, DMSO-$d_6$) δ 12.53 (s, 1H), 7.82 (d, 1H), 7.75 (d, 1H), 7.55-7.46 (m, 3H), 6.87 (d, 1H), 6.66 (d, 1H), 5.19 (s, 1H), 4.52 (s, 3H), 3.59-3.51 (m, 1H), 3.33-3.28 (m, 1H), 3.04-2.91 (m, 1H), 2.75 (dd, 1H), 2.29-2.18 (m, 1H), 1.18-1.04 (m, 6H), 0.97 (d, 3H).

Example 52

(E)-3-(3,5-difluoro-4-((1S,3R/1R,3S)-2-(2-fluoro-2-methylpropyl)-6-(1-isobutyl-1H-pyrazol-4-yl)-3-methyl-1,2,3,4-tetrahydroisoquinolin-1-yl)phenyl) acrylic Acid

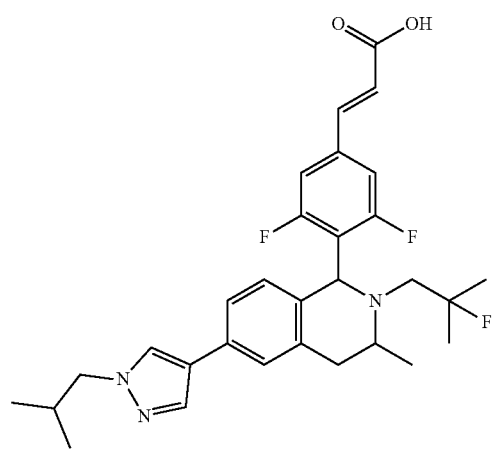

52

In accordance with the synthetic route of Example 10, the starting material 2-methyl-5-(4,4,5,5-tetramethyl-1,3,2-dioxaborolan-2-yl)thiazole 10b used in step 2 was replaced with 1-isobutyl-4-(4,4,5,5-tetramethyl-1,3,2-dioxaborolan-2-yl)-1H-pyrazol that was prepared by a method disclosed in the patent application publication "WO2014153214", accordingly, the title compound (E)-3-(3,5-difluoro-4-((1S,3R/1R,3S)-2-(2-fluoro-2-methylpropyl)-6-(1-isobutyl-1H-pyrazol-4-yl)-3-methyl-1,2,3,4-tetrahydroisoquinolin-1-yl)phenyl)acrylic acid 52 was prepared.

MS m/z (ESI): 526.6 [M+1]

$^1$H NMR (400 MHz, CD$_3$OD) δ 7.93 (s, 1H), 7.80 (s, 1H), 7.58 (d, 1H), 7.33 (s, 1H), 7.21 (t, 3H), 6.70 (d, 1H), 6.53 (d, 1H), 5.23 (s, 1H), 3.96 (d, 2H), 3.70-3.74 (m, 1H), 3.38-3.42 (dd, 1H), 3.01 (t, 1H), 2.63-2.68 (dd, 1H), 2.36-2.17 (m, 2H), 1.19-1.10 (dd, 6H), 1.03 (s, 3H), 0.93 (d, 6H).

Example 53

(E)-3-(3,5-difluoro-4-((1S,3R/1R,3S)-2-(2-fluoro-2-methylpropyl)-3-methyl-6-(3-methyl-1,2,4-oxadiazol-5-yl)-1,2,3,4-tetrahydroisoquinolin-1-yl)phenyl) acrylic Acid

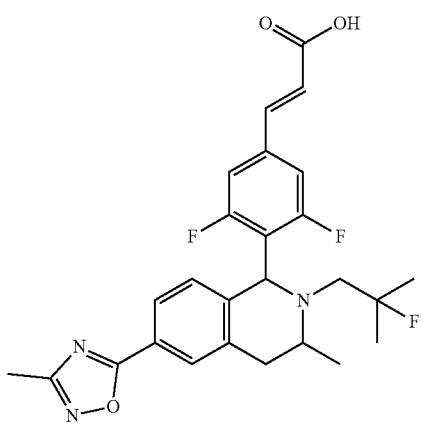

53

In accordance with the synthetic route of Example 19, the starting material N-hydroxy propionamidine used in step 2 was replaced with N-hydroxyacetamidine, accordingly, the title compound (E)-3-(3,5-difluoro-4-((1S,3R/1R,3S)-2-(2-fluoro-2-methylpropyl)-3-methyl-6-(3-methyl-1,2,4-oxadiazol-5-yl)-1,2,3,4-tetrahydroisoquinolin-1-yl)phenyl)acrylic acid 53 was prepared.

MS m/z (ESI): 486.0 [M+1]

$^1$H NMR (400 MHz, DMSO-d$_6$): δ 12.05 (s, 1H), 7.90 (s, 1H), 7.77 (d, 1H), 7.52-7.46 (m, 3H), 6.98 (d, 1H), 6.66 (d, 1H), 5.23 (s, 1H), 3.62-3.57 (m, 1H), 2.95 (t, 1H), 2.79 (d, 1H), 2.41 (s, 3H), 2.29-2.19 (m, 2H), 1.11 (dd, 6H), 0.97 (d, 3H)

Example 54

(E)-3-(3,5-difluoro-4-((1S,3R/1R,3S)-2-(2-fluoro-2-methylpropyl)-3-methyl-6-(oxazol-2-yl)-1,2,3,4-tetrahydroisoquinolin-1-yl)phenyl)acrylic Acid

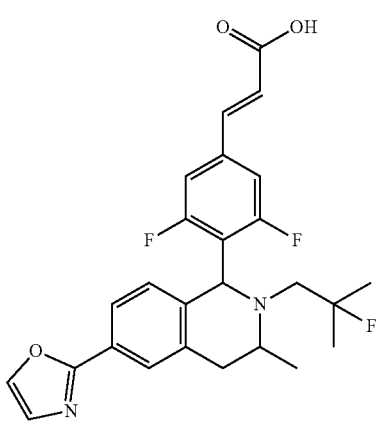

54

In accordance with the synthetic route of Example 10, the starting material 2-methyl-5-(4,4,5,5-tetramethyl-1,3,2-dioxaborolan-2-yl)thiazole 10b used in step 2 was replaced with oxazole, accordingly, the title compound (E)-3-(3,5-difluoro-4-((1S,3R/1R,3S)-2-(2-fluoro-2-methylpropyl)-3-methyl-6-(oxazol-2-yl)-1,2,3,4-tetrahydroisoquinolin-1-yl)phenyl)acrylic acid 54 was prepared.

MS m/z (ESI): 471.5[M+1]

$^1$H NMR (400 MHz, CD$_3$OD) δ 7.98 (s, 1H), 7.83 (s, 1H), 7.71 (d, 1H), 7.57 (d, 1H), 7.30 (s, 1H), 7.23 (d, 2H), 6.89 (d, 1H), 6.55 (d, 1H), 5.30 (s, 1H), 3.78-3.74 (m, 1H), 3.47-3.42 (m, 1H), 3.06-2.99 (m, 1H), 2.77-2.72 (m, 1H), 2.38-2.27 (m, 1H), 1.20-1.04 (m, 9H).

Example 55

(E)-3-(3,5-difluoro-4-((1S,3R/1R,3S)-2-(2-fluoro-2-methylpropyl)-3-methyl-6-(1-methyl-1H-pyrazol-4-yl)-1,2,3,4-tetrahydroisoquinolin-1-yl)phenyl)acrylic Acid

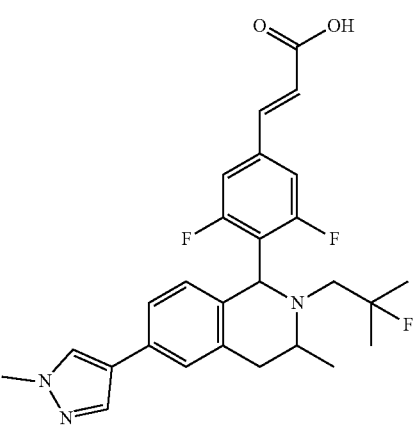

55

In accordance with the synthetic route of Example 10, the starting material 2-methyl-5-(4,4,5,5-tetramethyl-1,3,2-dioxaborolan-2-yl)thiazole 10b used in step 2 was replaced with 4-(4,4,5,5-tetramethyl-1,3,2-dioxaborolan-2-yl)-1H-pyrazol, accordingly, the title compound (E)-3-(3,5-difluoro-4-((1S,3R/1R,3S)-2-(2-fluoro-2-methylpropyl)-3-methyl-6-(1-methyl-1H-pyrazol-4-yl)-1,2,3,4-tetrahydroisoquinolin-1-yl)phenyl)acrylic acid 55 was prepared.

MS m/z (ESI): 484.5 [M+1]

$^1$H NMR (400 MHz, CD$_3$OD) δ 7.99 (s, 1H), 7.84 (s, 1H), 7.63-7.40 (m, 5H), 7.06-7.00 (m, 1H), 6.63 (d, 1H), 6.10-6.02 (m, 1H), 4.09-4.00 (m, 1H), 3.93 (s, 3H), 3.43-3.37 (m, 2H), 3.17-3.10 (m, 2H), 1.56-1.44 (m, 9H).

Example 56 and Example 57

(E)-3-(3,5-difluoro-4-((1R,3S)-2-(2-fluoro-2-methylpropyl)-3-methyl-6-(1-methyl-1H-pyrazol-4-yl)-1,2,3,4-tetrahydroisoquinolin-1-yl)phenyl)acrylic Acid (E)-3-(3,5-difluoro-4-((1S,3R)-2-(2-fluoro-2-methylpropyl)-3-methyl-6-(1-methyl-1H-pyrazol-4-yl)-1,2,3,4-tetrahydroisoquinolin-1-yl)phenyl)acrylic Acid

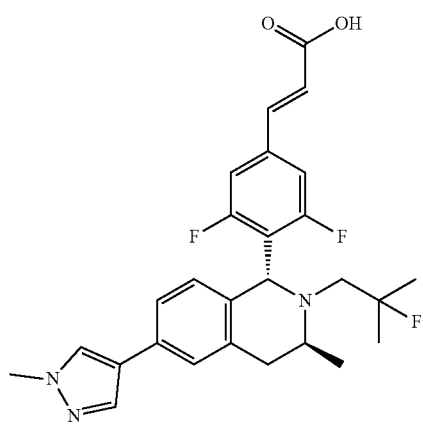

56

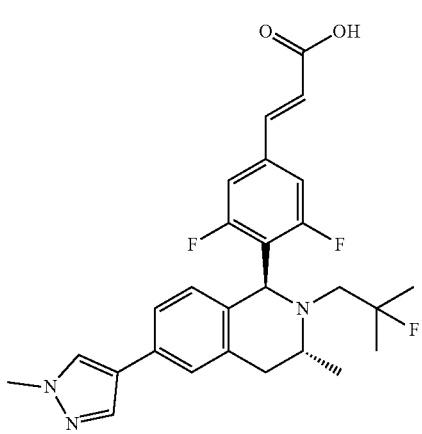

57

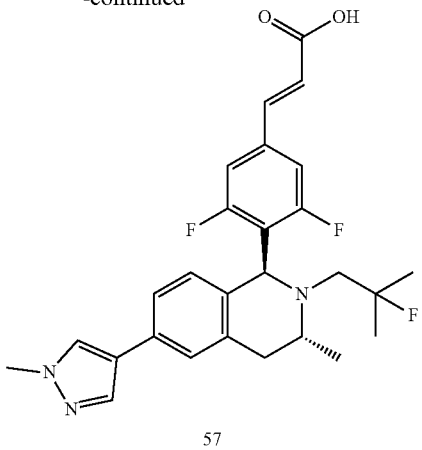

57

(E)-3-(3,5-difluoro-4-((1S,3R/1R,3S)-2-(2-fluoro-2-methylpropyl)-3-methyl-6-(1-methyl-1H-pyrazol-4-yl)-1,2,3,4-tetrahydroisoquinolin-1-yl)phenyl)acrylic acid 55 (605 mg, 1.25 mmol) was separated chirally (separation conditions: chiral preparative column CHIRALPAK AD-H, 0.46 cm I.D.×25 cm L; mobile phase: ethanol:TFA=100:0.1, flow rate: 1.0 mL/min). The corresponding fractions were collected and concentrated under reduced pressure to obtain the title compounds (E)-3-(3,5-difluoro-4-((1R,3S)-2-(2-fluoro-2-methylpropyl)-3-methyl-6-(1-methyl-1H-pyrazol-4-yl)-1,2,3,4-tetrahydroisoquinolin-1-yl)phenyl)acrylic acid 56 (419.7 mg) as a yellow solid and (E)-3-(3,5-difluoro-4-((1S,3R)-2-(2-fluoro-2-methylpropyl)-3-methyl-6-(1-methyl-1H-pyrazol-4-yl)-1,2,3,4-tetrahydroisoquinolin-1-yl)phenyl)acrylic acid 57 (325.8 mg) as a yellow solid.

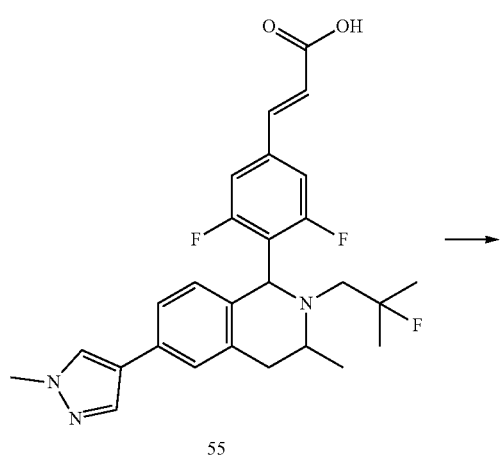

55

→

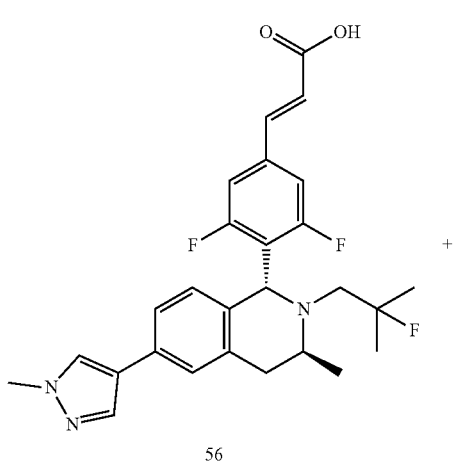

56

+

Example 56

MS m/z (ESI): 484.5 [M+1];

Chiral HPLC analysis: retention time: 6.654 minutes, chiral purity: 99.20% (chromatographic column: CHIRALPAK IE, 0.46 cm I.D.×15 cm L), mobile phase: ethanol/TFA=100/0.1 (V/V/V);

$^1$H NMR (400 MHz, CD$_3$OD) δ 8.00 (s, 1H), 7.85 (s, 1H), 7.62 (d, 1H), 7.51 (s, 1H), 7.43-7.40 (m, 3H), 7.02 (m, 1H), 6.63 (d, 1H), 5.98 (s, 1H), 4.04 (s, 1H), 3.95 (s, 3H), 3.62-3.58 (m, 1H), 3.44-3.38 (dd, 1H), 3.15-3.08 (m, 2H), 1.52-1.32 (m, 9H).

Example 57

MS m/z (ESI): 484.5 [M+1]

Chiral HPLC analysis: retention time 11.021 minutes, chiral purity: 99.9% (column: CHIRALPAK IE, 0.46 cm I.D.×15 cm L, mobile phase: ethanol/TFA=100/0.1 (V/V/V));

$^1$H NMR (400 MHz, CD$_3$OD) δ 8.00 (s, 1H), 7.85 (s, 1H), 7.62 (d, 1H), 7.51 (s, 1H), 7.43-7.40 (m, 3H), 7.02 (m, 1H), 6.63 (d, 1H), 5.98 (s, 1H), 4.04 (s, 1H), 3.95 (s, 3H), 3.62-3.58 (m, 1H), 3.44-3.38 (dd, 1H), 3.15-3.08 (m, 2H), 1.52-1.32 (m, 9H).

Example 58

(E)-3-(4-((1S,3R/1R,3S)-6-(1-cyclopropyl-1H-pyrazol-4-yl)-2-(2-fluoro-2-methylpropyl)-3-methyl-1,2,3,4-tetrahydroisoquinolin-1-yl)-3,5-difluorophenyl)acrylic Acid

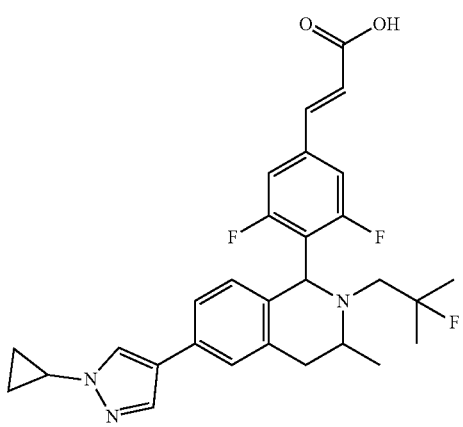

In accordance with the synthetic route of Example 10, the starting material 2-methyl-5-(4,4,5,5-tetramethyl-1,3,2-dioxaborolan-2-yl)thiazole 10b used in step 2 was replaced with 1-cyclopropyl-4-(4,4,5,5-tetramethyl-1,3,2-dioxaborolan-2-yl)-1H-pyrazole, accordingly, the title compound (E)-3-(4-((1S,3R/1R,3S)-6-(1-cyclopropyl-1H-pyrazol-4-yl)-2-(2-fluoro-2-methylpropyl)-3-methyl-1,2,3,4-tetrahydroisoquinolin-1-yl)-3,5-difluorophenyl)acrylic acid 58 was prepared.

MS m/z (ESI): 510.5 [M+1]

$^1$H NMR (400 MHz, CD$_3$OD) δ 8.04 (s, 1H), 7.82 (s, 1H), 7.57 (d, 1H), 7.48 (s, 1H), 7.37-7.33 (m, 3H), 6.96 (s, 1H), 6.61 (d, 1H), 5.96 (s, 1H), 3.99 (s, 1H), 3.71-3.67 (m, 1H), 3.44-3.38 (dd, 1H), 3.25-3.23 (m, 1H), 3.15-2.88 (m, 2H), 1.64-1.21 (m, 9H), 1.14-1.08 (m, 4H).

Example 59

(E)-3-(3,5-difluoro-4-((1S,3R/1R,3S)-2-(2-fluoro-2-methylpropyl)-3-methyl-6-phenyl-1,2,3,4-tetrahydroisoquinolin-1-yl)phenyl)acrylic Acid

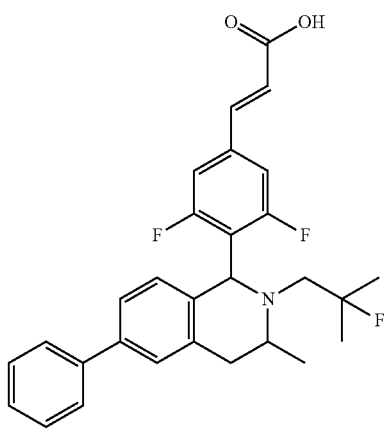

In accordance with the synthetic route of Example 10, the starting material 2-methyl-5-(4,4,5,5-tetramethyl-1,3,2-dioxaborolan-2-yl)thiazole 10b used in step 2 was replaced with phenylboronic acid, accordingly, the title compound (E)-3-(3,5-difluoro-4-((1S,3R/1R,3S)-2-(2-fluoro-2-methylpropyl)-3-methyl-6-phenyl-1, 2,3,4-tetrahydroisoquinolin-1-yl)phenyl)acrylic acid 59 was prepared.

MS m/z (ESI): 480.5[M+1]

$^1$H NMR (400 MHz, CD$_3$OD) δ 8.12 (s, 1H), 7.78-7.76 (s, 1H), 7.66-7.62 (m, 1H), 7.46-7.44 (m, 2H), 7.30 (s, 1H), 7.24-7.14 (m, 4H), 6.77-6.67 (m, 2H), 5.23 (s, 1H), 3.74-3.72 (m, 1H), 3.43-3.38 (m, 1H), 3.03-2.96 (m, 1H), 2.70-2.68 (m, 1H), 2.35-2.20 (m, 1H), 1.77-0.99 (m, 9H)

Example 60

(E)-3-(3,5-difluoro-4-((1S,3R/1R,3S)-2-(2-fluoro-2-methylpropyl)-3-methyl-6-(4-morpholinophenyl)-1,2,3,4-tetrahydroisoquinolin-1-yl)phenyl)acrylic Acid

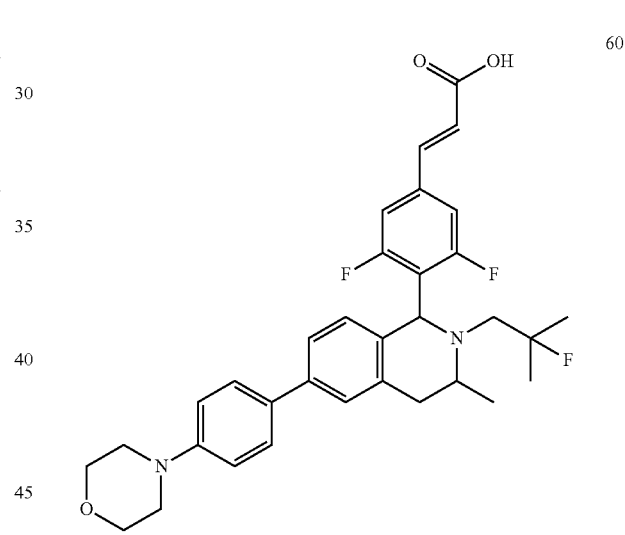

In accordance with the synthetic route of Example 10, the starting material 2-methyl-5-(4,4,5,5-tetramethyl-1,3,2-dioxaborolan-2-yl)thiazole 10b used in step 2 was replaced with 4-(4-(4,4,5,5-tetramethyl-1,3,2-dioxaborolan-2-yl)phenyl) morpholine, accordingly, the title compound (E)-3-(3,5-difluoro-4-((1S,3R/1R,3S)-2-(2-fluoro-2-methylpropyl)-3-methyl-6-(4-morpholinophenyl)-1,2,3,4-tetrahydroisoquinolin-1-yl)phenyl)acrylic acid 60 was prepared.

MS m/z (ESI): 565.5 [M+1]

$^1$H NMR (400 MHz, CDCl$_3$) δ 7.56-7.55 (m, 2H), 7.54-7.36 (m, 3H), 7.30 (m, 1H), 7.00-6.98 (m, 2H), 6.87-6.81 (m, 2H), 6.43 (d, 1H), 5.27 (s, 1H), 3.92 (s, 4H), 3.48 (d, 1H), 3.25 (d, 4H), 3.00 (t, 1H), 2.68 (d, 1H), 2.36-2.25 (m, 1H), 1.48 (s, 1H), 1.30-1.15 (m, 6H), 1.07-1.06 (m, 3H).

Example 61

(E)-3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl)acrylic Acid

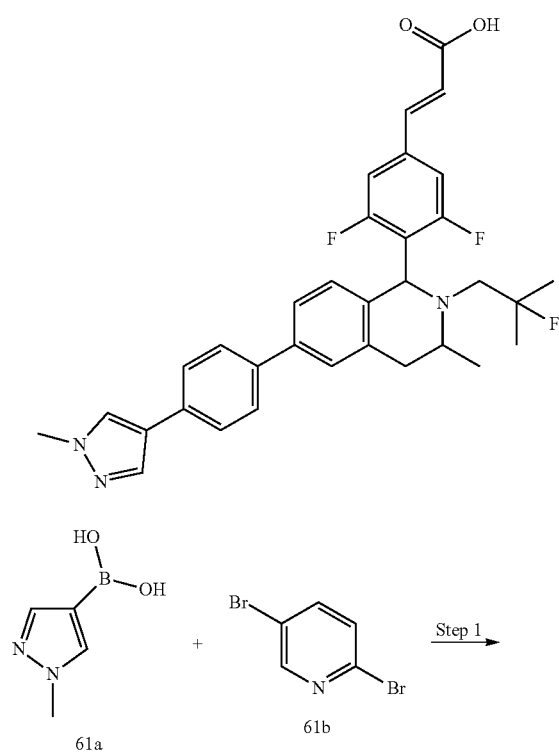

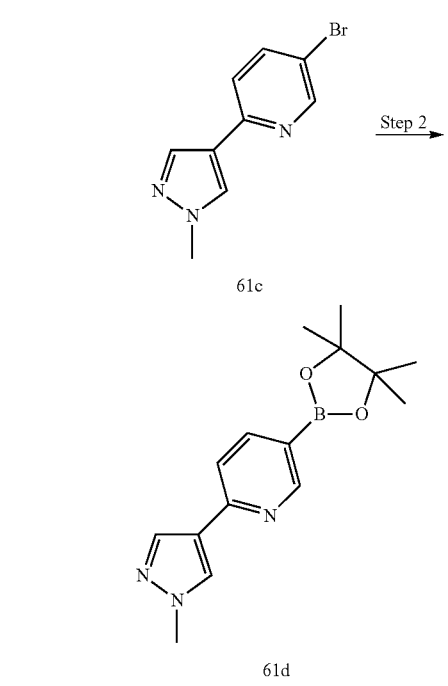

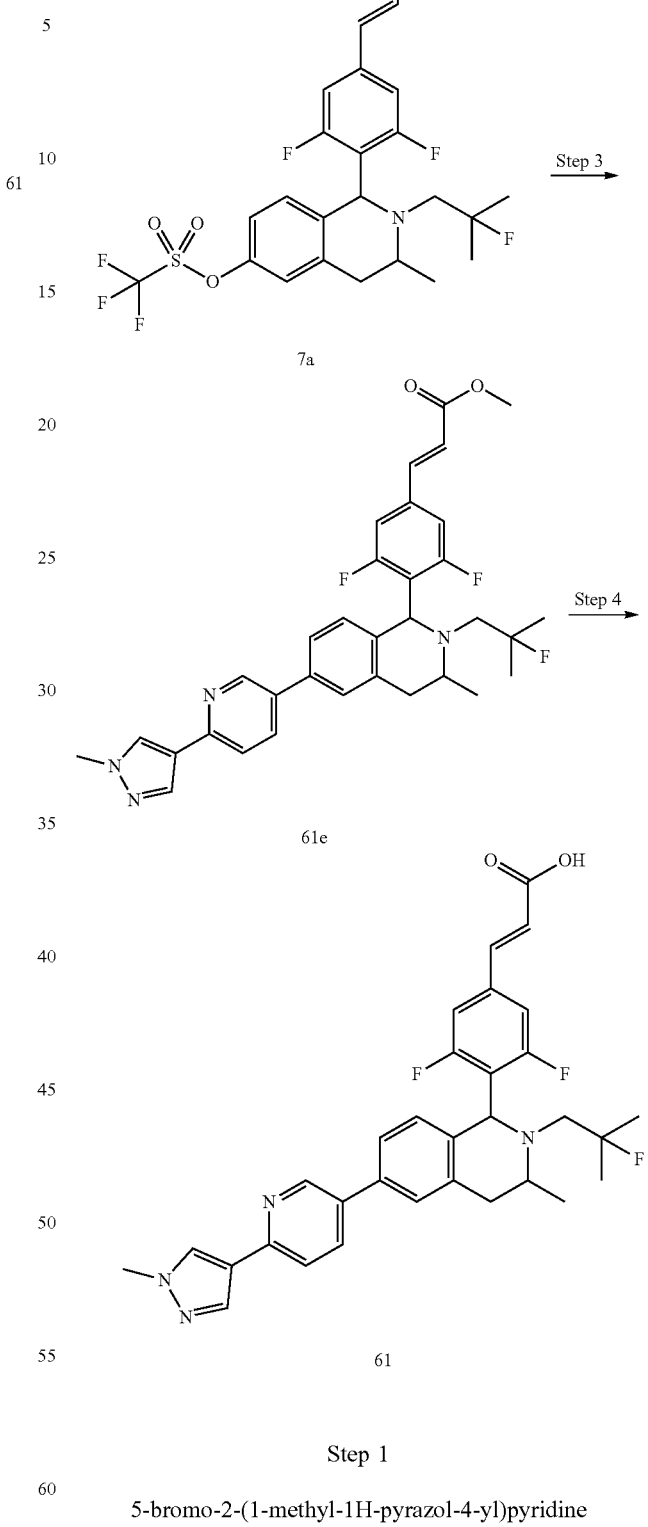

Step 1

5-bromo-2-(1-methyl-1H-pyrazol-4-yl)pyridine (1-methyl-1H-pyrazol-4-yl)boronic acid 61a (0.1 g, 0.794 mmol) was dissolved in 5.5 mL of a mixture of 1,4-dioxane and water (V/V=10:1), then 2,5-dibromopyridine 61b (0.188 g, 0.784 mmol), tetrakis(triphenylphosphine)palladium (92 mg, 0.796 mmol) and sodium carbonate (0.168 g, 1.585 mmol) were added. The mixture was warmed up to 85° C. and stirred for 12 hours. After cooling to room temperature, 20 mL of ethyl acetate was added. The reaction mixture was washed with water, dried over anhydrous sodium sulfate and filtered. The filtrate was concentrated under reduced pressure, and the resulting residue was purified by silica gel column chromatography with elution system B to obtain the title compound 5-bromo-2-(1-methyl-1H-pyrazol-4-yl)pyridine 61c (0.13 g, yield 68%) as a white solid.

Step 2

2-(1-methyl-1H-pyrazol-4-yl)-5-(4,4,5,5-tetramethyl-1,3,2-dioxaborolan-2-yl)pyridine 5-bromo-2-(1-methyl-1H-pyrazol-4-yl)pyridine 61c (0.12 g, 0.504 mmol) was dissolved in 3 mL of 1,4-dioxane, then bis(pinacolato)diboron (0.192 g, 0.756 mmol), [1,1'-Bis(diphenylphosphino)ferrocene]dichlorophalladium (II) (22.13 mg, 0.0302 mmol) and potassium acetate (0.15 g, 1.528 mmol) were added. The reaction was warmed up to 85° C. and stirred for 12 hours. After cooling to room temperature, the reaction mixture was filtered. The filtrate was concentrated under reduced pressure, and the resulting residue was purified by thin-layer chromatography with elution system A to obtain the title compound 2-(1-methyl-1H-pyrazol-4-yl)-5-(4,4,5,5-tetramethyl-1,3,2-dioxaborolan-2-yl)pyridine 61d (35 mg, yield 24%) as a yellow oil.

Step 3

(E)-methyl 3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl) acrylate (E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl)acrylate 7a (69 mg, 0.122 mmol) was dissolved in 3.3 mL of a mixture of 1,4-dioxane and water (V/V=10:1), then 2-(1-methyl-1H-pyrazol-4-yl)-5-(4,4,5,5-tetramethyl-1,3,2-dioxaborolan-2-yl)pyridine 61d (35 mg, 0.123 mmol), tetrakis(triphenylphosphine)palladium (14.1 mg, 0.122 mmol) and sodium carbonate (25.9 g, 0.244 mmol) were added. The reaction was warmed up to 85° C. and stirred for 12 hours. After cooling to room temperature, 20 mL of ethyl acetate was added. The reaction mixture was washed with water, dried over anhydrous sodium sulfate and filtered. The filtrate was concentrated under reduced pressure, and the resulting residue was purified by thin layer chromatography with elution system B to obtain the title compound (E)-methyl 3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl)acrylate 61e (25 mg, yield 36%) as a yellow oil.

Step 4

(E)-3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl)acrylic Acid (E)-methyl 3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl)acrylate 61e (25 mg, 0.0435 mmol) was dissolved in 4 mL of a mixture of tetrahydrofuran and methanol (V/V=3:1), then 0.22 mL of 1 M lithium hydroxide solution was added. The reaction was stirred for 2 hours at room temperature. Then, 10% citric acid solution was added to adjust the pH to 3-4. Ethyl acetate (20 mL) was added, then the reaction mixture was dried over anhydrous sodium sulfate and filtered. The filtrate was concentrated under reduced pressure, and the resulting residue was purified by thin layer chromatography with elution system A to obtain the title compound (E)-3-(3,5-difluoro-4-((1S,3R/1R,3S)-2-(2-fluoro-2-methylpropyl)-3-methyl-6-(6-(1-methyl-1H-pyrazol-4-yl)pyridin-3-yl)-1,2,3,4-tetrahydroisoquinolin-1-yl)phenyl)acrylic acid 61 (10 mg, yield 41%) as a yellow solid.

MS m/z (ESI): 561.5 [M+1]

$^1$H NMR (400 MHz, CD$_3$OD) δ 8.73 (s, 1H), 8.27 (s, 1H), 8.19 (s, 2H), 7.74-7.72 (d, 1H), 7.59-7.55 (d 1H), 7.48 (s 1H), 7.39-7.37 (d 1H), 7.24-7.22 (d 2H), 6.88-6.86 (d, 1H), 6.57-6.53 (d 1H), 5.30 (s, 1H), 3.99 (s, 3H), 3.77 (s 1H), 3.49-3.45 (m 1H), 3.07-3.00 (m, 1H), 2.77-2.74 (m, 1H), 2.38-2.28 (m, 1H), 1.16-0.92 (m, 9H).

Example 62

(E)-3-(3,5-difluoro-4-((1S,3R/1R,3S)-2-(2-fluoro-2-methylpropyl)-3-methyl-6-(quinolin-3-yl)-1,2,3,4-tetrahydroisoquinolin-1-yl)phenyl)acrylic Acid

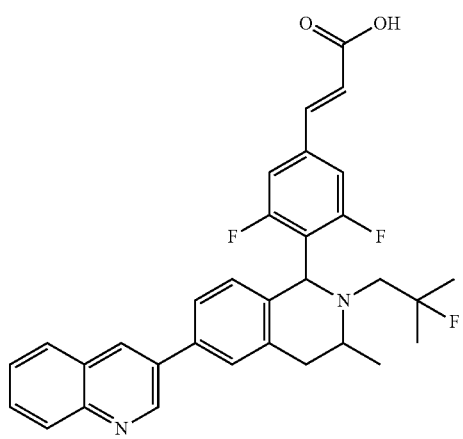

In accordance with the synthetic route of Example 10, the starting material 2-methyl-5-(4,4,5,5-tetramethyl-1,3,2-dioxaborolan-2-yl)thiazole 10b used in step 2 was replaced with 3-(4,4,5,5-tetramethyl-1,3,2-dioxaborolan-2-yl)quinoline that was prepared by a well-known method disclosed in "*Organic & Biomolecular Chemistry*, 2014, 12(37), 7318-7327", accordingly, the title compound (E)-3-(3,5-difluoro-4-((1S,3R/1R,3S)-2-(2-fluoro-2-methylpropyl)-3-methyl-6-(quinolin-3-yl)-1,2,3,4-tetrahydroisoquinolin-1-yl)phenyl) acrylic acid 62 was prepared.

MS m/z (ESI): 531.5 [M+1]

$^1$H NMR (400 MHz, CD$_3$OD) δ 9.16 (s, 1H), 8.59 (s, 1H), 8.09-8.03 (m, 2H), 7.80-7.78 (m 1H), 7.68-7.53 (m 4H), 7.26-7.23 (d, 2H), 6.94-6.92 (d 1H), 6.58-6.54 (d 1H), 5.33 (s, 1H), 3.79 (s 1H), 3.52-3.49 (m 1H), 3.09-3.01 (m, 1H), 2.82-2.79 (m, 1H), 2.40-2.29 (m, 1H), 1.18-0.90 (m, 9H).

Example 63

(E)-3-(3,5-difluoro-4-((1S,3R/1R,3S)-2-(2-fluoro-2-methylpropyl)-3-methyl-6-(quinolin-6-yl)-1,2,3,4-tetrahydroisoquinolin-1-yl)phenyl)acrylic Acid

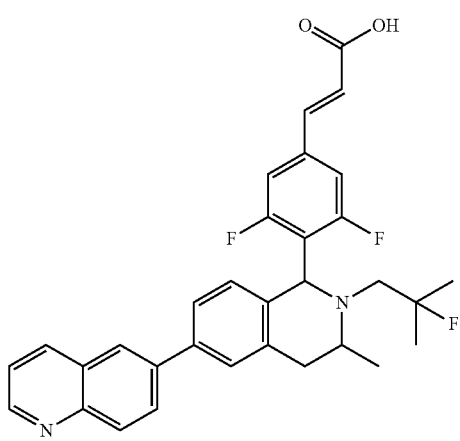

63

In accordance with the synthetic route of Example 10, the starting material 2-methyl-5-(4,4,5,5-tetramethyl-1,3,2-dioxaborolan-2-yl)thiazole 10b used in step 2 was replaced with 6-(4,4,5,5-tetramethyl-1,3,2-dioxaborolan-2-yl)quinoline, accordingly, the title compound (E)-3-(3,5-difluoro-4-((1S,3R/1R,3S)-2-(2-fluoro-2-methylpropyl)-3-methyl-6-(quinolin-6-yl)-1,2,3,4-tetrahydroisoquinolin-1-yl)phenyl)acrylic acid 63 was prepared.

MS m/z (ESI): 531.6 [M+1]

$^1$H NMR (400 MHz, CD$_3$OD) δ 8.85 (dd, 1H), 8.45 (dd, 1H), 8.19 (t, 1H), 8.10 (d, 2H), 7.62-7.55 (m, 3H), 7.50 (dd, 1H), 7.23 (d, 2H), 6.88 (d, 1H), 6.55 (d, 1H), 5.33 (s, 1H), 3.78 (s, 1H), 3.49 (dd, 1H), 3.05 (t, 1H), 2.78 (dd, 1H), 2.40-2.29 (t, 1H), 1.21-1.12 (t, 6H), 1.08 (t, 3H).

Example 64 and Example 65

(E)-3-(3,5-difluoro-4-((1S,3R)-2-(2-fluoro-2-methylpropyl)-3-methyl-6-(quinolin-6-yl)-1,2,3,4-tetrahydroisoquinolin-1-yl)phenyl)acrylic Acid (E)-3-(3,5-difluoro-4-((1R,3S)-2-(2-fluoro-2-methylpropyl)-3-methyl-6-(quinolin-6-yl)-1,2,3,4-tetrahydroisoquinolin-1-yl)phenyl)acrylic Acid

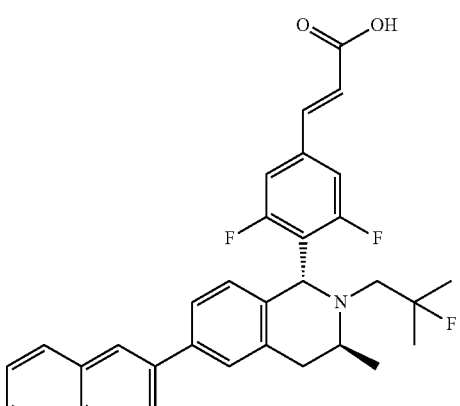

65

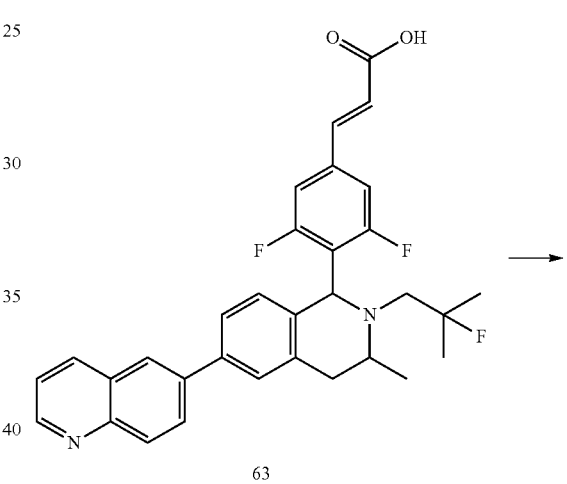

63 →

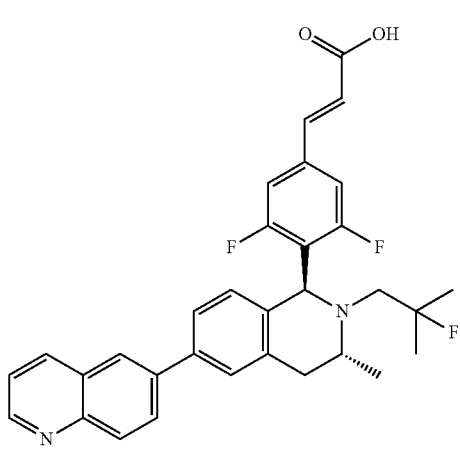

64

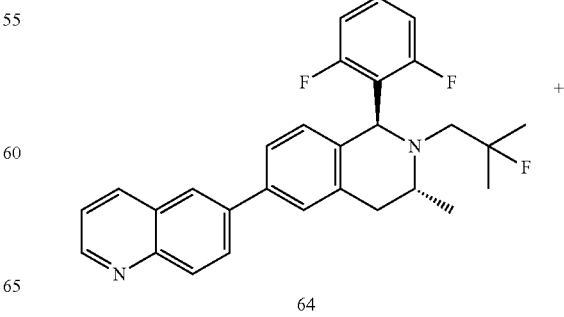

64 +

133

-continued

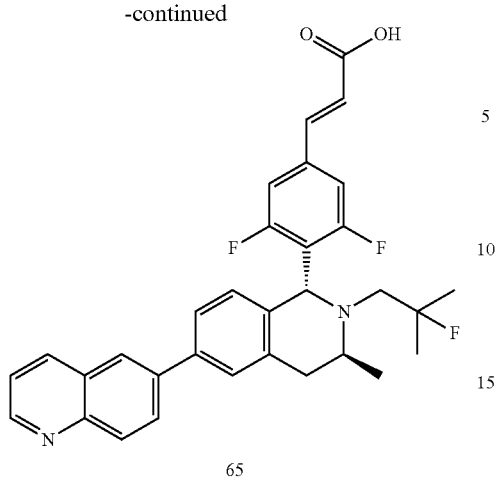

63

(E)-3-(3,5-difluoro-4-((1S,3R/1R,3S)-2-(2-fluoro-2-methylpropyl)-3-methyl-6-(quinolin-6-yl)-1,2,3,4-tetrahydroisoquinolin-1-yl)phenyl)acrylic acid 63 (290 mg, 0.547 mmol) was separated chirally (separation conditions: chiral preparative column CHIRALPAK AD-H, 0.46 cm I.D.×25 cm L; mobile phase: n-hexane:ethanol:TFA=70:30:0.1, flow rate: 1.0 mL/min). The corresponding fractions were collected and concentrated under reduced pressure to obtain the title compounds (E)-3-(3,5-difluoro-4-((1S,3R)-2-(2-fluoro-2-methylpropyl)-3-methyl-6-(quinolin-6-yl)-1,2,3,4-tetrahydroisoquinolin-1-yl)phenyl)acrylic acid 64 (210 mg) as a white solid and (E)-3-(3,5-difluoro-4-((1R,3S)-2-(2-fluoro-2-methylpropyl)-3-methyl-6-(quinolin-6-yl)-1,2,3,4-tetrahydroisoquinolin-1-yl)phenyl)acrylic acid 65 (248 mg) as a white solid.

Example 64

MS m/z (ESI): 531.5 [M+1];

Chiral HPLC analysis: retention time 6.604 minutes, chiral purity: 100% (chromatographic column: CHIRALPAK IE, 0.46 cm I.D.×15 cm L, mobile phase: n-hexane/ethanol/TFA=70/30/0.1 (V/V/V);

$^1$H NMR (400 MHz, CD$_3$OD) δ 9.16 (s, 1H), 8.59 (s, 1H), 8.09-8.03 (m, 2H), 7.80-7.78 (m 1H), 7.68-7.53 (m 4H), 7.26-7.23 (d, 2H), 6.94-6.92 (d 1H), 6.58-6.54 (d 1H), 5.33 (s, 1H), 3.79 (s 1H), 3.52-3.49 (m 1H), 3.09-3.01 (m, 1H), 2.82-2.79 (m, 1H), 2.40-2.29 (m, 1H), 1.18-0.90 (m, 9H).

Example 65

MS m/z (ESI): 531.5 [M+1];

Chiral HPLC analysis: retention time 10.592 minutes, chiral purity: 99.2% (chromatographic column: CHIRALPAK IE, 0.46 cm I.D.×15 cm L, mobile phase: n-hexane/ethanol/TFA=70/30/0.1 (V/V/V);

$^1$H NMR (400 MHz, CD$_3$OD) δ 9.16 (s, 1H), 8.59 (s, 1H), 8.09-8.03 (m, 2H), 7.80-7.78 (m 1H), 7.68-7.53 (m 4H), 7.26-7.23 (d, 2H), 6.94-6.92 (d 1H), 6.58-6.54 (d 1H), 5.33 (s, 1H), 3.79 (s 1H), 3.52-3.49 (m 1H), 3.09-3.01 (m, 1H), 2.82-2.79 (m, 1H), 2.40-2.29 (m, 1H), 1.18-0.90 (m, 9H).

134

Example 66

(E)-3-(3,5-difluoro-4-((1S,3R/1R,3S)-2-(2-fluoro-2-methylpropyl)-3-methyl-6-(2-methylbenzo[d]thiazol-6-yl)-1,2,3,4-tetrahydroisoquinolin-1-yl)phenyl)acrylic Acid

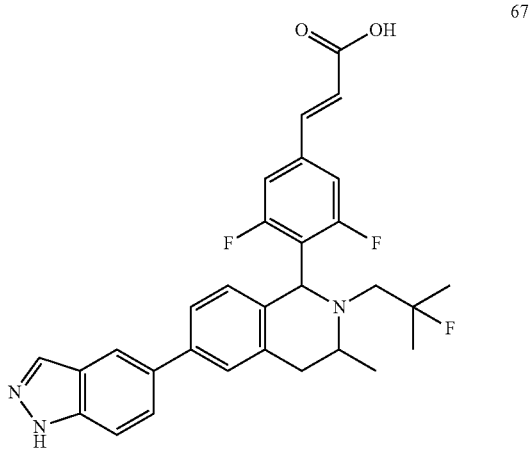 [SMILES: CC1Cc2cc(-c3ccc4[nH]ncc4c3)ccc2C(c2c(F)cc(/C=C/C(=O)O)cc2F)N1CC(C)(C)F]

66

In accordance with the synthetic route of Example 10, the starting material 2-methyl-5-(4,4,5,5-tetramethyl-1,3,2-dioxaborolan-2-yl)thiazole 10b used in step 2 was replaced with 2-methyl-6-(4,4,5,5-tetramethyl-1,3,2-dioxaborolan-2-yl) benzo[d]thiazole that was prepared by a well-known method disclosed in "Journal of the American Chemical Society, 2014, 136(11), 4287-4299", accordingly, the title compound (E)-3-(3,5-difluoro-4-((1S,3R/1R,3S)-2-(2-fluoro-2-methylpropyl)-3-methyl-6-(2-methylbenzo[d]thiazol-6-yl)-1,2,3,4-tetrahydroisoquinolin-1-yl)phenyl) acrylic acid 66 was prepared.

MS m/z (ESI): 551.0 [M+1]

$^1$H NMR (400 MHz, CD$_3$OD) δ 8.13 (s, 1H), 7.91 (d, 1H), 7.73 (d, 1H), 7.58 (d, 1H), 7.46 (s, 1H), 7.36 (d, 1H), 7.20 (d, 2H), 6.82 (d, 1H), 6.53 (d, 1H), 5.29 (s, 1H), 3.75 (s, 1H), 3.45 (d, 1H), 3.03 (t, 1H), 2.86 (s, 3H), 2.73 (d, 1H), 2.38-2.27 (m, 1H), 1.20-1.11 (m, 6H), 1.05 (d, 3H).

Example 67

(E)-3-(3,5-difluoro-4-((1S,3R/1R,3S)-2-(2-fluoro-2-methylpropyl)-6-(1H-indazol-5-yl)-3-methyl-1,2,3,4-tetrahydroisoquinolin-1-yl)phenyl)acrylic Acid In accordance with the synthetic route of Example 10, the starting material 2-methyl-5-(4,4,5,5-tetramethyl-1,3,2-dioxaborolan-2-yl)thiazole 10b used in step 2 was replaced with 5-(4,4,5,5-tetramethyl-1,3,2-dioxaborolan-2-yl)-1H-indole that was prepared by a well-known method disclosed in "*Organic Letters,* 2012, 14(2), 600-603"), accordingly, the title compound (E)-3-(3,5-difluoro-4-((1S,3R/1R,3S)-2-(2-fluoro-2-methylpropyl)-6-(1H-indazol-5-yl)-3-methyl-1,2,3,4-tetrahydroisoquinolin-1-yl)phenyl)acrylic acid 67 was prepared.

MS m/z (ESI): 520.5 [M+1]

$^1$H NMR (400 MHz, CD$_3$OD) δ 8.10 (s, 1H), 7.99 (s, 1H), 7.71-7.09 (m, 1H), 7.68-7.59 (m 2H), 7.56 (s 1H), 7.37-7.35 (d 2H), 7.22-7.20 (d, 2H), 6.82-6.80 (d 1H), 6.57-6.53 (d 1H), 5.29 (s, 1H), 3.77 (s 1H), 3.50-3.45 (m 1H), 3.08-3.00 (m, 1H), 2.76-2.72 (m, 1H), 2.39-2.28 (m, 1H), 1.20-1.06 (m, 9H).

Example 68 and Example 69

(E)-3-(3,5-difluoro-4-((1R,3R)-2-(2-fluoro-2-methylpropyl)-3-methyl-1,2,3,4-tetrahydro benzofuro[2,3-c]pyridin-1-yl)phenyl)acrylic Acid (E)-3-(3,5-difluoro-4-((1S,3S)-2-(2-fluoro-2-methylpropyl)-3-methyl-1,2,3,4-tetrahydro benzofuro[2,3-c]pyridin-1-yl)phenyl)acrylic Acid

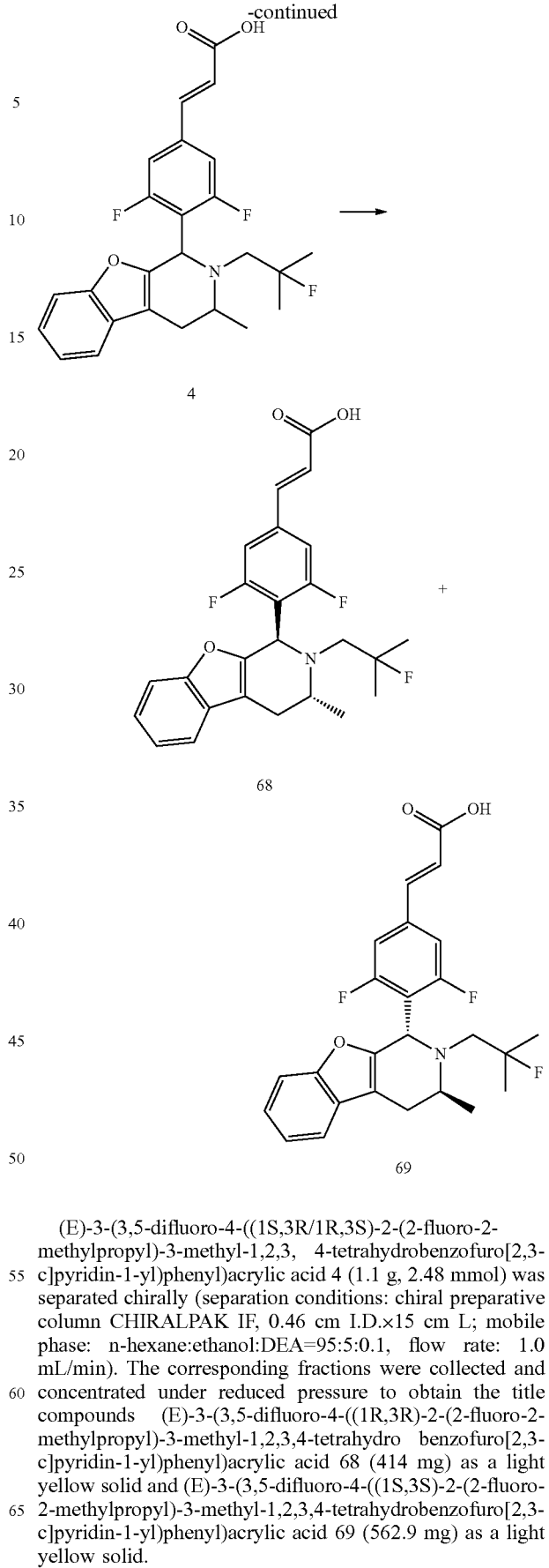

(E)-3-(3,5-difluoro-4-((1S,3R/1R,3S)-2-(2-fluoro-2-methylpropyl)-3-methyl-1,2,3, 4-tetrahydrobenzofuro[2,3-c]pyridin-1-yl)phenyl)acrylic acid 4 (1.1 g, 2.48 mmol) was separated chirally (separation conditions: chiral preparative column CHIRALPAK IF, 0.46 cm I.D.×15 cm L; mobile phase: n-hexane:ethanol:DEA=95:5:0.1, flow rate: 1.0 mL/min). The corresponding fractions were collected and concentrated under reduced pressure to obtain the title compounds (E)-3-(3,5-difluoro-4-((1R,3R)-2-(2-fluoro-2-methylpropyl)-3-methyl-1,2,3,4-tetrahydro benzofuro[2,3-c]pyridin-1-yl)phenyl)acrylic acid 68 (414 mg) as a light yellow solid and (E)-3-(3,5-difluoro-4-((1S,3S)-2-(2-fluoro-2-methylpropyl)-3-methyl-1,2,3,4-tetrahydrobenzofuro[2,3-c]pyridin-1-yl)phenyl)acrylic acid 69 (562.9 mg) as a light yellow solid.

Example 68

MS m/z (ESI): 444.2 [M+1];

Chiral HPLC analysis: retention time 6.878 minutes, chiral purity: 99.52% (chromatographic column: CHIRAL-PAK AD-H, 0.46 cm I.D.×25 cm L, mobile phase: n-hexane/methanol/ethanol/TFA=90/5/5/0.01 (V/V/V/V).

$^1$H NMR (400 MHz, CD$_3$OD) δ 7.61 (d, 1H), 7.53-7.51 (m, 1H), 7.34-7.21 (m, 5H), 6.57 (d, 1H), 5.28 (s, 1H), 3.73-3.71 (m, 1H), 3.03-2.94 (m, 2H), 2.64-2.59 (m, 1H), 2.49-2.39 (m, 1H), 1.31-1.14 (m, 9H).

Example 69

MS m/z (ESI): 444.4 [M+1];

Chiral HPLC analysis: retention time 5.320 minutes, chiral purity: 98.99% (chromatographic column: CHIRAL-PAK AD-H, 0.46 cm I.D.×25 cm L, mobile phase: n-hexane/methanol/ethanol/TFA=90/5/5/0.01 (V/V/V/V);

$^1$H NMR (400 MHz, CD$_3$OD) δ 7.61 (d, 1H), 7.53-7.51 (m, 1H), 7.34-7.21 (m, 5H), 6.57 (d, 1H), 5.28 (s, 1H), 3.73-3.71 (m, 1H), 3.03-2.94 (m, 2H), 2.64-2.59 (m, 1H), 2.49-2.39 (m, 1H), 1.31-1.14 (m, 9H).

Example 70

(E)-3-(3,5-difluoro-4-((6S,8R/6R,8S)-7-(2-fluoro-2-methylpropyl)-8-methyl-6,7,8,9-tetrahydro-3H-pyrazolo[4,3-f]isoquinolin-6-yl)phenyl)acrylic Acid

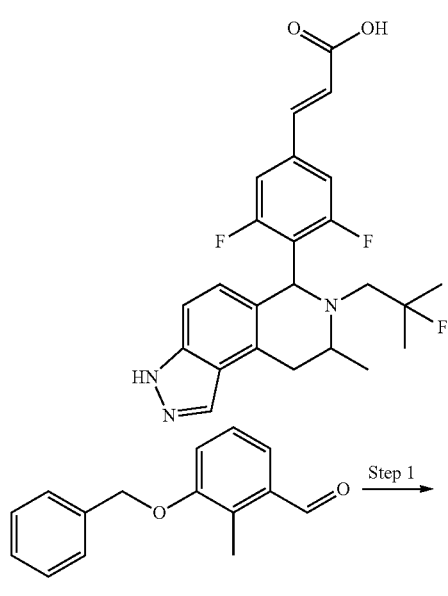

70

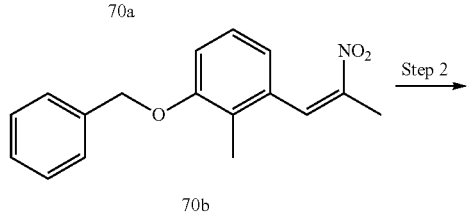

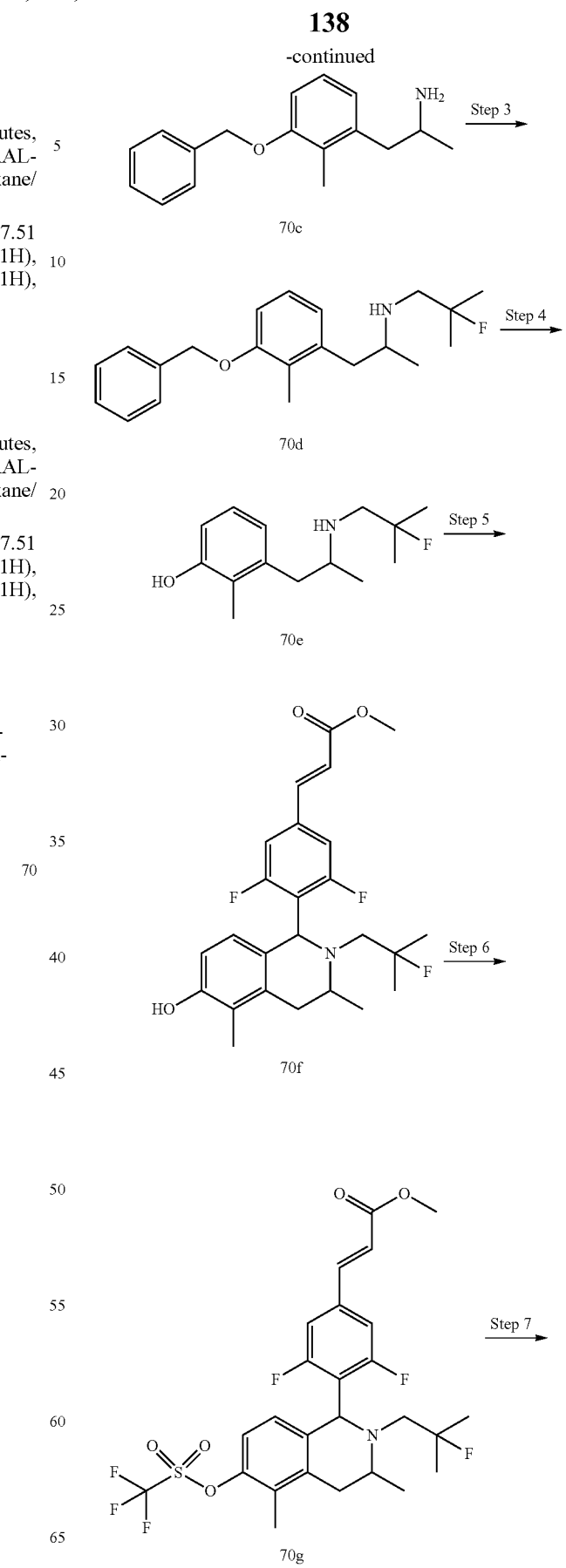

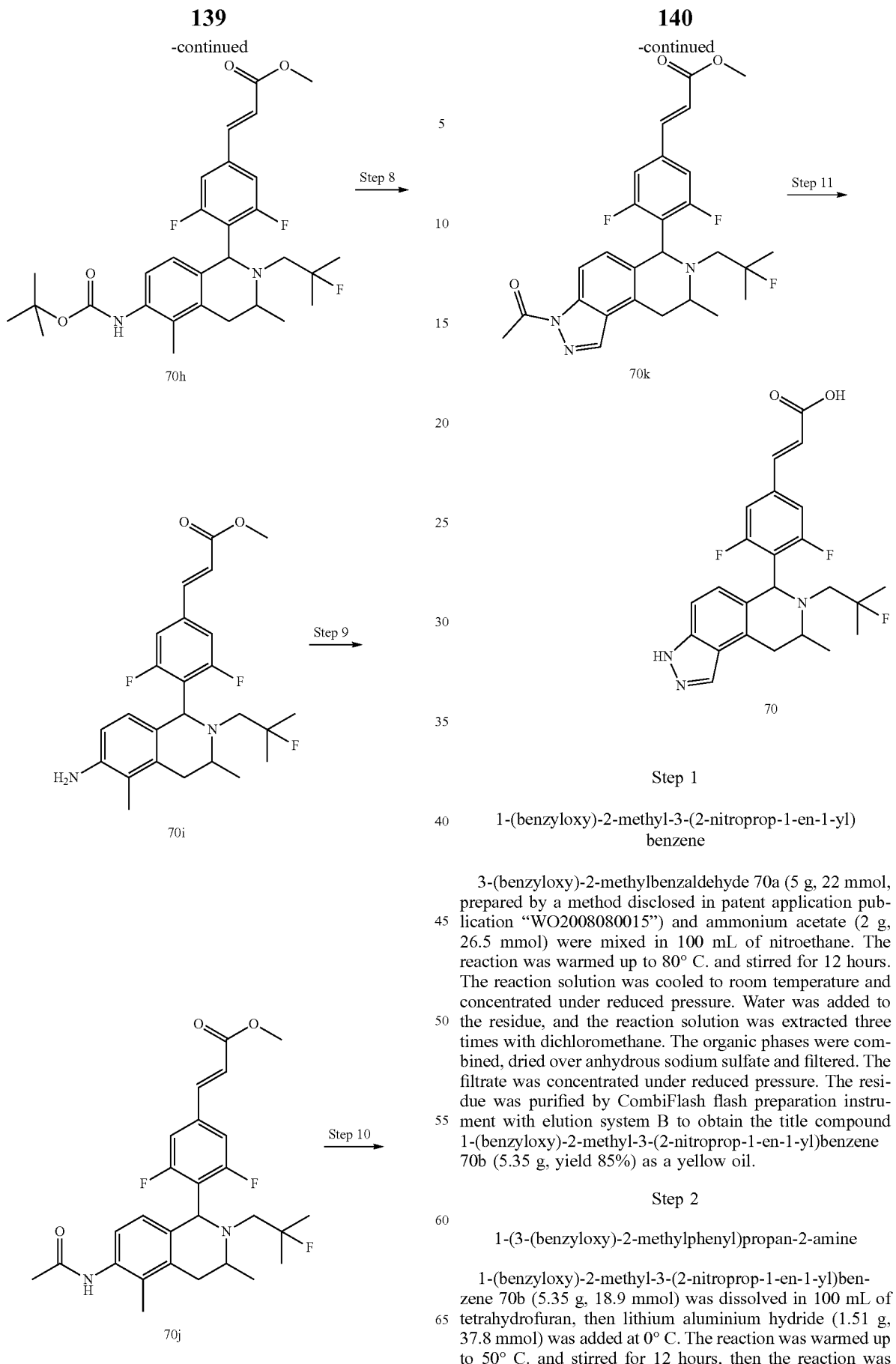

Step 1

1-(benzyloxy)-2-methyl-3-(2-nitroprop-1-en-1-yl)
benzene 3-(benzyloxy)-2-methylbenzaldehyde 70a (5 g, 22 mmol, prepared by a method disclosed in patent application publication "WO2008080015") and ammonium acetate (2 g, 26.5 mmol) were mixed in 100 mL of nitroethane. The reaction was warmed up to 80° C. and stirred for 12 hours. The reaction solution was cooled to room temperature and concentrated under reduced pressure. Water was added to the residue, and the reaction solution was extracted three times with dichloromethane. The organic phases were combined, dried over anhydrous sodium sulfate and filtered. The filtrate was concentrated under reduced pressure. The residue was purified by CombiFlash flash preparation instrument with elution system B to obtain the title compound 1-(benzyloxy)-2-methyl-3-(2-nitroprop-1-en-1-yl)benzene 70b (5.35 g, yield 85%) as a yellow oil.

Step 2

1-(3-(benzyloxy)-2-methylphenyl)propan-2-amine 1-(benzyloxy)-2-methyl-3-(2-nitroprop-1-en-1-yl)benzene 70b (5.35 g, 18.9 mmol) was dissolved in 100 mL of tetrahydrofuran, then lithium aluminium hydride (1.51 g, 37.8 mmol) was added at 0° C. The reaction was warmed up to 50° C. and stirred for 12 hours, then the reaction was stopped. After cooling to room temperature, sodium sulfate decahydrate was added to quench the reaction. The reaction solution was filtered, and the filtrate was concentrated under reduced pressure to obtain the crude title compound 1-(3-(benzyloxy)-2-methylphenyl)propan-2-amine 70c (4.78 g) as a light yellow oil, which was used directly in the next step without further purification.

Step 3

N-(1-(3-(benzyloxy)-2-methylphenyl)propan-2-yl)-2-fluoro-2-methylpropan-1-amine

The crude 1-(3-(benzyloxy)-2-methylphenyl)propan-2-amine 70c (4.78 g, 18.7 mmol), 2-fluoro-2-methylpropyl trifluoromethanesulfonate 1b (8.4 g, 37.4 mmol) and N,N-diisopropylethylamine (7.24 g, 56.1 mmol) were dissolved in 80 mL of 1,4-dioxane. The reaction was warmed up to 100° C. and stirred for 12 hours, then the reaction was stopped. The reaction solution was cooled to room temperature and concentrated under reduced pressure. The residue was purified by CombiFlash flash preparation instrument with elution system B to obtain the title compound N-(1-(3-(benzyloxy)-2-methylphenyl)propan-2-yl)-2-fluoro-2-methylpropan-1-amine 70d (1.25 g, yield 20%) as a yellow brown oil.

Step 4

3-(2-((2-fluoro-2-methylpropyl)amino)propyl)-2-methylphenol

N-(1-(3-(benzyloxy)-2-methylphenyl)propan-2-yl)-2-fluoro-2-methylpropan-1-amine 70d (1.2 g, 3.64 mmol) was dissolved in 50 mL of methanol, then ammonium formate (4.5 g, 72.8 mmol) and Pd/C (300 mg, 10%) were added. The reaction was warmed up to reflux and stirred for 5 hours, then the reaction was stopped. The reaction solution was cooled to room temperature and filtered. The filtrate was concentrated under reduced pressure. The residue was purified by CombiFlash flash preparation instrument with elution system A to obtain the title compound 3-(2-((2-fluoro-2-methylpropyl) amino)propyl)-2-methylphenol 70e (740 mg, yield 91%) as a yellow oil.

Step 5

(E)-methyl 3-(3,5-difluoro-4-((1S,3R/1R,3S)-2-(2-fluoro-2-methylpropyl)-6-hydroxy-3,5-dimethyl-1,2,3,4-tetrahydroisoquinolin-1-yl)phenyl)acrylate 3-(2-((2-fluoro-2-methylpropyl)amino)propyl)-2-methylphenol 70e (740 mg, 3.1 mmol) was dissolved in 30 mL of methanol, then (E)-methyl 3-(3,5-difluoro-4-formylphenyl)acrylate 1e (1.05 g, 4.6 mmol) and acetic acid (560 mg, 9.3 mmol) were added. The reaction mixture was warmed up to 90° C. and stirred for 12 hours, then the reaction was stopped. The reaction solution was cooled to room temperature and concentrated under reduced pressure. The residue was purified by CombiFlash flash preparation instrument with elution system B to obtain the title compound (E)-methyl 3-(3,5-difluoro-4-(2-(2-fluoro-2-methylpropyl)-6-hydroxy-3,5-dimethyl-1,2,3,4-tetrahydroisoquinolin-1-yl) phenyl)acrylate 70f (900 mg, yield 65%) as a yellow solid.

Step 6

(E)-methyl 3-(3,5-difluoro-4-((1S,3R/1R,3S)-2-(2-fluoro-2-methylpropyl)-3,5-dimethyl-6-(((trifluoromethyl)sulfonyl)oxy)-1,2,3,4-tetrahydroisoquinolin-1-yl) phenyl)acrylate (E)-methyl 3-(3,5-difluoro-4-(2-(2-fluoro-2-methylpropyl)-6-hydroxy-3,5-dimethyl-1, 2,3,4-tetrahydroisoquinolin-1-yl)phenyl)acrylate 70f (900 mg, 2 mmol) was dissolved in 50 mL of dichloromethane, then 2,6-dimethylpyridine (428 mg, 4 mmol) and trifluoromethanesulfonic anhydride (850 mg, 3 mmol) were added at 0° C. The reaction mixture was stirred for 1.5 hours at 0° C., then the reaction was stopped. The reaction solution was warmed up to room temperature and concentrated under reduced pressure. The residue was purified by CombiFlash flash preparation instrument with elution system B to obtain the title compound (E)-methyl 3-(3,5-difluoro-4-((1S,3R/1R,3S)-2-(2-fluoro-2-methylpropyl)-3,5-dimethyl-6-(((trifluoromethyl)sulfonyl)oxy)-1,2,3,4-tetrahydroisoquinolin-1-yl)phenyl)acrylate 70g (955 mg, yield 82%) as a colorless oil.

Step 7

(E)-methyl 3-(4-((1S,3R/1R,3S)-6-((tert-butoxycarbonyl)amino)-2-(2-fluoro-2-methylpropyl)-3,5-dimethyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-3,5-dimethyl-6-(((trifluoromethyl) sulfonyl)oxy)-1,2,3,4-tetrahydroisoquinolin-1-yl)phenyl) acrylate 70g (250 mg, 0.43 mmol), tert-butyl carbamate (76 mg, 0.65 mmol), tris(dibenzylideneacetone)dipalladium (79 mg, 0.086 mmol), 4,5-bis(diphenylphosphino)-9,9-dimethylxanthene (100 mg, 0.172 mmol), cesium carbonate (280 mg, 0.86 mmol) and 3 mL of 1,4-dioxane were placed in a microwave tube. The mixture was warmed up to 125° C. and stirred in a microwave for 55 minutes, then the reaction was stopped. The reaction solution was cooled to room temperature and filtered. The filtrate was concentrated under reduced pressure. The residue was purified by CombiFlash flash preparation instrument with elution system B to obtain the title compound (E)-methyl 3-(4-((1S,3R/1R,3S)-6-((tert-butoxycarbonyl)amino)-2-(2-fluoro-2-methylpropyl)-3,5-dimethyl-1,2,3,4-tetrahydroisoquinolin-1-yl)-3,5-difluorophenyl)acrylate 70h (117 mg, yield 50%) as a yellow oil.

Step 8

(E)-methyl 3-(4-((1S,3R/1R,3S)-6-amino-2-(2-fluoro-2-methylpropyl)-3,5-dimethyl-1,2,3,4-tetrahydroisoquinolin-1-yl)-3,5-difluorophenyl)acrylate (E)-methyl 3-(4-((1S,3R/1R,3S)-6-((tert-butoxycarbonyl) amino)-2-(2-fluoro-2-methylpropyl)-3,5-dimethyl-1,2,3,4-tetrahydroisoquinolin-1-yl)-3,5-difluorophenyl)acrylate 70h (50 mg, 0.0915 mmol) was dissolved in 10 mL of dichloromethane, then 5 mL TFA was added. After stirring for 2 hours, the reaction was stopped. The reaction solution was concentrated under reduced pressure. The residue was dissolved in dichloromethane. Saturated sodium carbonate solution was added until the pH of this system is alkaline. The reaction solution was extracted with dichloromethane three times. The organic phases were combined, dried over anhydrous sodium sulfate and filtered. The filtrate was concentrated under reduced pressure to obtain the crude title compound (E)-methyl 3-(4-((1S,3R/1R,3S)-6-amino-2-(2-fluoro-2-methylpropyl)-3,5-dimethyl-1,2,3,4-tetrahydroisoquinolin-1-yl)-3,5-difluorophenyl)acrylate 70i (35 mg) as a brown oil, which was used directly in the next step without further purification.

Step 9

(E)-methyl 3-(4-((1S,3R/1R,3S)-6-acetamido-2-(2-fluoro-2-methylpropyl)-3,5-dimethyl-1,2,3,4-tetrahydroisoquinolin-1-yl)-3,5-difluorophenyl)acrylate (E)-methyl 3-(4-((1S,3R/1R,3S)-6-amino-2-(2-fluoro-2-methylpropyl)-3,5-dimethyl-1,2,3,4-tetrahydroisoquinolin-1-yl)-3,5-difluorophenyl)acrylate 70i (70 mg, 0.16 mmol) was dissolved in 10 mL of dichloromethane, then acetic anhydride (80 mg, 0.78 mmol) and N,N-diisopropylethylamine (100 mg, 0.78 mmol) were added. After stirring for 12 hours, the reaction was stopped. The reaction solution was concentrated under reduced pressure. The residue was purified by CombiFlash flash preparation instrument with elution system B to obtain the title compound (E)-methyl 3-(4-((1S,3R/1R,3S)-6-acetamido-2-(2-fluoro-2-methylpropyl)-3,5-dimethyl-1,2,3,4-tetrahydroisoquinolin-1-yl)-3,5-difluorophenyl)acrylate 70j (50 mg, yield 64%) as a yellow solid.

Step 10

(E)-methyl 3-(4-((6S,8R/6R,8S)-3-acetyl-7-(2-fluoro-2-methylpropyl)-8-methyl-6,7,8, 9-tetrahydro-3H-pyrazolo[4,3-f]isoquinolin-6-yl)-3,5-difluorophenyl)acrylate (E)-methyl 3-(4-((1S,3R/1R,3S)-6-acetamido-2-(2-fluoro-2-methylpropyl)-3,5-dimethyl-1,2,3,4-tetrahydroisoquinolin-1-yl)-3,5-difluorophenyl)acrylate 70j (10 mg, 0.02 mmol) was dissolved in 1.5 mL of ethyl acetate, then acetic anhydride (6 mg, 0.06 mmol), tetrabutylammonium bromide (0.6 mg, 0.002 mmol), potassium acetate (5 mg, 0.05 mmol) and 3-methyl-1-nitrobutane (5 mg, 0.04 mmol) were added. After stirring for 48 hours, the reaction was stopped. The reaction solution was concentrated under reduced pressure. The residue was purified by CombiFlash flash preparation instrument with elution system B to obtain the title compound (E)-methyl 3-(4-((6S,8R/6R,8S)-3-acetyl-7-(2-fluoro-2-methylpropyl)-8-methyl-6,7,8,9-tetrahydro-3H-pyrazolo[4,3-f]isoquinolin-6-yl)-3,5-difluorophenyl) acrylate 70k (7 mg, yield 70%) as a yellow solid.

Step 11

(E)-3-(3,5-difluoro-4-((6S,8R/6R,8S)-7-(2-fluoro-2-methylpropyl)-8-methyl-6,7,8,9-tetrahydro-3H-pyrazolo[4,3-f]isoquinolin-6-yl)phenyl)acrylic Acid (E)-methyl 3-(4-((6S,8R/6R,8S)-3-acetyl-7-(2-fluoro-2-methylpropyl)-8-methyl-6,7, 8, 9-tetrahydro-3H-pyrazolo[4,3-f]isoquinolin-6-yl)-3,5-difluorophenyl)acrylate 70k (5 mg, 0.01 mmol) was dissolved in 10 mL of methanol, then 5 mL of 0.2 M sodium hydroxide solution were added. After stirring for 2 hours, the reaction was stopped. Then, 10% citric acid was added until the pH of the reaction solution was acidic. The mixture was extracted with dichloromethane three times. The organic phases were combined, dried over anhydrous sodium sulfate and filtered. The filtrate was concentrated under reduced pressure. The residue was purified by thin layer chromatography with elution system B to obtain the title compound (E)-3-(3,5-difluoro-4-((6S,8R/6R, 8S)-7-(2-fluoro-2-methylpropyl)-8-methyl-6,7,8,9-tetrahydro-3H-pyrazolo[4,3-f]isoquinolin-6-yl)phenyl)acrylic acid 70 (3 mg, yield 68%) as a yellow solid.

MS m/z (ESI): 444.5 [M+1]

$^1$H NMR (400 MHz, CD$_3$OD) δ 8.10 (s, 1H), 7.58 (d, 1H), 7.25-7.19 (m, 2H), 6.76 (d, 1H), 6.54 (d, 1H), 5.35 (s, 1H), 3.82 (s, 1H), 3.50-3.45 (m, 1H), 3.08-2.99 (m, 2H), 2.42-2.35 (m, 1H), 2.06 (s, 1H), 1.22-1.07 (m, 9H).

Example 71 and Example 72

(E)-3-(3,5-difluoro-4-((5S,7R)-6-(2-fluoro-2-methylpropyl)-7-methyl-5,6,7,8-tetrahydro-[1,3]dioxolo[4,5-g]isoquinolin-5-yl)phenyl)acrylic Acid (E)-3-(3,5-difluoro-4-((5R,7S)-6-(2-fluoro-2-methylpropyl)-7-methyl-5,6,7,8-tetrahydro-[1,3]dioxolo[4,5-g]isoquinolin-5-yl)phenyl)acrylic Acid

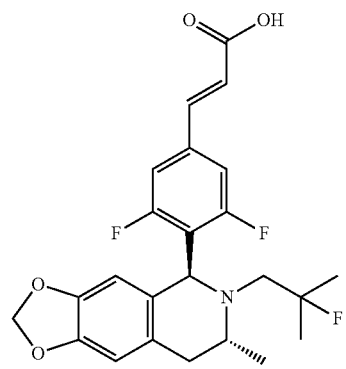

71

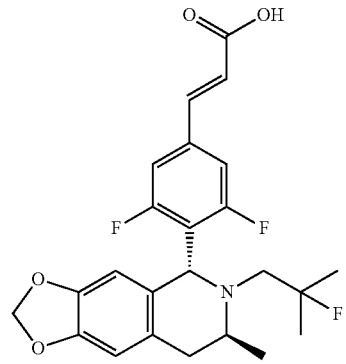

72

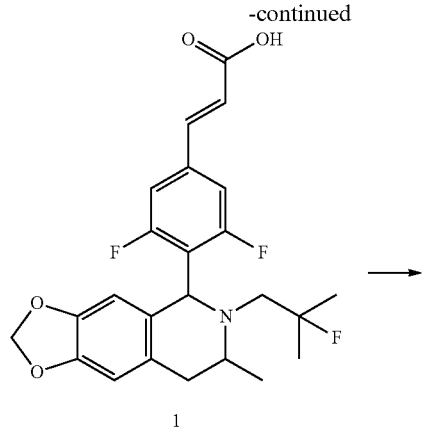

(E)-3-(3,5-difluoro-4-((5S,7R/5R,7S)-6-(2-fluoro-2-methylpropyl)-7-methyl-5,6,7, 8-tetrahydro-[1,3]dioxolo[4,5-g]isoquinolin-5-yl)phenyl)acrylic acid 1 (595 mg, 1.33 mmol) was separated chirally (separation conditions: chiral preparative column CHIRALPAK AD, 5.0 cm I.D.×25 cm L; mobile phase: methanol/CO₂/TFA=20:80:0.1, flow rate: 60 mL/min). The corresponding fractions were collected and concentrated under reduced pressure to obtain the title compounds (E)-3-(3,5-difluoro-4-((5S,7R)-6-(2-fluoro-2-methylpropyl)-7-methyl-5,6,7,8-tetrahydro-[1,3]dioxolo[4,5-g]isoquinolin-5-yl)phenyl)acrylic acid 71 (278 mg) as a yellow solid and (E)-3-(3,5-difluoro-4-((5R,7S)-6-(2-fluoro-2-methylpropyl)-7-methyl-5,6,7,8-tetrahydro-[1,3]dioxolo[4,5-g]isoquinolin-5-yl)phenyl)acrylic acid 72 (249 mg) as a yellow solid.

Example 71

MS m/z (ESI): 448.4 [M+1];
Chiral HPLC analysis: retention time 3.307 minutes, chiral purity: 96.79% (chromatographic column: CHIRALPAK AD-H, 0.46 cm I.D.×15 cm L, mobile phase: methanol/CO₂ O₂/TFA=20:80:0.1 (V/V/V));
$^1$H NMR (400 MHz, CDCl₃) δ 7.55 (d, 1H), 7.07 (s, 2H), 6.69 (s, 1H), 6.42-6.36 (m, 2H), 6.09 (s, 1H), 5.97 (s, 2H), 4.35 (s, 1H), 3.37-3.25 (m, 3H), 2.93-2.83 (m, 1H), 1.73 (d, 3H), 1.51 (m, 6H).

Example 72

MS m/z (ESI): 448.4 [M+1];
Chiral HPLC analysis: retention time 2.173 minutes, chiral purity: 99.37% (chromatographic column: CHIRALPAK AD-H, 0.46 cm I.D.×25 cm L, mobile phase: methanol/CO₂ O₂/TFA=20:80:0.1 (V/V/V));
$^1$H NMR (400 MHz, CDCl₃) δ 7.54 (d, 1H), 7.06 (d, 2H), 6.67 (s, 1H), 6.39 (d, 1H), 6.33 (s, 1H), 5.97-5.95 (m, 3H), 4.25 (s, 1H), 3.39-3.27 (m, 2H), 3.11 (t, 1H), 2.79-2.72 (m, 1H), 1.66 (d, 3H), 1.48-1.43 (m, 6H).

Example 73

(E)-3-(3,5-difluoro-4-((1R,3R/1S,3S)-5-fluoro-2-(2-fluoro-2-methylpropyl)-3-methyl-1, 2,3,4-tetrahydrobenzofuro[2,3-c]pyridin-1-yl)phenyl)acrylic Acid

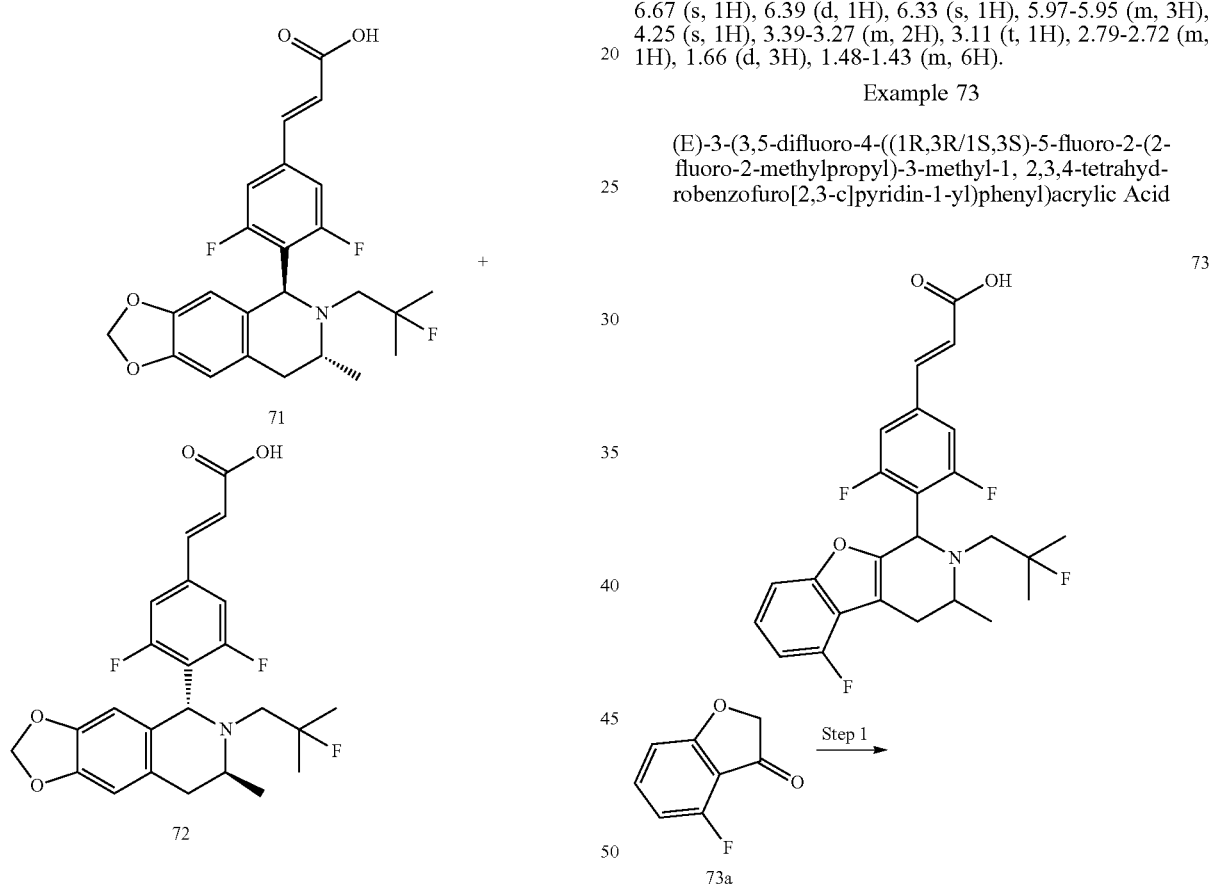

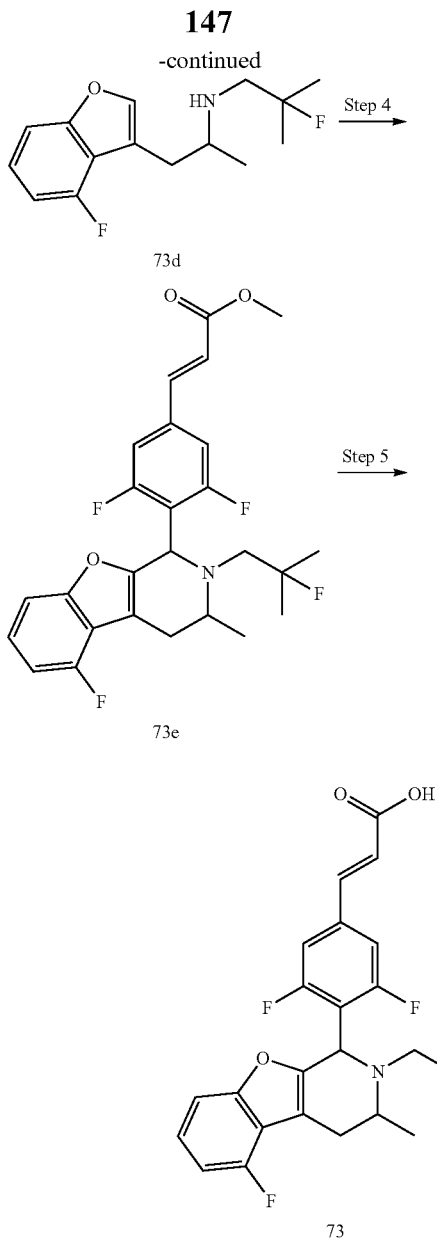

Step 2

1-(4-fluorobenzofuran-3-yl)propan-2-amine 1-(4-fluorobenzofuran-3-yl)propan-2-one 73b (300 mg, 1.56 mmol), ammonium acetate (1.2 g, 15.6 mmol), and sodium acetate (128 mg, 1.56 mmol) were dissolved in 10 mL of methanol, then sodium cyanoborohydride (147 mg, 2.34 mmol) was added, and 0.5 mL of acetic acid was added dropwise. After stirring for 12 hours, the reaction was stopped. Water was added, and the reaction solution was extracted with dichloromethane three times. The organic phases were combined, dried over anhydrous sodium sulfate and filtered. The filtrate was concentrated under reduced pressure. The residue was purified by CombiFlash flash preparation instrument with elution system A to obtain the title compound 1-(4-fluorobenzofuran-3-yl)propan-2-amine 73c (300 mg, yield 66.7%) as a yellow oil.

Step 3

2-fluoro-N-(1-(4-fluorobenzofuran-3-yl)propan-2-yl)-2-methylpropan-1-amine 1-(4-fluorobenzofuran-3-yl)propan-2-amine 73c (200 mg, 1 mmol), 2-fluoro-2-methylpropyl trifluoromethanesulfonate 1b (448 mg, 2 mmol) and N,N-diisopropylethylamine (384 mg, 3 mmol) were dissolved in 10 mL of 1,4-dioxane. The reaction solution was warmed up to 90° C. and was stirred for 12 hours, then the reaction was stopped. The reaction solution was cooled to room temperature and concentrated under reduced pressure. The residue was purified by silica gel column chromatography with elution system A to obtain the title compound 2-fluoro-N-(1-(4-fluorobenzofuran-3-yl)propan-2-yl)-2-methylpropan-1-amine 73d (200 mg, yield 74%) as a yellow oil.

Step 4

(E)-methyl 3-(3,5-difluoro-4-((1R,3R/1S,3S)-5-fluoro-2-(2-fluoro-2-methylpropyl)-3-methyl-1,2,3,4-tetrahydrobenzofuro[2,3-c]pyridin-1-yl)phenyl)acrylate 2-fluoro-N-(1-(4-fluorobenzofuran-3-yl)propan-2-yl)-2-methylpropan-1-amine 73d (200 mg, 0.75 mmol), (E)-methyl 3-(3,5-difluoro-4-formylphenyl)acrylate 1e (254 mg, 1.12 mmol) and triisopropylsilyl chloride (723 mg, 3.75 mmol) were dissolved in 5 mL of N,N-dimethylformamide and placed in a sealed tube. The reaction was heated to 130° C. and reacted for 3 hours, then the reaction was stopped. The reaction solution was cooled to room temperature and concentrated under reduced pressure. The resulting residue was purified by thin layer chromatography with elution system A to obtain the title compound (E)-methyl 3-(3,5-difluoro-4-((1R,3R/1S,3S)-5-fluoro-2-(2-fluoro-2-methylpropyl)-3-methyl-1,2,3,4-tetrahydrobenzofuro[2,3-c]pyridin-1-yl)phenyl)acrylate 73e (300 mg, yield 84%) as a yellow oil.

Step 5

(E)-3-(3,5-difluoro-4-((1R,3R/1S,3S)-5-fluoro-2-(2-fluoro-2-methylpropyl)-3-methyl-1,2,3,4-tetrahydrobenzofuro[2,3-c]pyridin-1-yl)phenyl)acrylic Acid (E)-methyl 3-(3,5-difluoro-4-((1R,3R/1S,3S)-5-fluoro-2-(2-fluoro-2-methylpropyl)-3-methyl-1,2,3,4-tetrahydroben-

Step 1

1-(4-fluorobenzofuran-3-yl)propan-2-one 4-fluorobenzofuran-3(2H)-one 73a (500 mg, 3.29 mmol, prepared with a well-known method disclosed in "*Journal of Medicinal Chemistry*, 2011, 54(15), 5395-5402"), acetonyltriphenylphosphonium chloride (1.754 g, 4.93 mmol), and N,N-diisopropylethylamine (1.27 g, 9.87 mmol) were dissolved in 15 mL of dimethylbenzene. The reaction was warmed up to 140° C. and stirred for 12 hours at 140° C., then the reaction was stopped. The reaction solution was cooled to room temperature and concentrated under reduced pressure. The residue was purified by CombiFlash flash preparation instrument with elution system B to obtain the title compound 1-(4-fluorobenzofuran-3-yl)propan-2-one 73b (350 mg, yield 55%) as a light yellow solid.

zofuro[2,3-c]pyridin-1-yl)phenyl)acrylate 73e (300 mg, 0.63 mmol) was dissolved in 20 mL of methanol, then 10 mL of 0.6 M sodium hydroxide solution were added. After stirring for 12 hours, the reaction was stopped. Then, 10% citric acid was added until the pH of the reaction solution is acidic. The mixture was extracted with dichloromethane three times. The organic phases were combined, dried over anhydrous sodium sulfate and filtered. The filtrate was concentrated under reduced pressure. The residue was purified by thin layer chromatography with elution system A to obtain the title compound (E)-3-(3,5-difluoro-4-((1R,3R/1S,3S)-5-fluoro-2-(2-fluoro-2-methylpropyl)-3-methyl-1,2,3,4-tetrahydrobenzo furo[2,3-c]pyridin-1-yl)phenyl)acrylic acid 73 (200 mg, yield 69%) as a yellow solid.

MS m/z (ESI): 462.4 [M+1]

¹H NMR (400 MHz, CD₃OD) δ 7.62 (d, 1H), 7.33-7.22 (m, 4H), 7.00-6.95 (m, 1H), 6.60 (d, 1H), 5.50 (s, 1H), 3.79 (d, 1H), 3.23-3.12 (m, 2H), 2.88-2.83 (m, 1H), 2.68 (s, 1H), 1.40-1.24 (m, 9H).

Example 74 and Example 75

(E)-3-(3,5-difluoro-4-((1R,3R)-5-fluoro-2-(2-fluoro-2-methylpropyl)-3-methyl-1,2,3,4-tetrahydrobenzofuro[2,3-c]pyridin-1-yl)phenyl)acrylic Acid (E)-3-(3,5-difluoro-4-((1S,3S)-5-fluoro-2-(2-fluoro-2-methylpropyl)-3-methyl-1,2,3,4-tetrahydrobenzofuro[2,3-c]pyridin-1-yl)phenyl)acrylic Acid

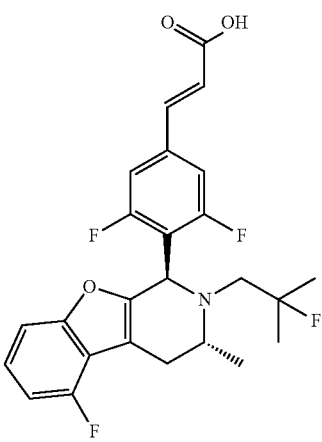

74

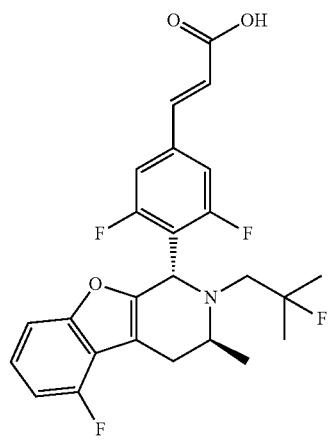

75

(E)-3-(3,5-difluoro-4-((1R,3R/1S,3S)-5-fluoro-2-(2-fluoro-2-methylpropyl)-3-methyl-1,2,3,4-tetrahydrobenzofuro[2,3-c]pyridin-1-yl)phenyl)acrylic acid 73 (410 mg, 0.89 mmol) was separated chirally (separation conditions: chiral preparative column CHIRALPAK IF, 5.0 cm I.D.×25 cm L; mobile phase: n-hexane:ethanol:TFA=95:5:0.1, flow rate: 60 mL/min). The corresponding fractions were collected and concentrated under reduced pressure to obtain the title compounds (E)-3-(3,5-difluoro-4-((1R,3R)-5-fluoro-2-(2-fluoro-2-methylpropyl)-3-methyl-1,2,3,4-tetrahydrobenzofuro[2,3-c]pyridin-1-yl)phenyl)acrylic acid 74 (110 mg) as a yellow solid and (E)-3-(3,5-difluoro-4-((1S,3S)-5-fluoro-2-(2-fluoro-2-methylpropyl)-3-methyl-1,2,3,4-tetrahydrobenzofuro[2,3-c]pyridin-1-yl)phenyl)acrylic acid 75 (200 mg) as a yellow solid.

Example 74

MS m/z (ESI): 462.4 [M+1];

Chiral HPLC analysis: retention time 8.381 minutes, chiral purity: 99.54% (chromatographic column: CHIRALPAK IF, 0.46 cm I.D.×15 cm L, mobile phase: n-hexane:ethanol:TFA=95:5:0.1 (V/V/V));

¹H NMR (400 MHz, CD₃OD) δ 7.62 (d, 1H), 7.33-7.22 (m, 4H), 7.00-6.95 (m, 1H), 6.60 (d, 1H), 5.50 (s, 1H), 3.79 (d, 1H), 3.23-3.12 (m, 2H), 2.88-2.83 (m, 1H), 2.68 (s, 1H), 1.40-1.24 (m, 9H).

Example 75

MS m/z (ESI): 462.4 [M+1];

Chiral HPLC analysis: retention time 5.321 minutes, chiral purity: 99.56% (chromatographic column: CHIRALPAK IF, 0.46 cm I.D.×15 cm L, mobile phase: n-hexane:ethanol:TFA=95:5:0.1 (V/V/V));

¹H NMR (400 MHz, CD₃OD) δ 7.62 (d, 1H), 7.33-7.22 (m, 4H), 7.00-6.95 (m, 1H), 6.60 (d, 1H), 5.50 (s, 1H), 3.79 (d, 1H), 3.23-3.12 (m, 2H), 2.88-2.83 (m, 1H), 2.68 (s, 1H), 1.40-1.24 (m, 9H).

Example 76

(E)-3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic Acid

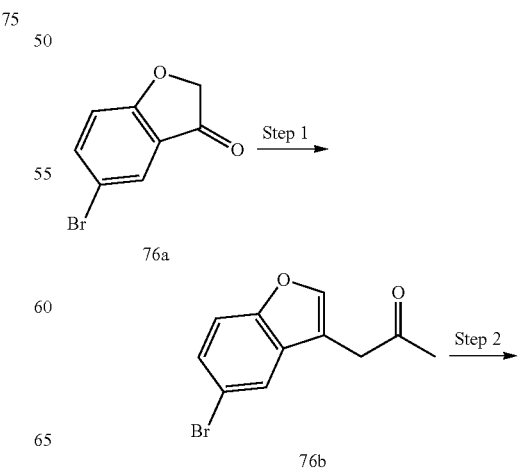

-continued

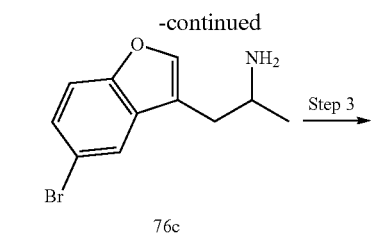
76c

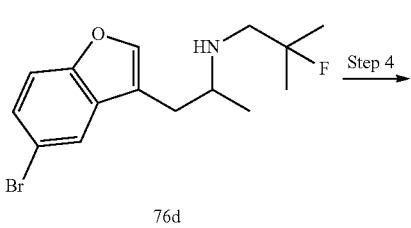
76d

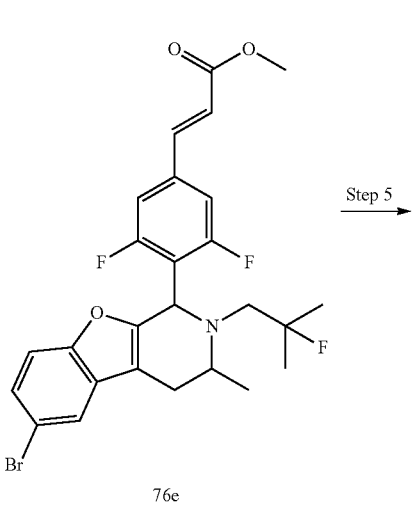
76e

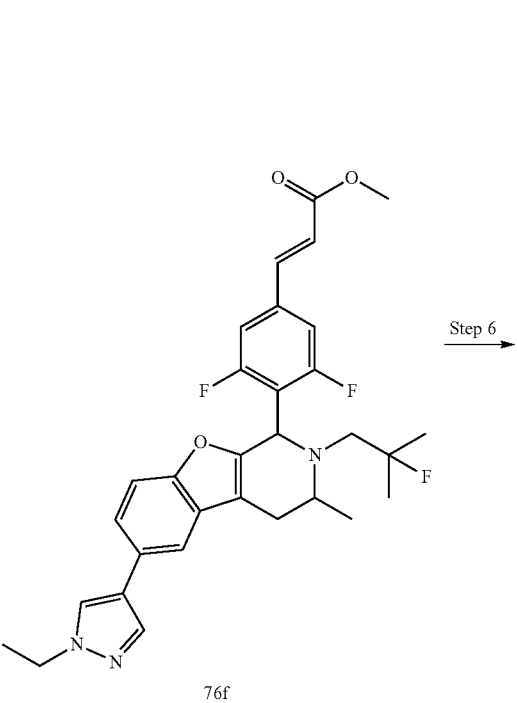
76f

-continued

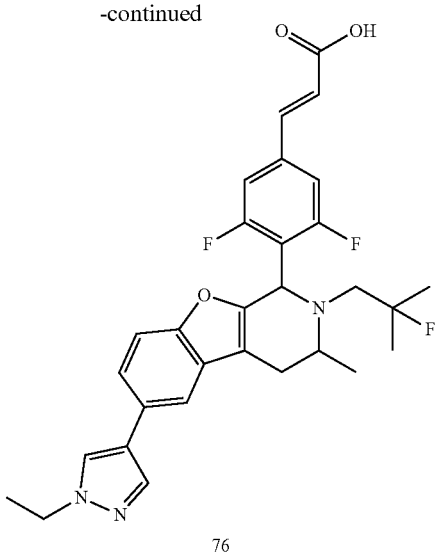
76

Step 1

1-(5-bromobenzofuran-3-yl)propan-2-one 5-bromobenzofuran-3(2H)-one 76a (5 g, 23.471 mmol, prepared by a method disclosed in the patent application "WO2008068974"), acetonyltriphenylphosphonium chloride (12.5 g, 35.206 mmol), and N,N-diisopropylethylamine (9.1 g, 70.413 mmol) were dissolved in 60 mL of dimethylbenzene. The mixture was warmed up to 120° C. and stirred for 12 hours, then the reaction was stopped. The reaction solution was cooled to room temperature and concentrated under reduced pressure. The residue was purified by silica gel column chromatography with elution system B to obtain the title compound 1-(5-bromobenzofuran-3-yl)propan-2-one 76b (3.1 g, yield 53%) as a yellow oil.

Step 2

1-(5-bromobenzofuran-3-yl)propan-2-amine 1-(5-bromobenzofuran-3-yl)propan-2-one 76b (3.1 g, 12.249 mmol), ammonium acetate (9.4 g, 122.486 mmol) and sodium acetate (1 g, 12.249 mmol) were dissolved in 10 mL of methanol, then sodium cyanoborohydride (1.15 g, 18.374 mmol) was added, and 30 drops of acetic acid was added dropwise. After stirring 3 hours, the reaction was stopped. Water was added, then the reaction solution was extracted three times with ethyl acetate. The organic phases were combined, dried over anhydrous sodium sulfate and filtered. The filtrate was concentrated under reduced pressure. The residue was purified by silica gel column chromatography with elution system A to obtain the title compound 1-(5-bromobenzofuran-3-yl)propan-2-amine 76c (1.2 g, yield 39%) as a yellow oil.

Step 3

N-(1-(5-bromobenzofuran-3-yl)propan-2-yl)-2-fluoro-2-methylpropan-1-amine 1-(5-bromobenzofuran-3-yl)propan-2-amine 76c (1.2 g, 4.722 mmol), 2-fluoro-2-methylpropyl trifluoromethanesulfonate 1b (1.59 g, 7.083 mmol) and N,N-diisopropylethylamine (1.83 g, 14.166 mmol) were dissolved in 25 mL of 1,4-dioxane. The mixture was warmed up to 90° C. and stirred for 12 hours, then the reaction was stopped. The reaction solution was cooled to room temperature and concentrated under reduced pressure. The residue was purified by silica gel column chromatography with elution system B to obtain the title compound N-(1-(5-bromobenzofuran-3-yl)propan-2-yl)-2-fluoro-2-methylpropan-1-amine 76d (1.3 g, yield 84%) as a yellow oil.

Step 4

(E)-methyl 3-(4-((1R,3R/1S,3S)-6-bromo-2-(2-fluoro-2-methylpropyl)-3-methyl-1,2,3,4-tetrahydrobenzofuro[2,3-c]pyridin-1-yl)-3,5-difluorophenyl)acrylate N-(1-(5-bromobenzofuran-3-yl)propan-2-yl)-2-fluoro-2-methylpropan-1-amine 76d (1.3 g, 3.961 mmol), (E)-methyl 3-(3,5-difluoro-4-formylphenyl)acrylate 1e (1.34 g, 5.941 mmol) and triisopropylsilyl chloride (3.8 g, 19.805 mmol) were dissolved in 6 mL of N,N-dimethylformamide and placed in a sealed tube. The reaction was heated to 120° C. and reacted for 3 hours, then the reaction was stopped. The reaction solution was cooled to room temperature, and water was added. The reaction solution was extracted with ethyl acetate, and the organic phase was concentrated under reduced pressure. The residue was purified by silica gel column chromatography with elution system B to obtain the title compound (E)-methyl 3-(4-((1R,3R/1S,3S)-6-bromo-2-(2-fluoro-2-methylpropyl)-3-methyl-1,2,3,4-tetrahydrobenzofuro[2,3-c]pyridin-1-yl)-3,5-difluorophenyl)acrylate 76e (460 mg, yield 22%) as a yellow solid.

Step 5

(E)-methyl 3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylate (E)-methyl 3-(4-((1R,3R/1S,3S)-6-bromo-2-(2-fluoro-2-methylpropyl)-3-methyl-1,2,3,4-tetrahydrobenzofuro[2,3-c]pyridin-1-yl)-3,5-difluorophenyl)acrylate 76e (200 mg, 0.373 mmol), 1-ethyl-4-(4,4,5,5-tetramethyl-1,3,2-dioxaborolan-2-yl)-1H-pyrazole 17a (166 mg, 0.746 mmol) and potassium carbonate (154 mg, 1.119 mmol) were dissolved in 6 mL of a mixture of 1,4-dioxane and water (V/V=5:1), then [1,1'-bis(diphenylphosphino)ferrocene]dichloropalladium (II) (27 mg, 0.037 mmol) was added. The mixture was warmed up to 85° C. and was stirred for 12 hours, then the reaction was stopped. The reaction solution was cooled to room temperature and filtered. The filtrate was concentrated under reduced pressure. The residue was purified by silica gel column chromatography with elution system B to obtain the title compound (E)-methyl 3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylate 76f (110 mg, yield 53%) as a yellow oil.

MS m/z (ESI): 551.9 [M+1]

Step 6

(E)-3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic Acid (E)-methyl 3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylate 76f (110 mg, 0.199 mmol) was dissolved in 5 mL of methanol, then 1 mL of 2 M sodium hydroxide was added. The reaction mixture was warmed up to 40° C. and was stirred for 1 hour at 40° C., then the reaction was stopped. The reaction solution was cooled to room temperature, then 1 M citric acid was added to adjust the pH to 5-6. The reaction solution was extracted with ethyl acetate. The organic phases were combined, dried over anhydrous sodium sulfate and filtered. The filtrate was concentrated under reduced pressure. The residue was purified by high performance liquid chromatography to obtain the title compound (E)-3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-di fluorophenyl)acrylic acid 76 (100 mg, yield 93%) as a yellow solid.

MS m/z (ESI): 535.8 [M−1]

$^1$H NMR (400 MHz, CD$_3$OD) δ 8.04 (s, 1H), 7.87 (s, 1H), 7.69 (s, 1H), 7.62 (d, 1H), 7.49 (d, 1H), 7.39-7.32 (m, 3H), 6.61 (d, 1H), 5.62 (s, 1H), 4.30-4.22 (m, 2H), 3.88 (s, 1H), 3.27-3.13 (m, 2H), 2.82-2.79 (m, 2H), 1.52 (t, 3H), 1.39-1.31 (m, 9H).

Example 77

(E)-3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl)phenyl)acrylic Acid

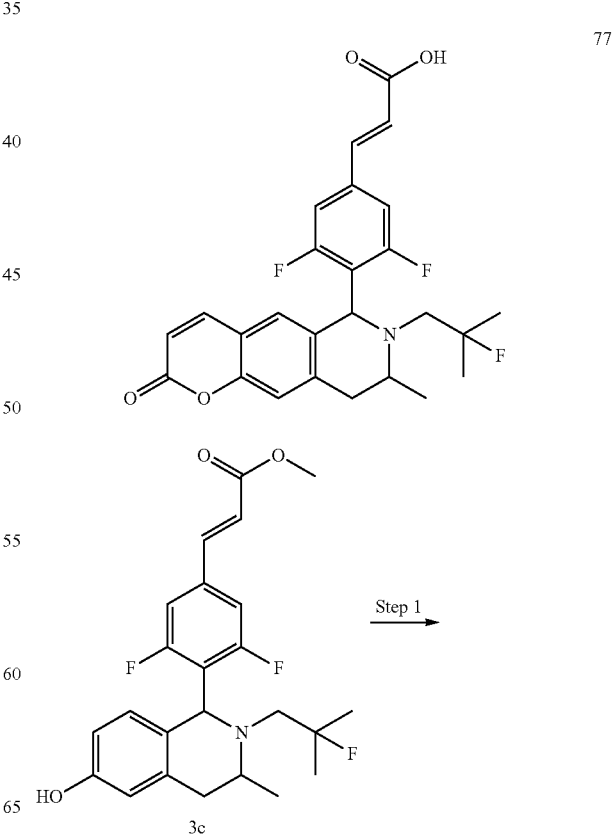

155

-continued

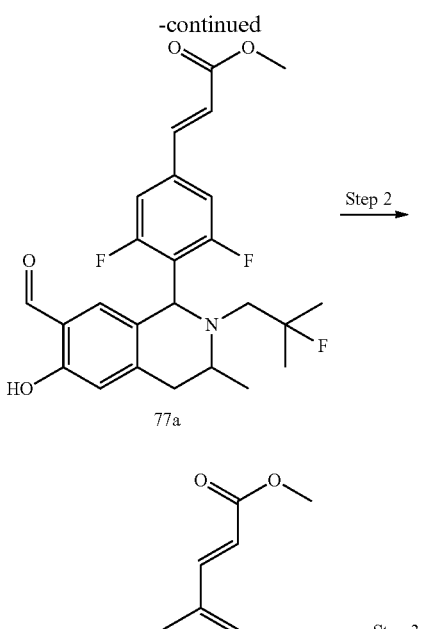

77a

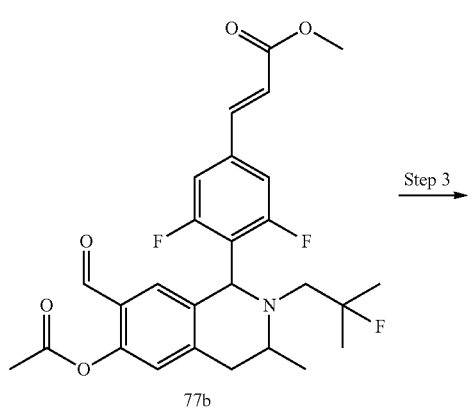

77b

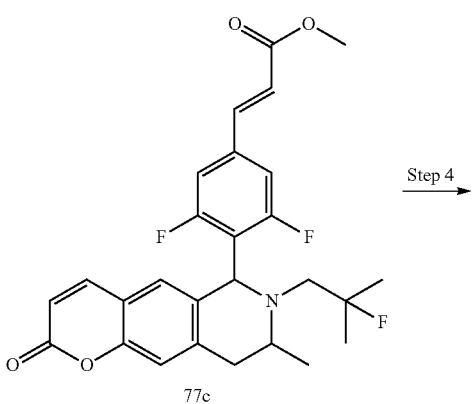

77c

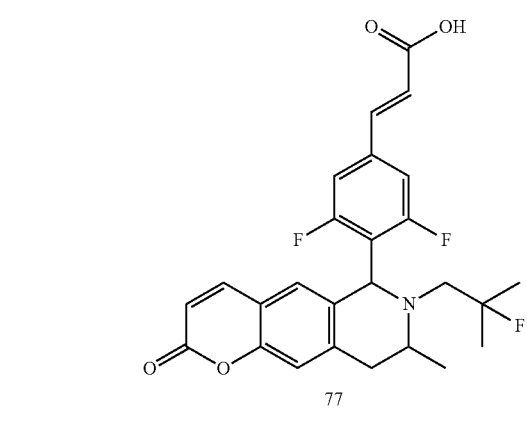

77

156

Step 1

(E)-methyl 3-(3,5-difluoro-4-((1S,3R/1R,3S)-2-(2-fluoro-2-methylpropyl)-7-formyl-6-hydroxy-3-methyl-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (1 g, 2.3 mmol), paraformaldehyde (692.5 mg, 2.3 mmol), magnesium chloride (658 mg, 6.93 mmol) and triethylamine (1.168 g, 11.5 mmol) were dissolved in 33 mL of tetrahydrofuran. The reaction mixture was warmed up to reflux for 4 hours. After cooling to room temperature, ice water was added to quench the reaction. The reaction mixture was extracted with dichloromethane (50 mL×3). The organic phases were combined, dried over anhydrous sodium sulfate and filtered. The filtrate was concentrated under reduced pressure to obtain the crude title compound (E)-methyl 3-(3,5-difluoro-4-((1S,3R/1R, 3S)-2-(2-fluoro-2-methylpropyl)-7-formyl-6-hydroxy-3-m ethyl-1,2,3,4-tetrahydroisoquinolin-1-yl)phenyl)acrylate 77a (1 g) as a light yellow solid, which was used directly in the next step without further purification.

Step 2

(E)-methyl 3-(4-((1S,3R/1R,3S)-6-acetoxy-2-(2-fluoro-2-methylpropyl)-7-formyl-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-7-formyl-6-hydroxy-3-methyl-1,2,3,4-tetrahydroisoquinolin-1-yl) phenyl)acrylate 77a (300 mg, 0.65 mmol) and sodium acetate (160 mg, 1.95 mmol) were dissolved in 9 mL of acetic anhydride. The reaction mixture was warmed up to 150° C. and stirred for 12 hours. The reaction solution was cooled to room temperature and concentrated under reduced pressure. The residue was purified by silica gel column chromotography with elution system B to obtain the title compound (E)-methyl 3-(4-((1S,3R/1R, 3S)-6-acetoxy-2-(2-fluoro-2-methylpropyl)-7-formyl-3-methyl-1,2,3,4-tetrahydroisoquinolin-1-yl)-3,5-difluorophenyl)acrylate 77b (150 mg, yield 47.5%) as a colorless oil.

Step 3

(E)-methyl 3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl)phenyl)acrylate (E)-methyl 3-(4-((1S,3R/1R,3S)-6-acetoxy-2-(2-fluoro-2-methylpropyl)-7-formyl-3-methyl-1,2,3,4-tetrahydroisoquinolin-1-yl)-3,5-difluorophenyl)acrylate 77b (150 mg, 0.3 mmol) and sodium acetate (150 mg, 1.8 mmol) were mixed, warmed up to 180° C., and stirred for 8 hours. The reaction solution was cooled to room temperature. The residue was purified by thin layer chromatography with elution system B to obtain the title compound (E)-methyl 3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl) phenyl)acrylate 77c (70 mg, yield 48.1%) as a colorless oil.

Step 4

(E)-3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl)phenyl)acrylic Acid (E)-methyl 3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl)phenyl)acrylate 77c (60 mg, 0.124 mmol) was dissolved in 2.4 mL of a mixture of tetrahydrofuran and methanol (V/V=3:1). The reaction mixture was cooled to 0° C., and 0.62 mL of 1M lithium hydroxide solution was added. The reaction mixture was naturally warmed up to room temperature and was stirred for 0.5 hour. The reaction solution was concentrated under reduced pressure to remove methanol and tetrehydrofuran. Then, 0.5 M HCl was added to adjust the pH to 5, and the mixture was extracted by ethyl acetate (5 mL×3). The organic phases were combined, dried over anhydrous sodium sulfate and filtered. The filtrate was concentrated under reduced pressure, and the residue was purified by high performance liquid chromatography to obtain the title compound (E)-3-(3,5-difluoro-4-((6S,8R/6R,8S)-7-(2-fluoro-2-methylpropyl)-8-methyl-2-oxo-6,7,8,9-tetrahydro-2H-pyrano[2,3-g]isoquinolin-6-yl)phenyl)acrylic acid 77 (30 mg, yield 51.5%) as a white solid.

MS m/z (ESI): 472.4 [M+1]

$^1$H NMR (400 MHz, CD$_3$OD) δ 7.79 (d, 1H), 7.61 (dd, 1H), 7.29 (d, 2H), 7.23 (s, 1H), 7.16 (s, 1H), 6.58 (d, 1H), 6.35 (d, 1H), 5.54 (s, 1H), 3.84 (s, 1H), 3.47 (dd, 1H), 3.29-3.15 (m, 1H), 2.91 (dd, 2H), 1.30-1.16 (m, 9H).

Example 78 and Example 79

(E)-3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylic Acid (E)-3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylic Acid

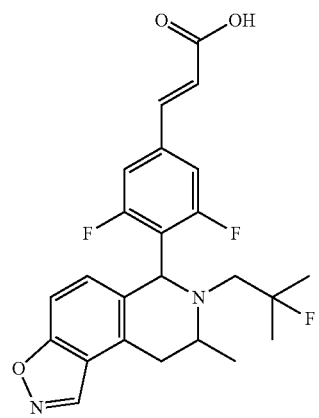

78

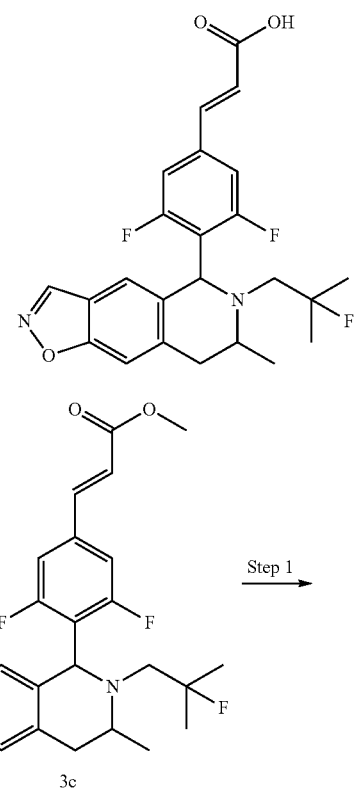

79

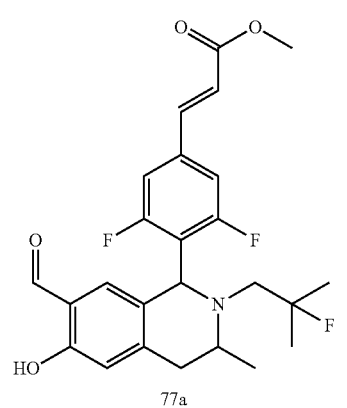

3c

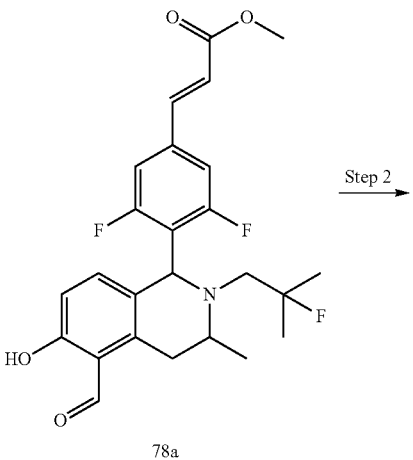

77a

78a

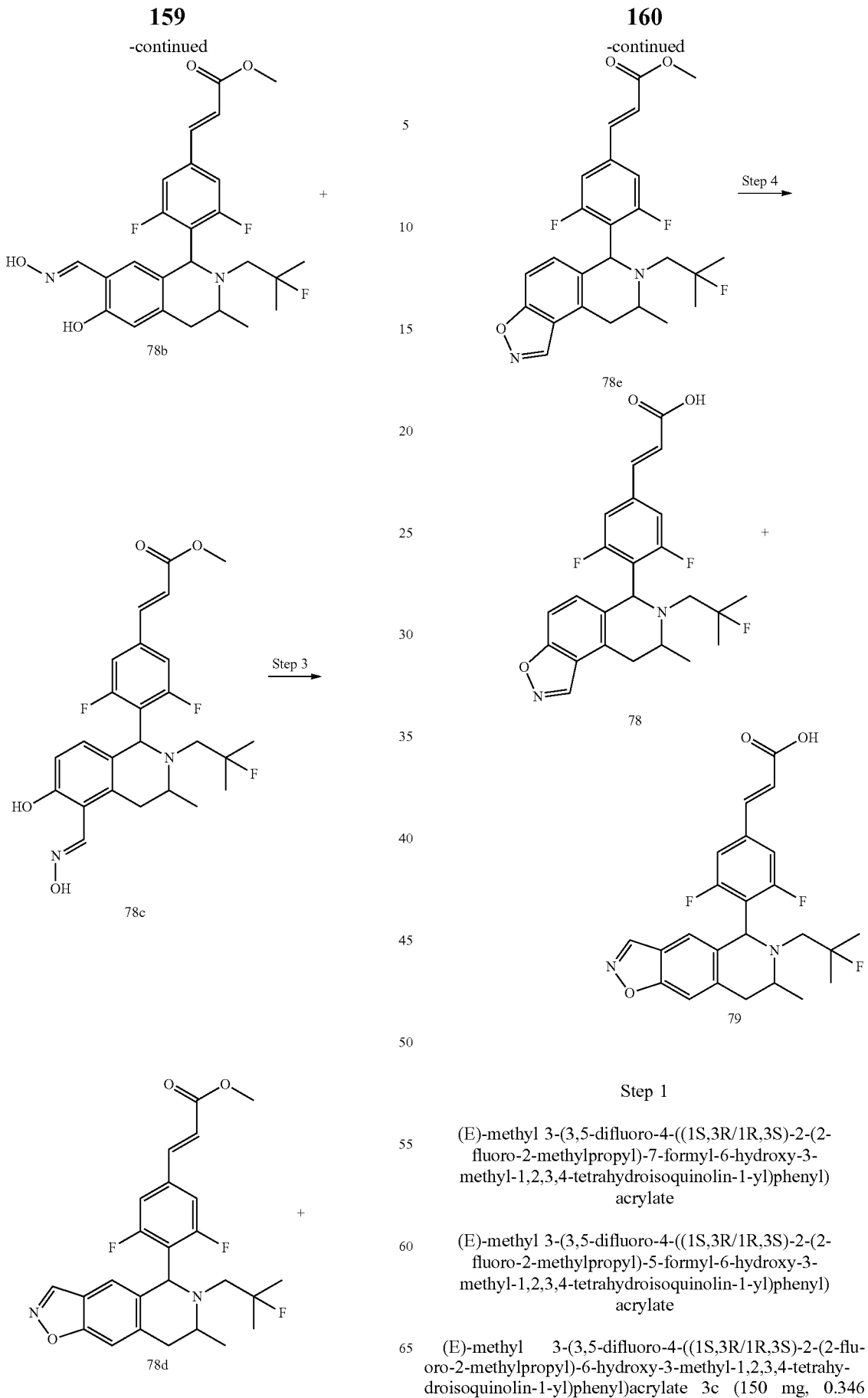
Step 1
(E)-methyl 3-(3,5-difluoro-4-((1S,3R/1R,3S)-2-(2-fluoro-2-methylpropyl)-7-formyl-6-hydroxy-3-methyl-1,2,3,4-tetrahydroisoquinolin-1-yl)phenyl)acrylate
(E)-methyl 3-(3,5-difluoro-4-((1S,3R/1R,3S)-2-(2-fluoro-2-methylpropyl)-5-formyl-6-hydroxy-3-methyl-1,2,3,4-tetrahydroisoquinolin-1-yl)phenyl)acrylate
(E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (150 mg, 0.346 mmol), paraformaldehyde (104 mg, 3.464 mmol) and magnesium chloride (99 mg, 1.03 mmol) were dissolved in 10 mL of tetrahydrofuan. The reaction mixture was warmed up to 65° C. and stirred for 12 hours. After cooling to room temperature, ice water was added to quench the reaction. The reaction mixture was extracted with dichloromethane (50 mL×3). The organic phases were combined, dried over anhydrous sodium sulfate and filtered. The filtrate was concentrated under reduced pressure to obtain the crude title compounds: a mixture of (E)-methyl 3-(3,5-difluoro-4-((1S,3R/1R,3S)-2-(2-fluoro-2-methylpropyl)-7-formyl-6-hydroxy-3-methyl-1,2,3,4-tetrahydroisoquinolin-1-yl)phenyl)acrylate 77a and (E)-methyl 3-(3,5-difluoro-4-((1S,3R/1R,3S)-2-(2-fluoro-2-methylpropyl)-5-formyl-6-hydroxy-3-methyl-1,2,3,4-tetrahydroisoquinolin-1-yl)phenyl)acrylate 78a (150 mg) as a yellow solid, which was used directly in the next step without further purification.

Step 2

(E)-methyl 3-(3,5-difluoro-4-((1S,3R/1R,3S)-2-(2-fluoro-2-methylpropyl)-6-hydroxy-7-((hydroxyimino)methyl)-3-methyl-1,2,3,4-tetrahydroisoquinolin-1-yl)phenyl)acrylate (E)-methyl 3-(3,5-difluoro-4-(2-(2-fluoro-2-methylpropyl)-6-hydroxy-5-((hydroxyimino)methyl)-3-methyl-1,2,3,4-tetrahydroisoquinolin-1-yl)phenyl) acrylate The crude mixture of (E)-methyl 3-(3,5-difluoro-4-((1S,3R/1R,3S)-2-(2-fluoro-2-methylpropyl)-7-formyl-6-hydroxy-3-methyl-1,2,3,4-tetrahydroisoquinolin-1-yl)phenyl)acrylate 77a and (E)-methyl 3-(3,5-difluoro-4-((1S,3R/1R,3S)-2-(2-fluoro-2-methylpropyl)-5-formyl-6-hydroxy-3-methyl-1,2,3,4-tetrahydroisoquinolin-1-yl)phenyl) acrylate 78a (150 mg, 0.325 mmol) and hydroxylamine hydrochloride (27 mg, 0.390 mmol) were dissolved in 4 mL of pyridine, then the mixture was stirred for 2.5 hours at room temperature. The reaction solution was concentrated under reduced pressure, added with ethyl acetate, washed with saturated sodium carbonate solution and water, dried over anhydrous sodium sulfate and filtered. The filtrate was concentrated under reduced pressure to obtain the crude title compounds: a mixture of (E)-methyl 3-(3,5-difluoro-4-((1S,3R/1R,3S)-2-(2-fluoro-2-methylpropyl)-6-hydroxy-7-((hydroxyimino)methyl)-3-methyl-1,2,3,4-tetrahydroisoquinolin-1-yl)phenyl)acrylate 78b and (E)-methyl 3-(3,5-difluoro-4-(2-(2-fluoro-2-methylpropyl)-6-hydroxy-5-((hydroxyimino)methyl)-3-methyl-1,2,3,4-tetrahydroisoquinolin-1-yl)phenyl)acrylate 78c (120 mg) as a yellow solid, which was used directly in the next step without further purification.

Step 3

(E)-methyl 3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylate (E)-methyl 3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylate The mixture of (E)-methyl 3-(3,5-difluoro-4-((1S,3R/1R,3S)-2-(2-fluoro-2-methylpropyl)-6-hydroxy-7-((hydroxyimino)methyl)-3-methyl-1,2,3,4-tetrahydroisoquinolin-1-yl)phenyl)acrylate 78b and (E)-methyl 3-(3,5-difluoro-4-(2-(2-fluoro-2-methylpropyl)-6-hydroxy-5-((hydroxyimino)methyl)-3-methyl-1,2,3,4-tetrahydroisoquinolin-1-yl)phenyl) acrylate 78c (120 mg, 0.252 mmol) and triphenylphosphine (142 mg, 0.504 mmol) were dissolved in 10 mL of tetrahydrofuran, then diethyl azodicarboxylate (88 mg, 0.504 mmol) was added slowly. The reaction solution was warmed up to 40° C. and stirred for 1 hour, then concentrated under reduced pressure. The residue was purified by silica gel column chromatography with elution system B to obtain the title compounds: a mixture of (E)-methyl 3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylate 78d and (E)-methyl 3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylate 78e (40 mg, yield 35%) as a transparent oil.

Step 4

(E)-3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylic Acid (E)-3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylic Acid The mixture of (E)-methyl 3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylate 78d and (E)-methyl 3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylate 78e (40 mg, 0.087 mmol) was dissolved in 5 mL of methanol, then sodium hydroxide (35 mg, 0.873 mmol) was added. The reaction mixture was warmed up to 30° C. and stirred for 1 hour. Then, 1 M HCl was added to adjust the pH to 5, and the reaction solution was extracted with ethyl acetate. The organic phases were dried over anhydrous sodium sulfate and filtered. The filtrate was concentrated under reduced pressure, and the resulting residue was purified by silica gel column chromatography with elution system A to obtain the title compounds, (E)-3-(3,5-difluoro-4-((6S,8R/6R,8S)-7-(2-fluoro-2-methylpropyl)-8-methyl-6,7,8,9-tetrahydroisoxazolo[4,5-f]isoquinolin-6-yl)phenyl)acrylic acid 78 (7.9 mg) as a white solid and (E)-3-(3,5-difluoro-4-((5S,7R/5R,7S)-6-(2-fluoro-2-methylpropyl)-7-methyl-5,6,7,8-tetrahydroisoxazolo[5,4-g]isoquinolin-5-yl)phenyl)acrylic acid 79 (7.8 mg) as a white solid, and the overall yield was 40.3%.

Example 78

MS m/z (ESI): 445.2 [M+1]
$^1$H NMR (400 MHz, CD$_3$OD) δ 7.60 (d, 1H), 7.31 (d, 2H), 7.00 (s, 1H), 6.77 (d, 1H), 6.59 (d, 1H), 5.58 (s, 1H), 3.87 (s, 1H), 3.50-3.36 (m, 1H), 3.00-2.96 (m, 1H), 2.85-2.42 (m, 2H), 1.36-1.25 (m, 9H).

Example 79

MS m/z (ESI): 445.2 [M+1]
$^1$H NMR (400 MHz, CD$_3$OD) δ 7.67 (s, 1H), 7.62 (d, 1H), 7.31 (d, 2H), 7.11 (s, 1H), 6.82 (d, 1H), 6.60 (d, 1H), 5.62 (s, 1H), 3.85 (s, 1H), 3.36-3.38 (m, 1H), 2.69-3.88 (m, 3H), 1.37-1.23 (m, 9H).

Example 80

(E)-3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylic Acid

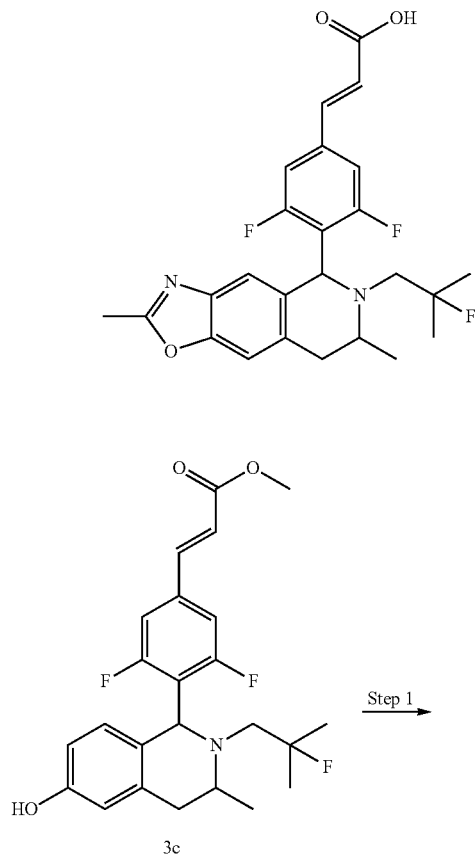

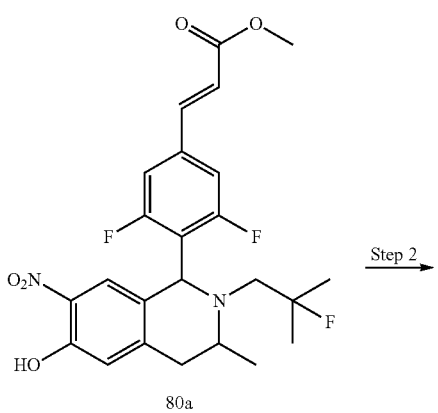

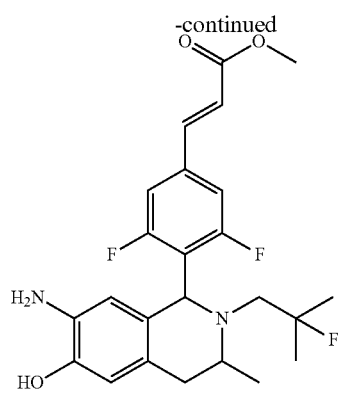

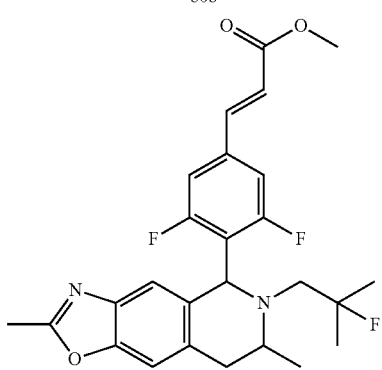

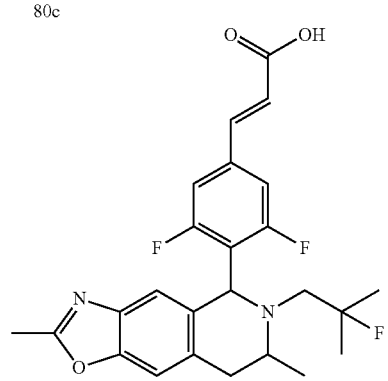

Step 1

(E)-methyl 3-(3,5-difluoro-4-((1S,3R/1R,3S)-2-(2-fluoro-2-methylpropyl)-6-hydroxy-3-methyl-7-nitro-1,2,3,4-tetrahydroisoquinolin-1-yl)phenyl)acrylate (E)-methyl 3-(3,5-difluoro-4-((1S,3R/1R,3S)-2-(2-fluoro-2-methylpropyl)-6-hydroxy-3-methyl-1,2,3,4-tetrahydroisoquinolin-1-yl)phenyl)acrylate 3c (1.3 g, 3 mmol) was dissolved in 13 mL of acetic acid, then nitric acid (189 mg, 3.6 mmol) was added. The reaction solution was stirred for 30 minutes at room temperature. Ice water was added into the reaction solution, and ammonia was added until the pH was alkaline. The reaction solution was extracted with dichloromethane. The organic phase was dried over anhydrous sodium sulfate and filtered. The filtrate was concentrated under reduced pressure, and the resulting residue was purified by silica gel column chromatography with elution system B to obtain the title compound (E)-methyl 3-(3,5- difluoro-4-((1S,3R/1R,3S)-2-(2-fluoro-2-methylpropyl)-6-hydroxy-3-methyl-7-nitro-1,2,3,4-tetrahydroisoquinolin-1-yl)phenyl)acrylate 80a (460 mg, yield 32%) as a yellow oil.

Step 2

(E)-methyl 3-(4-((1S,3R/1R,3S)-7-amino-2-(2-fluoro-2-methylpropyl)-6-hydroxy-3-methyl-1,2,3,4-tetrahydroisoquinolin-1-yl)-3,5-difluorophenyl)acrylate (E)-methyl 3-(3,5-difluoro-4-((1S,3R/1R,3S)-2-(2-fluoro-2-methylpropyl)-6-hydroxy-3-methyl-7-nitro-1,2,3,4-tetrahydroisoquinolin-1-yl)phenyl)acrylate 80a (460 mg, 0.961 mmol) was dissolved in 15 mL of dichloromethane, then tin tetrachloride (365 mg, 1.923 mmol) was added. The reaction solution was warmed up to 50° C. and stirred for 2 hours at 50° C., then cooled to room temperature and concentrated under reduced pressure. Ethanol (10 mL) was added, followed by one drop of concentrated HCl and Fe powder (161 mg, 2.883 mmol). The reaction solution was warmed up to 80° C. and stirred for 2 hours at 50° C., then cooled to room temperature and filtered. The filtrate was concentrated under reduced pressure to obtain the title compound (E)-methyl 3-(4-((1S,3R/1R,3S)-7-amino-2-(2-fluoro-2-methylpropyl)-6-hydroxy-3-methyl-1,2,3,4-tetrahydroisoquinolin-1-yl)-3,5-difluorophenyl)acrylate 80b (400 mg) as a black solid, which was used directly in the next step without further purification.

Step 3

(E)-methyl 3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylate (E)-methyl 3-(4-((1S,3R/1R,3S)-7-amino-2-(2-fluoro-2-methylpropyl)-6-hydroxy-3-methyl-1,2,3,4-tetrahydroisoquinolin-1-yl)-3,5-difluorophenyl)acrylate 80b (100 mg, 0.223 mmol), trimethyl orthoacetate (80 mg, 0.669 mmol) and pyridinium p-toluenesulfonate (6 mg, 0.022 mmol) were dissolved in 3 mL of N,N-dimethylformamide. The reaction solution was warmed up to 80° C. and stirred for 1 hour at 80° C., then cooled to room temperature, added with water, and extracted with ethyl acetate. The organic phase was dried over anhydrous sodium sulfate and filtered. The filtrate was concentrated under reduced pressure, and the residue was purified by thin layer chromatography with elution system B to obtain the title compound (E)-methyl 3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylate 80c (20 mg, yield 19%) as a yellow solid.

Step 4

(E)-3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylic Acid (E)-methyl 3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylate 80c (20 mg, 0.042 mmol) was dissolved in 5 mL of methanol, then sodium hydroxide (17 mg, 0.423 mmol) was added. The reaction solution was warmed up to 30° C. and the reaction was stirred for 1 hour at 30° C. Then, 1 M of HCl was added to adjust the pH to 5. The reaction solution was extracted with ethyl acetate, and the organic phase was dried over anhydrous sodium sulfate and filtered. The filtrate was concentrated under reduced pressure, and the resulting residue was purified by silica gel column chromatography with elution system A to obtain the title compound (E)-3-(3,5-difluoro-4-((5S,7R/5R,7S)-6-(2-fluoro-2-methylpropyl)-2,7-dimethyl-5,6,7,8-tetrahydrooxazolo[5,4-g]isoquinolin-5-yl)phenyl)acrylic acid 80 (4 mg, yield 20%) as a white solid.

MS m/z (ESI): 459.2 [M+1]

$^1$H NMR (400 MHz, CD$_3$OD) δ 7.34 (s, 1H), 7.27 (d, 1H), 7.10 (d, 2H), 6.96 (s, 1H), 6.52 (d, 1H), 5.34 (s, 1H), 3.73 (s, 1H), 3.49-3.47 (m, 1H), 3.01 (t, 1H), 2.77 (d, 1H), 2.60 (s, 3H), 2.34-2.27 (m, 1H), 1.15 (t, 6H), 1.04 (d, 3H).

Example 81

(E)-3-(3,5-difluoro-4-((5S,7R/5R,7S)-6-(2-fluoro-2-methylpropyl)-7-methyl-5,6,7,8-tetrahydrooxazolo[5,4-g]isoquinolin-5-yl)phenyl)acrylic Acid

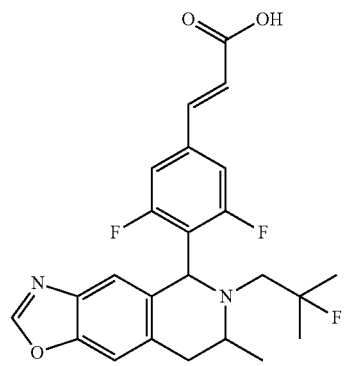

81

In accordance with the synthetic route of Example 80, the starting material trimethyl orthoacetate in step 3 was replaced with trimethyl orthoformate, accordingly, the title compound (E)-3-(3,5-difluoro-4-((5S,7R/5R,7S)-6-(2-fluoro-2-methylpropyl)-7-methyl-5,6,7,8-tetrahydrooxazolo[5,4-g]isoquinolin-5-yl)phenyl)acrylic acid 81 was prepared.

MS m/z (ESI): 445.2 [M+1]

$^1$H NMR (400 MHz, CD$_3$OD) δ 8.35 (s, 1H), 7.46 (s, 1H), 7.32 (d, 1H), 7.15-7.12 (m, 3H), 6.53 (d, 1H), 5.39 (s, 1H), 3.75 (s, 1H), 3.53-3.51 (m, 1H), 3.23-3.21 (m, 1H), 3.02 (t, 1H), 2.83 (d, 1H), 1.21 (t, 6H), 1.15 (d, 3H).

Example 82

(E)-3-(3,5-difluoro-4-((6S,8R/6R,8S)-7-(2-fluoro-2-methylpropyl)-8-methyl-6,7,8,9-tetrahydro-[1,3]dioxolo[4,5-f]isoquinolin-6-yl)phenyl)acrylic Acid

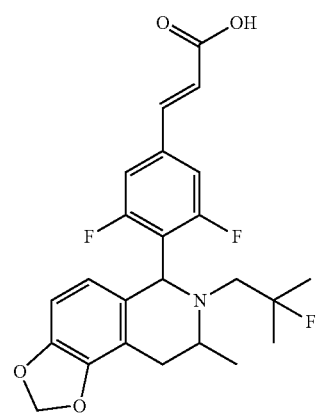

82

In accordance with the synthetic route of Example 35, the starting material (E)-methyl 3-(4-formylphenyl)acrylate 35a used in step 1 was replaced with (E)-methyl 3-(3,5-difluoro-4-formylphenyl)acrylate 1e, and the starting material dimethyl sulfate used in step 2 was replaced with dibromomethane, accordingly, the title compound (E)-3-(3,5-difluoro-4-((6S,8R/6R,8S)-7-(2-fluoro-2-methylpropyl)-8-methyl-6,7,8,9-tetrahydro-[1,3]dioxolo[4,5-f]isoquinolin-6-yl)phenyl)acrylic acid 82 was prepared.

MS m/z (ESI): 448.4 [M+1]

$^1$H NMR (400 MHz, CD$_3$OD) δ 7.59-7.55 (d, 1H), 7.20-7.18 (d, 2H), 6.71-6.51 (m 2H), 6.24-6.22 (d 1H), 5.97-5.96 (m 2H), 5.21 (s, 1H), 3.68 (s 1H), 3.04-2.88 (m 1H), 2.68-2.63 (m, 1H), 2.34-2.23 (m, 2H), 1.19-0.90 (m, 9H).

Example 83

(E)-3-(4-(6-(2-fluoro-2-methylpropyl)-7-methyl-5,6,7,8-tetrahydro-[1,3]dioxolo[4,5-g]isoquinolin-5-yl)phenyl)acrylic Acid

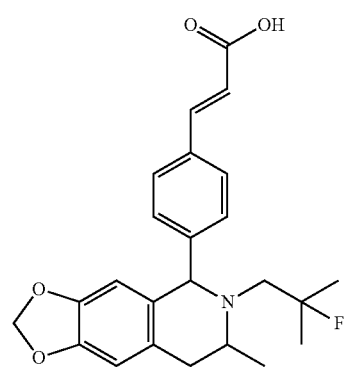

83

In accordance with the synthetic route of Example 1, the starting material (E)-methyl 3-(3,5-difluoro-4-formylphenyl)acrylate 1e used in step 3 was replaced with (E)-methyl 3-(4-formylphenyl)acrylate 35a, accordingly, the title compound (E)-3-(4-(6-(2-fluoro-2-methylpropyl)-7-methyl-5,6,7,8-tetrahydro-[1,3]dioxolo[4,5-g]isoquinolin-5-yl)phenyl)acrylic acid 83 was prepared.

MS m/z (ESI): 412.3 [M+1]

$^1$H NMR (400 MHz, CD$_3$OD) δ 7.45-7.42 (m, 2H), 7.28-7.25 (m, 2H), 6.88 (d, 1H), 6.75 (s, 1H), 6.63 (s, 1H), 6.55 (d, 1H), 6.30 (s, 2H), 5.33 (s, 1H), 3.75 (s, 1H), 3.50 (dd, 1H), 3.03 (t, 1H), 2.75 (dd, 1H), 2.40-2.24 (t, 1H), 1.21-1.15 (t, 6H), 1.06 (t, 3H).

Example 84

(E)-3-(3,5-difluoro-4-((1R,3R/1S,3S)-8-fluoro-2-(2-fluoro-2-methylpropyl)-3-methyl-1,2,3,4-tetrahydrobenzofuro[2,3-c]pyridin-1-yl)phenyl)acrylic Acid

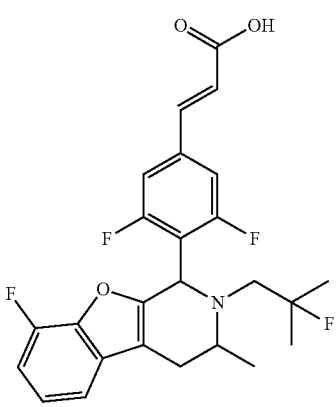

84

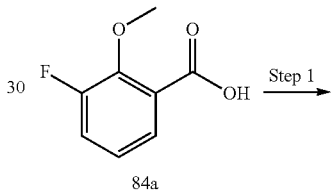 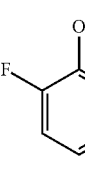 Step 1 →

84a

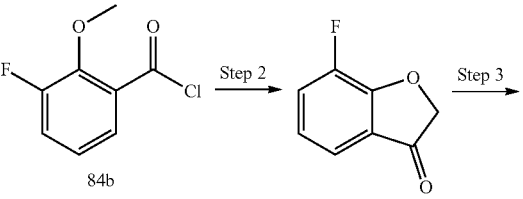

84b     84c

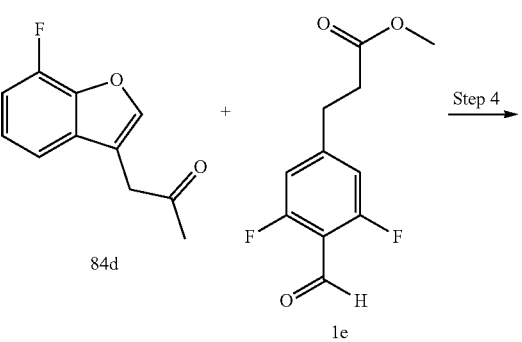 

84d     1e

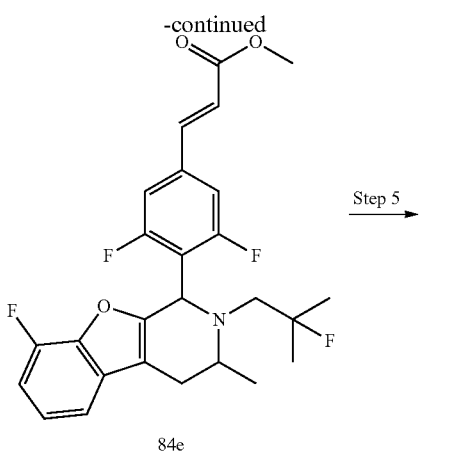

84e

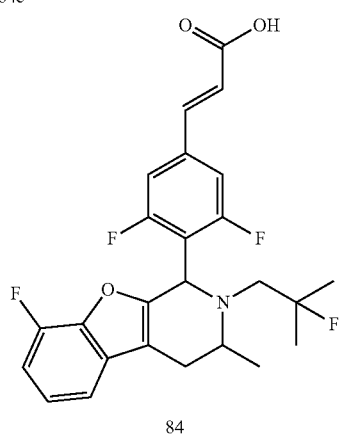

84

Step 1

3-fluoro-2-methoxybenzoyl Chloride 3-fluoro-2-methoxybenzoic acid 84a (1.5 g, 8.8 mmol, prepared by a method disclosed in the patent application publication "WO2014031937") was dissolved in 20 mL of dichloromethane, then 9 drops of N,N-dimethylformamide was added, followed by 1.4 mL of thionyl chloride in an ice bath. The reaction mixture was stirred for 12 hours at room temperature, then concentrated under reduced pressure to obtain the crude title compound 3-fluoro-2-methoxybenzoyl chloride 84b (1.86 g) as a yellow liquid, which was used directly in the next step without further purification.

Step 2

7-fluorobenzofuran-3 (2H)-one

The crude 3-fluoro-2-methoxybenzoyl chloride 84b (1.86 g, 8.8 mmol) was dissolved in 20 mL of ether, then 10 mL of a solution of 2 M (trimethylsilyl)diazomethane in n-hexane was added dropwise in an ice bath. The reaction solution was then stirred for 3 hours at room temperature, then concentrated under reduced pressure to remove the solvent. Then, 20 mL of acetic acid was added in an ice bath, and the reaction was stirred for 1 hour at room temperature. The reaction solution was concentrated under reduced pressure, then water was added. The reaction solution was extracted with ethyl acetate. The organic phase was washed with saturated sodium carbonate solution, dried over anhydrous sodium sulfate and filtered. The filtrate was concentrated under reduced pressure, and the resulting residue was purified by silica gel column chromatography with elution system B to obtain the title compound 7-fluorobenzofuran-3(2H)-one 84c (340 mg, yield 27%) as a yellow solid.

Step 3

1-(7-fluorobenzofuran-3-yl)propan-2-one 7-fluorobenzofuran-3(2H)-one 84c (340 mg, 2.2 mmol) and acetonyltriphenylphosphonium chloride (1.2 g, 3.3 mmol) were dissolved in 10 mL of xylene, then 1.1 mL of N,N-diisopropylethylamine were added. The reaction solution was warmed up to 140° C. and stirred for 12 hours, then cooled to room temperature, and water was added. The reaction solution was extracted with ethyl acetate. The organic phase was dried over anhydrous sodium sulfate and filtered. The filtrate was concentrated under reduced pressure, and the resulting residue was purified by silica gel column chromatography with elution system B to obtain the title compound 1-(7-fluorobenzofuran-3-yl)propan-2-one 84d (171 mg, yield 40%) as a red-brown liquid.

In accordance with the synthetic route of Example 4, the starting material N-(1-(benzofuran-3-yl)propan-2-yl)-2-fluoro-2-methylpropan-1-amine 4c used in step 3 was replaced with 1-(7-fluorobenzofuran-3-yl)propan-2-one 84d, accordingly, the title compound 1-(7-fluorobenzofuran-3-yl)propan-2-one 84 was prepared.

MS m/z (ESI): 462.2 [M+1]

$^{1}$H NMR (400 MHz, DMSO-$d_6$) δ 12.05 (s, 1H), 7.42 (d, 1H), 7.29-7.23 (m, 3H), 7.17 (t, 1H), 7.08 (d, 1H), 6.53 (d, 1H), 5.23 (s, 1H), 3.54-3.48 (m, 1H), 2.95-2.86 (m, 2H), 2.45-2.34 (m, 2H), 1.24 (d, 3H), 1.18 (d, 3H), 1.11 (d, 3H).

Example 85

(E)-3-(4-((1R,3R/1S,3S)-7-chloro-2-(2-fluoro-2-methylpropyl)-3-methyl-1,2,3,4-tetrahydrobenzofuro[2,3-c]pyridin-1-yl)-3,5-difluorophenyl)acrylic Acid

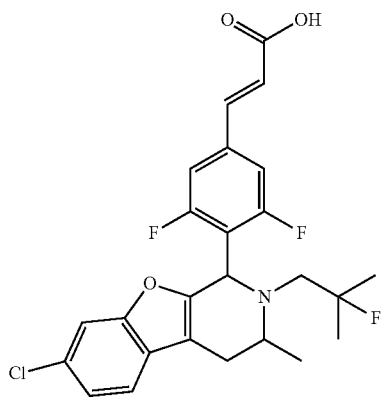

85

In accordance with the synthetic route of Example 84, the starting material 1-(7-fluorobenzofuran-3-yl)propan-2-one 84d was replaced with 1-(fluorobenzofuran-3-yl)propan-2-one, accordingly, the title compound (E)-3-(4-((1R,3R/1S,3S)-7-chloro-2-(2-fluoro-2-methylpropyl)-3-methyl-1,2,3,4-tetrahydrobenzofuro[2,3-c]pyridin-1-yl)-3,5-difluorophenyl)acrylic acid 85 was prepared.

MS m/z (ESI): 478.4 [M+1]

¹H NMR (400 MHz, CD₃OD) δ 7.50-7.42 (m, 3H), 7.27-7.20 (m, 3H), 6.57 (d, 1H), 5.27 (s, 1H), 3.70 (d, 1H), 3.27-2.92 (m, 2H), 2.63-2.38 (m, 2H), 1.43-1.13 (m, 9H).

Example 86

(E)-3-(3,5-difluoro-4-((1R,3R/1S,3S)-7-fluoro-2-(2-fluoro-2-methylpropyl)-3-methyl-1, 2,3,4-tetrahydrobenzofuro[2,3-c]pyridin-1-yl)phenyl)acrylic Acid

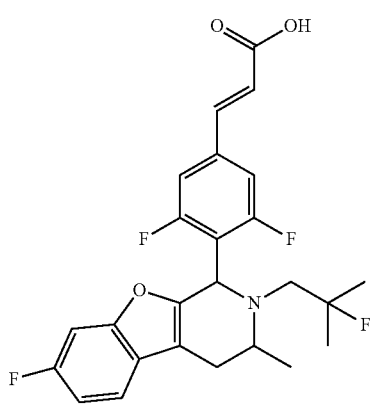

86

In accordance with the synthetic route of Example 84, the starting material 3-fluoro-2-methoxybenzoic acid 84a used in step 1 was replaced with 4-fluoro-2-methoxybenzoic acid that was prepared by a method disclosed in the patent application publication "WO201153359", accordingly, the title compound (E)-3-(3,5-difluoro-4-((1R,3R/1S,3S)-7-fluoro-2-(2-fluoro-2-methylpropyl)-3-methyl-1, 2,3,4-tetrahydrobenzofuro[2,3-c]pyridin-1-yl)phenyl)acrylic acid 86 was prepared.

MS m/z (ESI): 462.4[M+1]

¹H NMR (400 MHz, CD₃OD) δ 7.55 (d, 1H), 7.45 (dd, 1H), 7.20 (d, 2H), 7.11 (dd, 1H), 7.01 (m, 1H), 6.53 (d, 1H), 5.24 (s, 1H), 3.66 (m, 1H), 2.94 (m, 2H), 2.56 (dd, 1H), 2.41 (dd, 1H), 1.30-1.10 (m, 9H).

Example 87

(E)-3-(4-((1R,3R/1S,3S)-6-bromo-2-(2-fluoro-2-methylpropyl)-3-methyl-1,2,3,4-tetrahydrobenzofuro[2,3-c]pyridin-1-yl)-3,5-difluorophenyl)acrylic Acid

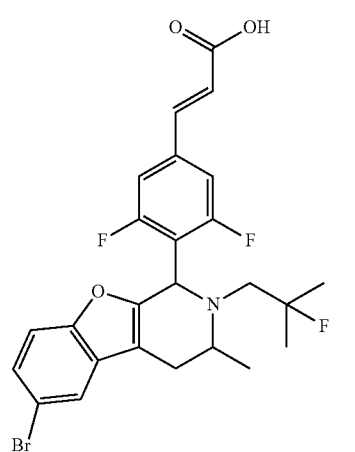

87

-continued

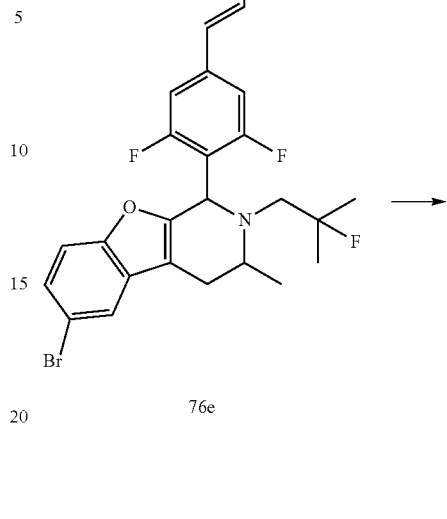

76e

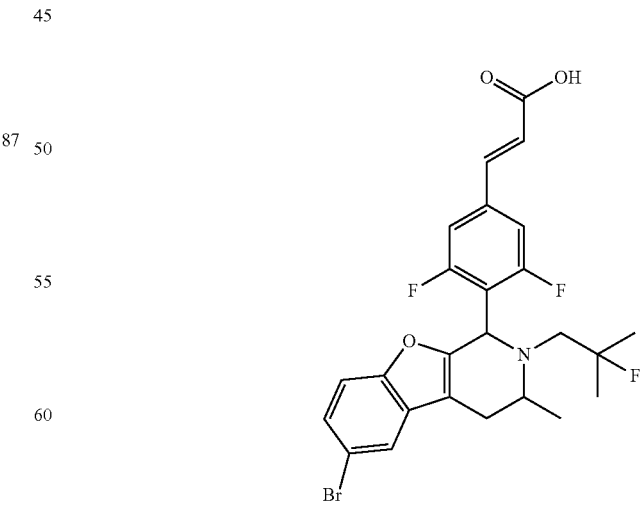

87

(E)-methyl 3-(4-(6-bromo-2-(2-fluoro-2-methylpropyl)-3-methyl-1,2,3,4-tetrahydrobenzofuro[2,3-c]pyridin-1-yl)-3,5-difluorophenyl)acrylate 76e (10 mg, 0.042 mmol) was dissolved in 5 mL of methanol, then sodium hydroxide (7 mg, 0.187 mmol) and 1 mL of water were added. The reaction mixture was stirred for 12 hours at room temperature. Then, 1M HCl was added dropwise to adjust the pH to 5. The reaction solution was extracted by dichloromethane. The organic phase was dried over anhydrous sodium sulfate and filtered. The filtrate was concentrated under reduced pressure, and the resulting residue was purified by silica gel column chromatography with elution system A to obtain the title compound (E)-3-(4-((1R,3R/1S,3S)-6-bromo-2-(2-fluoro-2-methylpropyl)-3-methyl-1,2,3,4-tetrahydrobenzofuro[2,3-c]pyridin-1-yl)-3,5-difluorophenyl)acrylic acid 87 (5 mg, yield 50%) as a yellow solid.

MS m/z (ESI): 523.3 [M+1]

¹H NMR (400 MHz, CD₃OD) δ 7.67 (s, 1H), 7.42 (d, 1H), 7.35-7.33 (dd, 1H), 7.28 (d, 1H), 7.18 (d, 2H), 6.57 (d, 1H), 5.26 (s, 1H), 3.69 (s, 1H), 3.02-2.92 (m, 2H), 2.60-2.56 (m, 1H), 2.48-2.38 (m, 1H), 1.20-1.11 (m, 9H).

Example 88

(E)-3-(3,5-difluoro-4-((1R,3R/1S,3S)-2-(2-fluoro-2-methylpropyl)-3-methyl-6-(1H-pyrazol-4-yl)-1,2,3,4-tetrahydrobenzofuro[2,3-c]pyridin-1-yl)phenyl)acrylic Acid

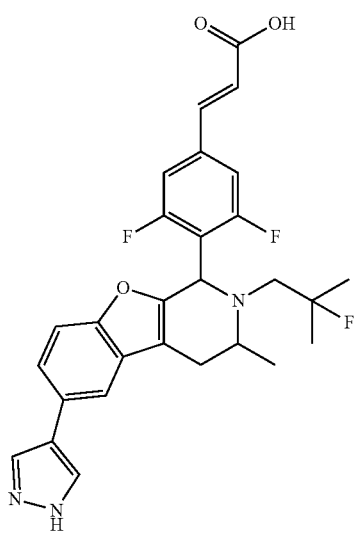

88

In accordance with the synthetic route of Example 76, the starting material, 1-ethyl-4-(4,4,5,5-tetramethyl-1,3,2-dioxaborolan-2-yl)-1H-pyrazole 17a used in step 5 was replaced with tert-butyl 4-(4,4,5,5-tetramethyl-1,3,2-dioxaborolan-2-yl)-1H-pyrazole-1-carboxylate, accordingly, the title compound (E)-3-(3,5-difluoro-4-((1R,3R/1S,3S)-2-(2-fluoro-2-methylpropyl)-3-methyl-6-(1H-pyrazol-4-yl)-1,2,3,4-tetrahydrobenzofuro[2,3-c]pyridin-1-yl)phenyl)acrylic acid 88 was prepared.

MS m/z (ESI): 510.5 [M+1]

¹H NMR (400 MHz, CD₃OD) δ 8.06 (s, 2H), 7.77 (s, 1H), 7.62 (d, 1H), 7.51 (d, 1H), 7.39-7.31 (m, 3H), 6.60 (d, 1H), 5.56 (s, 1H), 3.85 (s, 1H), 3.16-3.11 (m, 2H), 2.79-2.75 (m, 2H), 1.36-1.27 (m, 9H).

Example 89

(E)-3-(3,5-difluoro-4-((1R,3R/1S,3S)-2-(2-fluoro-2-methylpropyl)-3-methyl-6-(1-methyl-1H-pyrazol-4-yl)-1,2,3,4-tetrahydrobenzofuro[2,3-c]pyridin-1-yl)phenyl)acrylic Acid

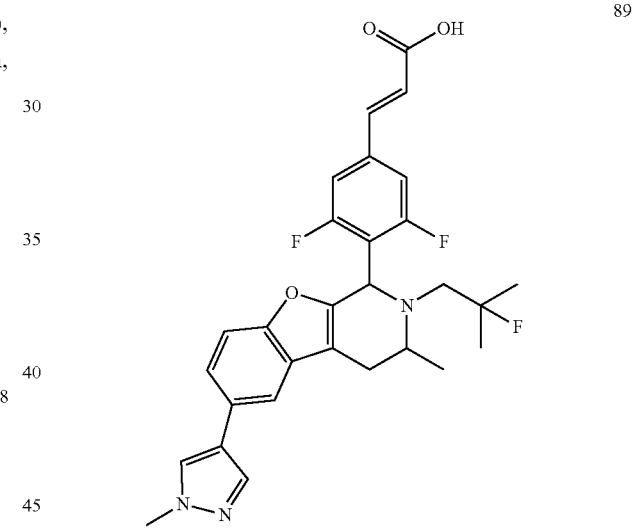

89

In accordance with the synthetic route of Example 76, the starting material 1-ethyl-4-(4,4,5,5-tetramethyl-1,3,2-dioxaborolan-2-yl)-1H-pyrazole 17a used in step 5 was replaced with 1-methyl-4-(4,4,5,5-tetramethyl-1,3,2-dioxaborolan-2-yl)-1H-pyrazole 16h, accordingly, the title compound (E)-3-(3,5-difluoro-4-((1R,3R/1S,3S)-2-(2-fluoro-2-methylpropyl)-3-methyl-6-(1-methyl-1H-pyrazol-4-yl)-1,2,3,4-tetrahydrobenzofuro[2,3-c]pyridin-1-yl)phenyl)acrylic acid 89 was prepared.

MS m/z (ESI): 524.5 [M+1]

¹H NMR (400 MHz, CD₃OD) δ 7.98 (s, 1H), 7.86 (s, 1H), 7.72 (s, 1H), 7.62 (d, 1H), 7.37-7.48 (m, 1H), 7.35-7.32 (m, 3H), 6.60 (d, 1H), 5.55 (s, 1H), 3.98 (s, 3H), 3.86 (s, 1H), 3.22-3.11 (m, 2H), 2.79-2.75 (m, 2H), 1.36-1.27 (m, 9H).

Example 90

(E)-3-(3,5-difluoro-4-((1R,3R/1S,3S)-2-(2-fluoro-2-methylpropyl)-3-methyl-6-(pyridin-3-yl)-1,2,3,4-tetrahydrobenzofuro[2,3-c]pyridin-1-yl)phenyl)acrylic Acid

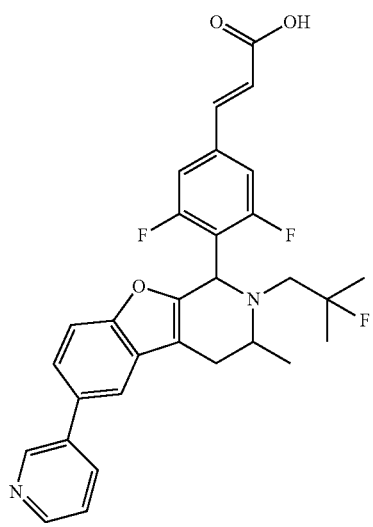

90

In accordance with the synthetic route of Example 76, the starting material, 1-ethyl-4-(4,4,5,5-tetramethyl-1,3,2-dioxaborolan-2-yl)-1H-pyrazole 17a used in step 5 was replaced with pyridin-3-ylboronic acid 28a, accordingly, the title compound (E)-3-(3,5-difluoro-4-((1R,3R/1S,3S)-2-(2-fluoro-2-methylpropyl)-3-methyl-6-(pyridin-3-yl)-1,2,3,4-tetrahydrobenzofuro[2,3-c]pyridin-1-yl)phenyl)acrylic acid 90 was prepared.

MS m/z (ESI): 521.5 [M+1]

$^1$H NMR (400 MHz, CD$_3$OD) δ 9.19 (s, 1H), 8.89-8.80 (m, 2H), 8.10 (t, 1H), 8.01 (s, 1H), 7.70-7.57 (m, 3H), 7.28 (d, 2H), 6.58 (d, 1H), 5.36 (s, 1H), 3.78 (s, 1H), 3.13-2.99 (m, 2H), 2.50 (d, 1H), 2.71-2.44 (m, 1H), 1.29-1.16 (m, 9H).

Example 91

(E)-3-(3,5-difluoro-4-((5S,7R/5R,7S)-6-(2-fluoro-2-methylpropyl)-7-methyl-5,6,7,8-tetrahydro-1H-pyrazolo[3,4-g]isoquinolin-5-yl)phenyl)acrylic Acid

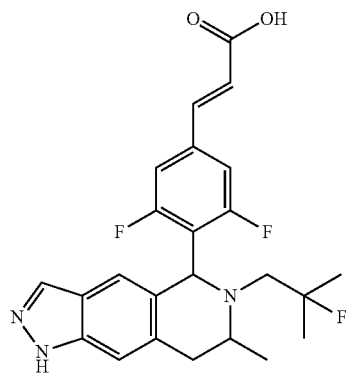

91

In accordance with the synthetic route of Example 70, the starting material 3-(benzyloxy)-2-methylbenzaldehyde 70a used in step 1 was replaced with 3-(benzyloxy)-4-methylbenzaldehyde, accordingly, the title compound (E)-3-(3,5-difluoro-4-((5S,7R/5R,7S)-6-(2-fluoro-2-methylpropyl)-7-methyl-5,6,7,8-tetrahydro-1H-pyrazolo[3,4-g]isoquinolin-5-yl)phenyl)acrylic acid 91 was prepared.

MS m/z (ESI): 444.5 [M+1]

$^1$H NMR (400 MHz, CD$_3$OD) δ 8.10 (d, 1H), 7.58-7.18 (m, 3H), 6.78 (s, 1H), 6.55 (d, 1H), 5.36 (s, 1H), 3.81 (s, 1H), 3.25-3.30 (m, 2H), 2.42-2.30 (m, 2H), 2.07 (s, 1H), 1.22-0.92 (m, 9H).

Example 92

(E)-3-(3,5-difluoro-4-((6S,8R/6R,8S)-(7-isobutyl-8-methyl-6,7,8,9-tetrahydro-3H-pyrazolo[4,3-f]isoquinolin-6-yl)phenyl)acrylic Acid

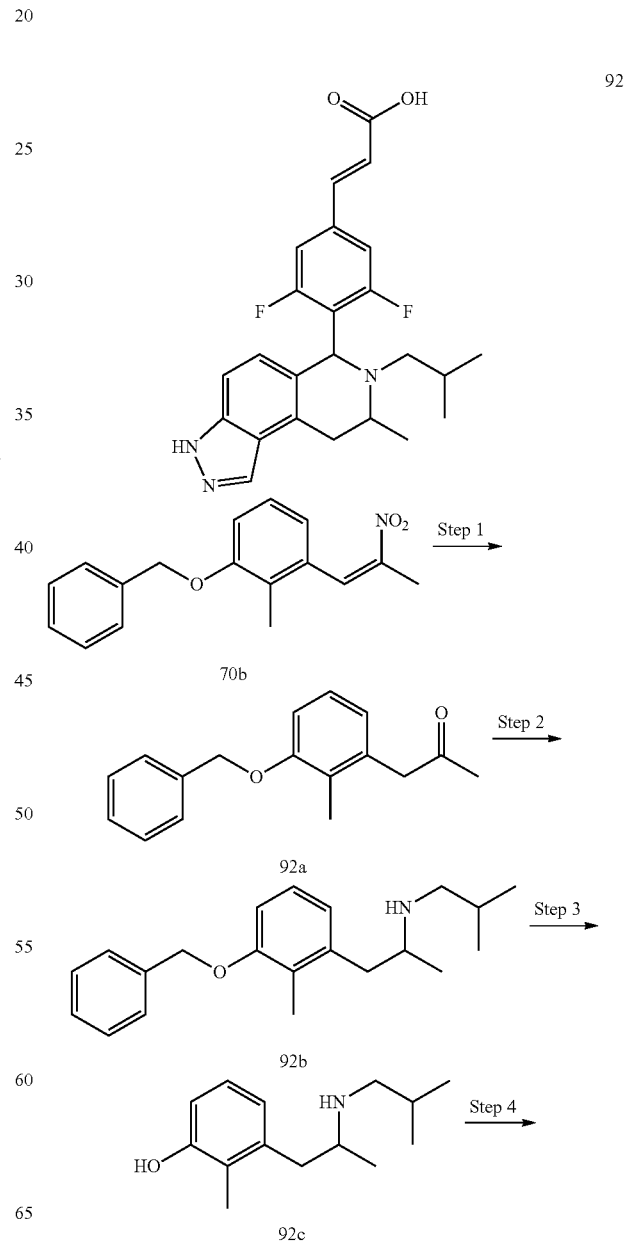

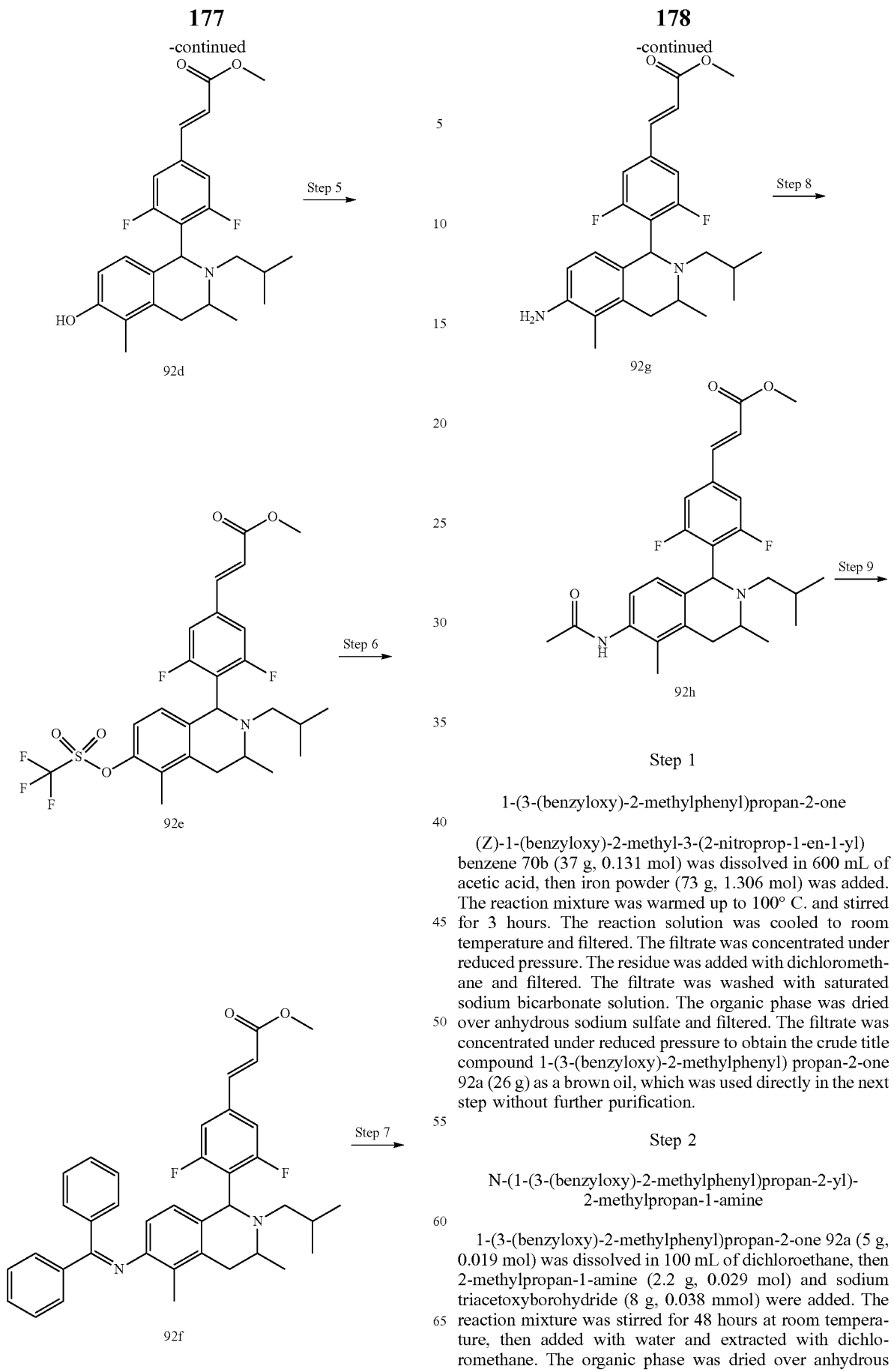

Step 1

1-(3-(benzyloxy)-2-methylphenyl)propan-2-one (Z)-1-(benzyloxy)-2-methyl-3-(2-nitroprop-1-en-1-yl) benzene 70b (37 g, 0.131 mol) was dissolved in 600 mL of acetic acid, then iron powder (73 g, 1.306 mol) was added. The reaction mixture was warmed up to 100° C. and stirred for 3 hours. The reaction solution was cooled to room temperature and filtered. The filtrate was concentrated under reduced pressure. The residue was added with dichloromethane and filtered. The filtrate was washed with saturated sodium bicarbonate solution. The organic phase was dried over anhydrous sodium sulfate and filtered. The filtrate was concentrated under reduced pressure to obtain the crude title compound 1-(3-(benzyloxy)-2-methylphenyl) propan-2-one 92a (26 g) as a brown oil, which was used directly in the next step without further purification.

Step 2

N-(1-(3-(benzyloxy)-2-methylphenyl)propan-2-yl)-2-methylpropan-1-amine 1-(3-(benzyloxy)-2-methylphenyl)propan-2-one 92a (5 g, 0.019 mol) was dissolved in 100 mL of dichloroethane, then 2-methylpropan-1-amine (2.2 g, 0.029 mol) and sodium triacetoxyborohydride (8 g, 0.038 mmol) were added. The reaction mixture was stirred for 48 hours at room temperature, then added with water and extracted with dichloromethane. The organic phase was dried over anhydrous sodium sulfate and filtered. The filtrate was concentrated under reduced pressure, and the resulting residue was purified by silica gel column chromatography with elution system A to obtain the title compound N-(1-(3-(benzyloxy)-2-methylphenyl)propan-2-yl)-2-methylpropan-1-amine 92b (5.2 g, yield 85%) as a light yellow oil.

Step 3

3-(2-(isobutylamino)propyl)-2-methylphenol

N-(1-(3-(benzyloxy)-2-methylphenyl)propan-2-yl)-2-methylpropan-1-amine 92b (5.2 g, 16.696 mmol) was dissolved in 50 mL of methanol, then palladium on activated carbon (1 g, 10%) was added. The reaction system was purged with hydrogen three times to remove air. The reaction solution was stirred for 12 hours at room temperature, then filtered. The filtrate was concentrated under reduced pressure to obtain the title compound 3-(2-(isobutylamino)propyl)-2-methylphenol 92c (4 g) as a light brown oil, which was used directly in the next step without further purification.

Step 4

(E)-methyl 3-(3,5-difluoro-4-((1S,3R/1R,3S)-6-hydroxy-2-isobutyl-3,5-dimethyl-1,2, 3,4-tetrahydroisoquinolin-1-yl)phenyl)acrylate 3-(2-(isobutylamino)propyl)-2-methylphenol 92c (3.7 g, 0.017 mmol) was dissolved in 50 mL of methanol, then (E)-methyl 3-(3,5-difluoro-4-formylphenyl)acrylate 1e (5.68 g, 0.025 mol) and acetic acid (2.04 g, 0.03 mmol) were added. The reaction solution was warmed up to 60° C. and stirred for 12 hours, then cooled to room temperature and concentrated under reduced pressure. The resulting residue was purified by silica gel column chromatography with elution system B to obtain the title compound (E)-methyl 3-(3,5-difluoro-4-((1S,3R/1R,3S)-6-hydroxy-2-isobutyl-3,5-dimethyl-1,2,3,4-tetrahydroisoquinolin-1-yl)phenyl)acrylate 92d (2.5 g, yield 34%) as a yellow oil.

Step 5

(E)-methyl 3-(3,5-difluoro-4-((1S,3R/1R,3S)-2-isobutyl-3,5-dimethyl-6-(((trifluoromethyl)sulfonyl)oxy)-1,2,3,4-tetrahydroisoquinolin-1-yl)phenyl)acrylate (E)-methyl 3-(3,5-difluoro-4-((1S,3R/1R,3S)-6-hydroxy-2-isobutyl-3,5-dimethyl-1, 2,3,4-tetrahydroisoquinolin-1-yl)phenyl)acrylate 92d (2.5 g, 5.821 mmol) was dissolved in 25 mL of dichloromethane, then 2,6-lutidine (1.25 g, 11.641 mmol) and trifluoromethanesulfonic anhydride (2.46 g, 8.732 mmol) were added at 0° C. The reaction solution was stirred for 2 hours at 0° C., then concentrated under reduced pressure. The resulting residue was purified by silica gel column chromatography with elution system B to obtain the title compound (E)-methyl 3-(3,5-difluoro-4-((1S,3R/1R,3S)-2-isobutyl-3,5-dimethyl-6-(((trifluoromethyl)sulfonyl)oxy)-1,2,3,4-tetrahydroisoquinolin-1-yl)phenyl)acrylate 92e (2.5 g, yield 76%) as a light yellow solid.

Step 6

(E)-methyl 3-(4-((1S,3R/1R,3S)-6-((diphenylmethylene) amino)-2-isobutyl-3,5-dimethyl-1,2,3,4-tetrahydroisoquinolin-1-yl)-3,5-difluorophenyl)acrylate (E)-methyl 3-(3,5-difluoro-4-((1S,3R/1R,3S)-2-isobutyl-3,5-dimethyl-6-(((trifluoromethyl)sulfonyl)oxy)-1,2,3,4-tetrahydroisoquinolin-1-yl)phenyl)acrylate 92e (2.5 g, 4.452 mmol), benzophenone imine (1.05 g, 5.787 mmol), palladium acetate (200 mg, 0.89 mmol), (R)-(+)-2,2'-bis(diphenylphosphino)-1,1'-binaphthyl (554 mg, 0.89 mmol), and cesium carbonate (2.9 g, 8.89 mmol) were dissolved in 40 mL of 1,4-dioxane. The reaction solution was warmed up to 100° C. and stirred for 12 hours, then cooled to room temperature and filtered. The filtrate was concentrated under reduced pressure. The resulting residue was purified by silica gel column chromatography with elution system B to obtain the title compound (E)-methyl 3-(4-((1S,3R/1R,3S)-6-((diphenylmethylene)amino)-2-isobutyl-3,5-dimethyl-1, 2,3,4-tetrahydroisoquinolin-1-yl)-3,5-difluorophenyl)acrylate 92f (1.8 g, yield 69%) as a light yellow oil.

Step 7

(E)-methyl 3-(4-((1S,3R/1R,3S)-6-amino-2-isobutyl-3,5-dimethyl-1,2,3,4-tetrahydroisoquinolin-1-yl)-3,5-difluorophenyl)acrylate (E)-methyl 3-(4-((1S,3R/1R,3S)-6-((diphenylmethylene)amino)-2-isobutyl-3,5-dimethyl-1,2,3,4-tetrahydroisoquinolin-1-yl)-3,5-difluorophenyl)acrylate 92f (1.8 g, 3.037 mmol) was dissolved in 30 mL of methanol. The reaction solution was cooled to 0° C., added with 10 mL of 1 M of HCl and stirred for 2 hours. Saturated sodium carbonate solution was added until the pH of the reaction solution was neutral. The reaction solution was extracted with dichloromethane, and the organic phase was dried over anhydrous sodium sulfate and filtered. The filtrate was concentrated under reduced pressure, and the resulting residue was purified by silica gel column chromatography with elution system B to obtain the title compound (E)-methyl 3-(4-((1S, 3R/1R,3S)-6-amino-2-isobutyl-3,5-dimethyl-1,2,3,4-tetrahydroisoquinolin-1-yl)-3,5-difluorophenyl)acrylate 92g (1.2 g, yield 92%) as a light yellow oil.

In accordance with the synthetic route of Example 70, the starting material (E)-methyl 3-(4-((1S,3R/1R,3S)-6-amino-2-(2-fluoro-2-methylpropyl)-3,5-dimethyl-1,2,3,4-tetrahydroisoquinolin-1-yl)-3,5-difluorophenyl)acrylate 70i used in step 9 was replaced with (E)-methyl 3-(4-((1S,3R/1R,3S)-6-amino-2-isobutyl-3,5-dimethyl-1,2,3,4-tetrahydroisoquinolin-1-yl)-3,5-difluorophenyl)acrylate 92g, accordingly, the title compound (E)-3-(3,5-difluoro-4-((6S,8R/6R,8S)-7-isobutyl-8-methyl-6,7,8,9-tetrahydro-3H-pyrazolo[4,3-f]isoquinolin-6-yl)phenyl)acrylic acid 92 was prepared.

MS m/z (ESI): 426.2 [M+1]

$^1$H NMR (400 MHz, CD$_3$OD) δ 8.07 (s, 1H), 7.22-7.30 (m, 2H), 7.08 (t, 2H), 6.77 (dd, 1H), 6.53 (dd, 1H), 5.23 (s, 1H), 3.54-3.58 (m, 1H), 3.36-3.42 (dd, 1H), 2.96-3.00 (dd, 1H), 2.51-3.56 (dd, 1H), 2.06-2.09 (m, 1H), 1.64-1.69 (m, 1H), 1.03 (d, 3H), 0.83 (d, 3H), 0.72 (d, 3H).

Example 93

(E)-3-(4-((1S,3R/1R,3S)-6-cyano-2-(2-fluoro-2-methylpropyl)-3-methyl-1,2,34-tetrahydroisoquinolin-1-yl)-3,5-difluorophenyl)acrylic Acid

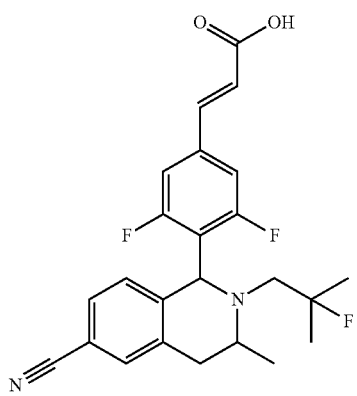

93

In accordance with the synthetic route of Example 10, the starting material 2-methyl-5-(4,4,5,5-tetramethyl-1,3,2-dioxaborolan-2-yl)thiazole 10b used in step 2 was replaced with zinc cyanide, accordingly, the title compound (E)-3-(4-((1S,3R/1R,3S)-6-cyano-2-(2-fluoro-2-methylpropyl)-3-methyl-1,2,3,4-tetrahydroisoquinolin-1-yl)-3,5-difluorophenyl)acrylic acid 93 was prepared.

MS m/z (ESI): 429.5 [M+1]

$^1$H NMR (400 MHz, CD$_3$OD) δ 7.60-7.55 (m, 2H), 7.40 (d, 1H), 7.23 (d, 2H), 6.93 (d, 1H), 6.56 (d, 1H), 5.30 (s, 1H), 3.78-3.70 (m, 1H), 3.67-3.41 (m, 1H), 3.04-2.96 (m, 1H), 2.75-2.70 (m, 1H), 2.36-2.25 (m, 1H), 1.33-1.01 (m, 9H).

Examples 94, 95

(E)-3-(3,5-difluoro-4-((6S,8R)-7-(2-fluoro-2-methylpropyl)-8-methyl-6,7,8,9-tetrahydro-3H-pyrazolo[4,3-f]isoquinolin-6-yl)phenyl)acrylic Acid (E)-3-(3,5-difluoro-4-((6R,8S)-7-(2-fluoro-2-methylpropyl)-8-methyl-6,7,8,9-tetrahydro-3H-pyrazolo[4,3-f]isoquinolin-6-yl)phenyl)acrylic Acid

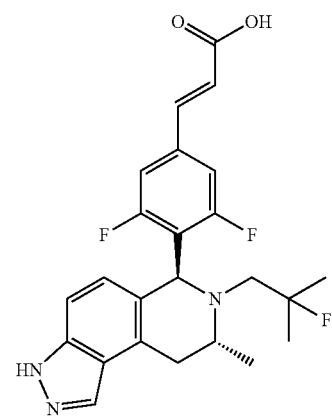

94

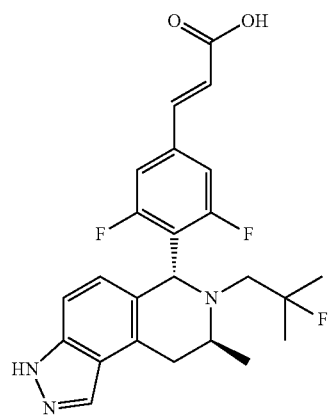

95

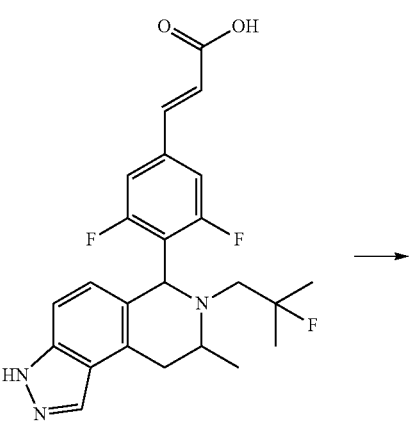

70

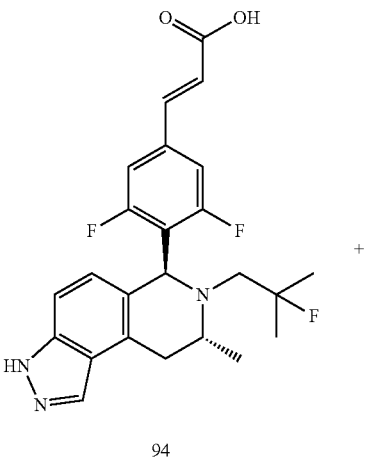

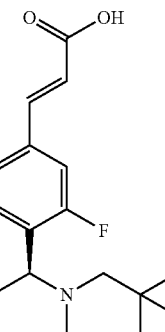

94

-continued

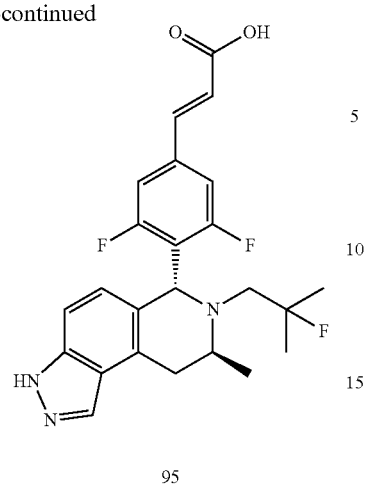

95

(E)-3-(3,5-difluoro-4-((6S,8R/6R,8S)-7-(2-fluoro-2-methylpropyl)-8-methyl-6,7,8, 9-tetrahydro-3H-pyrazolo[4,3-f]isoquinolin-6-yl)phenyl)acrylic acid 70 (250 mg, 0.56 mmol) was separated chirally (separation conditions: chiral preparative column Superchiral S-AD (Chiralway), 2 cm I.D.*25 cm Length, 5 μm; mobile phase: $CO_2$ $O_2$:ethanol=60:40, flow rate: 60 g/min). The corresponding fractions were collected and concentrated under reduced pressure to obtain the title compounds (E)-3-(3,5-difluoro-4-((6S,8R)-7-(2-fluoro-2-methylpropyl)-8-methyl-6,7,8,9-tetrahydro-3H-pyrazolo[4,3-f]isoquinolin-6-yl)phenyl)acrylic acid 94 (100 mg) as a yellow solid and (E)-3-(3,5-difluoro-4-((6R,8S)-7-(2-fluoro-2-methylpropyl)-8-methyl-6,7,8,9-tetrahydro-3H-pyrazolo[4,3-f]isoquinolin-6-yl)phenyl)acrylic acid 95 (100 mg) as a yellow solid.

Example 94

MS m/z (ESI): 444.5 [M+1];

Chiral HPLC analysis: retention time 5.299 minutes, chiral purity: 99.286% (chromatographic column: Superchiral S-AD, 0.46 cm I.D.×15 cm L; mobile phase: $CO_2O_2$: ethanol=60:40 (V/V));

$^1$H NMR (400 MHz, $CD_3OD$) δ 8.10 (s, 1H), 7.58 (d, 1H), 7.25-7.19 (m, 2H), 6.76 (d, 1H), 6.54 (d, 1H), 5.35 (s, 1H), 3.82 (s, 1H), 3.50-3.45 (m, 1H), 3.08-2.99 (m, 2H), 2.42-2.35 (m, 1H), 2.06 (s, 1H), 1.22-1.07 (m, 9H).

Example 95

MS m/z (ESI): 444.5 [M+1];

Chiral HPLC analysis: retention time 4.101 minutes, chiral purity: 99.649% (chromatographic column: Superchiral S-AD, 0.46 cm I.D.×15 cm L; mobile phase: $CO_2O_2$: ethanol=60:40 (V/V));

$^1$H NMR (400 MHz, $CD_3OD$) δ 8.10 (s, 1H), 7.58 (d, 1H), 7.25-7.19 (m, 2H), 6.76 (d, 1H), 6.54 (d, 1H), 5.35 (s, 1H), 3.82 (s, 1H), 3.50-3.45 (m, 1H), 3.08-2.99 (m, 2H), 2.42-2.35 (m, 1H), 2.06 (s, 1H), 1.22-1.07 (m, 9H).

Example 96 and Example 97

(E)-3-(4-((1S,3S)-6-(1-ethyl-1H-pyrazol-4-yl)-2-(2-fluoro-2-methylpropyl)-3-methyl-1, 2,3,4-tetrahydrobenzofuro[2,3-c]pyridin-1-yl)-3,5-difluorophenyl) acrylic Acid (E)-3-(4-((1R,3R)-6-(1-ethyl-1H-pyrazol-4-yl)-2-(2-fluoro-2-methylpropyl)-3-methyl-1, 2,3,4-tetrahydrobenzofuro[2,3-c]pyridin-1-yl)-3,5-difluorophenyl) acrylic Acid

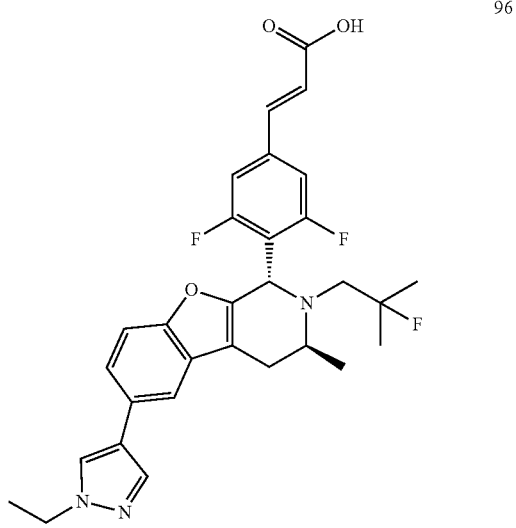

96

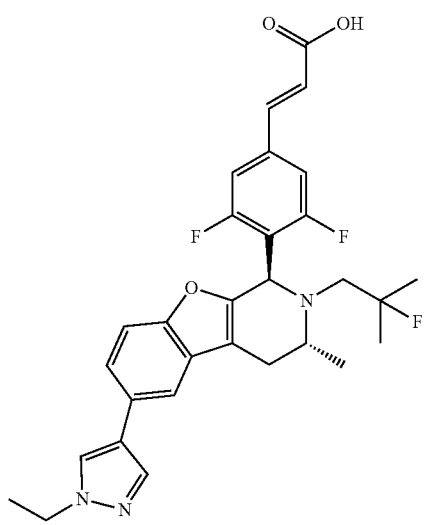

97

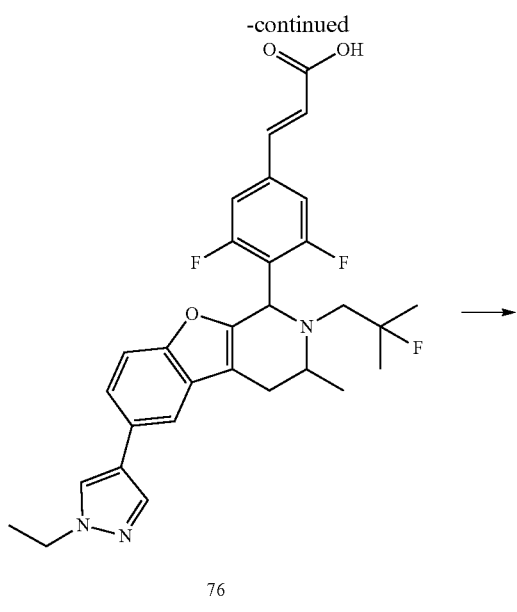

76

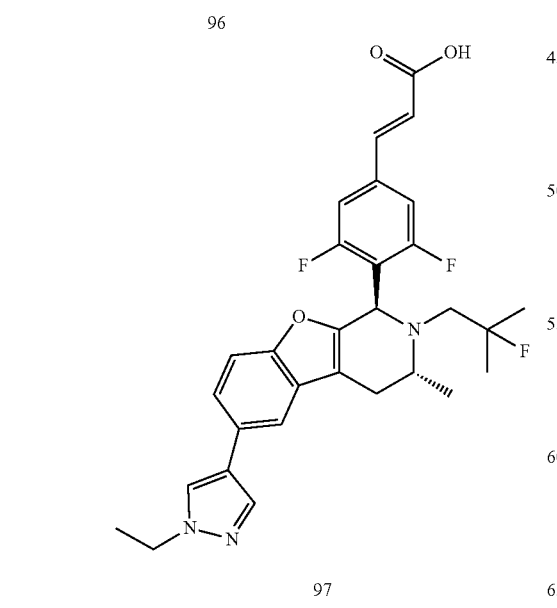

96

97

(E)-3-(4-((1R,3R/1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic acid 76 (160 mg, 0.3 mmol) was separated chirally (separation conditions: chiral preparative column CHIRALPAK AD, 2.5 cm I.D.*25 cm Length, 5 m; mobile phase: n-hexane: ethanol:TFA=60:40:0.1 (V/V/V), flow rate: 60 mL/min). The corresponding fractions were collected and concentrated under reduced pressure to obtain the title compounds (E)-3-(4-((1S,3S)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic acid 96 (124.4 mg) as a light yellow solid and (E)-3-(4-((1R,3R)-6-(1-ethyl-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic acid 97 (170 mg) as a light yellow solid.

Example 96

MS m/z (ESI): 538.2 [M+1];
Chiral HPLC analysis: retention time 8.909 minutes, chiral purity: 98.88% (chromatographic column: CHIRALPAK IC, 4.6 mm*250 mm 5 μm; mobile phase: n-hexane: ethanol:TFA=80:20:0.1 (V/V/V));
$^1$H NMR (400 MHz, CD$_3$OD) δ 8.03 (s, 1H), 7.86 (s, 1H), 7.72 (s, 1H), 7.61 (d, 1H), 7.47 (d, 1H), 7.30-7.37 (dd, 3H), 6.59 (d, 1H), 5.52 (s, 1H), 4.24 (q, 2H), 3.83 (s, 1H), 3.12 (d, 2H), 2.75 (d, 2H), 1.52 (t, 3H), 1.25-1.39 (m, 9H).

Example 97

MS m/z (ESI): 538.2 [M+1];
Chiral HPLC analysis: retention time 7.337 minutes, chiral purity: 98.82% (chromatographic column: CHIRALPAK IC, 4.6 mm*250 mm 5 m; mobile phase: n-hexane: ethanol:TFA=80:20:0.1 (V/V/V));
$^1$H NMR (400 MHz, CD$_3$OD) δ 8.03 (s, 1H), 7.86 (s, 1H), 7.72 (s, 1H), 7.61 (d, 1H), 7.47 (d, 1H), 7.30-7.37 (dd, 3H), 6.59 (d, 1H), 5.52 (s, 1H), 4.24 (q, 2H), 3.83 (s, 1H), 3.12 (d, 2H), 2.75 (d, 2H), 1.52 (t, 3H), 1.25-1.35 (m, 9H).

Example 98 and Example 99

(E)-3-(3,5-difluoro-4-((1S,3R)-2-(2-fluoro-2-methylpropyl)-3-methyl-1,2,3,4-tetrahydro-[6,6'-biisoquinolin]-1-yl)phenyl)acrylic Acid (E)-3-(3,5-difluoro-4-((1R,3S)-2-(2-fluoro-2-methylpropyl)-3-methyl-1,2,3,4-tetrahydro-[6,6'-biisoquinolin]-1-yl)phenyl)acrylic Acid

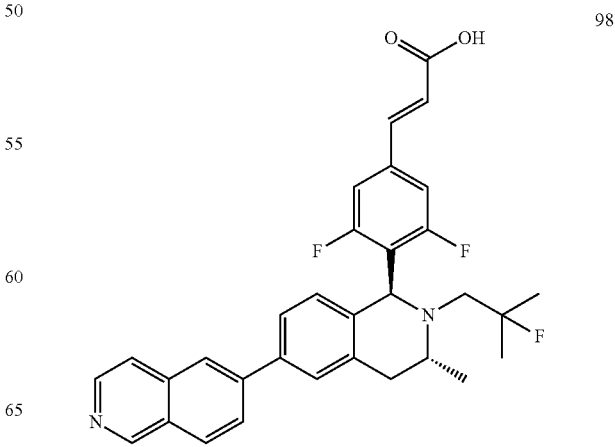

98

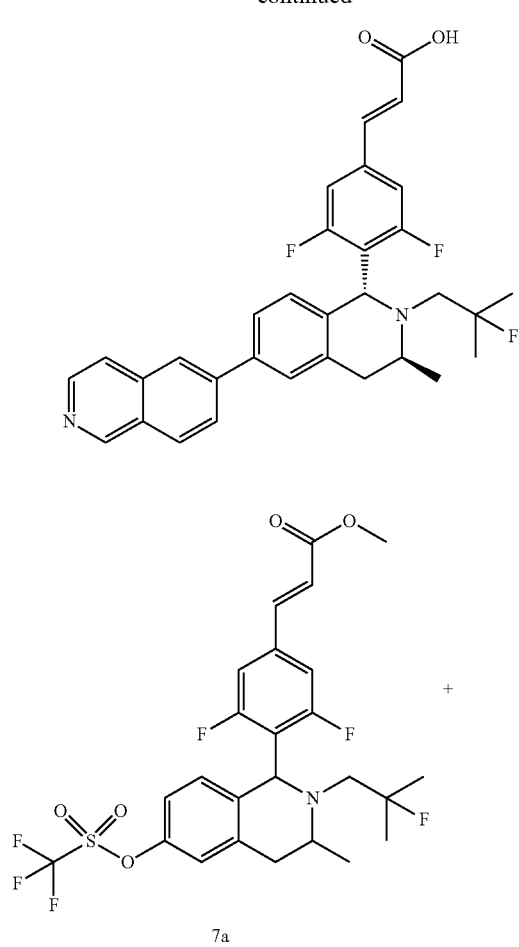
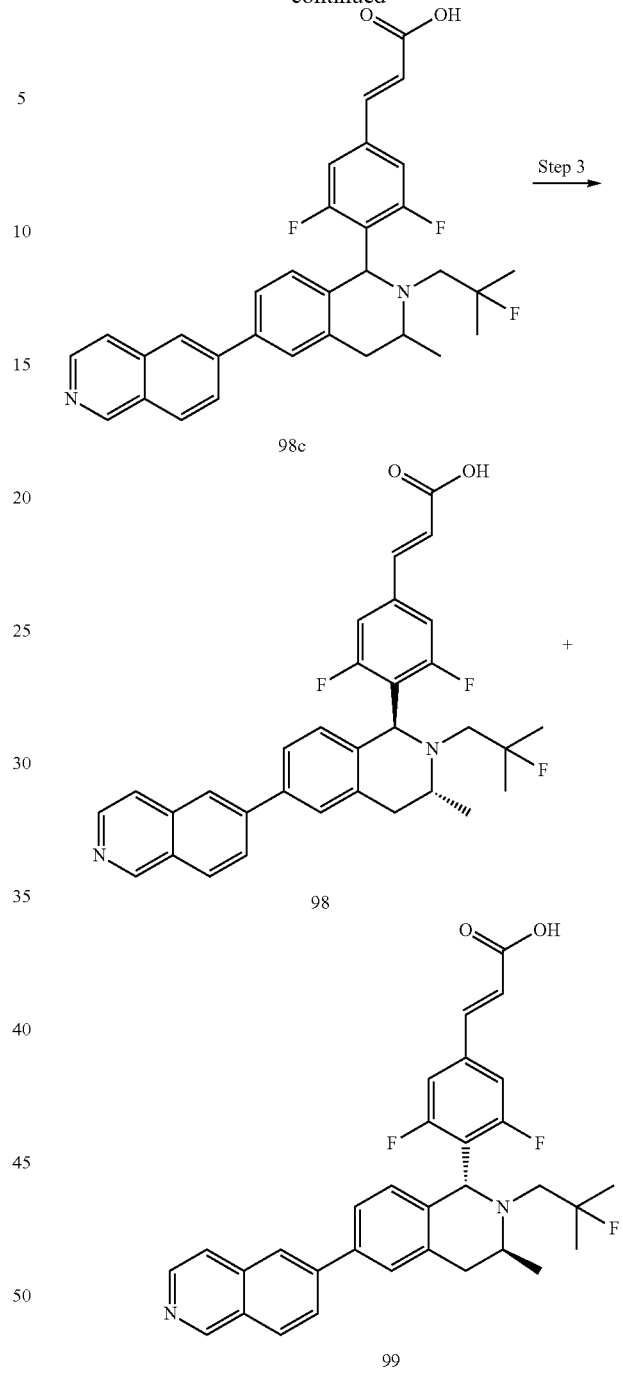
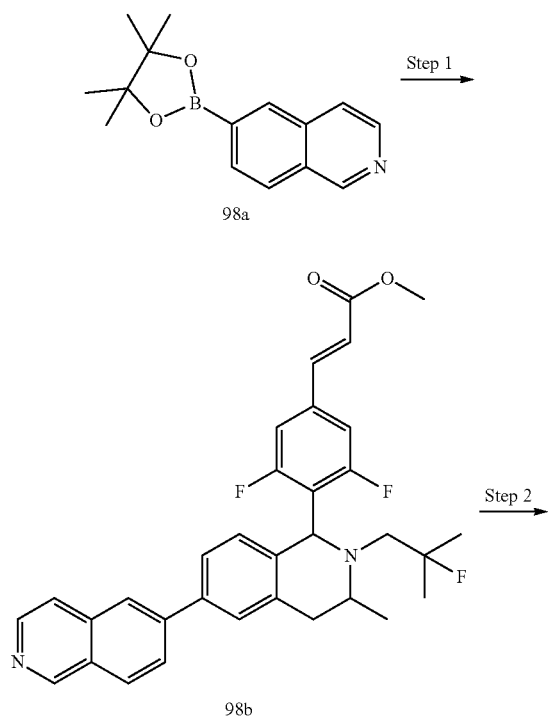
Step 1
(E)-methyl 3-(3,5-difluoro-4-((1S,3R/1R,3S)-2-(2-fluoro-2-methylpropyl)-3-methyl-1,2,3,4-tetrahydro-[6,6'-biisoquinolin]-1-yl)phenyl)acrylate
(E)-methyl 3-(3,5-difluoro-4-((1S,3R/1R,3S)-2-(2-fluoro-2-methylpropyl)-3-methyl-6-(((trifluoromethyl)sulfonyl)oxy)-1,2,3,4-tetrahydroisoquinolin-1-yl)phenyl) acrylate 7a (1.588 g, 2.8 mmol) was dissolved in 20 mL of a mixture of 1,4-dioxane and water (V/V=10:1), then 6-(4,4,5,5-tetramethyl-1,3,2-dioxaborolan-2-yl)isoquinoline 98a (0.862 g, 3.36 mmol), tetrakis (triphenylphosphine) palladium (0.324 g, 0.28 mmol) and sodium carbonate (0.89 g, 8.4 mmol). The reaction mixture was warmed up to 90° C. and stirred for 12 hours, then the reaction stopped. The reaction mixture was cooled to room temperature and filtered. The filtrate was concentrated under reduced pressure. The residue was purified by silica gel column chromatography with elution system B to obtain the title compound (E)-methyl 3-(3,5-difluoro-4-((1S,3R/1R,3S)-2-(2-fluoro-2-methylpropyl)-3-methyl-1,2,3,4-tetrahydro-[6,6'-biisoquinolin]-1-yl)phenyl)acrylate 98b (550 mg, yield 36%) as a white solid.

Step 2

(E)-3-(3,5-difluoro-4-(2-(2-fluoro-2-methylpropyl)-3-methyl-1,2,3,4-tetrahydro-[6,6'-biisoquinolin]-1-yl)phenyl)acrylic Acid (E)-methyl 3-(3,5-difluoro-4-((1S,3R/1R,3S)-2-(2-fluoro-2-methylpropyl)-3-methyl-1,2,3,4-tetrahydro-[6,6'-biisoquinolin]-1-yl)phenyl)acrylate 98b (550 mg, 1.01 mmol) was dissolved in 12 mL of a mixture of methanol and tetrahydrofuran (V/V=1:3), then sodium hydroxide (404 mg, 10.1 mmol) and 1.68 mL of water were added. The reaction mixture was stirred for 12 hours at room temperature. HCl (1 M) was added into the reaction mixture until the pH was 5-6, then 10 mL of water were added. The reaction mixture was extracted with ethyl acetate (15 mL×4). The organic phase was combined, dried over anhydrous sodium sulfate and filtered. The filtrate was concentrated under reduced pressure. The residue was purified by silica gel column chromatography with elution system A to obtain the title compound (E)-3-(3,5-difluoro-4-(2-(2-fluoro-2-methylpropyl)-3-methyl-1,2,3,4-tetrahydro-[6,6'-biisoquinolin]-1-yl)phenyl) acrylic acid 98c (450 mg, yield 83%) as a light yellow solid.

Step 3

(E)-3-(3,5-difluoro-4-((1S,3R)-2-(2-fluoro-2-methylpropyl)-3-methyl-1,2,3,4-tetrahydro-[6,6'-biisoquinolin]-1-yl)phenyl)acrylic Acid (E)-3-(3,5-difluoro-4-((1R,3S)-2-(2-fluoro-2-methylpropyl)-3-methyl-1,2,3,4-tetrahydro-[6,6'-biisoquinolin]-1-yl)phenyl)acrylic Acid (E)-3-(3,5-difluoro-4-(2-(2-fluoro-2-methylpropyl)-3-methyl-1,2,3,4-tetrahydro-[6, 6'-biisoquinolin]-1-yl)phenyl) acrylic acid 98c (300 mg, 0.565 mmol) was separated chirally (separation conditions: chiral preparative column Superchiral S-AD (Chiralway), 0.46 cm I.D.*25 cm Length, 5 µm; mobile phase: CO$_2$O$_2$/isopropanol/DEA=60:40:0.05 (V/V/V), flow rate: 2.5 mL/min). The corresponding fractions were collected and concentrated under reduced pressure to obtain the title compounds (E)-3-(3,5-difluoro-4-((1S,3R)-2-(2-fluoro-2-methylpropyl)-3-methyl-1,2,3,4-tetrahydro-[6,6'-biisoquinolin]-1-yl)phenyl)acrylic acid 98 (90 mg) as a white solid and (E)-3-(3,5-difluoro-4-((1R,3S)-2-(2-fluoro-2-methylpropyl)-3-methyl-1,2,3,4-tetrahydro-[6,6'-biisoquinolin]-1-yl)phenyl)acrylic acid 99 (90 mg) as a yellow crystal.

Example 98

MS m/z (ESI): 531.4 [M+1];

Chiral HPLC analysis: retention time 15.869 minutes, chiral purity: 100% (chromatographic column: CHIRALPAK IE, 4.6 mm*150 mm 5 m; mobile phase: n-hexane:ethanol:TFA=70:30:0.1 (V/V/V));

$^1$H NMR (400 MHz, CD$_3$OD) δ 9.27 (s, 1H), 8.45 (d, 1H), 8.20 (d, 2H), 8.03 (d, 1H), 7.92 (d, 1H), 7.60 (d, 2H), 7.51 (d, 1H), 7.24 (d, 2H), 6.90 (d, 1H), 6.55 (d, 1H), 5.32 (s, 1H), 3.77 (s, 1H), 3.48 (d, 1H), 3.05 (t, 1H), 2.78 (s, 1H), 2.29-2.40 (m, 1H), 1.16-1.21 (m, 6H), 1.08 (d, 3H).

Example 99

MS m/z (ESI): 531.4 [M+1];

Chiral HPLC analysis: retention time 14.020 minutes, chiral purity: 97.42% (chromatographic column: CHIRALPAK IE, 4.6 mm*150 mm 5 m; mobile phase: n-hexane:ethanol:TFA=70:30:0.1 (V/V/V));

$^1$H NMR (400 MHz, CD$_3$OD) δ 9.72 (s, 1H), 8.56 (t, 3H), 8.47 (d, 1H), 8.38 (d, 1H), 7.78 (s, 1H), 7.59-7.67 (m, 2H), 7.29 (d, 2H), 7.03 (d, 1H), 6.58 (d, 1H), 5.50 (s, 1H), 3.84 (s, 1H), 3.51 (d, 1H), 3.17 (t, 1H), 2.89 (d, 1H), 2.18-2.38 (m, 1H), 1.19-1.30 (m, 6H), 1.16 (d, 3H).

Example 100

(E)-3-(4-(6-(1-(difluoromethyl)-1H-pyrazol-4-yl)-2-(2-fluoro-2-methylpropyl)-3-methyl-1,2,3,4-tetrahydrobenzofuro[2,3-c]pyridin-1-yl)-3,5-difluorophenyl)acrylic Acid

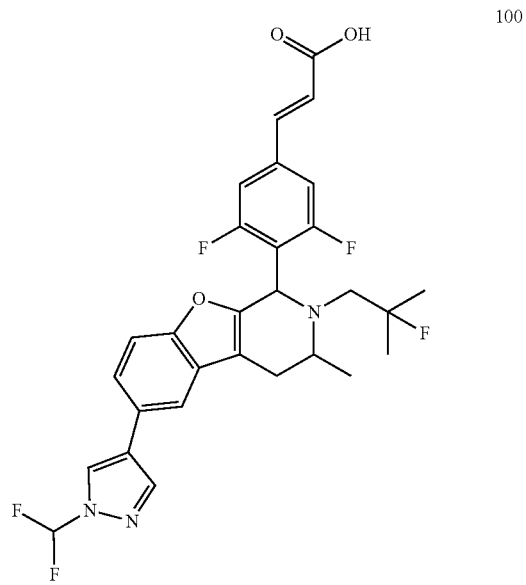

In accordance with the synthetic route of Example 76, the starting material 1-ethyl-4-(4,4,5,5-tetramethyl-1,3,2-dioxaborolan-2-yl)-1H-pyrazole 17a used in step 5 was replaced with 1-(difluoromethyl)-4n-(4,4,5,5-tetramethyl-1,3,2-dioxaborolan-2-yl)-1H-pyrazole 13a, accordingly, the title compound (E)-3-(4-(6-(1-(difluoromethyl)-1H-pyrazol-4-yl)-2-(2-fluoro-2-methylpropyl)-3-methyl-1,2,3,4-tetrahydrobenzofuro[2, 3-c]pyridin-1-yl)-3,5-difluorophenyl)acrylic acid 100 was prepared.

MS m/z (ESI): 557.8 [M−1]

¹H NMR (400 MHz, CD₃OD) δ 8.44 (s, 1H), 8.14 (s, 1H), 7.82 (d, 1H), 7.53-7.68 (m, 3H), 7.30-7.42 (m, 3H), 6.60 (m, 1H), 5.49 (s, 1H), 3.82 (s, 1H), 3.13 (d, 2H), 2.77 (d, 2H), 1.24-1.34 (m, 9H).

Example 101

(E)-3-(4-((6S,8R/6R,8S)-7-(2-fluoro-2-methylpropyl)-8-methyl-6,7,8,9-tetrahydro-3H-pyrazolo[4,3-f]isoquinolin-6-yl)phenyl)acrylic Acid

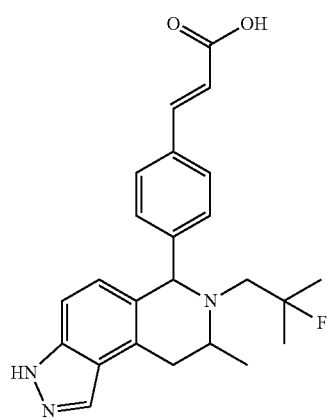

101

In accordance with the synthetic route of Example 92, the starting materials 3-(2-(isobutylamino)propyl)-2-methylphenol 92c and (E)-methyl 3-(3,5-difluoro-4-formylphenyl)acrylate 1e used in step 4 were replaced with 3-(2-((2-fluoro-2-methylpropyl)amino)propyl)-2-methylphenol 70e and (E)-methyl 3-(4-formylphenyl)acrylate 35a, accordingly, the title compound (E)-3-(4-((6S,8R/6R,8S)-7-(2-fluoro-2-methylpropyl)-8-methyl-6,7,8,9-tetrahydro-3H-pyrazolo[4,3-f]isoquinolin-6-yl)phenyl)acrylic acid 101 was prepared.

MS m/z (ESI): 408.4 [M+1]

¹H NMR (400 MHz, CD₃OD) δ 8.24 (s, 1H), 7.65-7.60 (m, 3H), 7.47 (d, 1H) 7.39 (d, 2H), 6.96 (d, 1H), 6.55 (d, 1H), 6.07 (s, 1H), 4.24 (m, 1H), 3.69 (m, 1H), 3.66 (m, 1H), 3.35 (m, 1H), 3.26 (m, 1H), 1.66-1.29 (m, 9H).

Example 102

(E)-3-(4-((6R,8R/6S,8S)-7-isobutyl-8-methyl-6,7,8,9-tetrahydro-3H-pyrazolo[4,3-f]isoquinolin-6-yl)phenyl)acrylic Acid

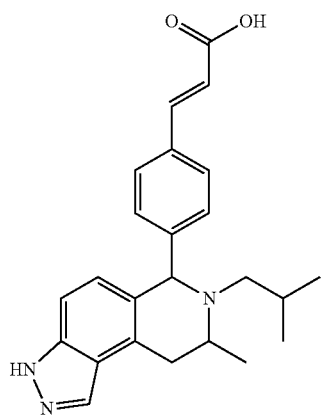

102

In accordance with the synthetic route of Example 92, the starting material (E)-methyl 3-(3,5-difluoro-4-formylphenyl)acrylate 1e used in step 4 was replaced with (E)-methyl 3-(4-formylphenyl)acrylate 35a, accordingly, the title compound (E)-3-(4-((6R,8R/6S,8S)-7-isobutyl-8-methyl-6,7,8,9-tetrahydro-3H-pyrazolo[4,3-f]isoquinolin-6-yl)phenyl) acrylic acid 102 was prepared.

MS m/z (ESI): 390.4 [M+1]

¹H NMR (400 MHz, CD₃OD) δ 8.10 (s, 1H), 7.52-7.47 (m, 3H), 7.29-7.26 (m, 3H), 6.87 (d, 1H), 6.50 (d, 1H), 3.54-3.51 (m, 1H), 3.29-3.25 (m, 1H), 3.00-2.99 (m, 1H), 2.50-2.47 (m, 1H), 2.23-2.20 (m, 1H), 1.97 (s, 1H), 1.82-1.87 (m, 1H), 1.12 (d, 3H), 0.95 (d, 3H), 0.82 (d, 3H).

Example 103

(E)-3-(4-((6S,8R/6R,8S)-7-cyclopentyl-8-methyl-6,7,8,9-tetrahydro-3H-pyrazolo[4,3-f]isoquinolin-6-yl)-3,5-difluorophenyl)acrylic Acid

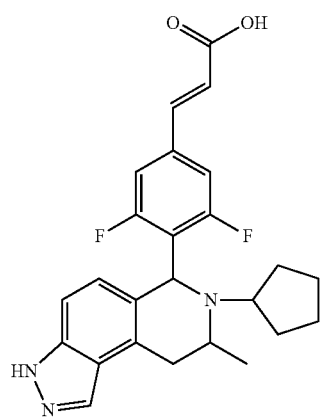

103

In accordance with the synthetic route of Example 92, the starting material 2-methylpropan-1-amine used in step 2 was replaced with cyclopentylamine, accordingly, the title compound (E)-3-(4-(7-cyclopentyl-8-methyl-6,7,8,9-tetrahydro-3H-pyrazolo[4,3-f]isoquinolin-6-yl)-3,5-difluorophenyl)acrylic acid 103 was prepared.

MS m/z (ESI): 438.4 [M+1]

$^1$H NMR (400 MHz, CD$_3$OD) δ 8.09 (s, 1H), 7.42 (d, 1H), 7.24 (d, 1H), 7.14 (d, 2H), 6.79 (d, 1H), 6.53 (d, 1H), 5.26 (s, 1H), 3.58 (s, 1H), 3.43-3.37 (m, 1H), 3.03-2.98 (m, 1H), 2.59-2.54 (m, 1H), 2.11-2.05 (m, 1H), 1.68-1.71 (m, 1H), 1.05 (d, 3H), 0.84 (d, 3H), 0.71 (d, 3H).

Biological Assay

The present invention will be further described with reference to the following test examples, but the examples should not be considered as limiting the scope of the invention.

Test Example 1. Inhibition Effect of the Compounds of the Present Invention on the Binding of Estrogen (E) to Estrogen Receptor (ER)

1. Experimental Object

The compounds of the present invention have an inhibition effect on the binding of E (estrogen) to ER (estrogen receptor), thereby blocking the binding of a complex of E and ER to ERE (estrogen responsive element), and subsequently blocking the expression of downstream luciferase protein.

The inhibition effect of the compounds on the binding of E to ER in vitro was tested by the following method.

The object of this experiment was to determine the inhibition effect of the compounds on the binding of E to ER, and the in vitro activity of the compounds was evaluated according to the IC$_{50}$ value.

2. Experimental Method

ERE was cloned upstream of the luciferase gene, and MCF-7/ERE-luciferase monoclonal cells were selected by transfection of MCF-7 (Cell Bank of Chinese Academy of Sciences typical culture preservation Committee, TCHu74). MCF-7/ERE-luciferase cells were inoculated into the MEM medium (hyclone, SH30024.01B) containing 10% charcoal stripped FBS (Moregate, FBSF), 1% sodium pyruvate (Sigma, Cat. No. S8636), 1% nonessential amino acids (Sigma, Cat. No. M7145) and 500 µg/ml G418 in a 96-well plate with a density of 30,000 cells/well, and the cells were incubated under the conditions of 37° C. and 5% CO$_2$. The drug was prepared as a 20 mM stock solution that was later diluted with 100% DMSO in 10 fold concentration gradient, and then diluted with 20-fold medium. After incubation for 24 hours, the medium was removed, then 0.1 nM estradiol (Sigma, Cat. No. E2758) and 10 µl of the drug diluted with the medium were added to each well, and the control group was added with DMSO. The plate was gently shaken and incubated in a incubator at 37° C., 5% CO$_2$. After 24 hours, the cell culture medium was discarded. Then, 50 µL of the prepared luciferase substrate (Promega, E6110) was added to each well, and the plate was placed in the dark at room temperature for 10-15 minutes, then the chemiluminescence signal value was determined.

3. Test Result

The inhibition effect of the compounds of the present invention on the binding of E to ER was tested by the experiment described above. The values of the chemiluminescence signal vs the logarithmic concentrations of the compounds were plotted using Graghpad Prism, and the IC$_{50}$ values are shown in Table 1.

TABLE 1

IC$_{50}$ value of inhibition effect of the compounds of the present invention on the binding of E to ER

| Example No. | IC$_{50}$ (nM) |
|---|---|
| 1 | 0.77 |
| 2 | 3.2 |
| 3 | 0.72 |
| 4 | 0.73 |
| 5 | 1.25 |
| 6 | 4.9 |
| 7 | 0.32 |
| 8 | 1.85 |
| 10 | 1.26 |
| 11 | 0.64 |
| 12 | 56.55 |
| 13 | 2.11 |
| 14 | 0.29 |
| 16 | 1.36 |
| 17 | 1.17 |
| 18 | 1.52 |
| 20 | 0.86 |
| 21 | 0.32 |
| 23 | 27.27 |
| 24 | 1.59 |
| 25 | 0.51 |
| 27 | 19.8 |
| 28 | 2.28 |
| 31 | 84.11 |
| 32 | 1.45 |
| 33 | 37.7 |
| 34 | 18.45 |
| 36 | 24.86 |
| 37 | 13.69 |
| 38 | 4.42 |
| 39 | 14.18 |
| 41 | 1.94 |
| 42 | 8.1 |
| 43 | 4.98 |
| 45 | 0.87 |
| 46 | 11.37 |
| 47 | 1.5 |
| 48 | 1.82 |
| 49 | 3.4 |
| 50 | 9.7 |
| 51 | 7.43 |
| 52 | 26 |
| 54 | 9.41 |
| 55 | 0.82 |
| 57 | 0.33 |
| 58 | 0.84 |
| 59 | 5.56 |
| 60 | 7.12 |
| 61 | 17.42 |
| 62 | 13.6 |
| 63 | 1.7 |
| 64 | 1.07 |
| 66 | 3.25 |
| 67 | 5.48 |
| 68 | 0.31 |
| 69 | 34 |
| 70 | 0.77 |
| 71 | 0.74 |
| 72 | 40.94 |
| 73 | 0.45 |
| 74 | 0.21 |
| 76 | 1.39 |
| 77 | 2.47 |
| 78 | 6.75 |
| 80 | 27.47 |
| 81 | 4.06 |
| 82 | 13.58 |
| 83 | 20.5 |
| 84 | 2.97 |
| 85 | 21.94 |
| 86 | 4.47 |
| 87 | 14.96 |
| 88 | 1.22 |
| 89 | 0.21 |

TABLE 1-continued

IC$_{50}$ value of inhibition effect of the compounds of the present invention on the binding of E to ER

| Example No. | IC$_{50}$ (nM) |
|---|---|
| 90 | 0.36 |
| 91 | 1.88 |
| 92 | 0.43 |
| 93 | 12.94 |
| 954 | 0.04 |
| 95 | 29.8 |
| 96 | 31.2 |
| 97 | 0.24 |
| 98 | 0.85 |
| 99 | 77.53 |
| 101 | 3.14 |
| 102 | 0.64 |
| 103 | 1.32 |

Conclusion: The compounds of the present invention have a remarkable inhibition effect on the binding of E to ER.

Test Example 2. Inhibition Effect of the Compounds of the Present Invention on the Proliferation of MCF7 Cells 1. Experimental Object The object of this experiment was to determine the inhibition effect of the compounds on the proliferation activity of MCF7 cells, and the in vitro activity of the compounds was evaluated according to the IC$_{50}$ value.

2. Experimental Method

MCF-7 cells (Cell Bank of Chinese Academy of Sciences typical culture preservation Committee, TChu 74) were inoculated into the MEM medium (hyclone, SH30024.01B) containing 10% FBS (Gibco, 10099-141), 1% sodium pyruvate (Sigma, Cat. No. S8636), and 1% nonessential amino acids (Sigma, Cat. No. M7145) in a 96-well plate with a density of 40,000 cells/well, and the cells were incubated under the conditions of 37° C. and 5% CO$_2$. The compound was prepared as a 20 mM stock solution that was later diluted to 1000× final concentration with 100% DMSO, and then diluted with 20-fold medium containing 2% FBS. After incubation for 24 hours, the medium was removed, then 90 μl of the medium containing 2% FBS and 10 μl of the drug were added to each well, 10 μl of DMSO were added to the control group, and the blank group contained only 100 μl medium containing 2% FBS. The plate was gently shaken and incubated in a incubator at 37° C., 5% CO$_2$. After 72 hours, 50 μl of mixed Cell Titer-Glo (Promega, Cat. No. G7571) were added to each well. The plate was shaken until the ingredients were well mixed, and placed at room temperature for 10 minutes, then the chemiluminescence signal value was determined.

3. Data Analysis

The values of the chemiluminescence signals vs the logarithmic concentrations of the compounds were plotted using Graghpad Prism to obtain IC$_{50}$ values. The results are shown in Table 2.

TABLE 2

IC$_{50}$ value of inhibition effect of the compounds of the present invention on the proliferation of MCF7 cells

| Example No. | IC$_{50}$ (nM) |
|---|---|
| 1 | 0.12 |
| 2 | 0.49 |
| 3 | 2.12 |
| 4 | 0.19 |
| 5 | 1.2 |
| 6 | 1.91 |
| 7 | 0.13 |
| 8 | 1.58 |
| 9 | 1.59 |
| 10 | 0.49 |
| 11 | 0.08 |
| 13 | 0.46 |
| 14 | 0.06 |
| 16 | 0.47 |
| 17 | 0.34 |
| 18 | 1.03 |
| 20 | 0.03 |
| 21 | 0.11 |
| 22 | 17.39 |
| 24 | 0.46 |
| 25 | 0.22 |
| 28 | 3.71 |
| 29 | 4.82 |
| 32 | 0.01 |
| 33 | 7.78 |
| 37 | 4.79 |
| 38 | 1.34 |
| 39 | 2.34 |
| 41 | 1.9 |
| 42 | 5 |
| 43 | 2.66 |
| 44 | 1.59 |
| 45 | 0.08 |
| 46 | 3.66 |
| 47 | 0.71 |
| 48 | 0.64 |
| 49 | 1.63 |
| 50 | 4.86 |
| 51 | 3.07 |
| 53 | 14.97 |
| 54 | 3.67 |
| 55 | 0.2 |
| 56 | 0.01 |
| 57 | 0.01 |
| 58 | 1.35 |
| 59 | 1.29 |
| 60 | 2.1 |
| 61 | 3.58 |
| 62 | 16.1 |
| 63 | 0.58 |
| 64 | 0.22 |
| 66 | 1.62 |
| 67 | 0.07 |
| 68 | 0.04 |
| 69 | 6.41 |
| 70 | 0.14 |
| 71 | 0.12 |
| 73 | 0.2 |
| 74 | 0.09 |
| 76 | 0.59 |
| 77 | 0.52 |
| 78 | 4.63 |
| 81 | 3.4 |
| 82 | 4.43 |
| 83 | 17.51 |
| 84 | 4.21 |
| 85 | 7.3 |
| 86 | 0.64 |
| 87 | 9.27 |
| 88 | 0.67 |
| 89 | 0.08 |
| 90 | 0.21 |
| 91 | 0.83 |
| 92 | 0.99 |
| 94 | 0.03 |
| 97 | 0.2 |
| 98 | 1.83 |

TABLE 2-continued

IC$_{50}$ value of inhibition effect of the compounds of the present invention on the proliferation of MCF7 cells

| Example No. | IC$_{50}$ (nM) |
|---|---|
| 101 | 2.07 |
| 102 | 4.99 |
| 103 | 2.95 |

Test Example 3. Degradation Effect of the Compounds of the Present Invention on ERα

1. Experimental Object

In order to determine the degradation effect on ER induced by the compounds of the present invention, the following method was used to determine the degradation effect of the compounds of the present invention on ER.

2. Materials and Instruments

BioTek Synergy HT Flatbed reader

MCF-7 cell line (TChu 74, Cell Bank of Chinese Academy of Sciences typical culture preservation Committee)

ERα Duoset Kit (#DYC5715E, R&D System)

3. Experimental Method

MCF-7 cells were incubated in DMEM/F-12 medium containing 10% FBS.

On the first day of the experiment, MCF-7 cells were resuspended in DMEM/F-12 medium containing 10% FBS treated by activated carbon, then inoculated into a 48-well plate with a density of 50,000 cells/well and incubated for 22-24 hours.

On the second day of the experiment, the test compound was diluted with medium and added to a 48-well plate. The ERα-capture antibody was diluted to 1 μg/ml with PBS, and added to a 96-well plate at 100 μl/well. The plate was sealed and coated overnight at room temperature.

On the third day of the experiment, the coated 96-well plate was washed twice with PBS, added with a sealing solution (1% BSA in PBS) at 110 μl/well and sealed for 1 hour at room temperature. The 48-well plate was washed once with PBS, and the residual liquid was removed. Then, 60 μl of lysis (6 M urea, 1 mM EDTA, 0.5% Triton X-100, 1 mM PMSF, Protease Inhibitor cocktail) was added to each well. After lysis on ice for 15 minutes, the diluent (1 mM EDTA, 0.5% TritonX-100 dissolved in PBS) was added. The cell-diluted lysate was transferred to a 96-well plate at 100 μl/well, then the plate was incubated at room temperature for 2 hours. The diluted primary antibody was added after the plate was washed 4 times with a washing liquid (PBST). After incubation for 1 hour, the 96-well plate was washed 4 times, and the second antibody was added, then the plate was incubated for 30 minutes. After the plate was washed with a washing liquid, TMB chromogenic solution was added and incubated for 15 minutes. The reaction was stopped by the addition of 1 M H$_2$SO$_4$, then the light absorption at 450 nm was read.

4. Test Result

The IC$_{50}$ values measured for the degradation effect of the compounds of the present invention on ERα are shown in Table 3.

TABLE 3

IC$_{50}$ value of the degradation effect of the compounds of the present invention on ERα

| Example No. | IC$_{50}$ (nM) |
|---|---|
| 1 | 0.11 |
| 2 | 0.95 |
| 4 | 0.56 |
| 5 | 3.94 |
| 6 | 1.92 |
| 7 | 2.71 |
| 10 | 6.58 |
| 11 | 2.02 |
| 13 | 6.93 |
| 14 | 0.64 |
| 16 | 3.11 |
| 17 | 1.43 |
| 18 | 4.2 |
| 20 | 0.82 |
| 21 | 0.67 |
| 24 | 0.12 |
| 25 | 0.21 |
| 32 | 0.41 |
| 41 | 0.36 |
| 45 | 2.12 |
| 47 | 3.54 |
| 48 | 7.36 |
| 49 | 6.29 |
| 55 | 0.69 |
| 57 | 0.1 |
| 58 | 1.79 |
| 59 | 6.25 |
| 60 | 7.35 |
| 64 | 4.72 |
| 67 | 6.69 |
| 68 | 0.11 |
| 70 | 0.77 |
| 71 | 0.06 |
| 73 | 0.76 |
| 74 | 1.35 |
| 76 | 2.43 |
| 77 | 2.21 |
| 78 | 0.37 |
| 81 | 1.62 |
| 86 | 7.13 |
| 88 | 1.61 |
| 89 | 0.31 |
| 90 | 2.42 |
| 91 | 2.33 |
| 94 | 0.02 |
| 97 | 6.11 |

Conclusion: The compounds of the present invention have a remarkable degradation effect on ERα.

Pharmacokinetics Assay

Test Example 4. The Pharmacokinetics Assay of the Compounds of Examples 10, 14, 20, 21, 57, 68, 71, 73, 74, 76 and 89 of the Present Invention 1. Abstract BALB/C nude mice were used as test animals. The drug concentration in plasma at different time points was determined by LC/MS/MS after intragastrical administration of the compounds of Examples 10, 14, 20, 21, 57, 68, 71, 73, 74, 76 and 89 to BALB/C nude mice. The pharmacokinetic behavior of the compounds of the present invention was studied and evaluated in BALB/C nude mice.

2. Protocol 2.1 Samples

Compounds of Examples 10, 14, 20, 21, 57, 68, 71, 73, 74, 76 and 89

2.2 Test Animals

Ninety-nine (99) female BALB/C nude mice were equally divided into 11 groups, which were purchased from SINO- BRITSH SIPPR/BK LAB. ANIMAL LTD., CO, with Certificate No.: SCXK (Shanghai) 2008-0016.

2.3 Preparation of the Test Compounds

The appropriate amount of each test compound was weighed, and successively added with 9% PEG400+0.5% tween 80+0.5% PVP+90% aqueous solution of 0.5% CMC.

2.4 Administration

After an overnight fast, 99 female BALB/C nude mice were equally divided into 11 groups, and administered the test compounds intragastrically at an administration volume of 0.2 mL/10 g.

3. Process

Blood (0.1 mL) was sampled (3 mice at each time point) at 0.5, 1.0, 2.0, 4.0, 6.0, 8.0, 11.0 and 24.0 hours after administration. The samples were stored in heparinized test tubes, and centrifuged for 10 minutes at 3,500 rpm to separate the blood plasma. The plasma samples were stored at −20° C. The plasma concentration of the test compounds in BALB/C nude mice after intragastrical administration was determined by LC/MS/MS.

4. Results of Pharmacokinetic Parameters in BALB/C Nude Mice

Pharmacokinetic parameters of the compounds of Examples 10, 14, 20, 21, 57, 68, 71, 73, 74, 76 and 89 of the present invention are shown below.

| | Pharmacokinetics Assay (3 mg/kg) | | | | | |
|---|---|---|---|---|---|---|
| Example No. | Plasma Conc. Cmax (ng/mL) | Area Under Curve AUC (ng/mL*hour) | Half-Life t1/2 (hour) | Mean Residence Time MRT (hour) | Clearance CL/F (1/hour/kg) | Apparent Distribution Volume Vz/F (1/kg) |
| 10 | 2597 | 15422 | 4.11 | 5.72 | 3.24 | 1152 |
| 14 | 6749 | 32690 | 4.74 | 5.93 | 1.53 | 627 |
| 20 | 3292 | 13049 | 3.27 | 4.07 | 3.83 | 1085 |
| 21 | 4300 | 10076 | 2.52 | 2.71 | 4.96 | 1081 |
| 57 | 5066 | 15087 | 2.78 | 3.23 | 3.31 | 798 |
| 68 | 3420 | 13184 | 2.32 | 3.7 | 6.32 | 1269 |
| 71 | 4130 | 8813 | 1.59 | 2.62 | 9.45 | 1304 |
| 73 | 1492 | 3954 | 1.47 | 2.45 | 12.6 | 1614 |
| 74 | 2527 | 5853 | 3.16 | 2.41 | 8.54 | 2339 |
| 76 | 5455 | 26945 | 4.53 | 5.7 | 1.86 | 728 |
| 89 | 1269 | 7706 | 3.97 | 5.69 | 6.49 | 2228 |

Conclusion: The compounds of the present invention are well absorbed and have a remarkable pharmacological absorption effect.

What is claimed is:

1. A method for treating an estrogen receptor mediated or dependent disease or condition in a subject in need thereof, wherein the estrogen receptor mediated or dependent disease or disorder is cancer selected from the group consisting of breast cancer, endometrial cancer, cervical cancer, prostate cancer, ovarian cancer, uterine cancer, the method comprising administering to the subject a pharmaceutical composition comprising one or more pharmaceutically acceptable carriers, diluents, or excipients, and a compound of formula (I):

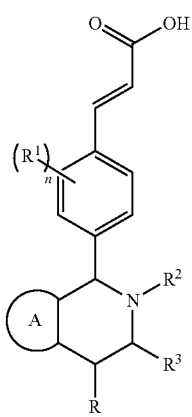

or a tautomer, mesomer, racemate, enantiomer, diastereomer, or mixture thereof, or a pharmaceutically acceptable salt thereof, wherein:

ring A is selected from the group consisting of:

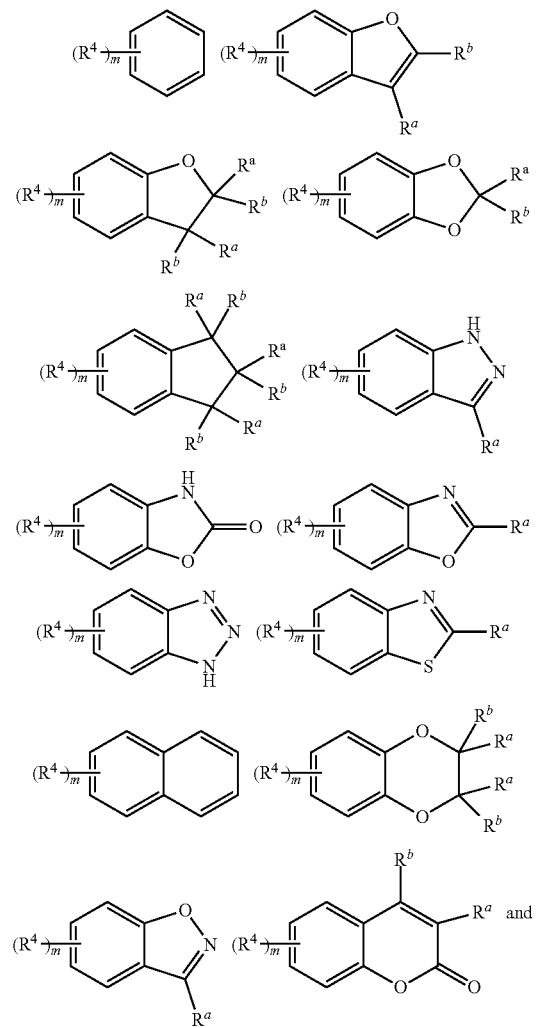

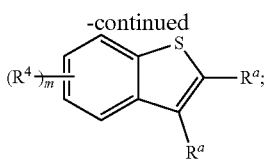

R is selected from the group consisting of hydrogen, alkyl and cycloalkyl, wherein the alkyl and cycloalkyl are each optionally substituted by one or more groups selected from the group consisting of halogen, amino, cyano, hydroxy, alkoxy, carboxy, cycloalkyl, aryl and heteroaryl;

each $R^1$ is identical or different and each is independently selected from the group consisting of hydrogen, alkyl, halogen, cyano and alkoxy, wherein the alkyl and alkoxy are each optionally substituted by one or more groups selected from the group consisting of halogen, amino, cyano and hydroxy;

$R^2$ is selected from the group consisting of alkyl, haloalkyl and cycloalkyl, wherein the alkyl and cycloalkyl are each optionally substituted by one or more groups selected from the group consisting of halogen, amino, cyano, hydroxy, alkoxy, carboxy, cycloalkyl, aryl and heteroaryl;

$R^3$ is selected from the group consisting of hydrogen, alkyl and cycloalkyl, wherein the alkyl and cycloalkyl are each optionally substituted by one or more groups selected from the group consisting of alkyl, halogen, amino, cyano, hydroxy, alkoxy, carboxy and cycloalkyl;

each $R^4$ is identical or different and each is independently selected from the group consisting of hydrogen, alkyl, cycloalkyl, alkoxy, amino, halogen, cyano, carboxy, alkenyl, alkynyl, heterocyclyl, aryl, heteroaryl, $-OR^5$, $-NHC(O)OR^5$ and $-NHC(O)NR^6R^7$, wherein the alkyl, alkenyl, alkynyl, cycloalkyl, alkoxy, heterocyclyl, aryl and heteroaryl are each optionally substituted by one or more groups selected from the group consisting of $R^c$, alkyl, haloalkyl, hydroxyalkyl, halogen, amino, nitro, cyano, hydroxy, oxo, hydroxyalkyl, alkoxy, cycloalkyl, heterocyclyl, aryl and heteroaryl;

$R^c$ is selected from the group consisting of alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl and $-C(O)NR^6R^7$;

$R^6$ and $R^7$ are identical or different and each is independently selected from the group consisting of hydrogen, alkyl, hydroxy, halogen, cyano, amino, nitro, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^a$ and $R^b$ are identical or different and each is independently selected from the group consisting of hydrogen, alkyl, hydroxy, halogen, cyano, amino, nitro, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, $-OR^5$, aryl and heteroaryl;

m is 0, 1, 2, 3 or 4; and n is 0, 1, 2, 3 or 4.

2. The method according to claim 1, wherein the cancer is breast cancer, ovarian cancer, endometrial cancer, or uterine cancer.

3. The method according to claim 1, wherein the cancer is breast cancer.

4. The method according to claim 1, $R^1$ is halogen.

5. The method according to claim 1, wherein $R^2$ is alkyl, and the alkyl is optionally substituted by one or more groups selected from the group consisting of halogen, amino, cyano, hydroxy, alkoxy, carboxy and cycloalkyl.

6. The method according to claim 1, wherein $R^3$ is alkyl.

7. The method according to claim 1, wherein R is hydrogen or alkyl.

8. The method according to claim 1, wherein ring A is selected from the group consisting of:

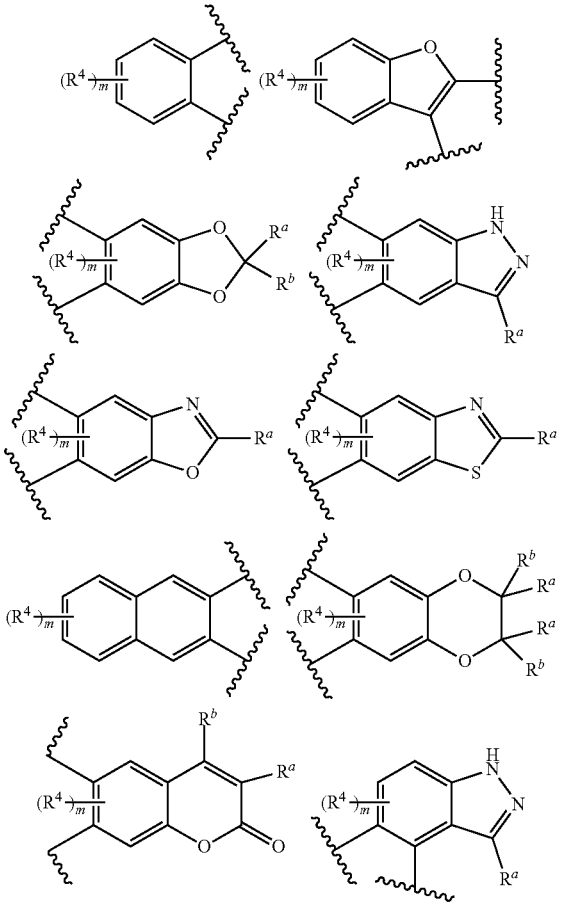

-continued

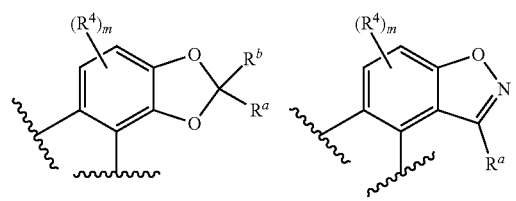

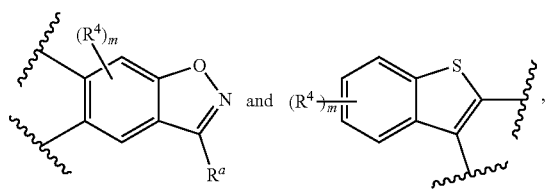

wherein:

R⁴, Rᵃ, Rᵇ and m are as defined in claim 1.

9. The method according to claim 1, wherein the compound of formula (I), or the tautomer, mesomer, racemate, enantiomer, diastereomer, or mixture thereof, or the pharmaceutically acceptable salt thereof is selected from the group consisting of a compound of formula (I-A), formula (I-B) and formula (I-C):

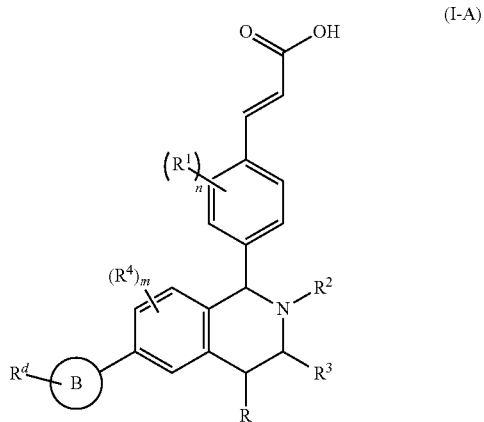

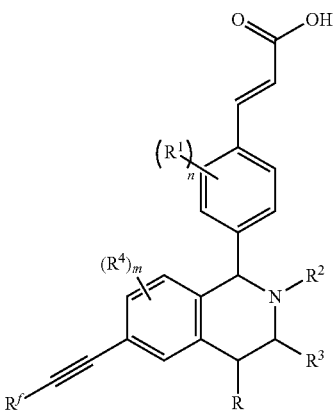

or a tautomer, mesomer, racemate, enantiomer, diastereomer, or mixture thereof, or a pharmaceutically acceptable salt thereof, wherein:
ring B is selected from the group consisting of cycloalkyl, heterocyclyl, aryl and heteroaryl;

$R^d$ is selected from the group consisting of hydrogen, alkyl, halogen, haloalkyl, hydroxyalkyl, oxo, amino, cyano, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^f$ is selected from the group consisting of hydrogen, alkyl, halogen, haloalkyl, hydroxyalkyl, hydroxyalkyl, amino, cyano, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl; and R to R⁵, m and n are as defined in claim 1.

10. The method according to claim 1, wherein the compound of formula (I), or the tautomer, mesomer, racemate, enantiomer, diastereomer, or mixture thereof, or the pharmaceutically acceptable salt thereof is selected from the group consisting of a compound of formula (II), formula (III) and formula (IV):

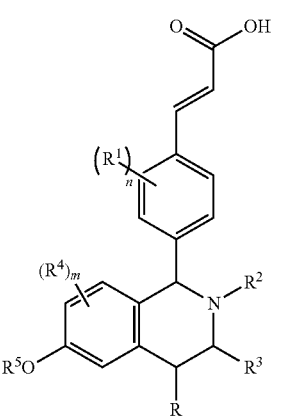

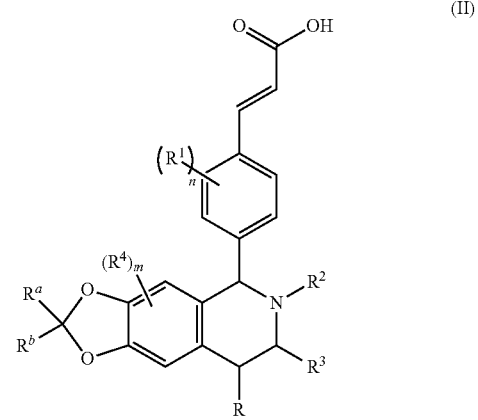

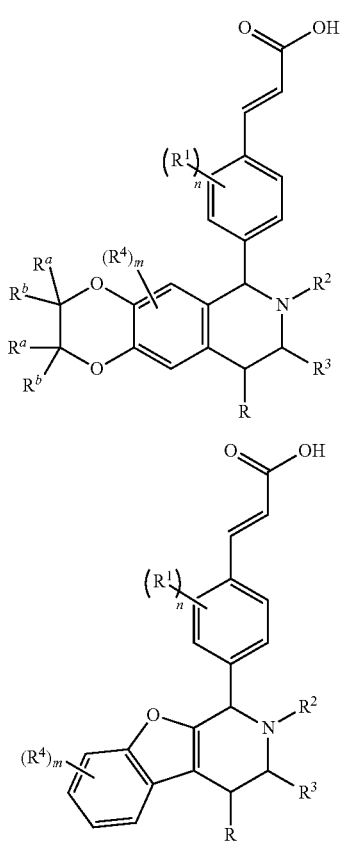

or a tautomer, mesomer, racemate, enantiomer, diastereomer, or mixture thereof, or a pharmaceutically acceptable salt thereof, wherein:

R to $R^3$, $R^a$, $R^b$, m and n are as defined in claim 1.

11. The method according to claim 1, wherein the compound of formula (I), or the tautomer, mesomer, racemate, enantiomer, diastereomer, or mixture thereof, or the pharmaceutically acceptable salt thereof is a compound of formula (I-D):

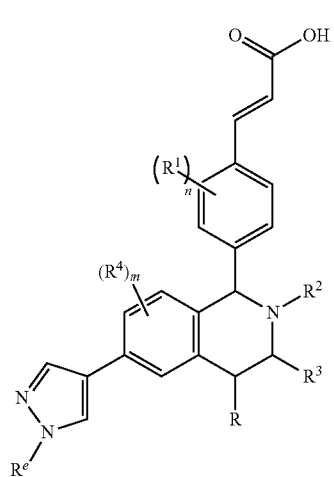

or a tautomer, mesomer, racemate, enantiomer, diastereomer, or mixture thereof, or a pharmaceutically acceptable salt thereof:

wherein:

$R^e$ is selected from the group consisting of alkyl, haloalkyl, hydroxyalkyl, alkoxy, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl; and R to $R^5$, m and n are as defined in claim 1.

12. The method according to claim 1, wherein the compound of formula (I), or the tautomer, mesomer, racemate, enantiomer, diastereomer, or mixture thereof, or the pharmaceutically acceptable salt thereof is a compound of formula (I-I):

(I-I)

[Structure I-I]

or a tautomer, mesomer, racemate, enantiomer, diastereomer, or mixture thereof, or a pharmaceutically acceptable salt thereof, wherein:

ring A, R to $R^3$ and n are as defined in claim 1.

13. The method according to claim 1, wherein the compound of formula (I), or the tautomer, mesomer, racemate, enantiomer, diastereomer, or mixture thereof, or the pharmaceutically acceptable salt thereof is selected from the group consisting of:

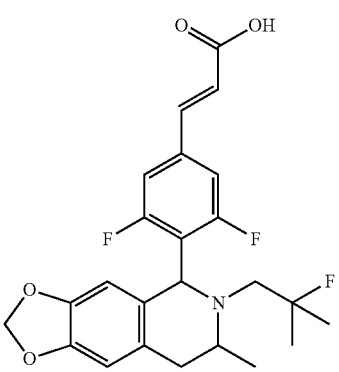

207
-continued
2
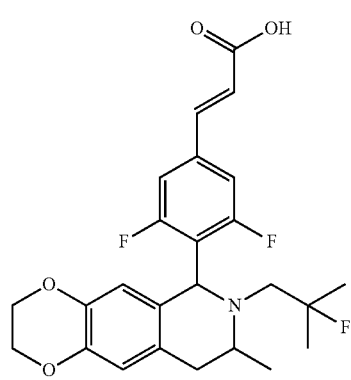
3
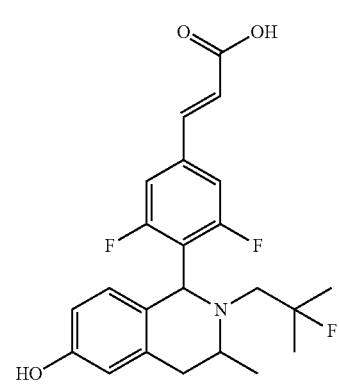
4
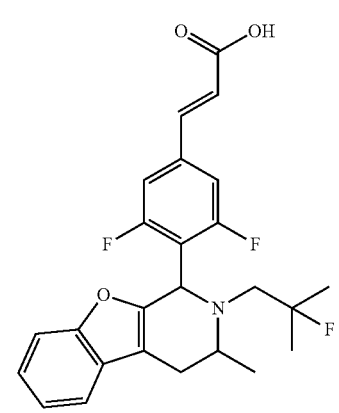
5
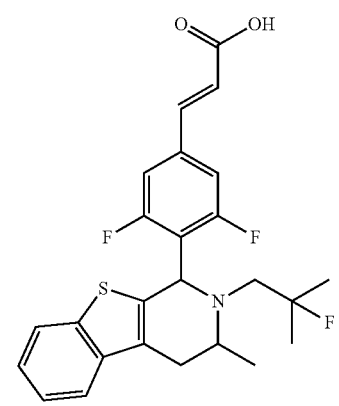
208
-continued
6
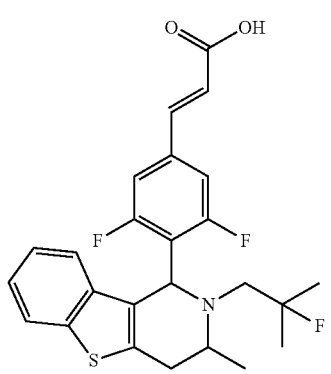
7
8

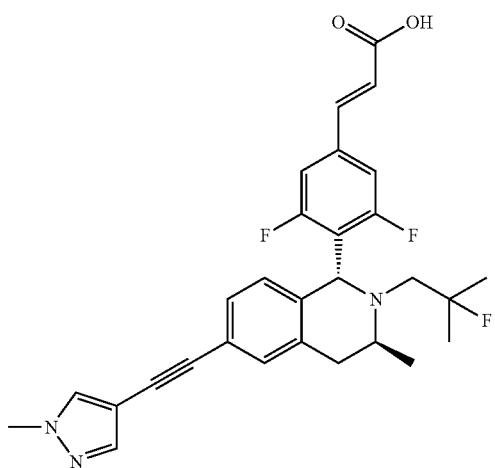
9
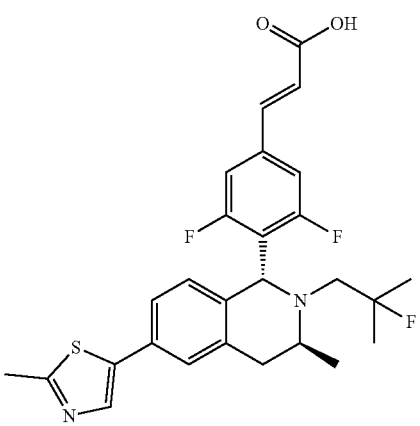
12
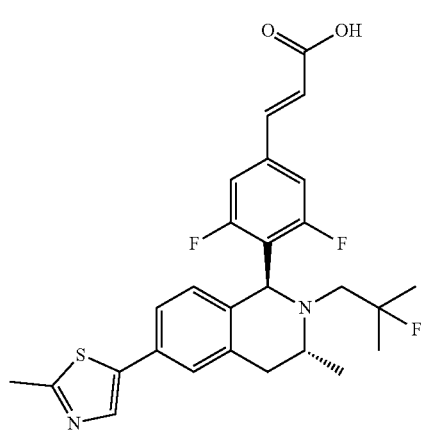
10
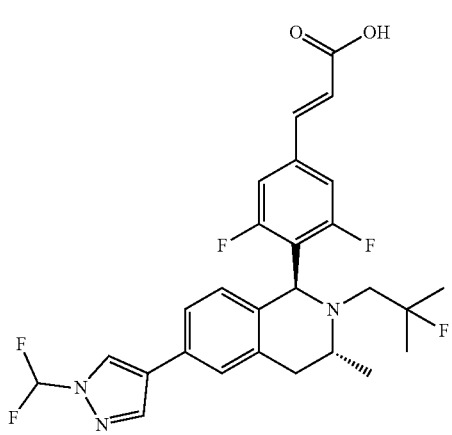
13
11
14

15
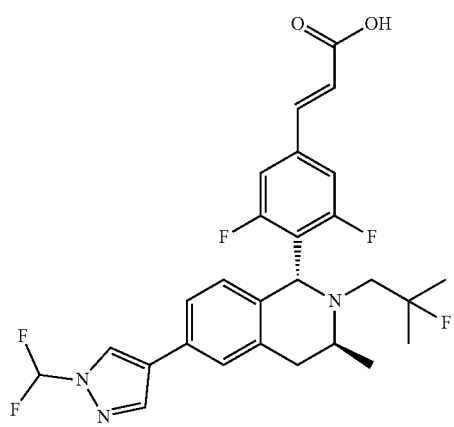
16
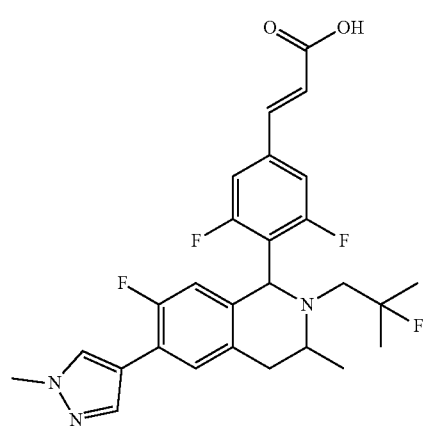
17
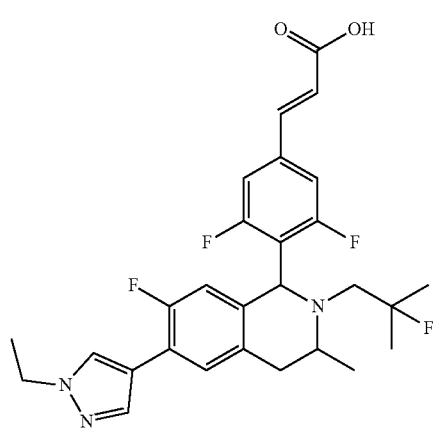
18
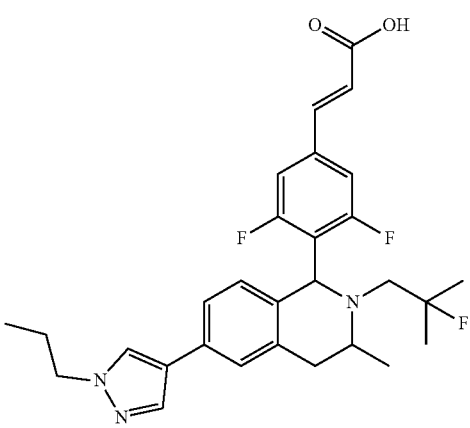
19
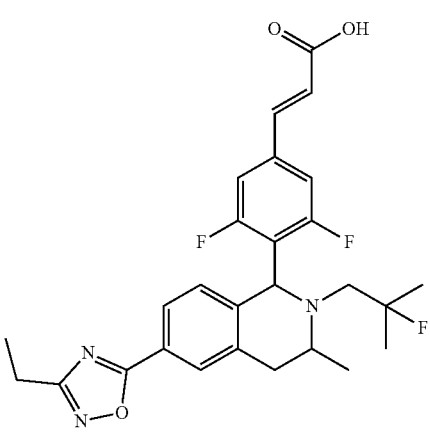
20
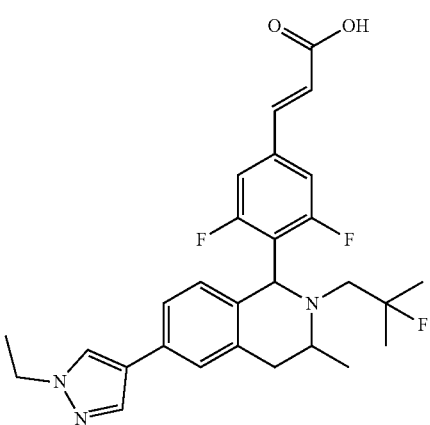

213
-continued
21
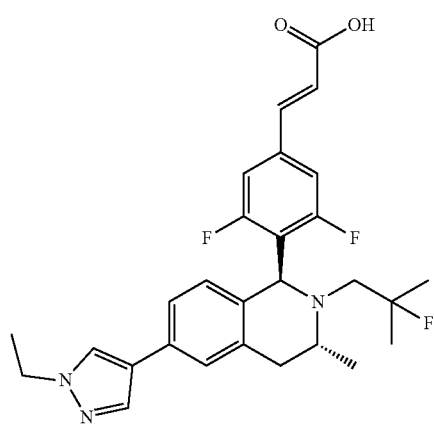
22
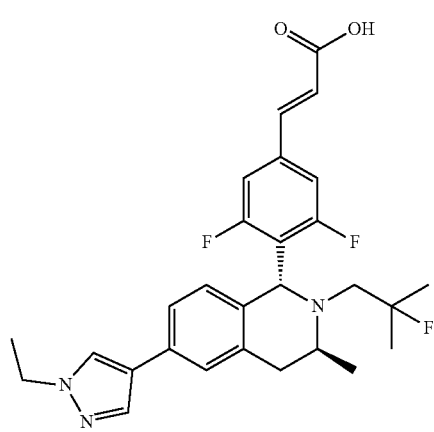
23
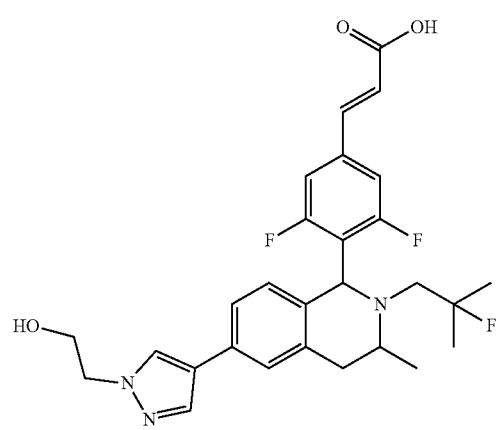
214
-continued
24
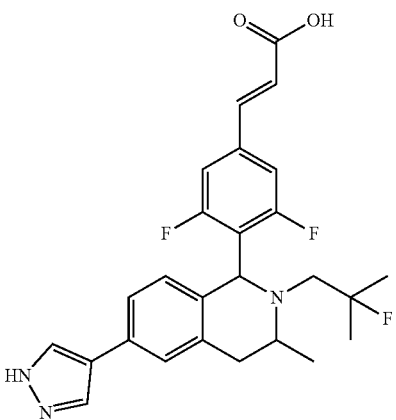
25
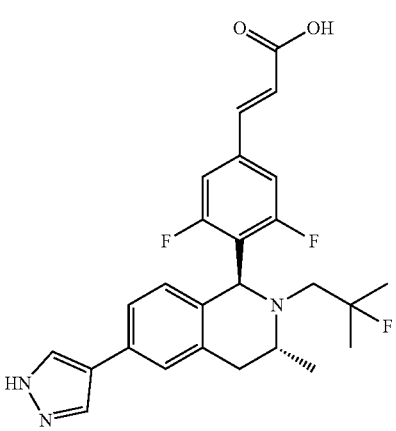
26
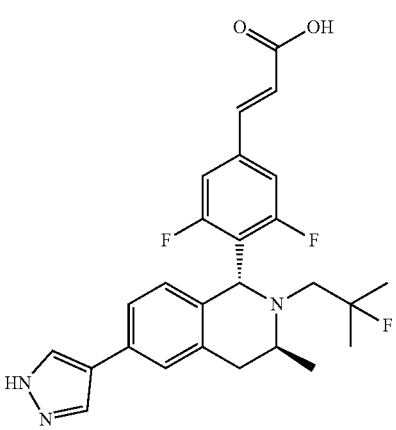

27
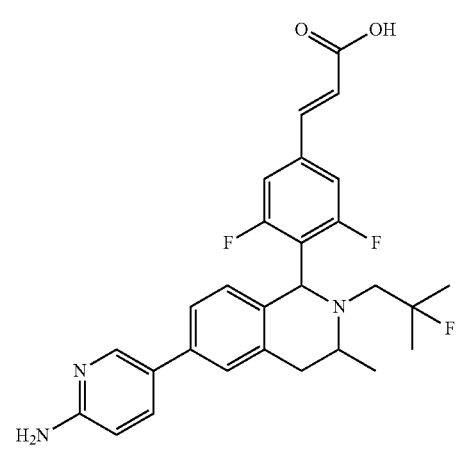
28
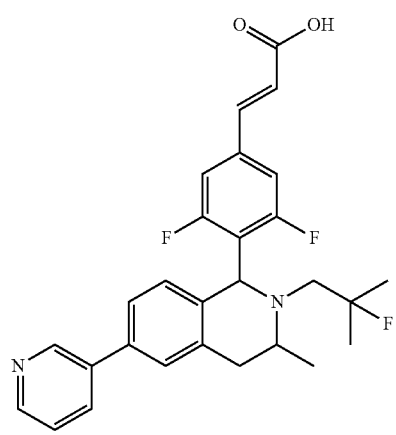
29
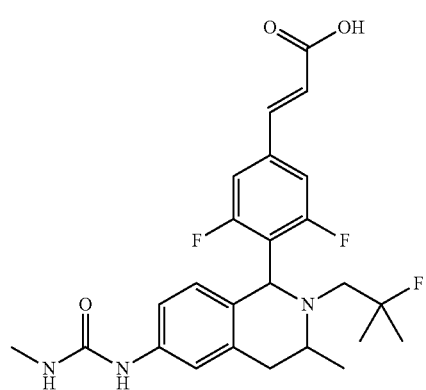
30
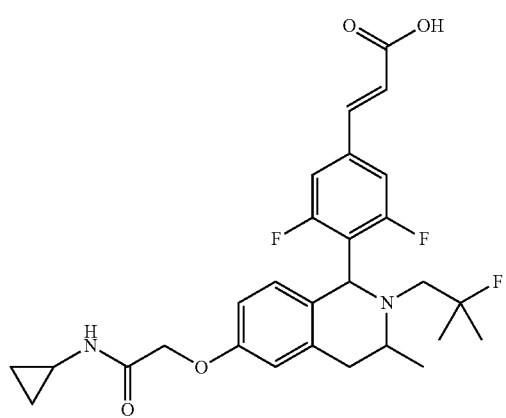
31
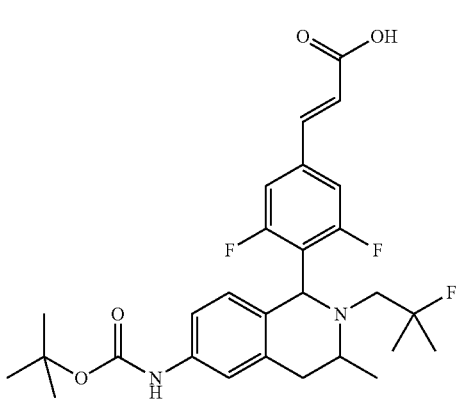
32
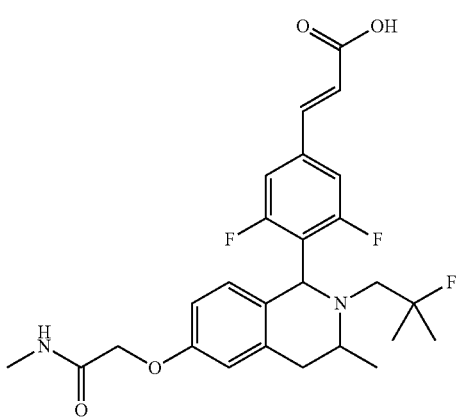
33
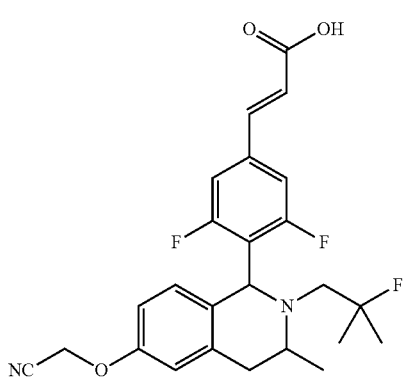
34
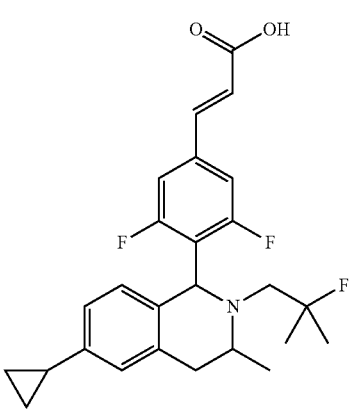

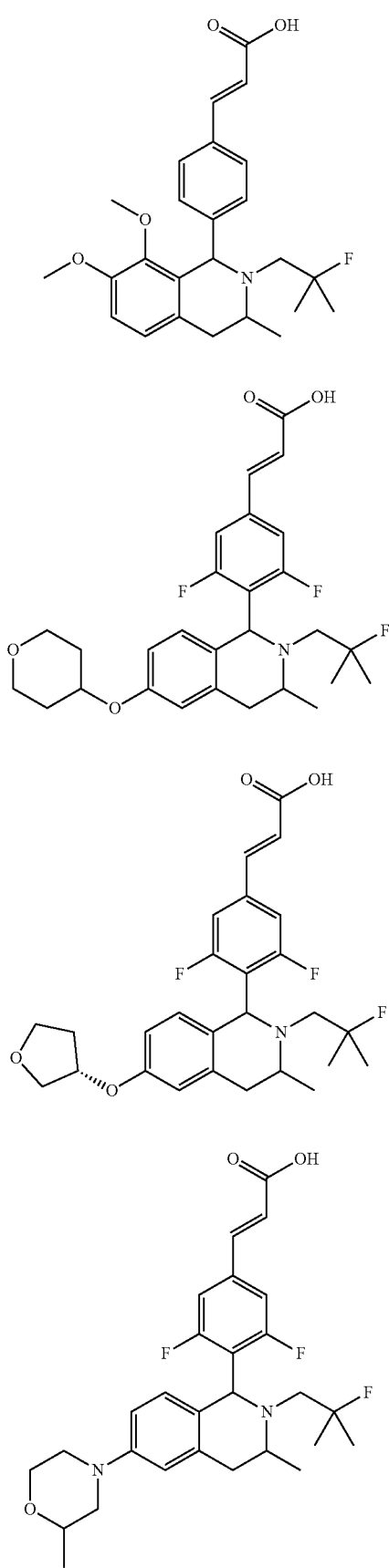
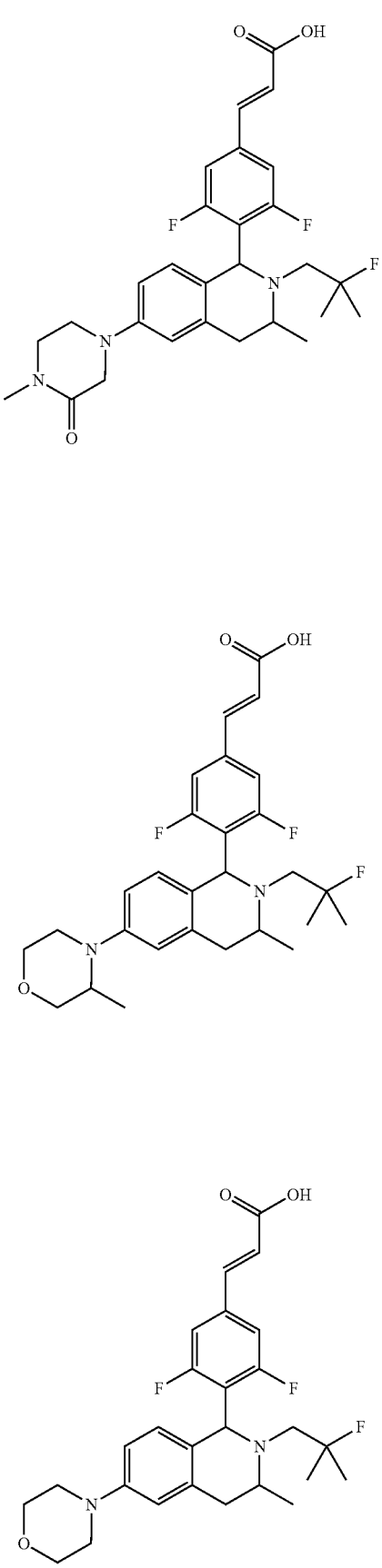

42
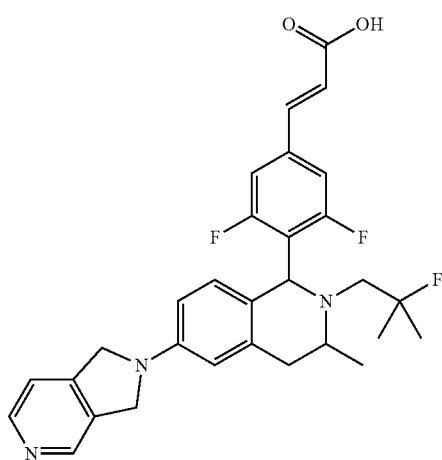
43
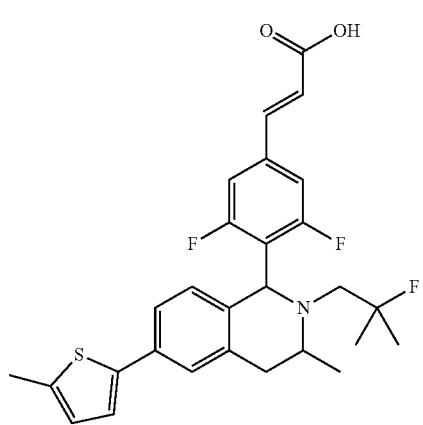
44
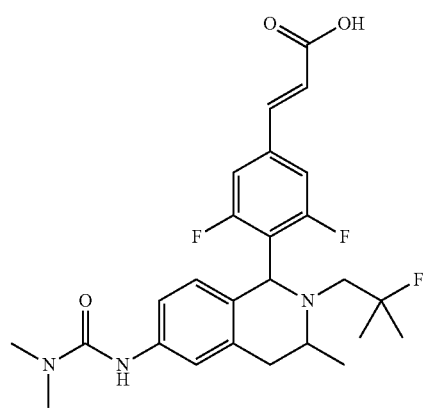
45
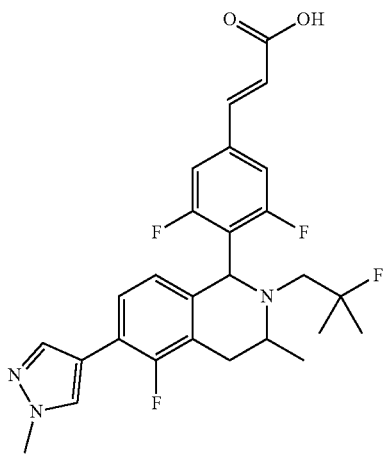
46
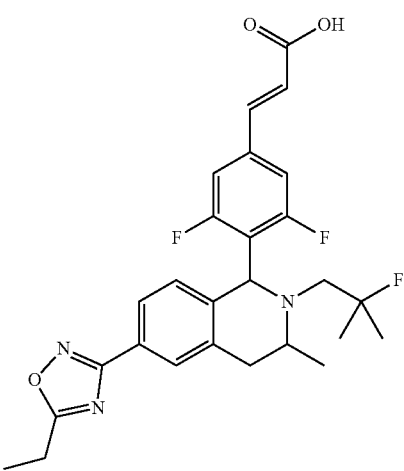
47
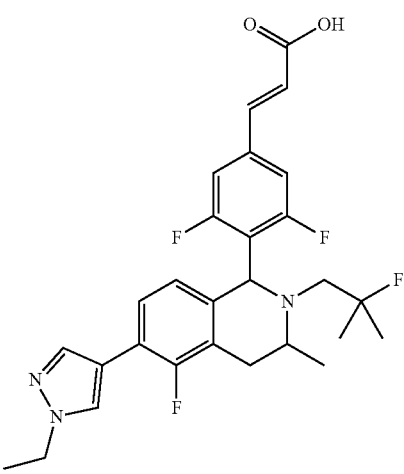

48
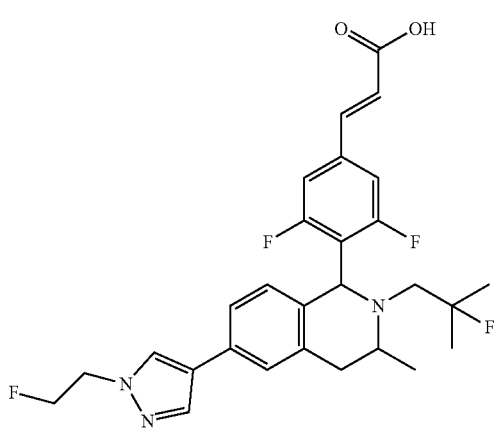
51
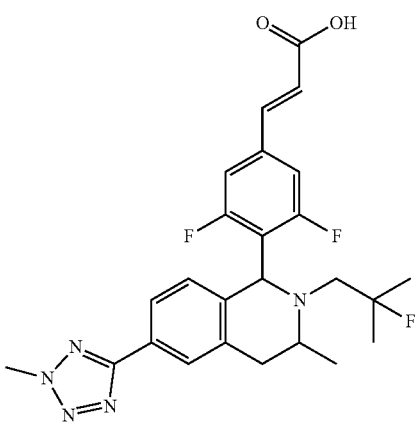
49
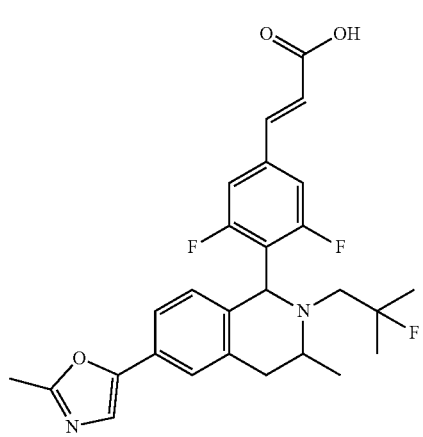
52
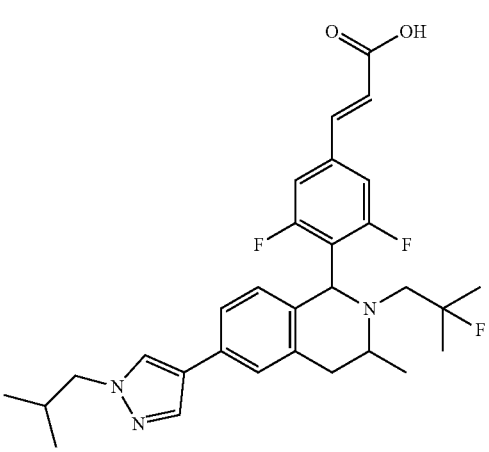
50
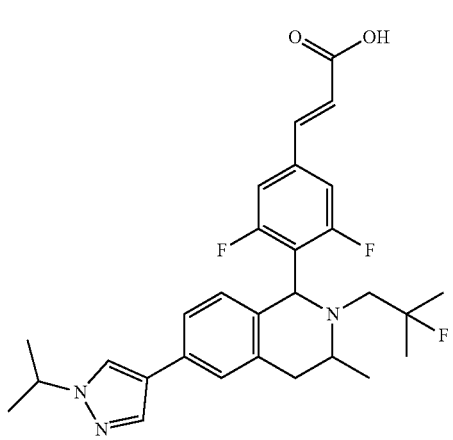
53
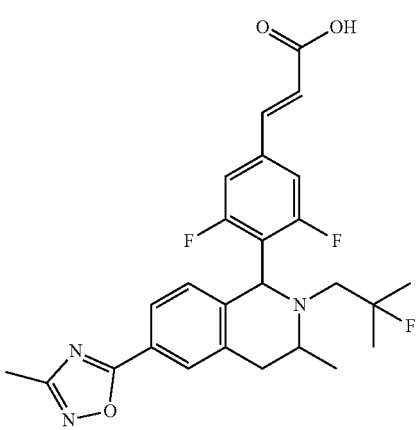

223
-continued
| 54 | 57 |
|---|---|
| 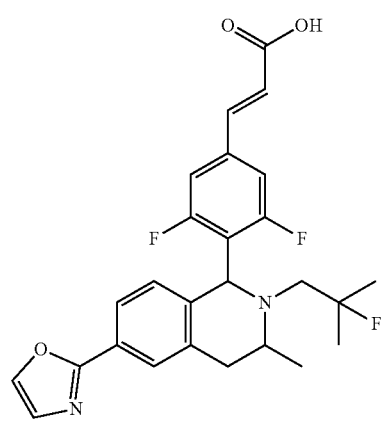 | 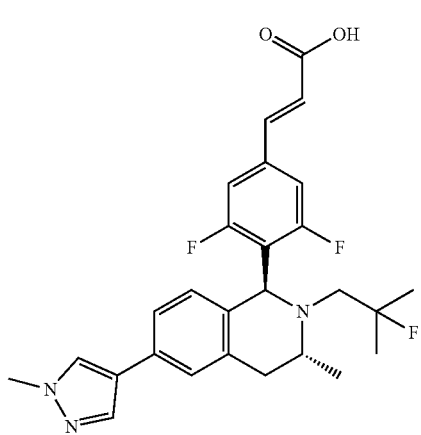 |
| 55 | 58 |
| 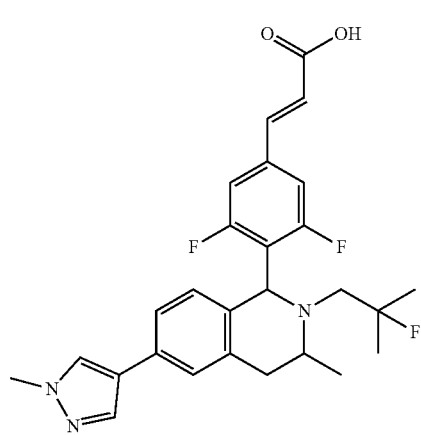 | 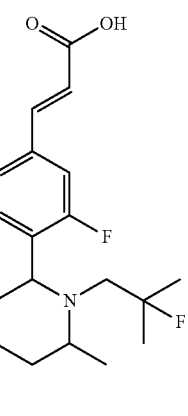 |
| 56 | 59 |
| 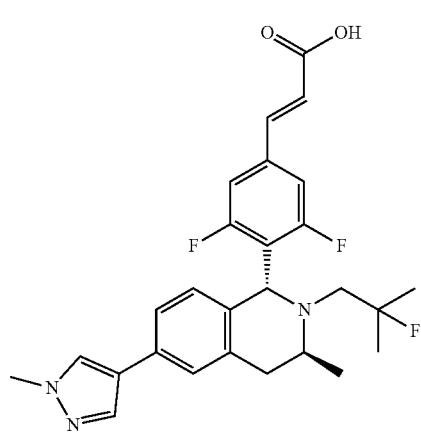 | 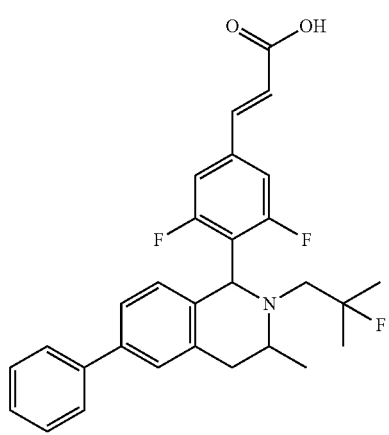 |
224
-continued 60
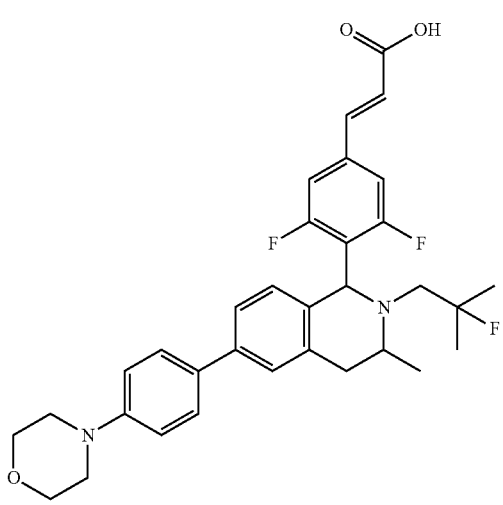
61
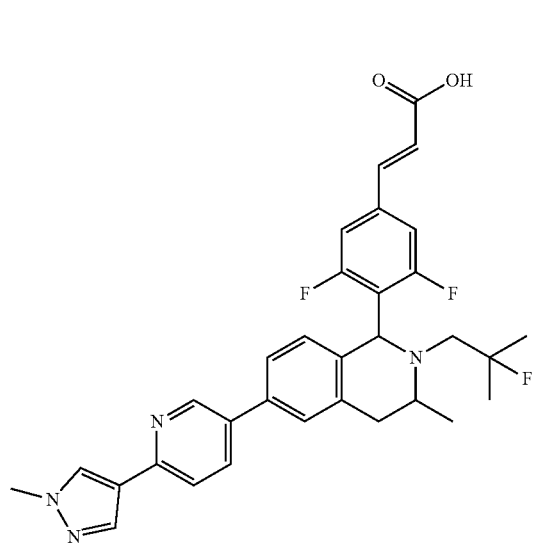
62
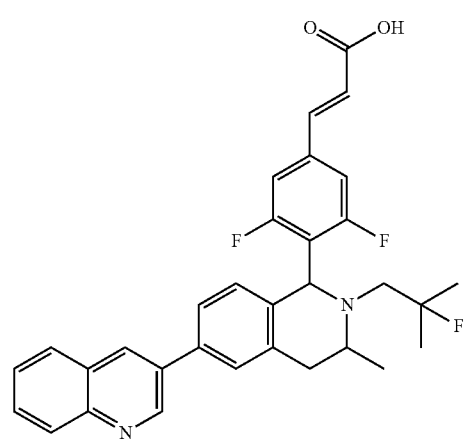
63
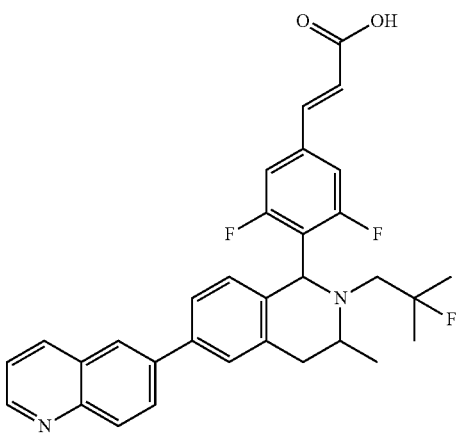
64
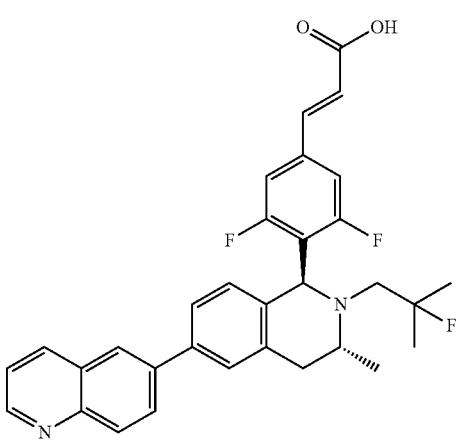
65
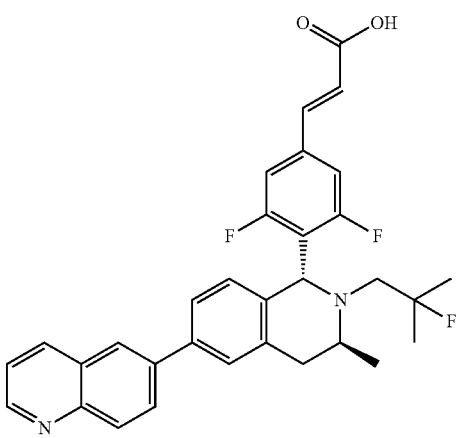

-continued
66
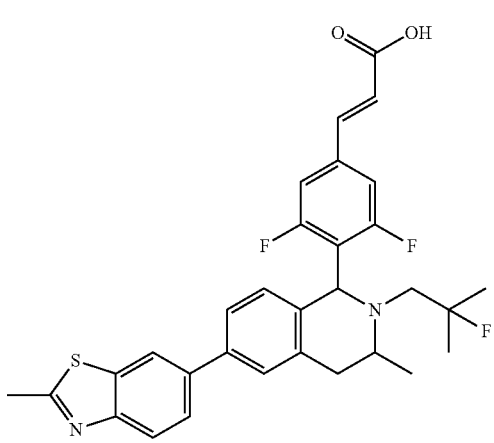
67
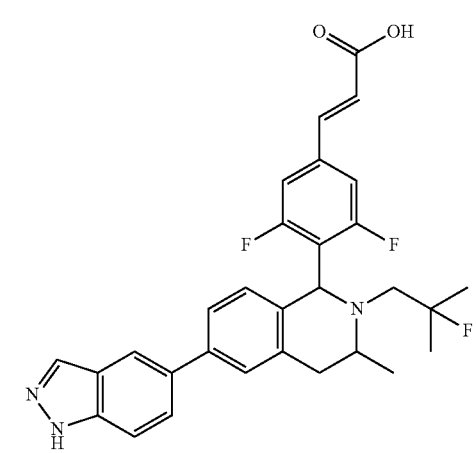
68
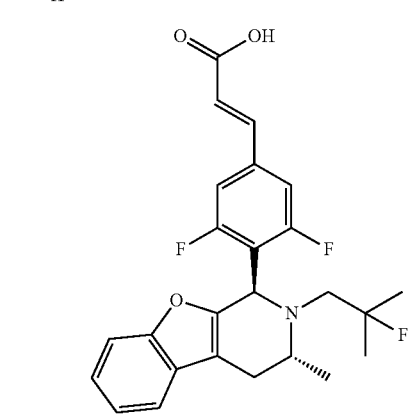
69
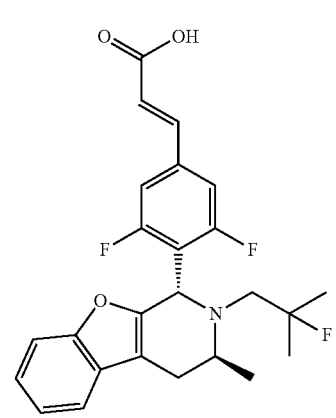
-continued
70
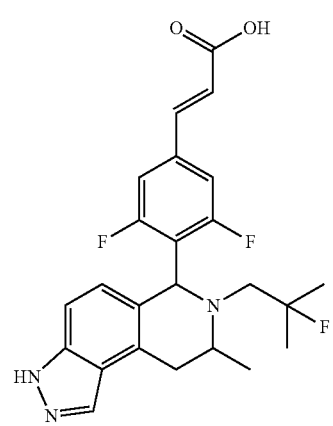
71
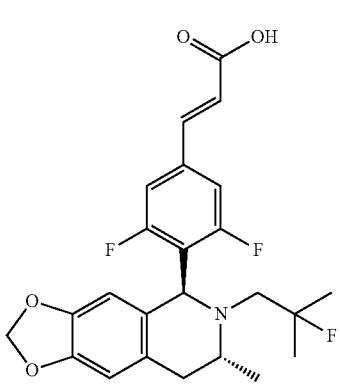
72
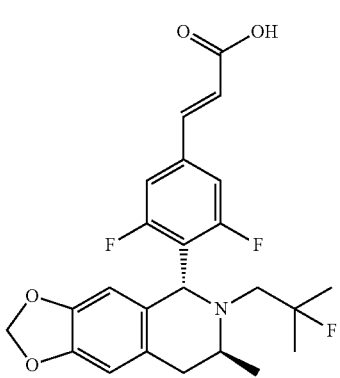
73
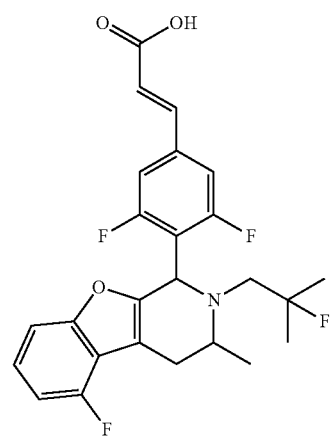

74
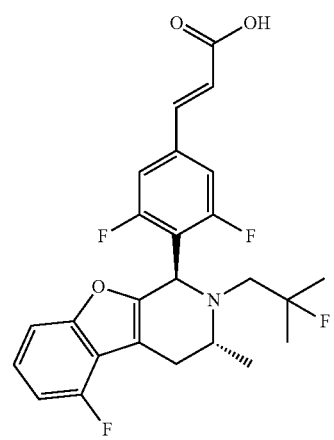
75
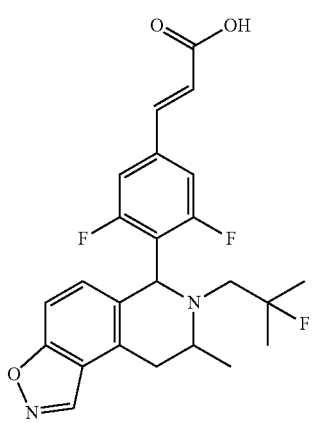
76
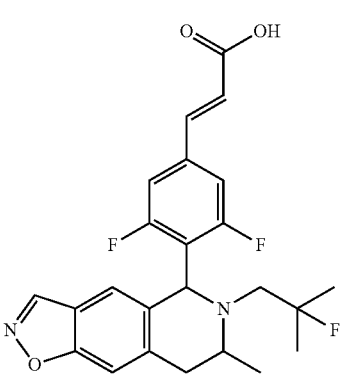
77
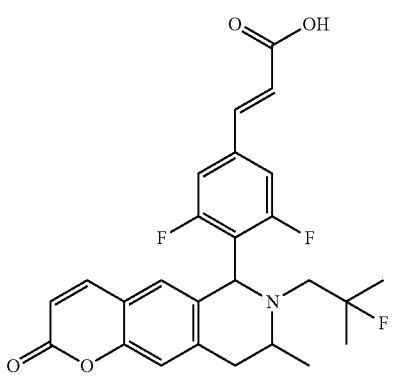
78
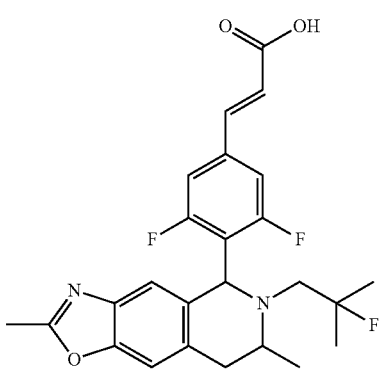
79
80

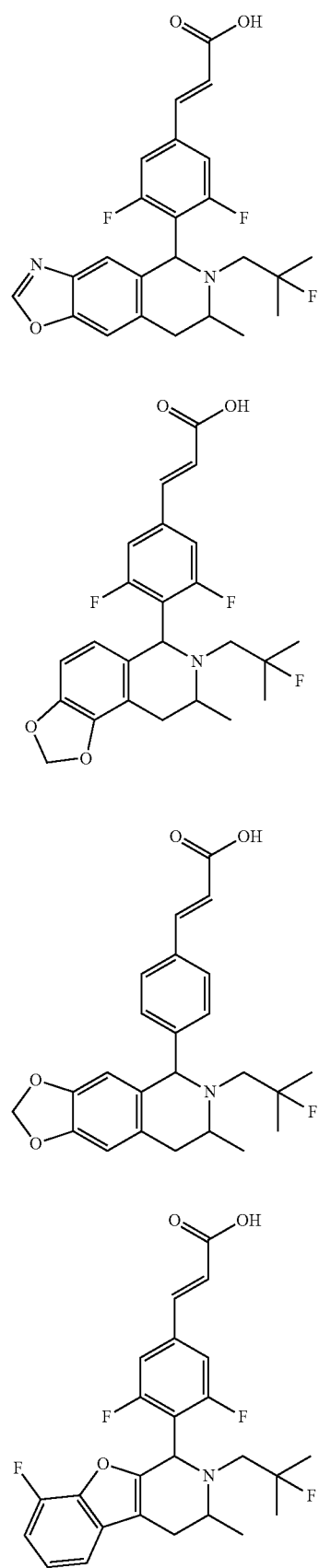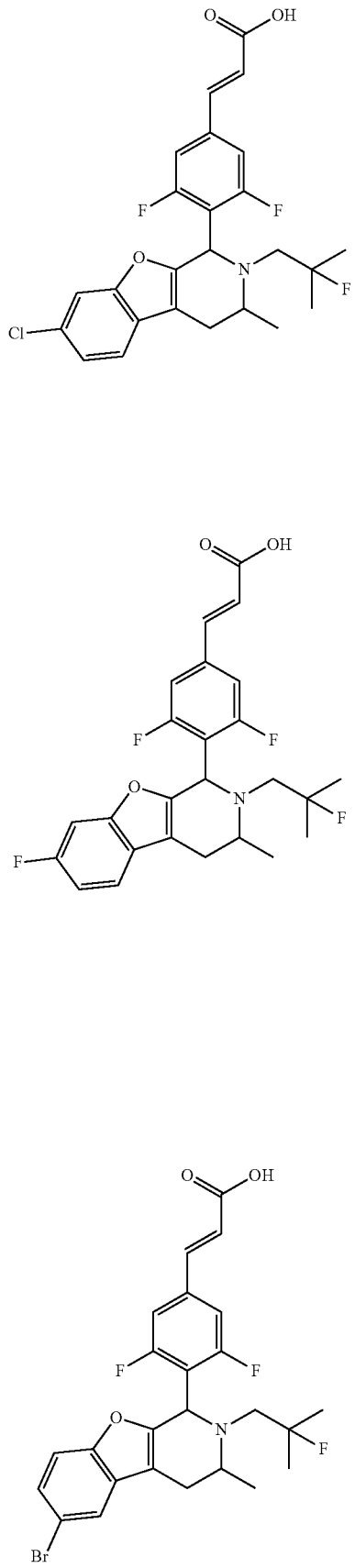

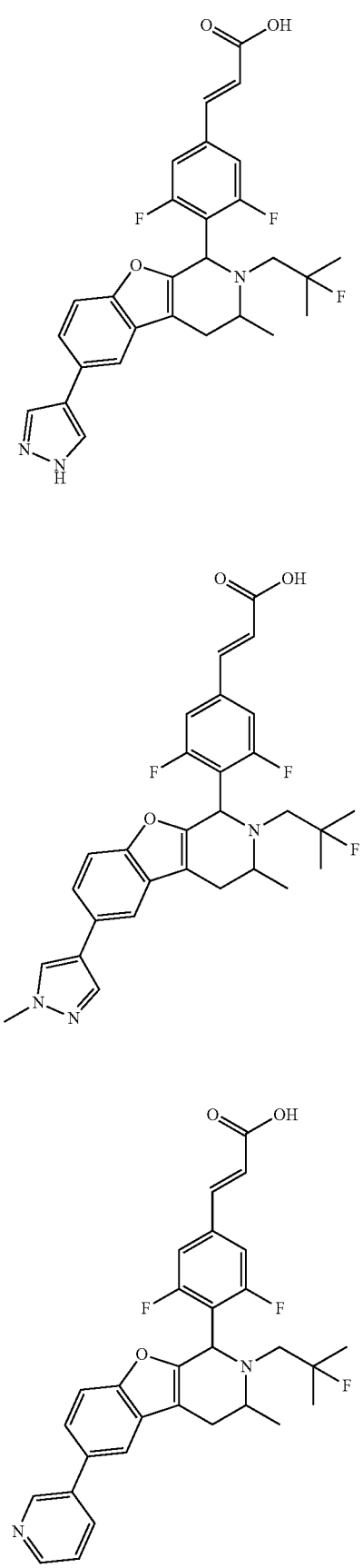
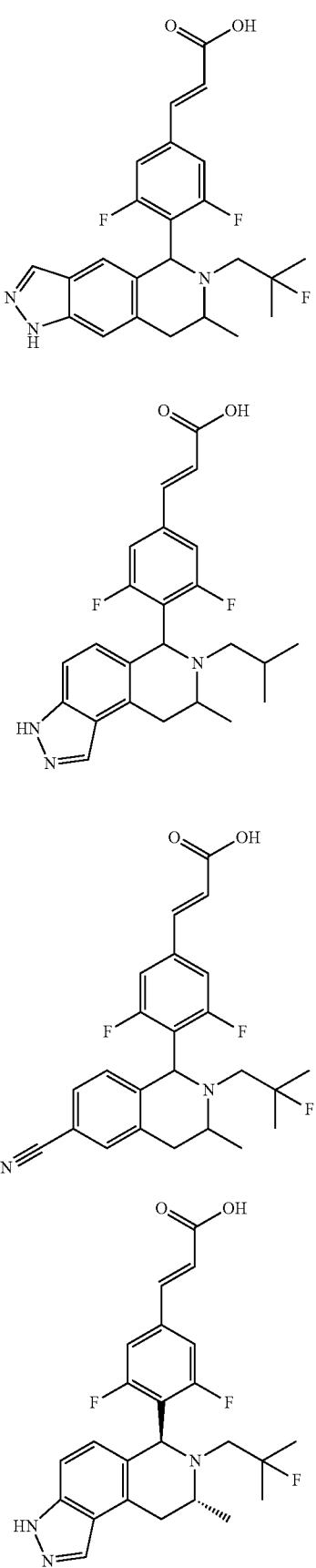

235
-continued
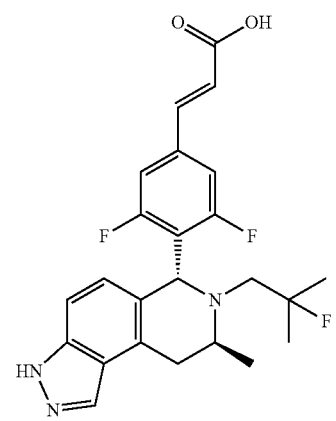
95
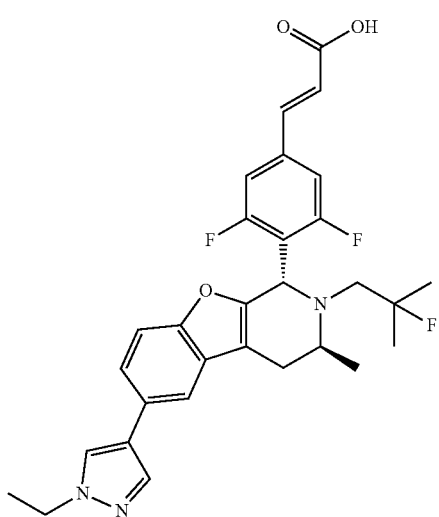
96
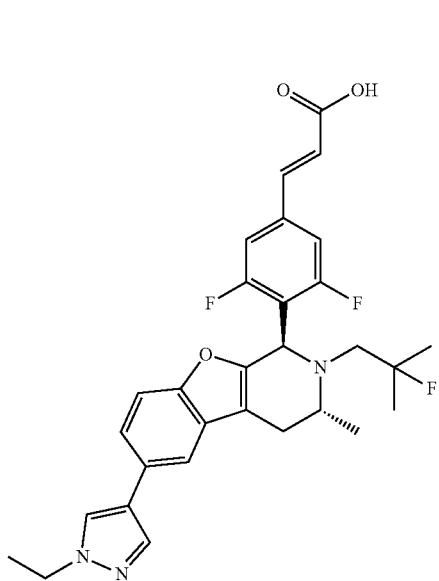
97
236
-continued
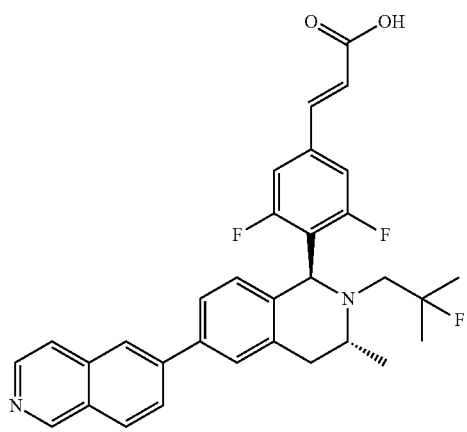
98
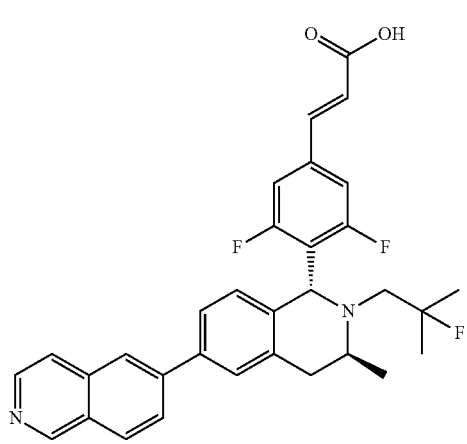
99
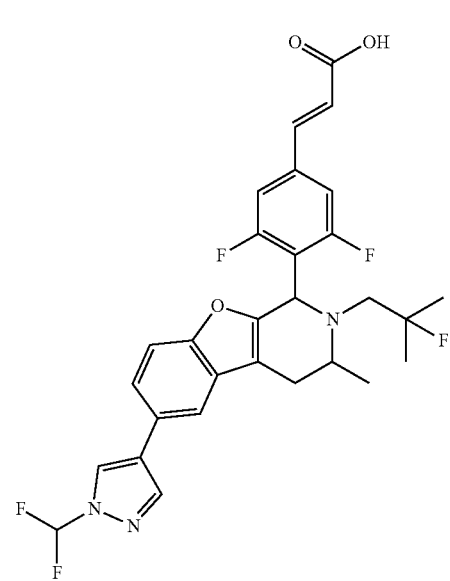
100

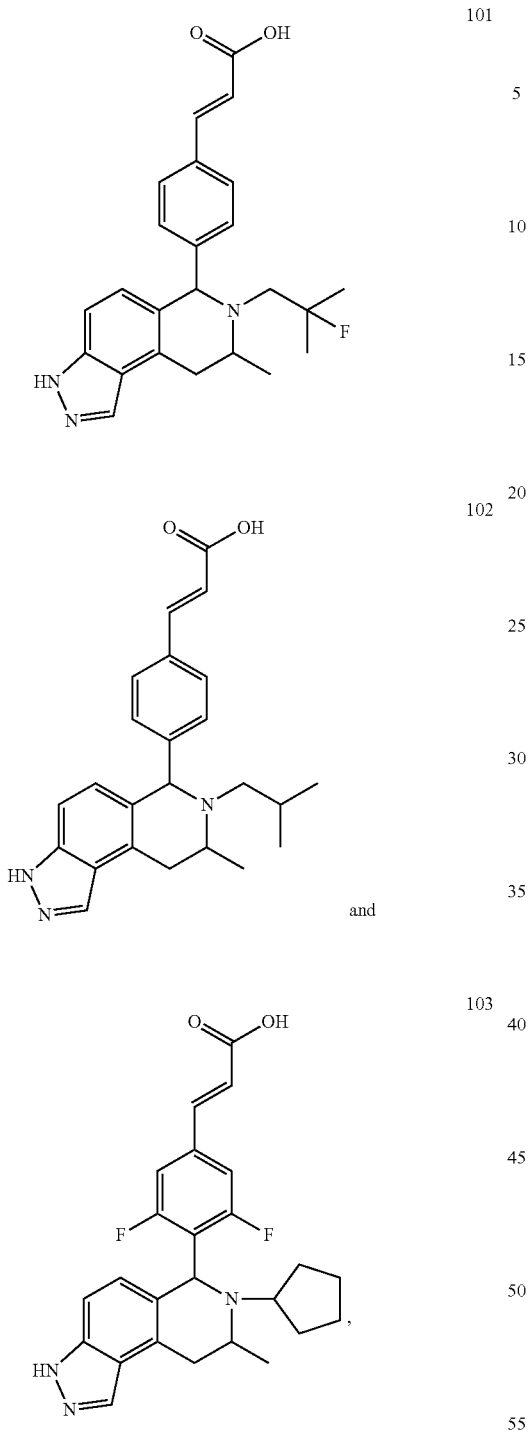

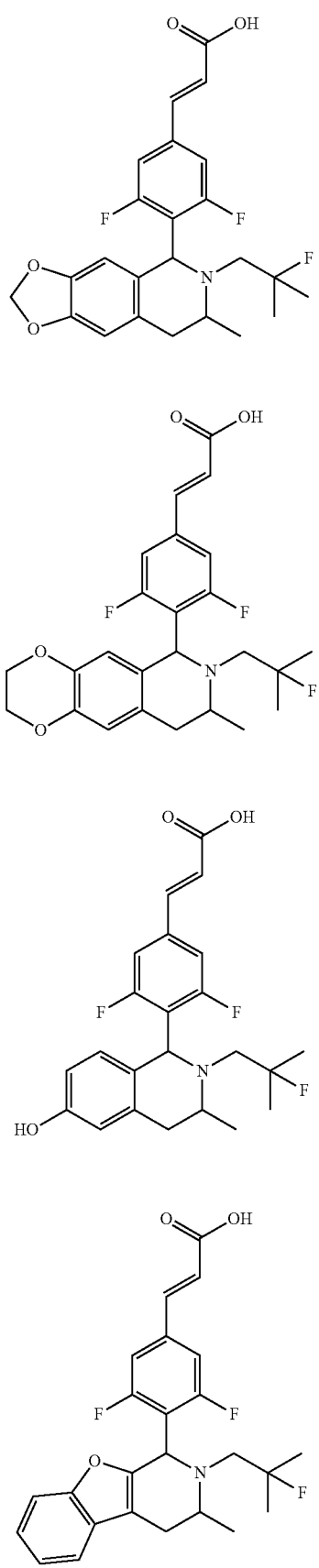

or a tautomer, mesomer, racemate, enantiomer, diastereomer, or mixture thereof, or a pharmaceutically acceptable salt thereof.

14. A method for treating cancer selected from the group consisting of breast cancer, ovarian cancer, and endometrial cancer in a subject in need thereof, the method comprising administering to the subject a pharmaceutical composition comprising one or more pharmaceutically acceptable carriers, diluents, or excipients, and a compound selected from the group consisting of:

5
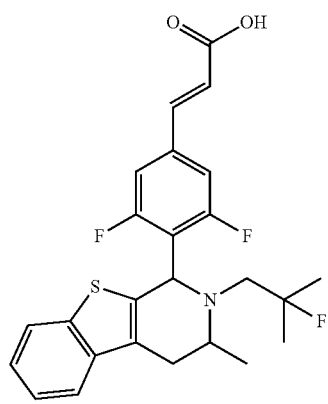
6
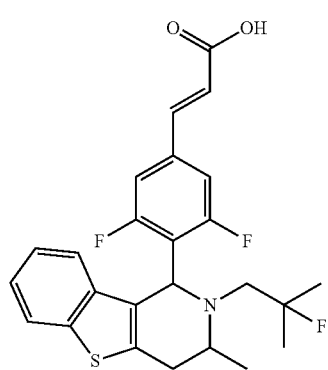
7
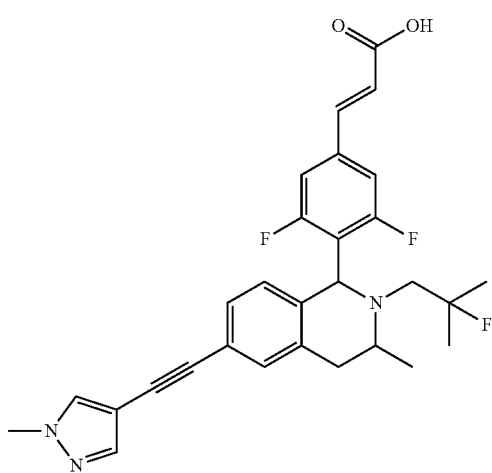
8
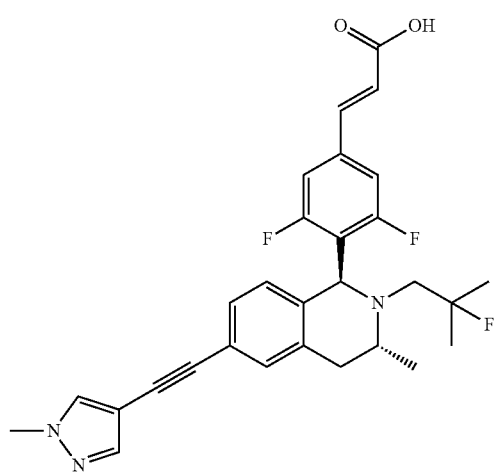
9
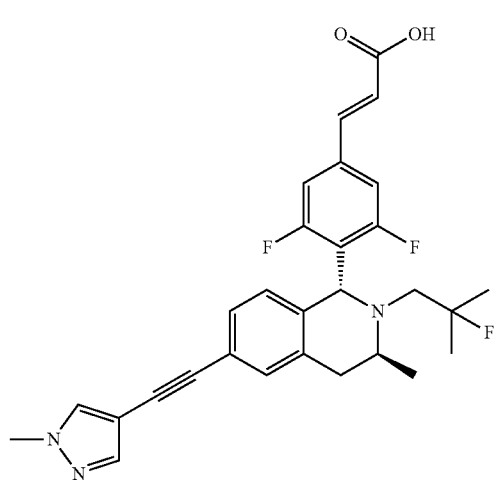
10
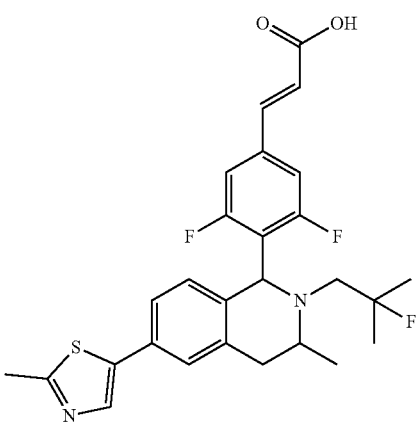

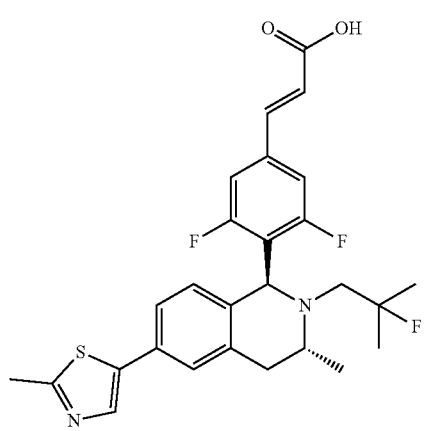
11
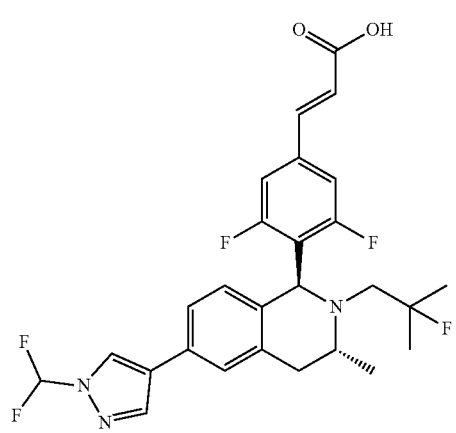
14
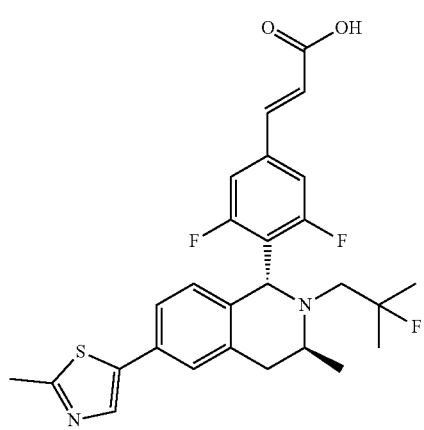
12
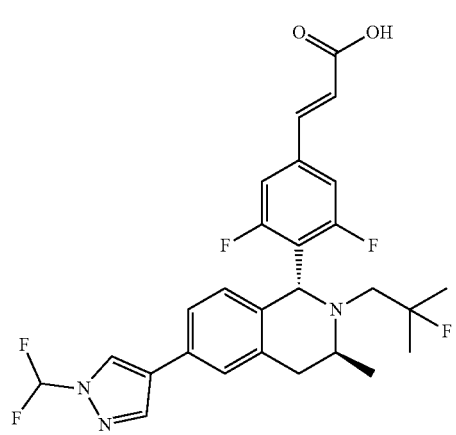
15
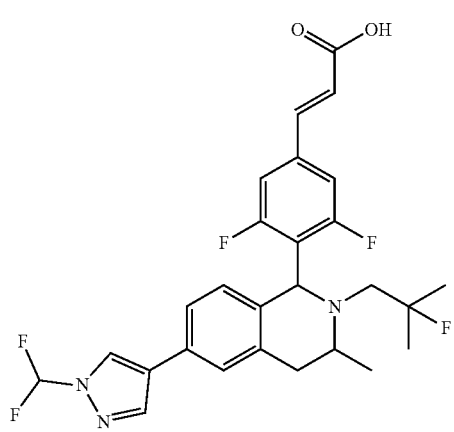
13
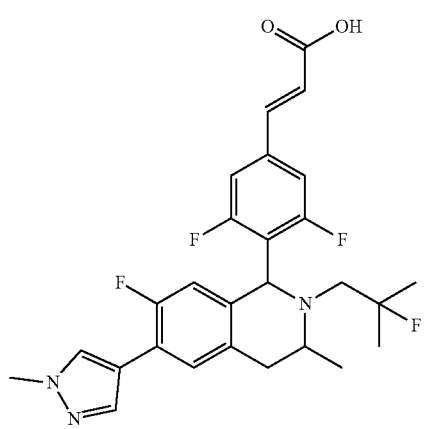
16

-continued
17
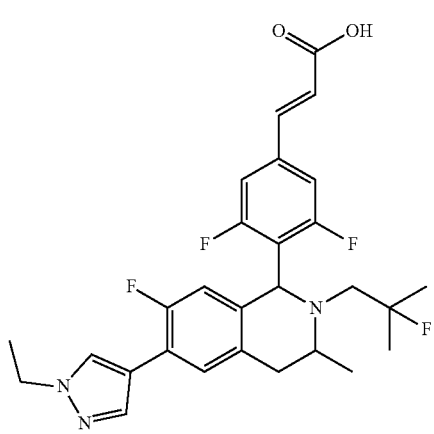
18
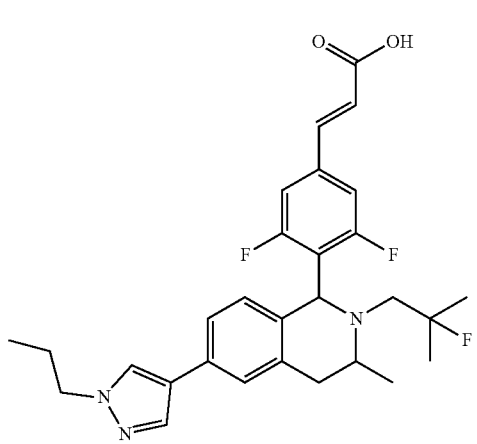
19
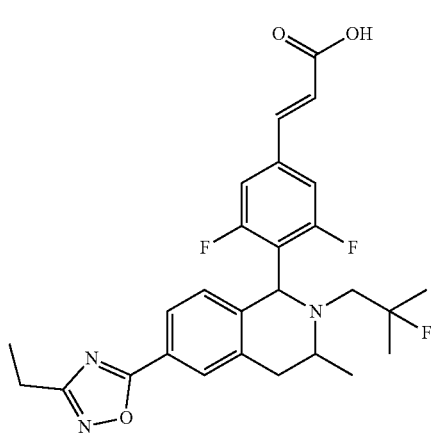
-continued
20
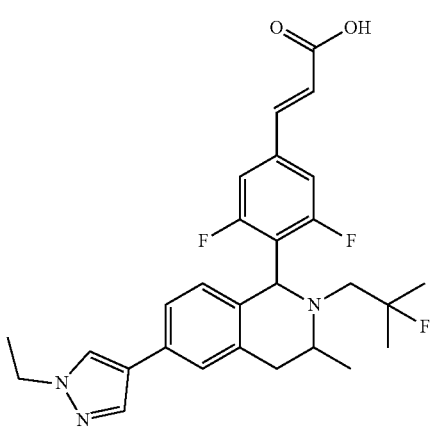
21
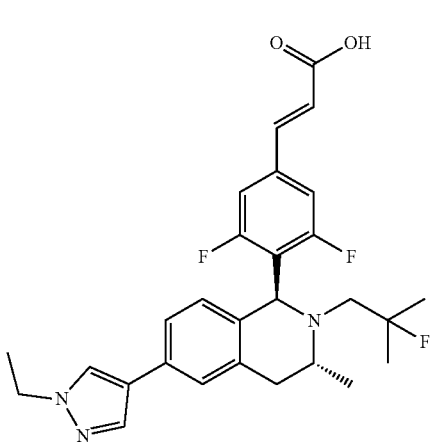
22
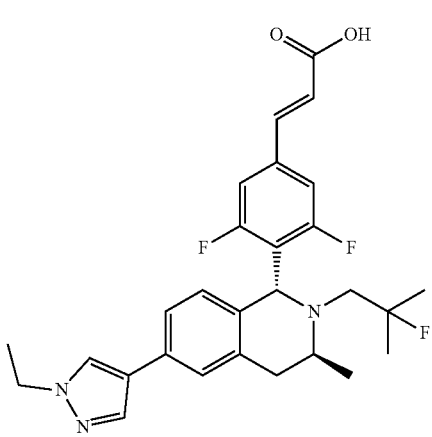

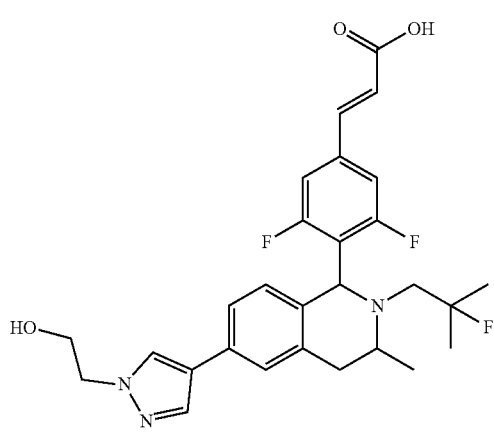
23
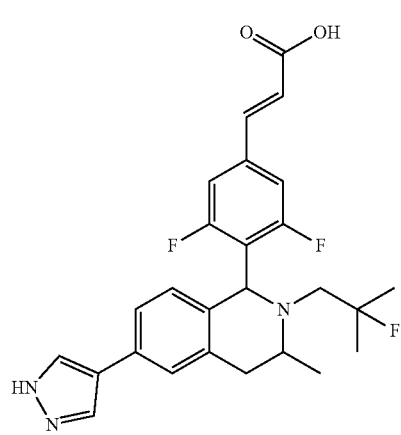
24
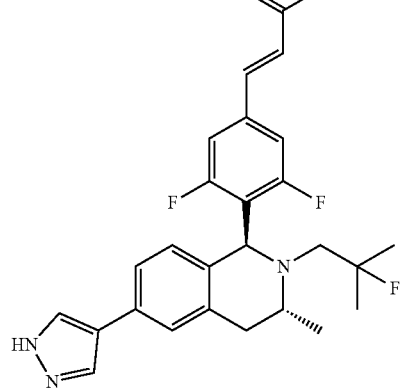
25
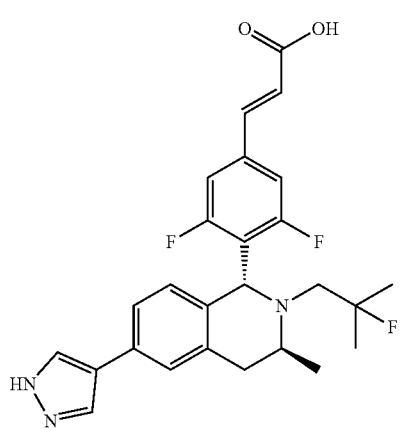
26
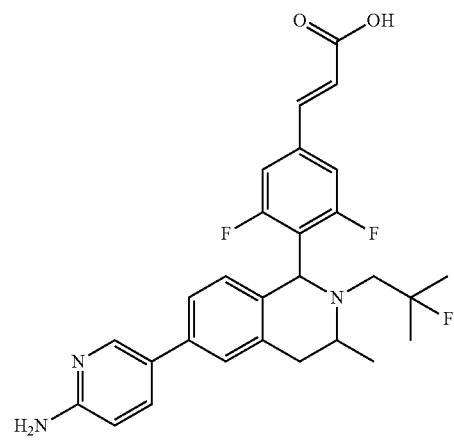
27
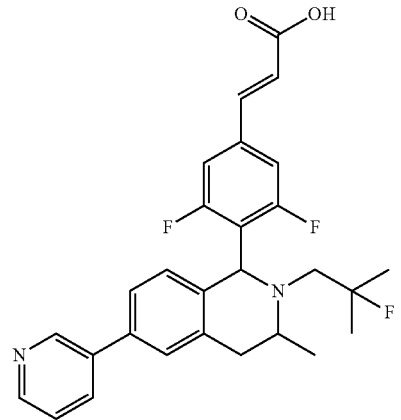
28
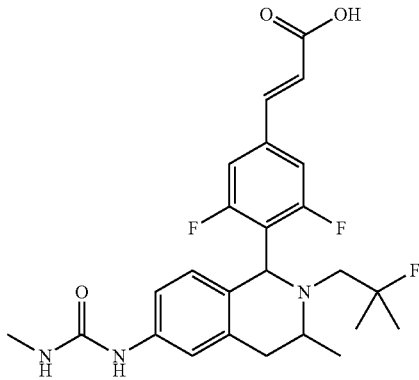
29

| | |
|---|---|
| 30 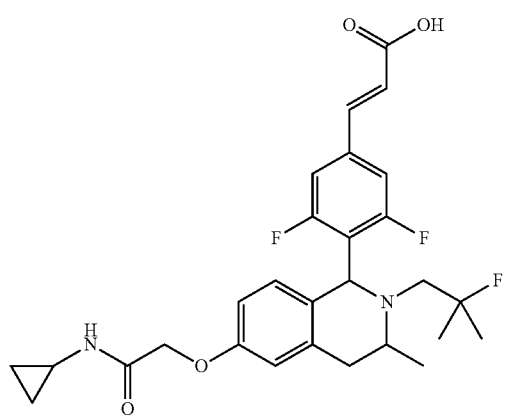 | 34 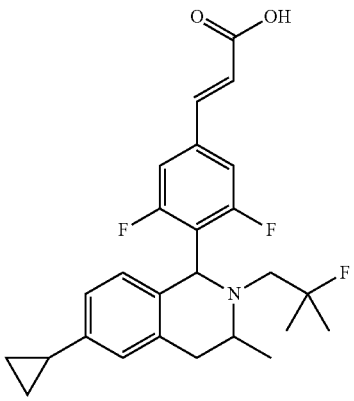 |
| 31 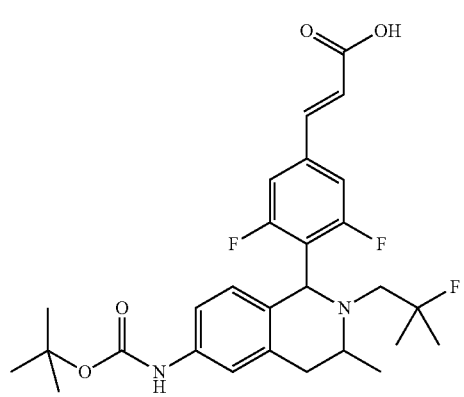 | 35 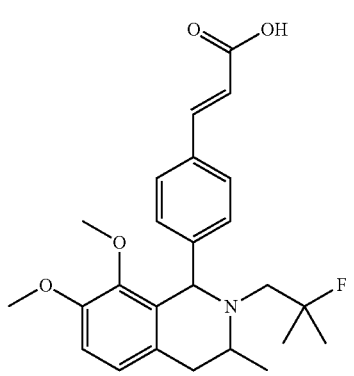 |
| 32 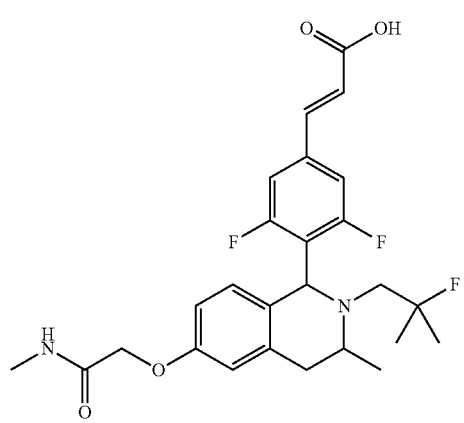 | 36 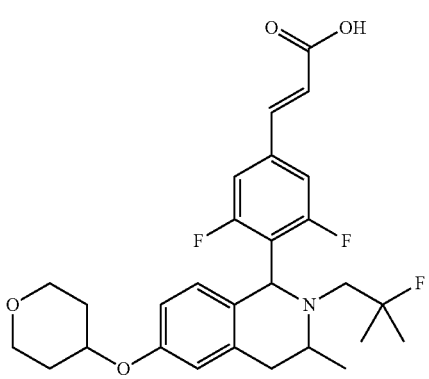 |
| 33 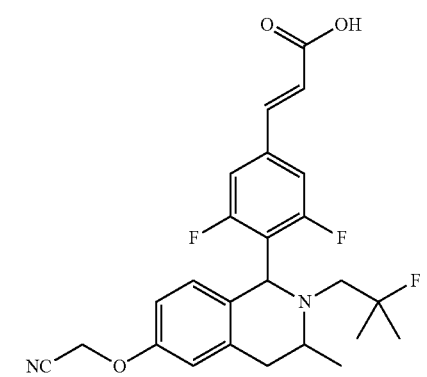 | 37 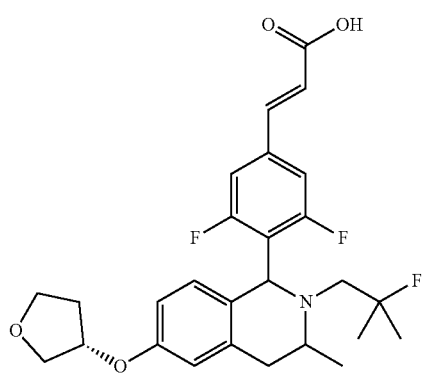 |

-continued
38
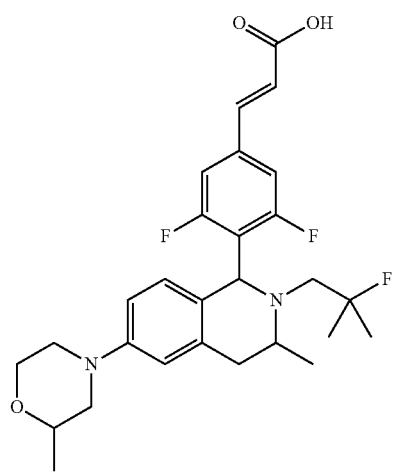
41
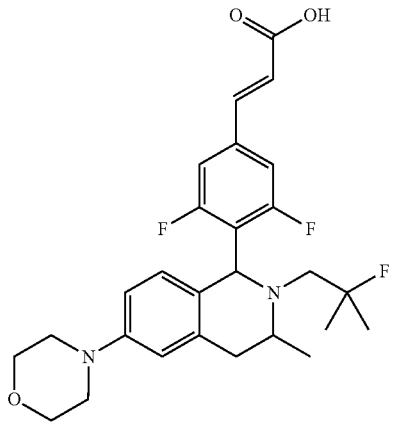
39
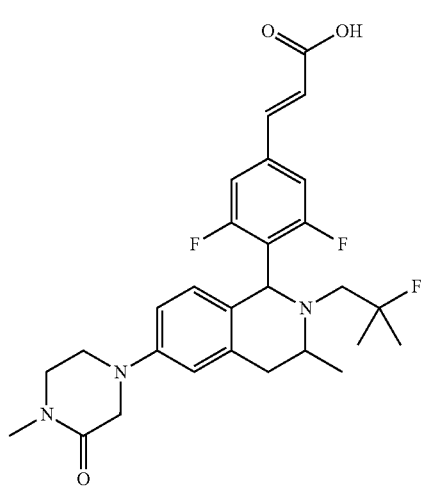
42
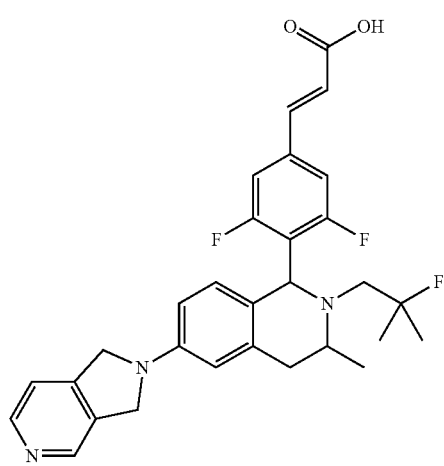
40
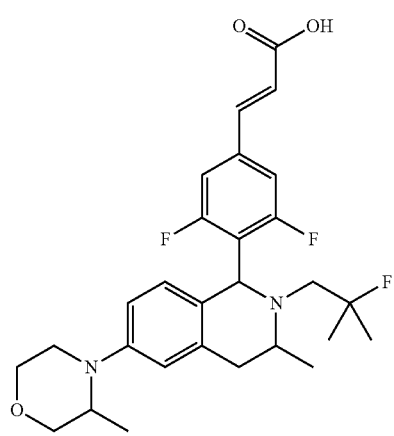
43
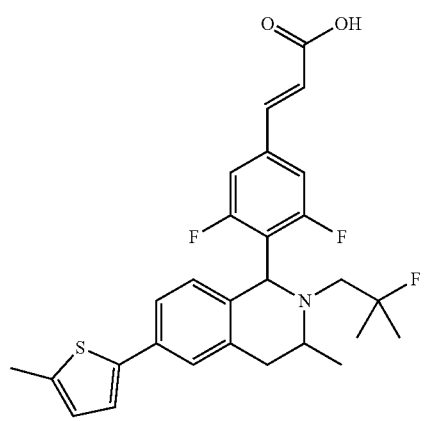

44
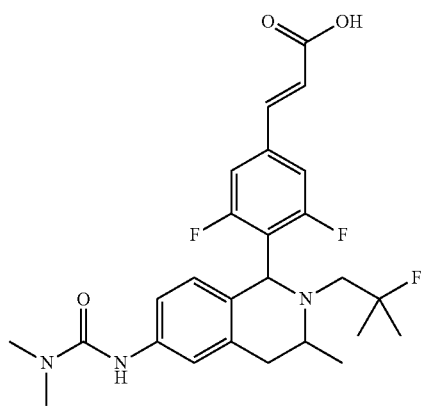
47
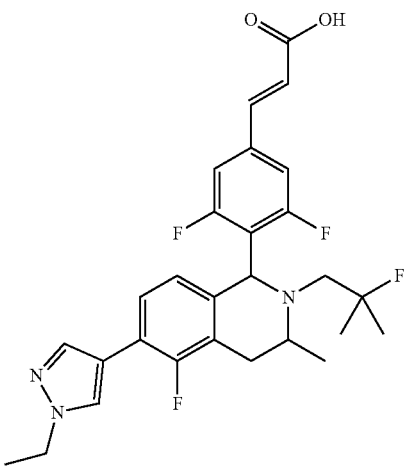
45
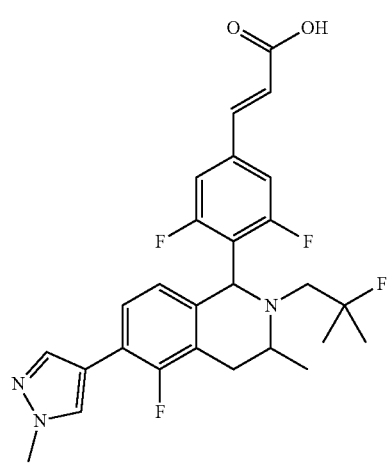
48
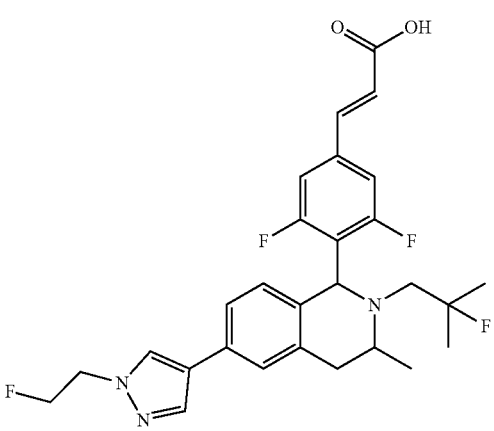
46
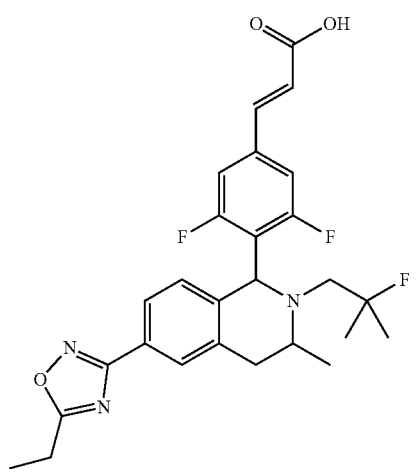
49
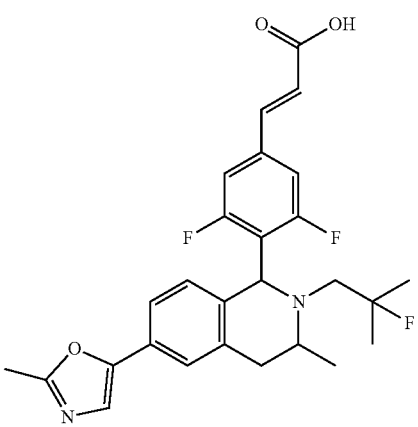

253
-continued
50
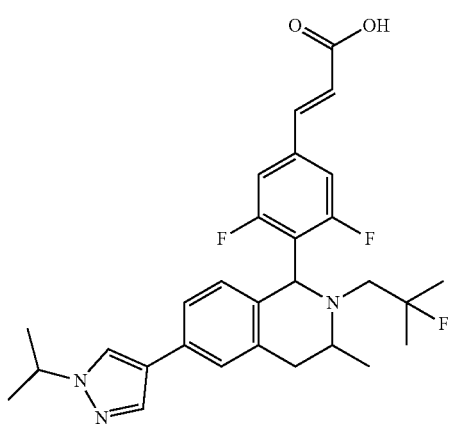
51
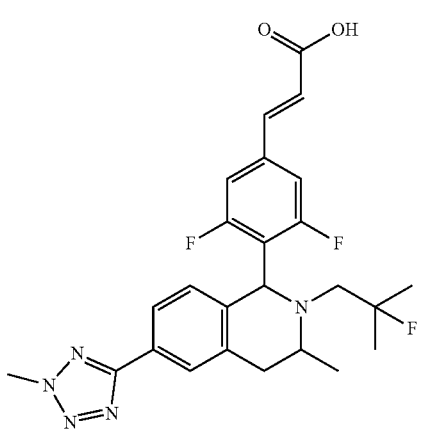
52
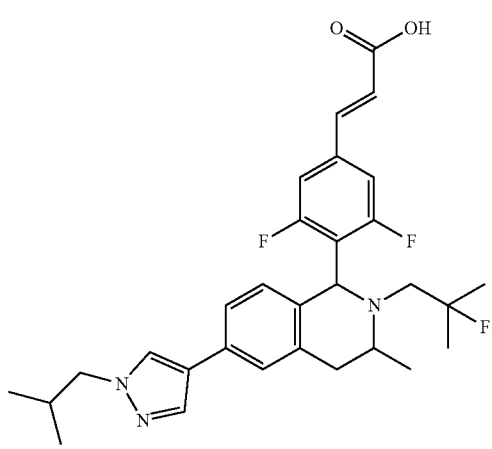
254
-continued
53
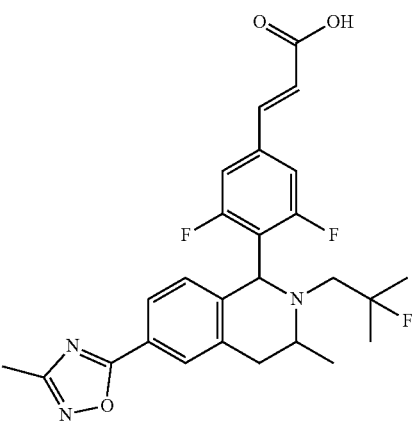
54
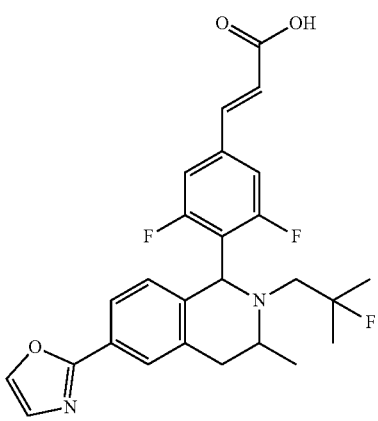
55
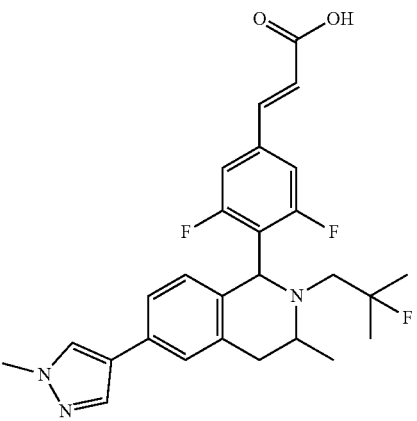

255
-continued
56
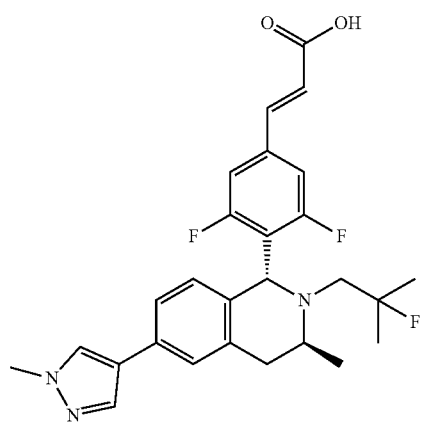
57
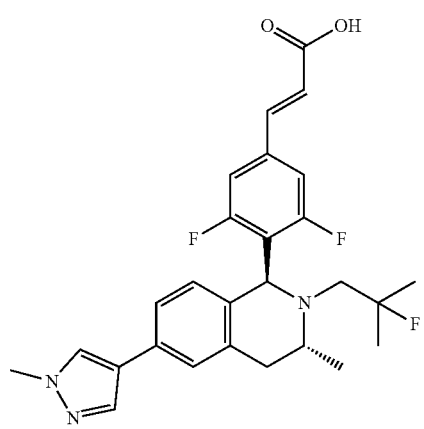
58
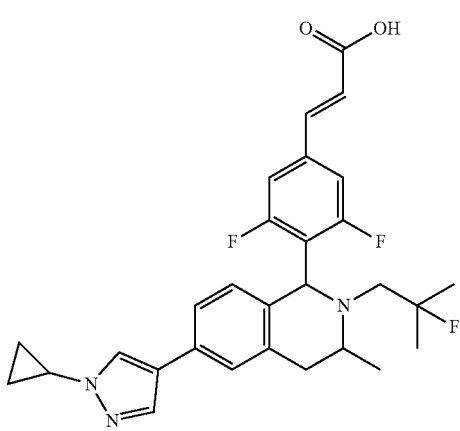
256
-continued
59
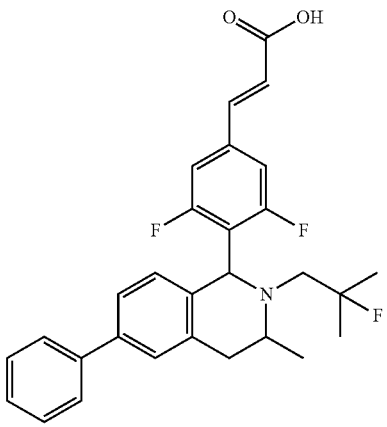
60
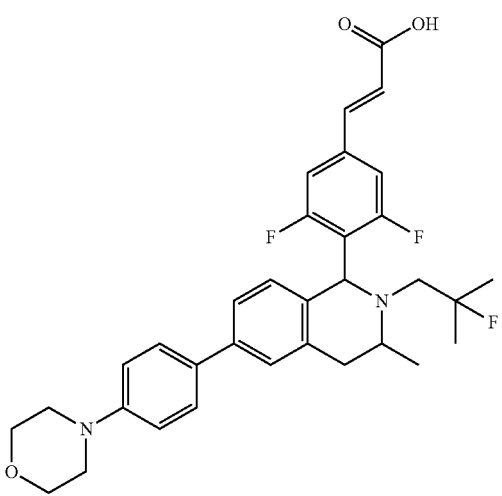
61
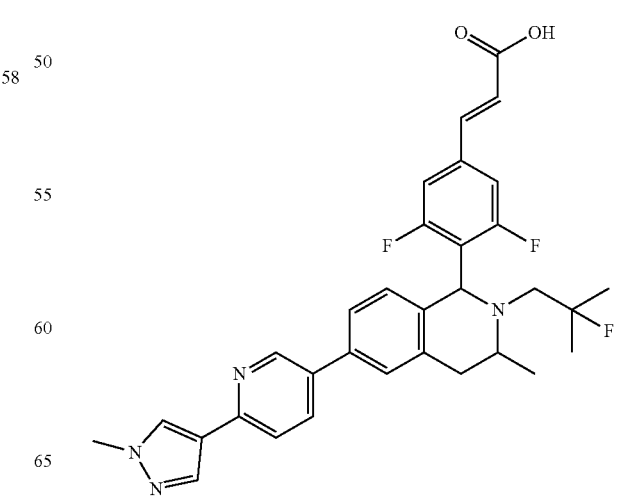

-continued
62
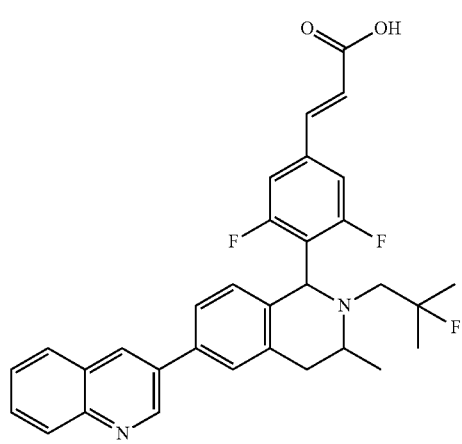
63
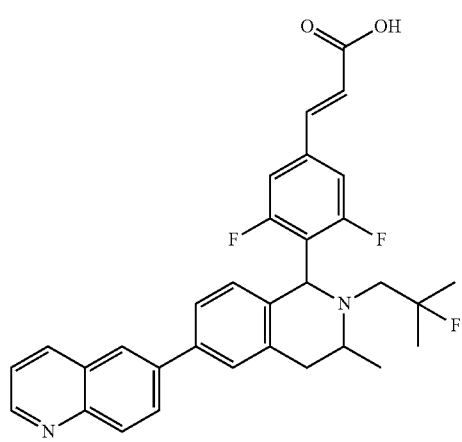
64
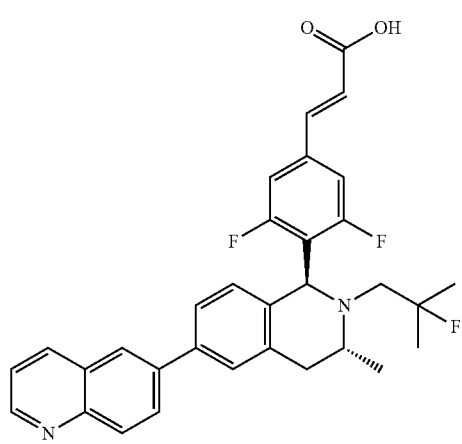
-continued
65
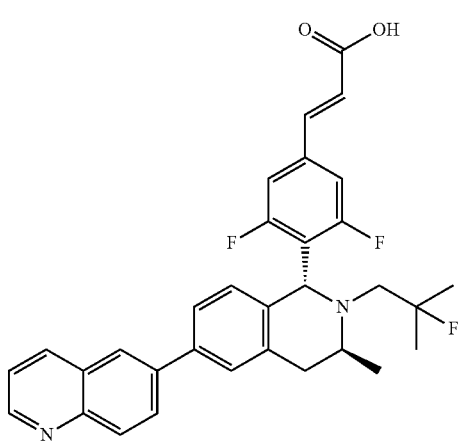
66
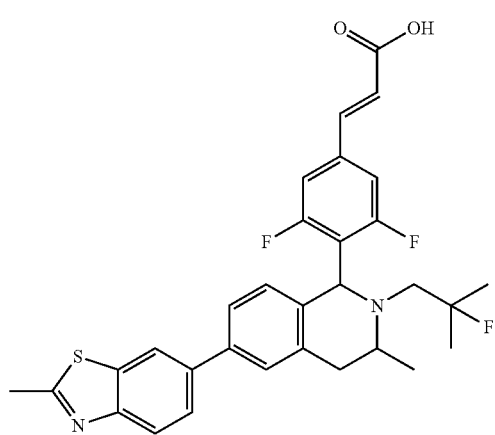
67
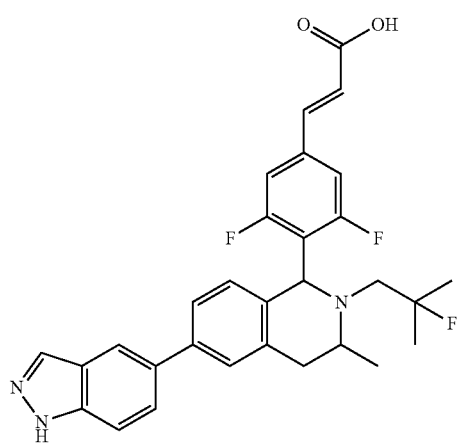

259
-continued
68
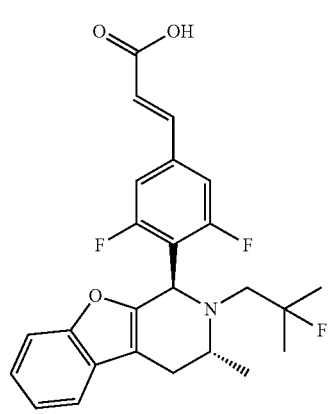
69
70
71
260
-continued
72
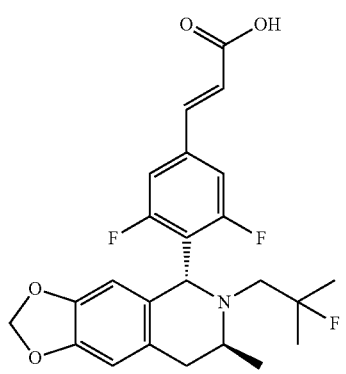
73
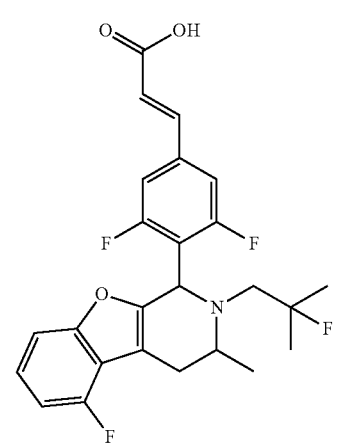
74
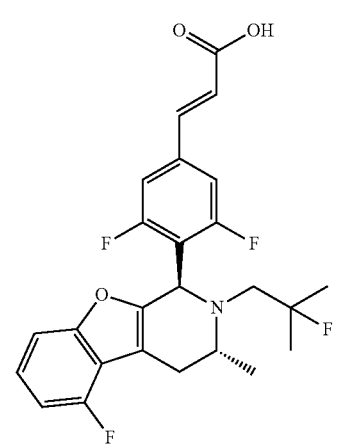
75
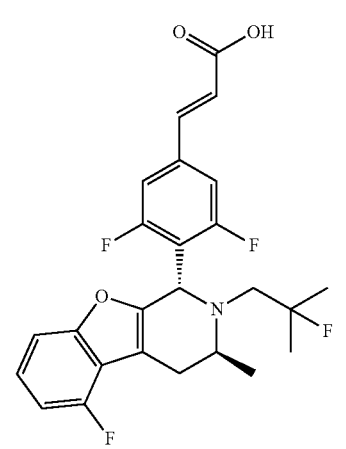 [SMILES: C[C@H]1Cc2c(oc3ccccc23)[C@H](c2c(F)cc(/C=C/C(=O)O)cc2F)N1CC(C)(C)F]

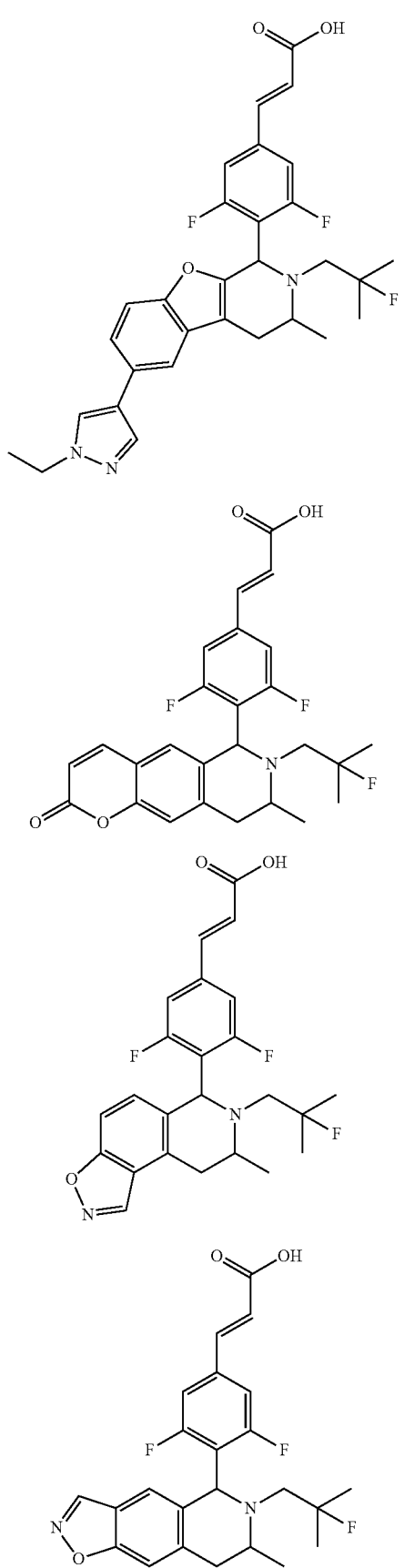
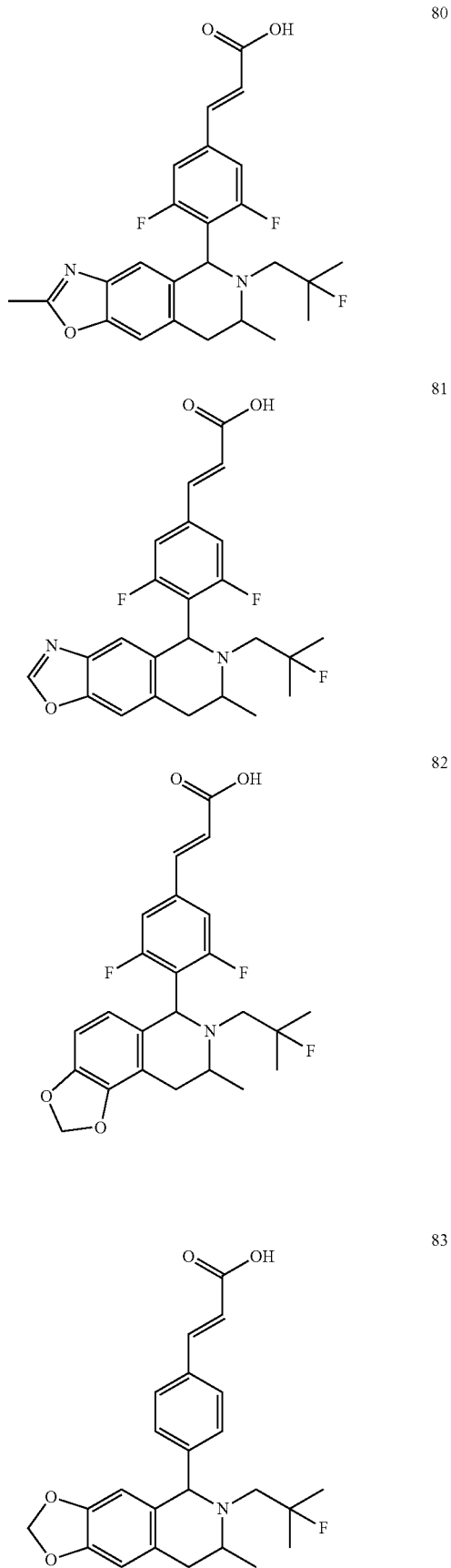

263
-continued
84
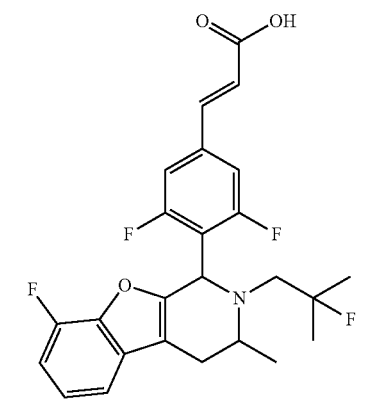
85
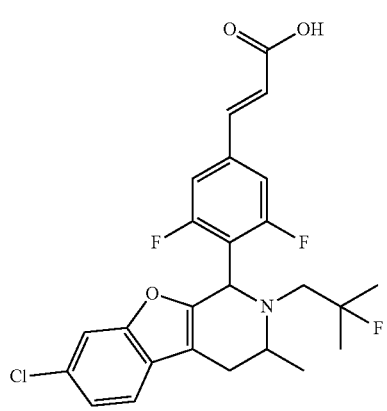
86
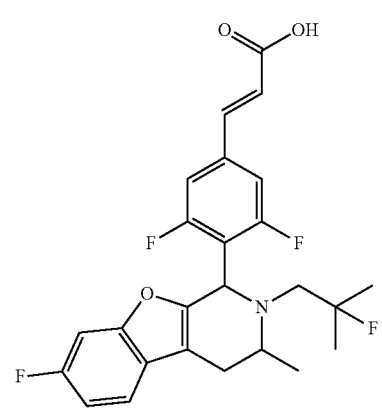
87
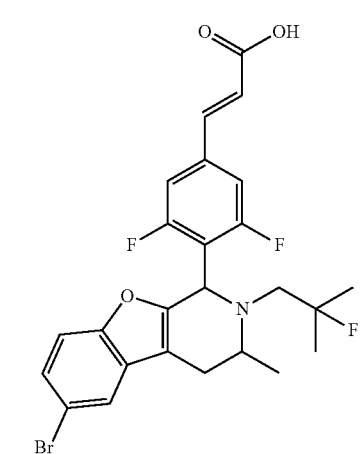
264
-continued
88
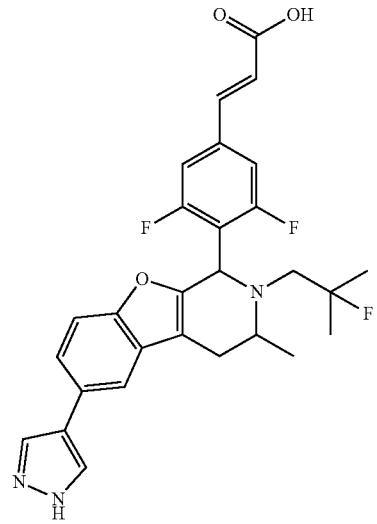
89
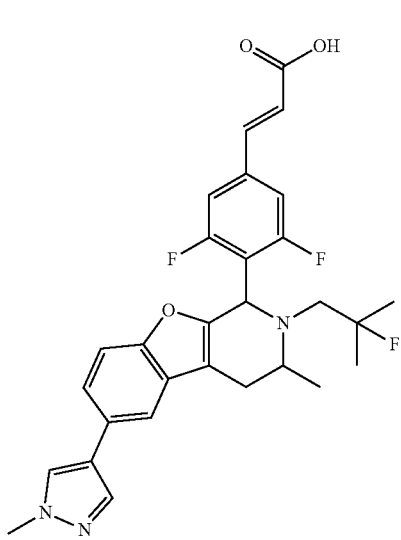
90
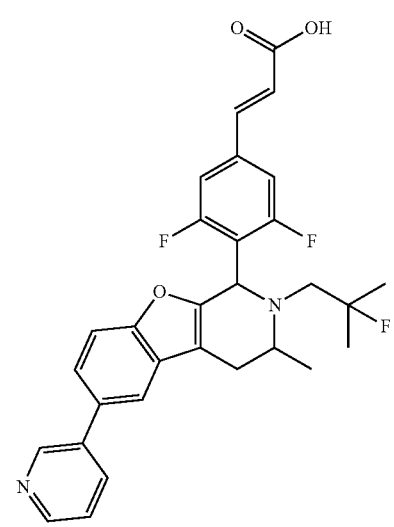

| | |
|---|---|
| 91 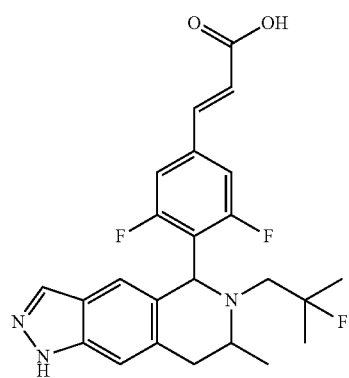 | 95 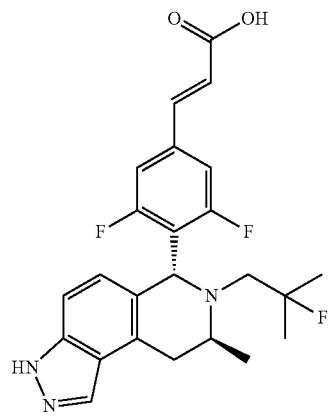 |
| 92 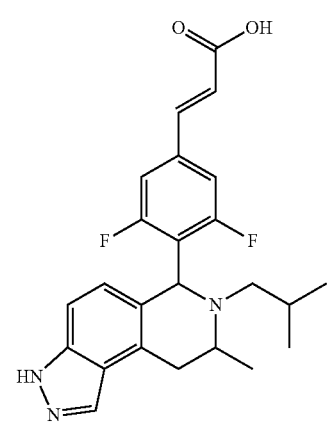 | 96 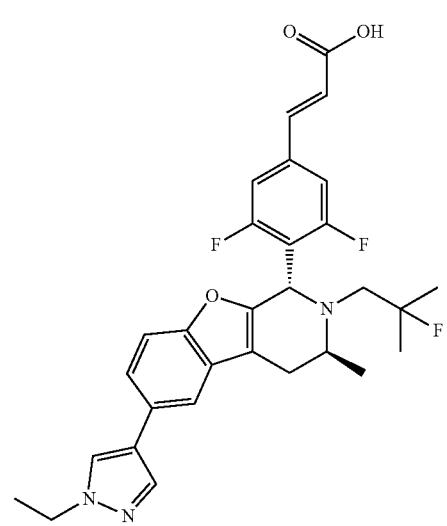 |
| 93 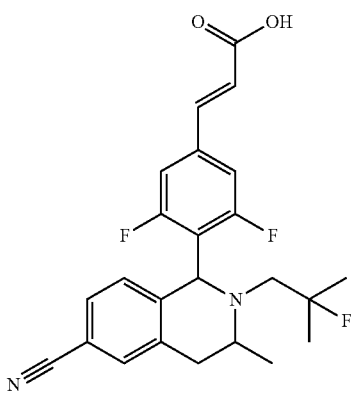 | |
| 94 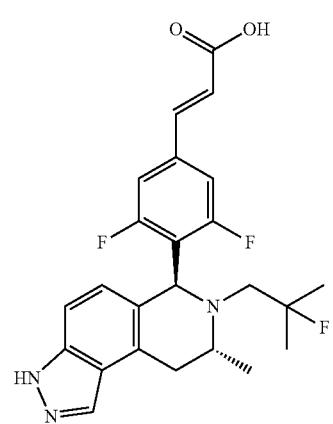 | 97 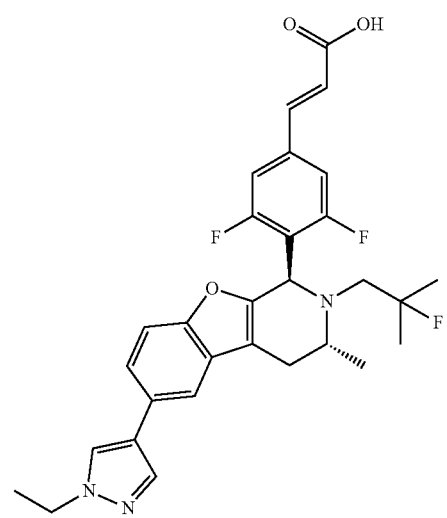 |

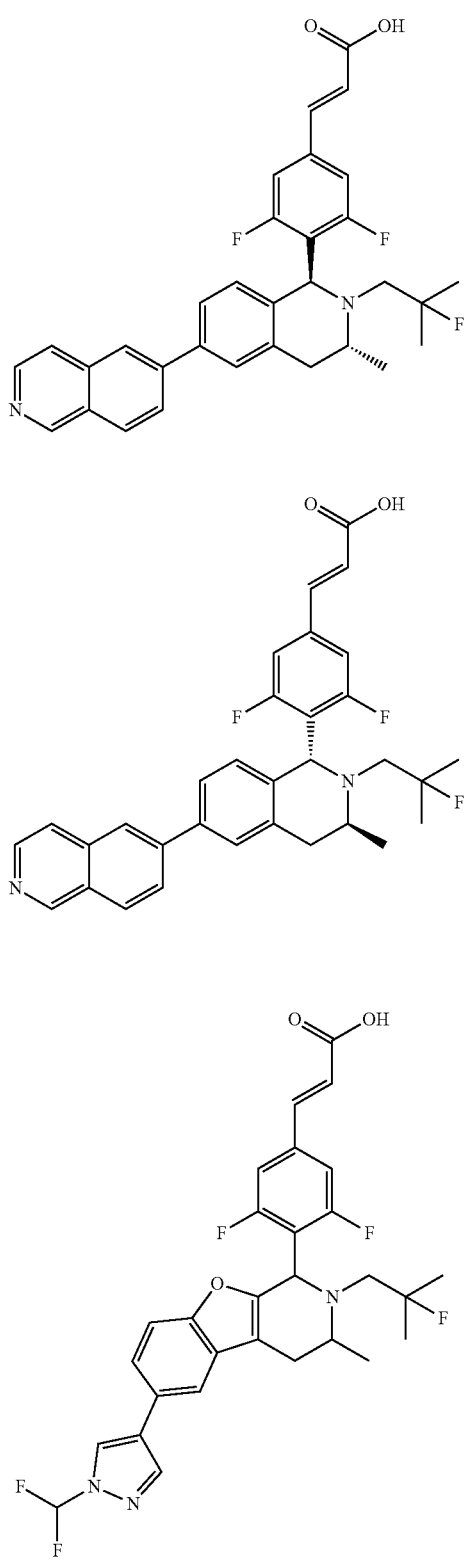
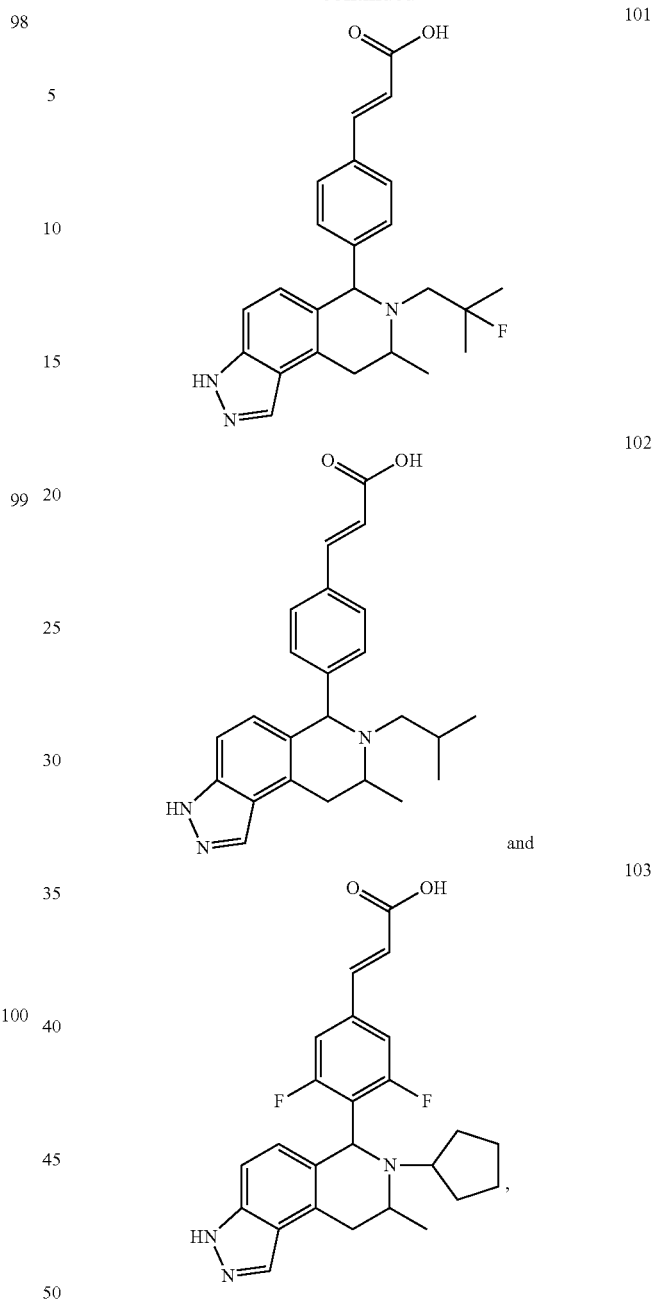
or a tautomer, mesomer, racemate, enantiomer, diastereomer, or mixture thereof, or a pharmaceutically acceptable salt thereof.
15. The method according to claim 14, wherein the cancer is breast cancer.
16. The method according to claim 14, wherein the cancer is ovarian cancer.
17. The method according to claim 14, wherein the cancer is endometrial cancer.
* * * * *